US009579351B2

(12) United States Patent
Kihm et al.

(10) Patent No.: US 9,579,351 B2
(45) Date of Patent: Feb. 28, 2017

(54) POSTPARTUM CELLS DERIVED FROM PLACENTAL TISSUE, AND METHODS OF MAKING AND USING THE SAME

(75) Inventors: Anthony J. Kihm, Princeton, NJ (US); Ian Ross Harris, Belle Mead, NJ (US); Sanjay Mistry, Bedminster, NJ (US); Alexander M. Harmon, Clinton, NJ (US); Darin J. Messina, Somerville, NJ (US); Agnieszka Seyda, New Brunswick, NJ (US); Chin-Feng Yi, Hillsborough, NJ (US); Anna Gosiewska, Skillman, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 1233 days.

(21) Appl. No.: 10/877,446

(22) Filed: Jun. 25, 2004

(65) Prior Publication Data
US 2005/0058631 A1  Mar. 17, 2005

Related U.S. Application Data

(60) Provisional application No. 60/483,264, filed on Jun. 27, 2003.

(51) Int. Cl.
| C12N 5/00 | (2006.01) |
| C12N 5/073 | (2010.01) |
| A61K 35/50 | (2015.01) |
| A61K 35/51 | (2015.01) |
| C12N 5/074 | (2010.01) |
| A61K 45/06 | (2006.01) |
| A61K 35/12 | (2015.01) |

(52) U.S. Cl.
CPC .............. *A61K 35/51* (2013.01); *A61K 45/06* (2013.01); *C12N 5/0605* (2013.01); *C12N 5/0607* (2013.01); *A61K 35/12* (2013.01); *C12N 2500/32* (2013.01); *C12N 2500/34* (2013.01); *C12N 2500/44* (2013.01); *C12N 2500/90* (2013.01); *C12N 2500/95* (2013.01); *C12N 2501/12* (2013.01); *C12N 2501/21* (2013.01); *C12N 2501/23* (2013.01); *C12N 2502/02* (2013.01); *C12N 2506/02* (2013.01); *C12N 2506/03* (2013.01); *C12N 2509/00* (2013.01); *C12N 2533/50* (2013.01)

(58) Field of Classification Search
CPC .... A61K 2300/00; A61K 35/50; A61K 35/12; C12N 5/0605; C12N 5/0668
See application file for complete search history.

(56) References Cited

U.S. PATENT DOCUMENTS

| 2,324,800 | A | * | 7/1943 | Richard Pasternack et al. ............................ 544/251 |
| 2,654,735 | A | * | 10/1953 | Casimir Funk et al. ...... 544/251 |
| 2,864,848 | A | * | 12/1958 | McArthur ...................... 558/145 |
| 2,912,332 | A | * | 11/1959 | Young et al. ................... 426/72 |
| 3,665,061 | A |   | 5/1972 | Eberly, Jr. |
| 3,930,954 | A |   | 1/1976 | Irie |
| 4,193,992 | A | * | 3/1980 | Fontaine ................ A61K 8/982 424/583 |
| 4,216,144 | A | * | 8/1980 | Ashmead ...................... 530/345 |
| 4,290,962 | A |   | 9/1981 | Tachi et al. |
| 4,352,883 | A |   | 10/1982 | Lim ................................ 435/178 |
| 4,393,240 | A | * | 7/1983 | Stille .............................. 568/13 |
| 4,465,776 | A | * | 8/1984 | Cidlowski et al. ........... 436/504 |
| 4,487,865 | A |   | 12/1984 | Balazs et al. |
| 4,544,516 | A |   | 10/1985 | Hughes et al. |
| 4,657,866 | A | * | 4/1987 | Kumar ................. C12N 5/0618 435/383 |
| 4,882,162 | A |   | 11/1989 | Ikada et al. ................... 424/444 |
| 4,925,677 | A |   | 5/1990 | Feijen |
| 4,963,489 | A |   | 10/1990 | Naughton et al. ......... 435/240.1 |
| 4,994,602 | A | * | 2/1991 | Seido et al. ................... 560/186 |
| 5,004,681 | A |   | 4/1991 | Boyse et al. ..................... 435/2 |
| 5,140,100 | A | * | 8/1992 | Braunstein et al. .......... 530/300 |
| 5,145,770 | A | * | 9/1992 | Tubo et al. ................... 435/1.3 |
| 5,192,553 | A |   | 3/1993 | Boyse et al. ................... 424/529 |
| 5,248,608 | A |   | 9/1993 | Van Dooren et al. |
| 5,284,766 | A |   | 2/1994 | Okano et al. |
| 5,286,632 | A |   | 2/1994 | Jones ........................... 435/91.2 |
| 5,320,962 | A |   | 6/1994 | Stiles et al. .................. 435/91.2 |
| 5,342,761 | A |   | 8/1994 | MacLeod ..................... 435/69.1 |
| 5,354,771 | A | * | 10/1994 | Walser .......................... 514/400 |
| 5,356,807 | A | * | 10/1994 | Blass et al. ................... 435/368 |

(Continued)

FOREIGN PATENT DOCUMENTS

| CN | 1407088 | 2/2003 |
| EP | 0 382 214 | 8/1990 |

(Continued)

OTHER PUBLICATIONS

Kawata M et al. 1984. Transcriptional control of HLA-A,B,C antigen in human placental cytotrophoblast isolated using trophoblast- and HLA-specific monoclonal antibodies and the fluorescence-activated cell sorter. Journal of Experimental Medicine 160: 633-651.*
"Iliac," "ilium," "ileal/ileac," and "ileum." Merriam-Webster MedlinePlus Online Medical Dictionary [online] [retrieved on Feb. 13, 2008]. Retrieved from the Internet: <URL://www.nlm.nih.gov/medlineplus/mplusdictionary.html>.*
"11885—DMEM, low glucose, pyruvate." Life Technologies. Available online at <http://www.lifetechnologies.com/us/en/home/technical-resources/media-formulation.48.html>, accessed Jul. 31, 2014. 2 pages.*
"MSCGM™ Mesenchymal Stem Cell Growth Medium." Lonza Group Ltd. Available online at <http://www.lonza.com/products-services/bio-research/stem-cells/adult-stem-cells-and-media/human-mesenchymal-stem-cells-media/mscgm-mesenchymal-stem-cell-growth-medium.aspx>. Accessed Aug. 27, 2015. 2 pages.*

(Continued)

*Primary Examiner* — Allison Fox
(74) *Attorney, Agent, or Firm* — Johnson & Johnson

(57) ABSTRACT

Cells derived from postpartum placenta and methods for their isolation are provided by the invention. The invention further provides cultures and compositions of the placenta-derived cells. The placenta-derived cells of the invention have a plethora of uses, including but not limited to research, diagnostic, and therapeutic applications.

44 Claims, No Drawings

(56) References Cited

U.S. PATENT DOCUMENTS

| | | | |
|---|---|---|---|
| 5,437,994 A | 8/1995 | Emerson et al. | 435/373 |
| 5,443,950 A | 8/1995 | Naughton et al. | |
| 5,466,233 A | 11/1995 | Weiner et al. | 604/890.1 |
| 5,474,987 A | 12/1995 | Cohen et al. | |
| 5,486,359 A | 1/1996 | Caplan et al. | 424/93.7 |
| 5,494,899 A * | 2/1996 | Kincade et al. | 514/10.2 |
| 5,506,134 A | 4/1996 | Soule et al. | |
| 5,580,777 A | 12/1996 | Bernard et al. | |
| 5,589,376 A | 12/1996 | Anderson et al. | 435/240.2 |
| 5,670,483 A | 9/1997 | Zhang et al. | 514/14 |
| 5,677,181 A | 10/1997 | Parish | 435/332 |
| 5,693,332 A | 12/1997 | Hansbrough | |
| 5,698,518 A | 12/1997 | Carson et al. | 514/12 |
| 5,707,643 A | 1/1998 | Ogura et al. | 424/428 |
| 5,718,922 A | 2/1998 | Herrero-Vanrell et al. | |
| 5,736,516 A | 4/1998 | Louis | 514/12 |
| 5,811,094 A | 9/1998 | Caplan et al. | 424/93.7 |
| 5,827,735 A | 10/1998 | Young et al. | 435/325 |
| 5,834,308 A | 11/1998 | Peck et al. | 435/325 |
| 5,840,580 A | 11/1998 | Terstappen et al. | 435/372 |
| 5,842,477 A | 12/1998 | Naughton et al. | |
| 5,843,780 A | 12/1998 | Thompson | 435/363 |
| 5,843,781 A | 12/1998 | Ballermann et al. | |
| 5,855,619 A | 1/1999 | Caplan et al. | |
| 5,869,079 A | 2/1999 | Wong et al. | 424/426 |
| 5,902,598 A | 5/1999 | Chen et al. | 424/423 |
| 5,902,741 A | 5/1999 | Purchio et al. | |
| 5,906,934 A | 5/1999 | Grande et al. | 435/325 |
| 5,914,265 A * | 6/1999 | Roop et al. | 435/320.1 |
| 5,919,702 A | 7/1999 | Purchio et al. | 435/378 |
| 5,928,214 A * | 7/1999 | Rubinstein | A01N 1/02 210/206 |
| 5,942,225 A | 8/1999 | Bruder et al. | 424/93.7 |
| 5,955,343 A | 9/1999 | Holmes et al. | 435/240.1 |
| 5,962,325 A | 10/1999 | Naughton et al. | 435/395 |
| 5,994,094 A | 11/1999 | Hötten et al. | 435/69.1 |
| 6,001,647 A | 12/1999 | Peck et al. | 435/325 |
| 6,022,743 A | 2/2000 | Naughton et al. | 435/395 |
| 6,059,968 A | 5/2000 | Wolf | |
| 6,140,039 A | 10/2000 | Naughton et al. | 435/1.1 |
| 6,153,591 A | 11/2000 | Cai et al. | |
| 6,171,610 B1 | 1/2001 | Vacanti et al. | 424/426 |
| 6,179,872 B1 | 1/2001 | Bell et al. | |
| 6,200,606 B1 | 3/2001 | Peterson et al. | 424/574 |
| 6,200,806 B1 | 3/2001 | Thomson | 435/366 |
| 6,214,369 B1 | 4/2001 | Grande et al. | 424/423 |
| 6,221,904 B1 | 4/2001 | Agus et al. | |
| 6,251,090 B1 | 6/2001 | Avery et al. | 604/9 |
| 6,261,600 B1 * | 7/2001 | Kirschner et al. | 424/466 |
| 6,261,841 B1 * | 7/2001 | Cohen | C12N 5/0644 435/2 |
| 6,291,240 B1 | 9/2001 | Mansbridge et al. | |
| 6,323,188 B1 | 11/2001 | Weissman | 514/52 |
| 6,326,201 B1 | 12/2001 | Fung et al. | 435/377 |
| 6,331,313 B1 | 12/2001 | Wong et al. | 424/427 |
| 6,333,029 B1 | 12/2001 | Vyakarnam et al. | |
| 6,355,239 B1 | 3/2002 | Bruder et al. | 424/93.1 |
| 6,355,699 B1 | 3/2002 | Vyakarnam et al. | 521/61 |
| 6,358,737 B1 | 3/2002 | Bonewald et al. | |
| 6,372,494 B1 | 4/2002 | Naughton et al. | |
| 6,375,972 B1 | 4/2002 | Guo et al. | 424/423 |
| 6,387,367 B1 | 5/2002 | Davis-Sproul et al. | 424/93.1 |
| 6,391,297 B1 | 5/2002 | Halvorsen | 424/93.7 |
| 6,429,013 B1 | 8/2002 | Halvorsen et al. | 435/377 |
| 6,436,704 B1 | 8/2002 | Roberts et al. | 435/366 |
| 6,495,645 B1 | 12/2002 | Okano et al. | |
| 6,497,875 B1 | 12/2002 | Sorrell et al. | 424/93.7 |
| 6,511,511 B1 | 1/2003 | Slivka et al. | |
| 6,528,245 B2 | 3/2003 | Sanchez-Ramos et al. | 435/1.1 |
| 6,534,084 B1 | 3/2003 | Vyakarnam et al. | |
| 6,555,374 B1 | 4/2003 | Gimble et al. | 435/371 |
| 6,592,623 B1 | 7/2003 | Bowlin et al. | |
| 6,599,323 B2 | 7/2003 | Melican et al. | 623/23.72 |
| 6,610,535 B1 | 8/2003 | Lu et al. | 435/325 |
| 6,638,765 B1 | 10/2003 | Rosenberg | 435/377 |
| 6,673,606 B1 | 1/2004 | Tennekoon et al. | 435/372 |
| 6,680,198 B1 | 1/2004 | Snyder et al. | 435/368 |
| 6,686,198 B1 | 2/2004 | Melton et al. | 435/377 |
| 6,703,017 B1 | 3/2004 | Peck et al. | 424/93.7 |
| 6,916,655 B2 | 7/2005 | Yasumoto et al. | 435/371 |
| 7,413,734 B2 | 8/2008 | Mistry et al. | |
| 7,468,276 B2 * | 12/2008 | Hariri | 435/325 |
| 7,510,873 B2 | 3/2009 | Mistry et al. | |
| 7,524,489 B2 | 4/2009 | Messina et al. | |
| 7,560,276 B2 | 7/2009 | Harmon et al. | |
| 7,875,272 B2 | 1/2011 | Messina et al. | |
| 7,875,273 B2 | 1/2011 | Messina et al. | |
| 8,277,796 B2 | 10/2012 | Messina et al. | |
| 8,318,483 B2 | 11/2012 | Mistry et al. | |
| 8,658,152 B2 | 2/2014 | Messina et al. | |
| 8,703,121 B2 | 4/2014 | Harris et al. | |
| 8,790,637 B2 | 7/2014 | Mistry et al. | |
| 2001/0024824 A1 | 9/2001 | Moss et al. | 435/366 |
| 2001/0031256 A1 | 10/2001 | Edge | 424/93.7 |
| 2001/0046489 A1 | 11/2001 | Habener et al. | 424/93.21 |
| 2001/0053362 A1 * | 12/2001 | Walters | 424/184.1 |
| 2002/0022676 A1 | 2/2002 | He et al. | 523/113 |
| 2002/0028510 A1 | 3/2002 | Sanberg et al. | 435/368 |
| 2002/0062151 A1 | 5/2002 | Altman et al. | 623/13.7 |
| 2002/0081725 A1 | 6/2002 | Tsang et al. | 435/366 |
| 2002/0098584 A1 | 7/2002 | Palmer et al. | 435/366 |
| 2002/0119565 A1 | 8/2002 | Clarke et al. | 435/366 |
| 2002/0123141 A1 | 9/2002 | Hariri | 435/366 |
| 2002/0150986 A1 | 10/2002 | Lau | 435/69.1 |
| 2002/0151056 A1 | 10/2002 | Sasai et al. | 435/368 |
| 2002/0160471 A1 | 10/2002 | Kisiday et al. | 435/177 |
| 2002/0160510 A1 * | 10/2002 | Hariri | 435/368 |
| 2002/0164307 A1 | 11/2002 | Habener et al. | 424/93.7 |
| 2002/0164791 A1 | 11/2002 | Van Der Kooy et al. | 435/366 |
| 2002/0168763 A1 | 11/2002 | Yan et al. | 435/325 |
| 2002/0182241 A1 | 12/2002 | Borenstein et al. | |
| 2002/0182728 A1 | 12/2002 | Ramiya et al. | 435/366 |
| 2002/0187550 A1 | 12/2002 | Dinsmore et al. | 435/377 |
| 2002/0192816 A1 | 12/2002 | Roberts et al. | 435/366 |
| 2003/0003574 A1 | 1/2003 | Toma et al. | 435/368 |
| 2003/0007954 A1 | 1/2003 | Naughton et al. | |
| 2003/0022369 A1 | 1/2003 | Fillmore et al. | 435/371 |
| 2003/0031657 A1 | 2/2003 | Habener et al. | 424/93.21 |
| 2003/0032178 A1 | 2/2003 | Hariri | 435/366 |
| 2003/0032179 A1 | 2/2003 | Hariri et al. | |
| 2003/0032183 A1 | 2/2003 | Sheridan | 435/370 |
| 2003/0049837 A1 | 3/2003 | Weiss et al. | 435/368 |
| 2003/0059939 A1 | 3/2003 | Page et al. | 435/366 |
| 2003/0082155 A1 | 5/2003 | Habener et al. | 424/93.21 |
| 2003/0082160 A1 | 5/2003 | Yu et al. | 424/93.21 |
| 2003/0096409 A1 | 5/2003 | Yasumoto et al. | 435/371 |
| 2003/0104997 A1 | 6/2003 | Black et al. | 514/12 |
| 2003/0109036 A1 | 6/2003 | Wu | 435/366 |
| 2003/0113910 A1 | 6/2003 | Levanduski | 435/325 |
| 2003/0118566 A1 | 6/2003 | Neuman et al. | 424/93.21 |
| 2003/0124721 A1 | 7/2003 | Cheatham et al. | 435/366 |
| 2003/0138948 A1 | 7/2003 | Fisk et al. | 435/366 |
| 2003/0138951 A1 | 7/2003 | Yin | 435/370 |
| 2003/0148513 A1 | 8/2003 | Sugaya et al. | 435/368 |
| 2003/0158089 A1 * | 8/2003 | Gallop et al. | 514/2 |
| 2003/0161818 A1 | 8/2003 | Weiss et al. | 424/93.21 |
| 2003/0162290 A1 | 8/2003 | Inoue et al. | 435/366 |
| 2003/0170215 A1 | 9/2003 | Tsang et al. | 424/93.21 |
| 2003/0175963 A1 | 9/2003 | Rosenberg | 435/375 |
| 2003/0180269 A1 | 9/2003 | Hariri | 424/93.21 |
| 2003/0186439 A1 | 10/2003 | Nakauchi et al. | 435/370 |
| 2003/0199447 A1 | 10/2003 | Goldman et al. | 514/12 |
| 2003/0203483 A1 | 10/2003 | Seshi | 435/366 |
| 2003/0203484 A1 | 10/2003 | Black et al. | 435/368 |
| 2003/0207450 A1 | 11/2003 | Young et al. | 435/368 |
| 2003/0211087 A1 | 11/2003 | Goldman | 424/93.21 |
| 2003/0211603 A1 * | 11/2003 | Earp et al. | 435/366 |
| 2003/0211605 A1 | 11/2003 | Lee et al. | 435/368 |
| 2003/0212024 A1 | 11/2003 | Keating et al. | 514/44 |
| 2003/0219894 A1 | 11/2003 | Seino et al. | 435/370 |
| 2003/0228295 A1 | 12/2003 | Svendsen | 424/93.21 |
| 2003/0235563 A1 | 12/2003 | Strom et al. | 424/93.21 |
| 2003/0235909 A1 | 12/2003 | Hariri et al. | 435/372 |
| 2004/0005704 A1 | 1/2004 | Csete et al. | 435/368 |

(56) References Cited

U.S. PATENT DOCUMENTS

| | | | |
|---|---|---|---|
| 2004/0009593 A1 | 1/2004 | Keirstead et al. | 435/368 |
| 2004/0014206 A1 | 1/2004 | Robl et al. | 435/325 |
| 2004/0014210 A1 | 1/2004 | Jessell et al. | 435/368 |
| 2004/0014211 A1 | 1/2004 | Ogle et al. | 435/368 |
| 2004/0014662 A1 | 1/2004 | Lindquist et al. | 514/12 |
| 2004/0028660 A1 | 2/2004 | Hariri et al. | |
| 2004/0029269 A1 | 2/2004 | Goldman et al. | 435/368 |
| 2004/0033597 A1 | 2/2004 | Toma et al. | 435/368 |
| 2004/0037818 A1 | 2/2004 | Brand et al. | 424/93.21 |
| 2004/0048372 A1 | 3/2004 | Hariri | 435/366 |
| 2004/0058412 A1 | 3/2004 | Ho et al. | 435/69.1 |
| 2004/0063202 A1 | 4/2004 | Petersen et al. | 435/368 |
| 2004/0072344 A1 | 4/2004 | Inoue et al. | 435/366 |
| 2004/0136967 A1 | 7/2004 | Weiss et al. | 424/93.7 |
| 2004/0204387 A1* | 10/2004 | McLaurin | 514/102 |
| 2004/0224401 A1* | 11/2004 | Ludwig et al. | 435/366 |
| 2005/0019865 A1 | 1/2005 | Kihm et al. | |
| 2005/0032209 A1 | 2/2005 | Messina et al. | 435/366 |
| 2005/0037491 A1 | 2/2005 | Mistry et al. | 435/366 |
| 2005/0054098 A1 | 3/2005 | Mistry et al. | 435/372 |
| 2005/0058629 A1 | 3/2005 | Harmon et al. | 424/93.7 |
| 2005/0058630 A1 | 3/2005 | Harris et al. | 424/93.7 |
| 2005/0058631 A1 | 3/2005 | Kihm et al. | 424/93.7 |
| 2005/0074435 A1 | 4/2005 | Casper et al. | 424/93.7 |
| 2005/0142660 A1 | 6/2005 | Lou et al. | |
| 2005/0148074 A1 | 7/2005 | Davies et al. | 435/372 |
| 2005/0249731 A1 | 11/2005 | Aslan et al. | 424/144.1 |
| 2006/0030039 A1 | 2/2006 | Chen et al. | |
| 2006/0128014 A1* | 6/2006 | Haggblad et al. | 435/368 |
| 2006/0153815 A1 | 7/2006 | Seyda et al. | |
| 2006/0153816 A1 | 7/2006 | Brown et al. | 424/93.7 |
| 2006/0153817 A1 | 7/2006 | Kihm et al. | 424/93.7 |
| 2006/0153818 A1 | 7/2006 | Dhanaraj et al. | 424/93.7 |
| 2006/0154366 A1 | 7/2006 | Brown et al. | 435/366 |
| 2006/0154367 A1 | 7/2006 | Kihm et al. | 435/366 |
| 2006/0166361 A1 | 7/2006 | Seyda et al. | |
| 2006/0171930 A1 | 8/2006 | Seyda et al. | |
| 2006/0188983 A1 | 8/2006 | Harris et al. | 435/366 |
| 2006/0223177 A1 | 10/2006 | Harris et al. | 435/325 |
| 2006/0233765 A1 | 10/2006 | Messina et al. | 424/93.7 |
| 2006/0233766 A1 | 10/2006 | Messina et al. | 424/93.7 |
| 2006/0234376 A1 | 10/2006 | Mistry et al. | 435/366 |
| 2006/0281793 A1* | 12/2006 | Gupta et al. | 514/356 |
| 2007/0009494 A1 | 1/2007 | Mistry et al. | 424/93.7 |
| 2007/0014771 A1 | 1/2007 | Mistry et al. | 424/93.7 |
| 2007/0036767 A1 | 2/2007 | Mistry et al. | 424/93.7 |
| 2007/0141700 A1 | 6/2007 | Harmon | |
| 2007/0160588 A1 | 7/2007 | Kihm | |
| 2007/0218549 A1 | 9/2007 | Mansbridge | |
| 2007/0264269 A1 | 11/2007 | Harmon et al. | |
| 2007/0264713 A1 | 11/2007 | Terstegge et al. | |
| 2007/0275362 A1 | 11/2007 | Edinger et al. | |
| 2008/0038782 A1* | 2/2008 | Borns | 435/91.2 |
| 2008/0064098 A1* | 3/2008 | Allickson | 435/366 |
| 2008/0112939 A1 | 5/2008 | Colter et al. | |
| 2008/0145934 A1 | 6/2008 | Harris et al. | |
| 2008/0159994 A1 | 7/2008 | Mantalaris et al. | |
| 2008/0166328 A1 | 7/2008 | Harmon et al. | |
| 2008/0226595 A1 | 9/2008 | Edinger et al. | |
| 2009/0123620 A1* | 5/2009 | Hiti et al. | 426/334 |
| 2009/0186358 A1* | 7/2009 | Melville et al. | 435/6 |
| 2010/0210013 A1 | 8/2010 | Mistry et al. | |
| 2010/0215714 A1 | 8/2010 | Messina et al. | |
| 2010/0260843 A1 | 10/2010 | Messina et al. | |
| 2012/0315251 A1 | 12/2012 | Harris et al. | |
| 2013/0022585 A1 | 1/2013 | Messina et al. | |
| 2014/0045263 A1 | 2/2014 | Mistry et al. | |
| 2014/0154226 A1 | 6/2014 | Messina et al. | |
| 2015/0064781 A1 | 3/2015 | Mistry et al. | |

FOREIGN PATENT DOCUMENTS

| | | |
|---|---|---|
| EP | 0 529 751 | 3/1993 |
| EP | 0 552 380 | 7/1993 |
| EP | 1 147 076 | 7/2000 |
| EP | 1 216 718 | 6/2002 |
| EP | 1 264 877 | 12/2002 |
| EP | 1 302 535 | 4/2003 |
| EP | 1 312 669 | 5/2003 |
| EP | 1 316 322 | 6/2003 |
| EP | 0 333 328 B1 | 12/2003 |
| EP | 1 405 649 | 4/2004 |
| JP | 2003-235549 | 8/2003 |
| JP | 2004-254682 | 9/2004 |
| WO | 90/11354 A1 | 10/1990 |
| WO | 92/03917 A1 | 3/1992 |
| WO | 93/04169 A1 | 3/1993 |
| WO | WO 94/25584 A1 | 11/1994 |
| WO | 95/17911 A1 | 7/1995 |
| WO | WO 95/23216 | 8/1995 |
| WO | WO 96/01316 A1 | 1/1996 |
| WO | WO 96/05309 A2 | 2/1996 |
| WO | WO 98/17791 A1 | 4/1998 |
| WO | WO 98/51317 | 11/1998 |
| WO | WO 99/03973 | 1/1999 |
| WO | WO 00/09666 | 2/2000 |
| WO | WO 00/38762 | 7/2000 |
| WO | WO-00/053795 A1 | 9/2000 |
| WO | 00/73421 A3 | 12/2000 |
| WO | WO 01/11011 A2 | 2/2001 |
| WO | WO 01/19379 A3 | 3/2001 |
| WO | WO 01/34775 A1 | 5/2001 |
| WO | WO 02/29971 A1 | 4/2002 |
| WO | WO 02/46373 A1 | 6/2002 |
| WO | WO 02/059278 A2 | 8/2002 |
| WO | WO 02/061053 | 8/2002 |
| WO | WO 02/062969 A2 | 8/2002 |
| WO | WO 02/063962 A1 | 8/2002 |
| WO | WO 02/064748 A2 | 8/2002 |
| WO | WO 02/064755 A2 | 8/2002 |
| WO | WO 02/086107 A2 | 10/2002 |
| WO | WO 03/023020 A1 | 3/2003 |
| WO | WO 03/025149 A2 | 3/2003 |
| WO | WO 03/029443 A1 | 4/2003 |
| WO | WO 03/029445 A1 | 4/2003 |
| WO | 03/039489 A3 | 5/2003 |
| WO | WO 03/042405 A2 | 5/2003 |
| WO | WO 03/048336 A2 | 6/2003 |
| WO | WO 03/054146 | 7/2003 |
| WO | WO 03/055992 A2 | 7/2003 |
| WO | WO 03/064601 A2 | 8/2003 |
| WO | WO 03/066832 A2 | 8/2003 |
| WO | WO 03/068937 A2 | 8/2003 |
| WO | WO 03/070749 | 8/2003 |
| WO | WO 03/070922 A1 | 8/2003 |
| WO | WO 03/072728 A2 | 9/2003 |
| WO | WO 03/080822 A1 | 10/2003 |
| WO | WO 03/087333 A2 | 10/2003 |
| WO | WO 03/087392 A2 | 10/2003 |
| WO | WO 03/089619 A2 | 10/2003 |
| WO | WO 03/010038 A1 | 12/2003 |
| WO | WO 03/102134 A2 | 12/2003 |
| WO | WO 03/102151 | 12/2003 |
| WO | WO 03/104442 A1 | 12/2003 |
| WO | WO 2004/003561 | 1/2004 |
| WO | WO 2004/007532 | 1/2004 |
| WO | WO 2004/011012 A2 | 2/2004 |
| WO | WO 2004/011621 A2 | 2/2004 |
| WO | WO 2004/016747 A2 | 2/2004 |
| WO | WO 2004/023100 A2 | 3/2004 |
| WO | 2004/072273 A1 | 8/2004 |
| WO | WO 2004/072104 | 8/2004 |
| WO | 2005/001076 A2 | 1/2005 |
| WO | 2005/001077 A2 | 1/2005 |
| WO | 2005/001078 A2 | 1/2005 |
| WO | 2005/001079 A2 | 1/2005 |
| WO | 2005/001080 A2 | 1/2005 |
| WO | 2005/003334 A2 | 1/2005 |
| WO | WO 2005/001076 A3 | 1/2005 |
| WO | WO 2005/021738 | 3/2005 |
| WO | 2005/038012 A2 | 4/2005 |
| WO | WO 2005/034624 | 4/2005 |
| WO | 2005/042703 A2 | 5/2005 |
| WO | WO 2005/001076 | 1/2006 |

(56) References Cited

FOREIGN PATENT DOCUMENTS

| WO | WO 2006/036826 | 4/2006 |
| WO | 2006/071773 A2 | 7/2006 |
| WO | 2006/071777 A2 | 7/2006 |
| WO | 2006/071778 A2 | 7/2006 |
| WO | 2006/071794 A2 | 7/2006 |
| WO | 2006/071802 A2 | 7/2006 |
| WO | WO 2006/083394 | 8/2006 |
| WO | WO 2007/073552 | 6/2007 |
| WO | WO 2008/045498 | 4/2008 |
| WO | WO 2008/060541 | 5/2008 |

OTHER PUBLICATIONS

Aboody, K.S., et al., "Neural stem cells display extensive tropism for pathology in adult brain: evidence from intracranial gliomase," PNAS, 2000, 97(23), 12846-12851.

Age-Related Eye Disease Study Research Group, "A randomized, placebo-controlled, clinical trial of high-dose supplementation with vitamins C and E, beta carotene, and zinc for age-related macular degeneration and vision loss," AREDS Report No. 8, Arch. Ophthalmal, 2001, 119, 1417-1436.

Allcock, H.R., et al., "Synthesis of poly[amino acid alkyl ester)phosphazenes]$^{1-3}$," Macromolecule, 1977, 10(4), 824-830.

Altman, G.H., et al., "Advanced bioreactor with controlled application of multi-dimensional strain for tissue engineering," J. Biomech. Eng., 2002, 124, 742-749.

Altman, R.D., et al., "Radiographic assessment of progression in osteoarthritis," Arthritis & Rheum., 1987, 30(11), 1214-1225.

Anseth, K.S., et al., "In situ forming degradable networks and their application in tissue engineering and drug delivery," J. of Control Release, 2002, 78, 199-209.

Avital, I., et al., "Isolation, characterization, and transplantation of bone marrow-derived hepatocyte stem cells," Biochem. & Biophys. Res. Comm., 2001, 288, 156-164.

Azizi, S.A., et al., "Engraftment and migration of human bone marrow stromal cells implanted in the brains of albino rats—similarities to astrocyte grafts," Proc. Natl. Acad. Sci. USA, 1998, 95, 3908-3913.

Baker, K.A., et al., "Intrastriatal and intranigral grafting of hNT neurons in the 6-OHDA rat model of Parkinson's Disease," Exper. Neurol., 2000, 162, 350-360.

Balis, F., et al., "Central nervous system pharmacology of antileukemic drugs," Am. J. of Pediatric. Hematol. Oncol., 1989, 11(1), 74-86.

Balkema, G.W., et al., "Impaired visual thresholds in hypopigmented animals," Visual Neuroscience, 1991, 6, 577-585.

Barberi, T., et al., "Neural subtype specification of fertilization and nuclear transfer embryonic stem cells and application in parkinsonian mice," Nature Biotechnology, 2003, 21(10), 1200-1207.

Beck, R.W., et al., "A clinical comparison of visual field testing with a new automated perimeter, the Humphrey field analyzer, and the Goldmann perimeter," Ophthalmology 1985, 92(1), 77-82.

Björklund, L.M., et al., "Embryonic stem cells develop into functional dopaminergic neurons after transplantation in a Parkinson rat model," PNAS, 2002, 99(4), 2344-2349.

Bouteiller, P.L., et al., "Soluble HLA-G1 at the materno-foetal interface—a review," Placenta, 2003, 24 (Suppl. A), S10-S15.

Brodsky, S.V., et al., "Coagulation, fibrinolysis and angiogenesis: new insights from knockout mice," Exp. Nephrol., 2002, 10, 299-306.

Brooks, P., "Inflammation as an important feature of osteoarthritis," Bull. World Health Org., 2003, 81 (9), 689-690.

Brown, J.A., et al., "Blockade of programmed death-1 ligands on dendritic cells enhances T cell activation and cytokine production," The J. of Immunology, 2003, 170, 1257-1266.

Burnstein, R.M., et al., "Differentiation and migration of long term expanded human neural progenitors in a partial lesion model of Parkinson's disease," Intern. J. of Biochem & Cell Biology, 2004, 36, 702-713.

Caballero, S., et al., "The many possible roles of stem cells in age-related macular degeneration," Graefe's Arch Clin. Exp. Ophthalmol, 2004, 242, 85-90.

Campbell, I.K., et al., "Human articular cartilage and chondrocytes produce hemopoietic colony-stimulating factors in culture in response to IL-1$^1$," J. of Immun., 1991, 147, 1238-1246.

Cao, Q., et al., "Stem cell repair of central nervous system injury," J. of Neuroscience Res., 2002, 68, 501-510.

Caplan, A.I., et al., "Mesenchymal stem cells: building blocks for molecular medicine in the 21$^{st}$ century," Trends in Molecular Med., 2001, 7(6), 259-264.

Chargracui, J., et al., "Fetal liver stroma consists of cells in epithelial-to-mesenchymal transition," Blood, 2003, 101, 2973-2982.

Chen, D., et al., "Differential roles for bone morphogenic protein (BMP) receptor type IB and IA in differentiation and specification of mesenchymal precursor cells to osteoblast and adipocyte lineages," J. Cell Biol., 1998, 142(1), 295-305.

Cheng, A., et al., "Nitric oxide acts in a positive feedback loop with BDNF to regulate neural progenitor cell proliferation and differentiation in the mammalian brain," Dev. Biol., 2003, 258, 319-333.

Coumans, B., et al., "Lymphoid cell apoptosis induced by trophoblastic cells: a model of active foeto-placental tolerance," J. of Immunological Methods, 1999, 224, 185-196.

D'Cruz, P.M., et al., "Mutation of the receptor tyrosine kinase gene Mertk in the retinal dystrophic RCS rat," Hum. Mol. Genet., 2000, 9(4), 645-651.

Danon, D., et al., "Macrophage treatment of pressure sores in paraplegia," J. of Wound Care, 1998, 7(6), 281-283.

Danon, D., et al., "Treatment of human ulcers by application of macrophages prepared from a blood unit," Exp. Gerontol., 1997, 32(6), 633-641.

Dimri, G.P., et al., "A biomarker that identifies senescent human cells in culture and in aging skin in vivo," Proc. Natl. Acad. Sci. USA, 1995, 92, 9363-9367.

Domb, A., et al., "Degradable polymers for site-specific drug delivery," Polymers for Advanced Technologies, 1992, 3, 279-292.

Doshi, S.N., et al., "Evolving role of tissue factor and its pathway inhibitor," Critical Care Med., 2002, 30(5), S241-S250.

Du, Y., et al., "Functional reconstruction of rabbit corneal epithelium by human limbal cells cultured on amniotic membrane," Molecular Vision, 2003, 9, 635-643.

Edlund, H., "Pancreatic organogenesis—developmental mechanisms and implications for therapy," Nat. Rev. Genet., 2002, 3, 524-532.

Efrat, S., et al., "Cell replacement therapy for type 1 diabetes," Trends in Molecular Medicine, 2002, 8(7), 334-339.

Ehtesham, M., et al., "Induction of glioblastoma apoptosis using neural stem cell-mediated delivery of tumor necrosis factor-related apoptosis-inducing ligand," Cancer Res., 2002, 62, 7170-7174.

Ehtesham, M., et al., "The use of interleukin 12-secreting neural stem cells for the treatment of intracranial glioma," Cancer Res., 2002, 5657-5663.

Ende, N., et al., "Parkinson's disease mice and human umbilical cord blood," J. Med., 2002, 33(1-4), 173-180, 1 page (Abstract).

Engstad, C.S., et al., "The effect of soluble β-1,3-glucan and lipopolysaccharide on cytokine production and coagulation activation in whole blood," Int. Immunopharmacol., 2002, 2, 1585-1597.

Enzmann, V., et al., "Enhanced induction of RPE lineage markers in pluripotent neural stem cells engrafted into the adult rat subretinal space," Investig. Ophthalmol. Visual Sci., 2003, 44, 5417-5422.

Fazeabas, A.T., et al., "Endometrial function: cell specific changes in the uterine environment," Mol. & Cellular. Endo., 2002, 186, 143-147.

Fiegel, H.C., et al., "Liver-specific gene expression in cultured human hematopoietic stem cells," Stem Cells, 2003, 21, 98-104.

Fischer, D., et al., "Lens-injury-stimulated axonal regeneration throughout the optic pathway of adult rats," Exp. Neurol., 2001, 172, 257-272.

Freed, C.R., et al., "Transplantation of embryonic dopamine neurons for severe Parkinson's disease," N. Engl. J. Med., 2001, 344(10), 710-719.

(56) References Cited

OTHER PUBLICATIONS

Frenkel, O., et al., "Activated macrophages for treating skin ulceration: gene expression in human monocytes after hypo-osmotic shock," *Clin. Exp. Immunol.*, 2002, 128, 59-66.
Friedman, J.A., et al., "Biodegradable polymer grafts for surgical repair of the injured spinal cord," *Neurosurgery*, 2002, 51(3), 742-751.
Fukuda, K., et al., "Reprogramming of bone marrow mesenchymal stem cells into cardiomyocytes," *C.R. Biol.*, 2002, 325, 1027-1038.
Gerdes, D., et al., "Cloning and tissue expression of two putative steroid membrane receptors," *Biol. Chem.*, 1998, 379, 907-911.
Gellersen, B., et al., "Cyclic AMP and progesterone receptor crosstalk in human endometrium: a decidualizing affair," *J. of Endocrinol.*, 2003, 178, 357-372.
Gökhan, Sç., et al., "Basic and clinical neuroscience applications of embryonic stem cells," *Anat. Rec. (New Anat)*, 2001, 265, 142-156.
Gosiewska, A., et al., "Development of a three-dimensional transmigration assay for testing cell-polymer interactions for tissue engineering applications," *Tissue Eng.*, 2001, 7(3), 267-277.
Gottlieb, D.I., "Large-scale sources of neural stem cells," *Ann. Rev. Neurosci.*, 2002, 25, 381-407.
Halvorsen, Y.D., et al., "Extracellular matrix mineralization and osteoblast gene expression by human adipose tissue-derived stromal cells," *Tissue Eng.*, 2001, 7, 729-741.
Hanahan, D., "Heritable formation of pancreatic β-cell tumours in transgenic mice expressing recombinant insulin/simian virus 40 oncogenes," *Nature*, 1985, 315, 115-122.
Haruta, M., et al., "In vitro and in vivo characterization of pigment epithelial cells differentiated from primate embryonic stem cells," *Investig. Ophthalmol. & Visual Sci.*, 2004, 45(3), 1020-1025.
Hayflick, L., "The longevity of cultured human cells," *J. Am. Geriatr. Soc.*, 1974, 22(1), 1-12.
Hayflick, L., "The strategy of senescence," *Gerontologist*, 1974, 14(1), 37-45.
Hongpaisan, J., "Inhibition of proliferation of contaminating fibroblasts by D-valine in cultures of smooth muscle cells from human myometrium," *Cell Biol. Int.*, 2000, 24, 1-7.
Hu, A., et al., "Hepatic differentiation from embryonic stem cells in vitro," *Chin. Med. J.*, 2003, 116(12), 1893-1897.
Hughes, G.C., et al., "Therapeutic angiogenesis in chronically ischemic procine myocardium: comparative effects of bFGF and VEGF," *Ann. Thorac. Surg.*, 2004, 77, 812-818.
Hutmacher, D.W., "Scaffold design and fabrication technologies for engineering tissues—state of the art and future perspectives," *J. Biomater. Sci. Polymer Edn.*, 2001, 12(1), 107-124.
Isacson, O., et al., "Specific axon guidance factors persist in the adult brain as demonstrated by pig neuroblasts transplanted to the rat," *Neurosci.*, 1996, 75(3), 827-837.
Isacson, O., "The production and use of cells as therapeutic agents in neurodegenerative diseases," *The Lancet (Neurology)*, 2003, 2, 417-424.
Ito, Y., et al., "A quantitative assay using basement membrane extracts to study tumor angiogenesis in vivo," *Int. J. Cancer*, 1996, 67, 148-152.
Jackson, J.A., et al., "Regeneration of ischemic cardiac muscle and vascular endothelium by adult stem cells," *J. Clin. Invest.*, 2001, 107, 1395-1402.
Janderova, L., et al., "Human mesenchymal stem cells as an in vitro model for human adipogenesis," *Obes. Res.*, 2003, 11(1), 65-74.
Jang, Y.K., et al., "Retinoic acid-mediated induction of neurons and glial cells from human umbilical cord-derived hematopoietic stem cells," *J. of Neurosci. Res.*, 2004, 75, 573-584.
Johe, K.K., et al., "Single factors direct the differentiation of stem cells from the fetal and adult central nervous system," *Genes & Devel.*, 1996, 10, 3129-3140.
Johnstone, B., et al., "In vitro chondrogenesis of bone-marrow-derived mesenchymal stem cells," *Exp. Cell Res.*, 1998, 238, 265-272.
Jones-Villeneuve, E.M., et al., "retinoic acid-induced neural differentiation of embryonal carcinoma cells," *Mol. & Cellu. Biol.*, 1983, 3(12), 2271-2279.
Kadiyala, S., et al., "Culture expanded canine mesenchymal stem cells possess osteochondrogenic potential in vivo and in vitro," *Cell Transplant*, 1997, 6(2), 125-134.
Kicic, A., et al., "Differentiation of marrow stromal cells into photoreceptors in the rat eye," *J. of Neurosci.*, 2003, 23(21), 7742-7749.
Kim, S.K., et al., "Intercellular signals regulating pancreas development and function," *Genes Dev.*, 2001, 15, 111-127.
Kim, J.-H., et al., "Dopamine neurons derived from embryonic stem cells function in an animal model of Parkinson's disease," *Nature*, 2002, 418, 50-56.
Kim, J.Y., et al., "Ocular surface reconstruction: limbal stem cell transplantation," *Ophthal. Clin. N Am.*, 2003, 16, 67-77.
Lang, K.J.D., et al., "Differentiation of embryonic stem cells to a neural fate: a route to re-building the nervous system," *J. of Neurosci. Res.*, 2004, 76, 184-192.
Le Belle, J.E., et al., "Stem cells for neurodegenerative disorders: where can we go from here?," *BioDrugs*, 2002, 16, 389-401.
Li, A., et al., "IL-8 directly enhanced endothelial cell survival, proliferation, and matrix metalloproteinases production and regulated angiogenesis," *J. Immunol.*, 2003, 170(6), 3369-3376.
Li, L.X., et al., "Inherited retinal dystrophy in the RCS rat: prevention of photoreceptor degeneration by pigment epithelial cell transplantation," *Exp. Eye Res.*, 1988, 47, 911-917.
Li, Y., et al., "Intracerebral transplantation of bone marrow stromal cells in a 1-methyl-4-phenyl-1,2,3,6-tetrahydropyridine mouse model of Parkinson's disease," *Neuroscience Letts.*, 2001, 315, 67-70.
Li, Y., et al., "Transplanted olfactory ensheathing cells promote regeneration of cut adult rat optic nerve axons," *J. of Neuro.*, 2003, 23(21), 7783-7788.
Liu, Y.-J., et al., "Molecular and genetic mechanisms of obesity: implications for future management," *Curr. Mol. Med.*, 2003, 3, 325-340.
Lockhart, et al., "Expression monitoring by hybridization to high-density oligonucleotide arrays," *Nat. Biotechnol.*, 1996, 14(13), 1675-1680.
Lund, R.D., et al., "Subretinal transplantation of genetically modified human cell lines attenuates loss of visual function in dystrophic rats," *Proc. Natl. Acad. Sci. USA*, 2001, 98(17), 9942-9947.
Lund, R.D., et al., "Cell transplantation as a treatment for retinal disease," *Progress in Retinal and Eye Research*, 2001, 20(4), 415-449.
Lund, R.L., et al., "Retinal transplantation: progress and problems in clinical application," *J. Leukocyte Biol.*, 2003, 74, 151-160.
Marx, W.F., et al., "Endovascular treatment of experimental aneurysms by use of biologically modified embolic devices: coil-mediated intraaneurysamal delivery of fibroblast tissue allografts," *Am. J. Neuroradiol.*, 2001, 22, 323-333.
Mason, A.J., et al., "The hypogonadal mouse: reproductive functions restored by gene therapy," *Science*, 1986, 234, 1372-1378.
Mayer-Proschel, M., et al., "Isolation of lineage-restricted neuronal precursors from multipotent neuroepithelial stem cells," *Neuron.*, 1997, 19, 773-785.
McDonald, J.A., et al., "Diminished responsiveness of male homosexual chronic hepatitis B virus carriers with HTLV-III antibodies to recombinant α-interferon," *Hepatology*, 1987, 7(4), 719-723.
Messina, D.J., et al., "Comparison of pure and mixed populations of human fetal-derived neural progenitors transplanted into intact and adult rat brain,", *Exper. Neurol.*, 2003, 184, 816-829.
Mitchell, J., et al., "Matrix cells from Wharton's jelly form neurons and glia," *Stem Cells*, 2003, 21, 50-60.
Moll, S., et al., "Monitoring warfarin therapy in patients with lupus anticoagulants," *Ann. Intern. Med.*, 1997, 127(3), 177-185.
Mombaerts, et al., "Creation of a large genomic deletion at the T-cell antigen receptor β-subunit locus in mouse embryonic stem cells by gene targeting," *Proc. Nat. Acad. Sci. USA*, 1991, 88, 3084-3087.
Nakamura, T., et al., "Ocular surface reconstruction using cultivated mucosal epithelial stem cells," *Cornea*, 2003, 22(Supp. 1), S75-S80.

(56) References Cited

OTHER PUBLICATIONS

Nicosia, R.F., et al., "Modulation of microvascular growth and morphogenesis by reconstituted basement membrane gel in three-dimensional cultures of rat aorta: a comparative study of angiogenesis in matrigal, collagen, fibrin, and plasma clot," in *Vitro Cell Dev. Biol.*, 1990, 26, 119-128.

Nishida K., et al., "Functional bioengineered corneal epithelial sheet grafts from corneal stem cells expanded ex vivo on a temperature-responsive cell culture surface," *Transplantation*, 2004, 77(3), 379-385.

Nixon, P.J., et al., "The contribution of cone responses to rat electroretinograms," *Clin. Experiment Ophthalmol.*, 2001, 29(3), 193-196.

Nusinowitz, S., et al., "Rod multifocal electroretinograms in mice," *Invest Ophthalmol Vis. Sci.*, 1999, 40(12), 2848-2858.

Oh, S.-H., et al., "Hepatocyte growth factor induces differentiation of adult rat bone marrow cells into a hepatocyte lineage in vitro," *Biochem. & Biophys. Res. Comm.*, 2000, 279, 500-504.

Okumoto, K., et al., "Differentiation of bone marrow cells into cells that express liver-specific genes in vitro: implication of the notch signals in differentiation," *Biochem. & Biophys. Res. Commun.*, 2003, 304, 691-695.

Orlic, D., et al., "Stem cells for myocardial regeneration," *Circ. Res.*, 2002, 91, 1092-1102.

Ornitz, D.M., et al., "Elastase I promoter directs expression of human growth hormone and SV40 T antigen genes to pancreatic acinar cells in transgenic mice," *Cold Spring Harbor Symp.Quant. Biol.*, 1985, vol. L, 399-409.

Osborne, N.N., et al., "Some current ideas on the pathogenesis and the role of neuroprotection in glaucomatous optic neuropathy," *Eur. J. Ophthalmol.*, 2003, 13 (*Supp. 3*), S19-S26.

Rabbany, S.Y., et al., "Molecular pathways regulating mobilization of marrow-derived stem cells for tissue revascularization," *Trends in Molecular Med.*, 2003, 9(3), 109-117.

Rafii, S., et al., "Therapeutic stem and progenitor cell transplantation for organ vascularization and regeneration," *Nature Med.*, 2003, 9(6), 702-712.

Raman-Cueto, A., et al., "Functional recovery of paraplegic rats and motor axon regeneration in their spinal cords by olfactory ensheathing glia," *Neuron*, 2000, 25, 425-435.

Readhead, C., et al., "Expression of a myelin basic protein gene in transgenic shiverer mice: correction of the dysmyelinating phenotype," *Cell*, 1987, 48, 703-712.

Refaie, A., et al., "Experimental islet cell transplantation in rats: optimization of the transplantation site," *Trans. Proc.*, 1998, 30, 400-403.

Reubinoff, B.E., et al., "Neural progenitors from human embryonic stem cells," *Nature Biotechnology*, 2001, 19, 1134-1140.

Rickard, D.J., et al., "Induction of rapid osteoblast differentiation in rat bone marrow stromal cell cultures by dexamethasone and BMP-2," *Dev. Biol.*, 1994, 161, 218-228.

Romanov, Y.A. et al., "Searching for alternative sources of postnatal human mesenchymal stem cells," *Stem Cells*, 2003, 21, 105-110.

Rosen, E.M., et al., "HGF/SF in angiogenesis," *Ciba Found. Symp.*, 1997, 212, 215-229.

Rutherford, A., et al., "Eyeing-up stem cell transplantation," *Trends in Molecular Medicine*, 2003, 7(1), p. 11.

Sahn, D.J., et al., "Recommendations regarding quantitation in M-Mode echocardiography: results of a survey of echocardiographic measurements," *Circulation*, 1978, 58, 1072-1083.

Sakariassen, K.S., et al., "Methods and models to evaluate shear-dependent and surface reactivity-dependent antithrombotic efficacy," *Thromb. Res.*, 2001, 104, 149-174.

Salcedo, et al., "Human endothelial cells express CCR2 and respond to MCP-1: direct role of MCP-1 in angiogenesis and tumor progression," *Blood*, 2000, 96(1), 34-40.

Sauve, Y., et al., "The relationship between full field electroretinogram and perimetry-like visual thresholds in RCS rats during photoreceptor degeneration and rescue by cell transplants," *Vision Res.*, 2004, 44(1), 9-18.

Schraermeyer, U., et al., "Subretinally transplanted embryonic stem cells rescue photoreceptor cells from degeneration in the RCS rats," *Cell Transplantation*, 2001, 10, 673-680.

Schwartz, R.E., et al., "Multipotent adult progenitor cells from bone marrow differentiate into functional hepatocyte-like cells," *J. of Clin. Invest.*, 2002, 109(10), 1291-1302.

Sebire, G., et al., "In vitro production of IL-6,IL-1 β, and tumor necrosis factor-alpha by human embryonic microglial and neural cells," *J. Immunol.*, 1993, 150, 1 517-1523.

Shani, M., "Tissue-specific expressin of rat myosin light-chain 2 gene in transgenic mice," *Nature*, 1985, 314, 283-286.

Shimizu, T., et al., "Cell sheet engineering for myocardial tissue reconstruction," *Biomaterials*, 2003, 24, 2309-2316.

Siminoff, R., et al., "Properties of reptilian cutaneous mechanoreceptors," *Exp. Neurol.*, 1968, 20(3), 403-414.

Sordillo, L.M., et al., "Culture of bovine mammary epithelial cells in D-valine modified medium: selective removal of contaminating fibroblasts," *Cell Biol. Int. Rep.*, 1988, 12, 355-364.

Storch, T.G., "Oxygen concentration regulates 5-azacytidine-induced myogenesis in $C_3H/10T1/2$ cultures," *Biochim. Biophys. Acta*, 1990, 1055, 126-129.

Street, C.N., et al., "Stem cells: a promising source of pancreatic islets for transplantation in type 1 diabetes," *Curr. Top Dev. Biol.*, 2003, 58, 111-136.

Svendsen, C.N., et al., "Long-term survival of human central nervous system progenitor cells transplanted into a rat model of Parkinson's disease," *Experim. Neurol.*, 1997, 148, 135-146.

Svendsen, C.N., "The amazing astrocyte," *Nature*, 2002, 417, 29-32.

Swift, G.H., et al., "Tissue-specific expression of the rat pancreatic elastase I gene in transgenic mice," *Cell*, 1984, 38, 639-646.

Tomita, M., et al., "Bone marrow-derived stem cells can differentiate into retinal cells in injured rat retina," *Stem Cells*, 2002, 20, 279-283.

Tresco, P.A., et al., "Cellular transplants as sources for therapeutic agents," *Advanced Drug Delivery Reviews*, 2000, 42, 3-27.

Tsonis, P.A., et al., "Lens and retina regeneration: transdifferentiation, stem cells and clinical applications," *Experim. Eye Res.*, 2004, 78, 161-172.

Turner, J.F., "Inherited retinal dystrophy in the RCS rat: prevention of photoreceptor degeneration by pigment epithelial cell transplantation," *Exp. Eye Res.*, 1988, 47, 911-917.

Tusher, V.G., et al., "Significance analysis of microarrays applied to the ionizing radiation response," *Proc. Natl. Acad. Sci. USA*, 2001, 98(9), 5116-5121.

Van Hoffelen, S.J., et al., "Incorporation of murine brain progenitor cells into the developing mammalian retina," *Invest. Ophthalmol. Vis. Sci.*, 2003, 44, 426-434.

Vassliopoulos, G., et al., "Transplanted bone marrow regenerates liver by cell fusion," *Nature*, 2003, 422, 901-904.

Villegas-Perez, M.P., et al., "Influences of peripheral nerve grafts on the survival and regrowth of axotomized retinal ganglion cells in adult rats," *J. of Neurosci.*, 1988, 8(1), 265-280.

Von Koskull, H., et al., "Induction of cytokeratin expression in human mesenchymal cells," *J. Cell Physiol.*, 1987, 133, 321-329.

Walboomers, X.F., et al., "Cell and tissue behavior on microgrooved surfaces," *Odontology*, 2001, 89, 2-11.

Wang, D., et al., "Synthesis and characterization of a novel degradable phosphate-containing hydrogel," *Biomaterials*, 2003, 24, 3969-3980.

Wang, X., et al., "Cell fusion is the principal source of bone-marrow-derived hepatocytes," *Nature*, 2003, 422, 897-900.

Wegman, A., et al., "Nonsteroidal anti-inflammatory drugs or acetaminophen for osteoarthritis of the hip or knee? A synstematic review of evidence and guidelines," *J. Rheumatol.*, 2004, 31, 344-354.

Weiss, M.L., et al., "Transplantation of porcine umbilical cord matrix cells into the rat brain," *Exp. Neur.*, 2003, 182, 288-299.

(56) References Cited

OTHER PUBLICATIONS

Wobus, A.M., et al., "Retinoic acid accelerates embryonic stem cell-derived cardiac differentiation and enhances development of ventricular cardiomyocytes," *J. Mol. Cell Cardiol.*, 1997, 29, 1525-1539.

Woodbury, D., et al., "Adult rat and human bone marrow stromal cells differentiate into neurons," *J. of Neurosci. Res.*, 2000, 61, 364-370.

Xu, C., et al., "Characterization and enrichment of cardiomyocytes derived from human embryonic stem cells," *Circ. Res.*, 2002, 91, 501-508.

Yang, H., et al., "Region-specific differentiation of neural tube-derived neuronal restricted progenitor cells after heterotopic transplantation," *PNAS*, 2000, 97(24), 13366-13371.

Yip, H.K., et al., "Axonal regeneration of retinal ganglion cells: effect of trophic factors," *Prog. Retin Eye Res.*, 2000, 19(5), 559-575.

Yu, M., et al., "Mid-trimester fetal blood-derived adherent cells share characteristics similiar to mesenchymal stem cells but full-term umbilical cord blood does not," *British J. of Haematology*, 2004, 124, 666-675.

Zangani, D., et al., "Multiple differentiation pathways of rat mammary stromal cells in vitro: acquisition of a fibroblast, adipocyte or endothelial phenotype is dependent on hormonal and extracellular matrix stimulation," *Differentiation*, 1999, 64, 91-101.

Zeng, B.Y., et al., "Regenerative and other responses to injury in the retinal stump of the optic nerve in adult albino rats: transaction of the intracranial optic nerve," *J. Anat.*, 1995, 186, 495-508.

Zhang, S.-C., et al., "In vitro differentiation of transplantable neural precursors from human embryonic stem cells," *Nature Biotechnology*, 2001, 1129-1133.

Eblenkamp, M. et al., "Umbilical cord stromal cells (UCSC). Cells featuring osteogenic differentiation potential," *Der Orthopade*, Dec. 2004, 33(12), 1338-1345.

Fukuchi, Y. et al., "Human Placenta-Derived Cells Have Mesenchymal Stem/Progenitor Cell Potential," *Stem Cells*, Alphamed Press, Dayton Ohio, 2004, 22(5), 649-658.

Wulf, G. G. et al., "Mesengenic Progenitor Cells Derived From Human Placenta," *Tissue Engineering*, Larchmont, NY, Jul. 2004, 10(7/8), 1136-1147.

Abbas, A.K., Lichtman, A.H., *Cellular and Molecular Immunology*, 5th Ed. (2003) Saunders, Philadelphia, p. 171.

Agbulut, O. et al., "Comparison of Human Skeletal Myoblasts and Bone Marrow-Derived CD133+ Progenitors for the Repair of Infarcted Myocardium," *Journal of the American College of Cardiology*, 2004, 44(2), 458-463.

Aldskogius, H. et al., "Strategies for repair of the deafferented spinal cord," *Brain Res. Rev.*, 2002, 20, 301-308.

Armulik A et al., "Endothelial/Pericyte Interactions," *Circ. Res.*, 2005, 97, 512-23.

Auda-Boucher, G., et al., "Staging of the commitment of murine cardiac cell progenitors," *Dev. Bio.*, 2000, 225(1), 214-225 (Abstract 2 pages).

Bao, Z.Z., et al., "Regulation of chamber-specific gene expression in the developing heart by Irx4," *Science*, 1999, 283(5405), 1161-1164 (Abstract 1 page).

Bhindi, R. et al., "Rat models of myocardial infarction," *Thromb Haemost*, 2006, 96, 602-610.

Constantini, S., et al., "The effects of methylprednisolone and the ganglioside GM1 on acute spinal cord injury in rats," *J. Neurosurg.*, 1994, 80(1), 97-111 (Abstract 2 pages).

Dawson, T.M., et al., "Neuroprotective and neurorestorative strategies for Parkinson's disease," *Nat. Neurosci.*, 2002, 5 Suppl., 1058-1061 (Abstract 1 page).

Doyle, J., "Spiraling complexity, robustness, and fragility in biology," http://www.cds.caltech.edu/~doyle/CmplxNets/Bio1.pdf, available online Feb. 28, 2004.

Eagle, H., "The specific amino acid requirements of a mammalian cell (strain L) in tissue culture," *J. Biol. Chem.*, Jun. 1955, 214(2), 839-852.

Edelstein, M. L. et al., "Gene therapy clinical trials worldwide 1989-2004—an overview," *J. Gene Med.*, Jun. 2004, 6(6), 597-602.

Eisenhofer, G., E., et al., "Tyrosinase: a developmentally specific major determinant of peripheral dopamine," *FASEB J.*, 2003, 1248-1255.

Foley, A. et al., "Heart induction: embryology to cardiomyocyte regeneration," *Trends Cardiovasc Med*, Apr. 2004, 14(3), 121-125.

Goodwin, H. S. et al., "Multilineage differentiation activity by cells isolated from umbilical cord blood: Expression of bone, fat and neural markers," *Biology of Blood and Marrow Transplantation*, 2001, 7, 581-588.

Hill, M. et al., "Treatment for swallowing difficulties (dysphagia) in chronic muscle disease," *Cochrane Database Syst Rev.*, 2004, (2):CD004303.

Holz, F. G. et al., "Intraocular microablation of choroidal tissue by a 308 nm AIDA excimer laser for RPE-transplantation in patients with age-related macular degeneration," *Biomed Tech* (Berlin), Apr. 2003, 48(4), 82-85.

Ishii, M. et al., "Molecular markers distinguish bone marrow mesenchymal stem cells from fibroblasts," *Biochemical and Biophysical Research Communications*, Jun. 24, 2005, 332(1), 297-303.

Jaffe, E. A. et al., "Culture of human endothelial cells derived from umbilical veins," *J Clin Invest*, 1973, 52, 2745-2756.

Jikuhara, T. et al., "Left atrial function as a reliable predictor of exercise capacity in patients with recent myocardial infarction," *Chest*, Apr. 1997, 111(4), 922-928.

Jomura, S., et al., "Potential Treatment of Cerebral Global Ischemia with Oct-4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2 pages.

Joussen, A. M., "Cell transplantation in age related macular degeneration: current concepts and future hopes," *Graefe's Arch. Clin. Exp. Ophthalmol.*, 2004, 242, 1-2.

Kirschstein R. et al., "Can stem cells repair a damaged heart?" *Stem Cells: Scientific Progress and Future Research Directions*, 2001, 87-92.

Klassen, H. et al., "Stem cells and retinal repair," *Prog. Retin. Eye Res.*, 2004, 23(2), 149-181 (Abstract 1 page).

Laface, D., et al., "Genetransfer into hematopoietic progenitor cells mediated by an adeno-associated virus vector," *Virology*, 1998, 162, 483-486.

Langeggen, H. et al., "HUVEC take up opsonized zymosan particles and secrete cytokines IL-6 and IL-8 in vitro," *FEMS Immunol. Med. Microbiol.*, 2003, 36, 55-61.

Lindvall, O. et al., "Stem cell therapy for human neurodegenerative disorders—how to make it work," *Nature Medicine*, Jul. 2004, 542-550.

Lodie, T. A. et al., "Systematic Analysis of Reportedly Distinct Populations of Mulitpotent Bone Marrow-Derived Stem Cells Reveals a Lack of Distinction," *Tissue Engineering*, Oct. 2002, 8(5), 739-751.

Luo, D. et al., "Synthetic DNA delivery systems," *Nat. Biotechnol.*, Jan. 2000, 18(1), 33-36.

Luyten, F. P. et al., "Skeletal tissue engineering: opportunities and challenges," *Best Pract. Res. Clin. Rheumatol.*, Dec. 2001, 15(5), 759-769.

MacDonald, R.J., "Expression of the pancreatic elastase I gene in transgenic mice,"*Hepatology*, 1987, 7(1), 42S-51S.

Medicetty, S. et al., "Transplantation of Human Umbilical Cord Matrix Stem Cells Alleviates Apomorphine-Induced Rotations in Parkinsonian Rats", 2003, XP-002383776, 1 page.

Medline Plus Online Medical Dictionary, definitions of "undifferentiated," and "differentiate," and "differentiation." Retrieved online Mar. 6, 2007. URL:www.nlm.nih.gov/medlineplus/mplusdictionary.html.

Merx, M. W. et al., "Transplantation of human umbilical vein endothelial cells improves left ventricular function in a rat model of myocardial infarction," *Basic Res. Cardiol.*, 2005, 100, 208-216.

Morgenstern, J. P., et al., "Advanced mammalian gene transfer: high titre retroviral vectors with multiple drug selection markers and a complementary helper-free packaging cell line," *Nucleic Acids Res.*, 1990, 18(12), 3587-3596.

(56) References Cited

OTHER PUBLICATIONS

Moulder, J. E., "Pharmacological intervention to prevent or ameliorate chronic radiation injuries," *Semin. Radiat. Oncol.*, 2003, 13, 73-84.
Nishishita, T. et al., "A potential pro-angiogenic cell therapy with human placenta-derived mesenchymal cells," *Biochemical and Biophysical Research Communications*, 2004, 325, 24-31.
Nork, T. M. et al., "Swelling and Loss of Photoreceptors in Chronic and Experimental Glaucomas," *Arch. Ophthalmol.*, 2000, 118, 235-245.
Palu, G. et al., "In pursuit of new developments for gene therapy of human disease," *J. Biotechnol.*, Feb. 1999, 68(1), 1-13.
Phipps, J. A. et al., "Paired-flash identification of rod and cone dysfunction in the diabetic rat," *Investigative Ophthalmology & Visual Science*, 2004, 45(12), 4592-4600.
Pittenger, M. F. et al., "Multilineage potential of adult human mesenchymal stem cells," *Science*, 1999, 284, 143-147 and seven pages of online supplementary material.
Pittenger, M. F. et al., "Mesenchymal Stem Cells and Their Potential as Cardiac Therapeutics," *Circ. Res.*, 2004, 95, 9-20.
Qian Ye et al., "Recovery of Placental-Derived Adherent Cells with Mesenchymal Stem Cell Characteristics", *Blood*, 2001, 98(11), 147B, XP-009026843.
Rehman, J. et al., "Secretion of Angiogenic and Antiapoptotic Factors by Human Adipose Stromal Cells," *Circulation*, 2004, 109, 1292-1298.
Reyes, M., et al., "Purification and ex vivo expansionof postnatal human marrow mesodermal progenitor cells," *Blood*, 2001, 98(9), 2615-2625.
Rezai, KA., et al., "Iris pigment epithelium transplantation," *Graefes Arch. Clin. Ophthalmol.*, 1997, 235, 558-562.
Rios, M., et al., "Catecholamine Synthesis is Mediated by Tyrosinase in the Absence of Tyrosine Hydroxylase," *J. Neurosci.*, 1999, 3519-3526.
Roskams, A. J. et al., "Directing stem cells and progenitor cells on the stage of spinal cord injury," *Exp. Neurol.*, 2005, 193, 267-272.
Salgado, A. J. et al., "Bone Tissue Engineering: State of the Art and Future Trends," *Macromol. Biosci.*, Aug. 2004, 4, 743-765.
Sethe, S. et al., "Aging of mesenchymal stem cells," *Ageing Research Reviews*, 2006, 5, 91-116.
Taylor, D. A. et al., "Regenerating functional myocardium: Improved performance after skeletal myoblast transplantation," *Nature Medicine*, Aug. 1998, 4(8), 929-933. Erratum in *Nature Medicine*, 4(10), 1200.
Taylor, D. A. et al., "Cardiac chimerism as a mechanism for self-repair: does it happen and if so to what degree?" *Circulation*, Jul. 2002, 106(1), 2-4.
Timmermans et al., "Stem cells for the heart, are we there yet?" *Cardiology*, 2003, 100(4), 176-185.
Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001, 19, 408-418.
Unigene entry for Hs.522632, *Homo sapiens* TMP metallopeptidase inhibitor 1 (TIMP1), printed from http://www.ncbi.nlm.nih.gov/UniGene on Oct. 12, 2006.
Urbich, C. et al., "Endothelial Progenitor Cells,", *Circ. Res.*, 2004, 95, 343-353.
Vajsar, J. et al., "Walker-Warburg syndrome," *Orphanet Journal of Rare Diseases*, 2006, 1, 29.
Verma, I. M. et al., "Gene therapy—promises, problems and prospects," *Nature*, Sep. 1997, 389(6648), 239-242.
Vermot-Desroches, C. et al., "Heterogeneity of antigen expression among human umbilical cord vascular endothelial cells: identification of cell subsets by co-expression of haemopoietic antigens," *Immunol. Lett.*, 1995, 48, 1-9.
Weiss, M. L. et al., "Human umbilical cord matrix stem cells: preliminary characterization and effect of transplantation in a rodent model of Parkinson's disease," *Stem Cells*, 2006, 24, 781-792.

Xu, Y., et al., "Dopamine, in the presence of tyrosinase, covalently modifies and inactivates tyrosine hydoxylase," *J. Neurosci. Res.*, 1998, 54(5), 691-697 (Abstract, 3 pages).
Yang Chen et al., "Enhancement of neovascularization with cord blood CD133+cell-derived endothelial progenitor cell transplantation," *Thrombosis and Haemostasis*, Jun. 2004, 91(6), 1202-1212.
Yokoo, T. et al., "Stem cell gene therapy for chronic renal failure," *Curr Gene Ther.*, 2003, 3, 387-394.
Zimmermann, S. et al., "Lack of telomerase activity in human mesenchymal stem cells," *Leukemia*, 2003, 17, 1146-1149.
Zuloff-Shani, A. et al., "Macrophage suspensions prepared from a blood unit for treatment of refractory human ulcers," *Transfus Apheresis Sci*. 2004, 30(2), 163-167.
Definition of "Iliac crest" provided by Wikipedia, the free encyclopedia; retrieved from the Internet at URL: http://en.wikipedia.org/wiki/Iliac_crest; downloaded on Dec. 11, 2007.
Aggarwal et al., "Human Mesenchymal Stem Cells Modulate Allogeneic Immune Cell Responses," *Blood*, 2005; 105(4):1815-1822.
Aston et al., "Repair of Articular Surfaces by Allografts of Articular and Growth-Plate Cartilage," *Journal of Bone and Joint Surgery*, 1986; 68-B(1):29-35.
Bai et al, "Dimerization of the Extracellular Calcium-sensing Receptor (CaR) on the Cell Surface of CaR-Transfected HEK293 Cells," *J. Biol Chem.*, 1998; 273(36): 23605-23610.
Blakemore et al., "Modelling Large Areas of Demyelination in the Rat Reveals the Potential and Possible Limitations of Transplanted GLIAL Cells for Remyelination In The CNS," *GLIA*, 2002; 38:155-68.
Bradley, B.A., The Role of HLA Matching in Transplantation, *Immunol. Lett.*, 1991; 29(1-2):55-59.
Bussolati et al., "Isolation of Renal Progenitor Cells from Adult Human Kidney," *American Journal of Pathology*, 2005; 166(2):545-555.
Carter, D. et al., "Characterization of MSC Potential to Treat GVHD Using Molecular Markers Linked to MSC-Mediated Immunosuppression in Vitro", *Blood*, 2005; 106(11) part 2, Abstract No. 4322, 160B.
"Cell Lysis, p. 2" http://www.piercenet.com/objects/view.cfm?type=Page&ID=1904ED25-8FA4-475C-8068-C2EB13D5F4E7; assessed Aug. 7, 2008.
Chen, H. et al., "The Effect of Hypothermia on Transient Middle Cerebral Artery Occlusion in the Rat," *J. Cereb. Blood Flow Metab.*, 1992; 12(4):621-28.
Chen, J. et al., "Therapeutic Benefit of Intravenous Administration of Bone Marrow Stromal Cells after Cerebral Ischemia in Rats," *Stroke*, 2001; 32(4):1005-11.
Davies, S.M. et al., "Engraftment and Survival After Unrelated-Donor Bone Marrow Transplantation: A Report from the National Marrow Donor Program," *Blood*, 2000; 96(13): 4096-4102.
Del Monte, Federica et al., "Improvement In Survival And Cardiac Metabolism After Gene Transfer Of Sarcoplasmic Reticulum Ca 2+ -ATPase In A Rat Model Of Heart Failure," *Circulation*, 2001;104;1424-1429.
Dickinson, A.M. et al., "Non-HLA Immunogenetics in Hematopoietic Stem Cell Transplantation," *Curr. Opin. Immunol.*, 2005; 17(5):517-25.
Fields, G.B., "Introduction of Protein-Like Molecular Architecture by Self-Assembly Processes," *Bioorg. Med. Chem.*, 1999; 7(1):75-81.
Franc, S. et al., "Microfibrillar Composition of Umbilical Cord Matrix: Characterization of Fibrillin, Collagen VI and Intact Collagen V", *PLACENTA*, 1988; 19:95-104.
Gupta et al., "Isolation and Characterization of Kidney-Derived Stem Cells," *Journal of American Society of Nephrology*, 2006; 17(11):3028-40.
Hartgerink, J.D. et al., "Peptide-Amphiphile Nanofibers: A Versatile Scaffold for the Preparation of Self-Assembling Materials," *PNAS*, 2002; 99(8):5133-38.
Herrera, M.B. et al., "Mesenchymal Stem Cells Contribute to the Renal Repair of Acute Tubular Epithelial Injury," *Int. J. Mol. Med.*, 2004; 14(6):1035-41.

(56) References Cited

OTHER PUBLICATIONS

Hill, D.P. et al., "Screening for Novel Pattern Formation Genes Using Gene Trap Approaches," *Methods in Enzymology*, 1993; 225:664-81.
Hishikawa, K. et al., "Musculin/MyoR is Expressed in Kidney Side Population Cells and Can Regulate Their Function," *Journal of Cell Biology*, 2005; 169:921-28.
Hoynowski, S.M. et al., "Characterization and Differentiation of Equine Umbilical Cord-Derived Matrix Cells," *Biochemical and Biophysical Research Communications*, 2007; 362:347-53.
In 'T Anker, et al., "Isolation of Mesenchymal Stem Cells of Fetal or Maternal Origin from Human Placenta," *Stem Cells*, 2004; 22:1338-45.
Iwasaki, T., "Recent Advances in the Treatment of Graft-Versus-Host Disease," *Clin. Med. Res.*, 2004; 2(4):243-52.
Jeras, M., "The Role of In Vitro Alloreactive T-Cell Functional Tests in the Selection of HLA Matched and Mismatched Haematopoietic Stem Cell Donors," *Transpl. Immunol.*, 2002; 10(2-3):205-14.
Jo, et al., "Use of Pharmasep Unit for Processing Microspheres," *AAPS PharmSciTech*, 2001; 2(1):Technical Notes.
Jones, J. et al., "Insulin-Like Growth Factors and their Binding Proteins: Biological Actions," *Endocrine Review*, 1995; 16(1):3-34.
Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, (2002); 277(9):7574-7580.
Kisiday, J. et al., "Self-Assembling Peptide Hydrogel Fosters Chondrocyte Extracellular Matrix Production and Cell Division: Implications For Cartilage Tissue Repair," *PNAS*, 2002; 99(15):9996-10001.
Kitamura et al., "Establishment and Characterization of Renal Progenitor Like Cells from S3 Segment of Nephron in Rat Adult Kidney," *The FASEB Journal*, (2005); 19(13):1789-1797.
Klahr, S et al., "Obstructive Nephropathy and Renal Fibrosis," *Am. J. Physiol Renal. Physiol.*, 2002; 283(5):F861-875.
Kokufuta, E. et al., "Effects of Surfactants on the Phase Transition of Poly(N-isopropylacrylamide) Gel," *Macromolecules*, 1993; 26:1053-59.
Kurtz et al., "Activity in Fetal Bovine Serum that Stimulates Erythroid Colony Formation in Fetal Mouse Livers is Insulinlike Growth Factor I," *J. Clin. Invest.*, (1985); 76:1643-1648.
Kushida, A., et al., "Decrease in Culture Temperature Releases Monolayer Endothelial Cell Sheets Together with Deposited Fibronectin Matrix from Temperature-Responsive Culture Surfaces," *J. of Biomedical Materials Research*, 1999; 45(4):355-62.
Le Blanc, K. et al., "Treatment of Severe Acute Graft-Versus-Host Disease With Third Party Haploidentical Mesenchymal Stem Cells," *Lancet*, 2004; 363(9419):1439-41.
Li, C.D. et al, "Mesenchymal Stem Cells Derived From Human Placenta Supress Allogenic Umbilical Cord Blood Lymphocyte Proliferation," *Cell Research*, 2005; 15(7):539-47.
Li, Y. et al., "Intact, Injured, Necrotic and Apoptotic Cells after Focal Cerebral Ischemia in the Rat," *J. Neurol. Sci.*, 1998; 156(2):119-32.
Li, Y. et al., "Ultrastructural and Light Microscopic Evidence of Apoptosis after Middle Cerebral Artery Occlusion in the Rat," *Am. J. Pathol.*, 1995; 146(5):1045-51.
Lindenlaub, et al., "Partial Sciatic Nerve Transection as a Model of Neuropathic Pain: A Qualitative and Quantitative Study," *PAIN*, 2000; 89(1): 97-106.
Ma, L. et al., "Human Umbilical Cord Wharton's Jelly-Derived Mesenchymal Stem Cells Differentiation into Nerve-Like Cells," *Chinese Med. Jour.*, 2005; 118(23):1987-93.
Ma, P.X. et al., "Synthetic Nano-Scale Fibrous Extracellular Matrix," *J. Biomed Mater Res.*, 1999; 46(1):60-72.
Mackay et al., "Chondrogenic Differentiation of Cultured Human Mesenchymal Stem Cells from Marrow," *Tissue Engineering*, 1998; 4(4):415-28.

Maeshima et al., "Adult Kidney Tubular Cell Population Showing Phenotypic Plasticity, Tubulogenic Capacity, and Integration Capability into Developing Kidney," *Journal of American Society of Nephrology*, 2006; 17(1):188-98.
Melero-Martin, J.J. et al., "Optimal In-Vitro Expansion of Chondroprogenitor Cells in Monolayer Culture," *Biotechnology and Bioengineering*, 2006; 93(3):519-33.
Merriam-Webster Online Dictionary $10^{th}$ Edition, Definition Of "Scaffold" [Retrieved on Sep. 8, 2008].
Moore, A.E. et al., "Parkinsonian Motor Deficits are Reflected by Proportional A9/A10 Dopamine Neuron Degeneration in the Rat," *Exp. Neurol.*, 2001; 172(2):363-76.
Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.
Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-06.
Ninichuk, V. et al., "Multipotent Mesenchymal Stem Cells Reduce Interstitial Fibrosis but do not Delay Progression of Chronic Kidney Disease in Collagen4a3-Deficient Mice," *Kidney Int.*, 2006; 70(1):121-29.
Nowak, A.P. et al., "Rapidly Recovering Hydrogel Scaffolds from Self-Assembling Diblock Copolypeptide Amphilphiles," *Nature*, 2002; 417(6887):424-28.
Oliver, J.A. et al., "The Renal Papilla is a Niche for Adult Kidney Stem Cells," *J. Clin Invest.*, 2004, 114(6):795-804.
Panepucci, R.A. et al., "Comparison of Gene Expression of Umbilical Cord Vein and Bone Marrow-Derived Mesenchymal Stem Cells," *Stem Cells*, 2004; 22(7):1263-78.
Pera, et al., Human Embryonic Stem Cells, J. Cell Science 2000; 113:5-10.
Petersdorf, E.W., "HLA Matching in Allogeneic Stem Cell Transplantation," *Curr. Op. Hematol.*, 2004; 11(6):386-91.
Pisharodi, et al., "An Animal Model for Neuron-Specfic Spinal Cord Lesions by the Microinjection of N-Methylaspartate, Kainic Acid, Quisqualic Acid," 1985; *Appl. Neurophysiol*, 48:226-33.
Pountos, I. et al., "Mesenchymal Stem Cell Tissue Engineering: Techniques for Isolation, Expansion and Application," *Injury*, 2007; 38(Supp. 4):S23-33.
Quaini, et al. "Chimerism The Transplated Heart", *NEJM*, 2002; 346:5-15.
Rahman et al., "Isolation and Primary Culture Urothelial Cells from Normal Human Bladder," *Urol. Research*, 1987; 15:315-20.
Russo, E., Cultivating Policy from Cell Types, *The Scientist*, 2001; 15(11):6.
Ryadnov, M.G. et al., "Engineering The Morphology Of A Self-Assembling Protein Fibre," *Nat. Mater.*, 2003; 2(5):329-32.
Sagrinati et al., "Isolation and Characterization of Multipotent Progenitor Cells from the Bowman's Capsule of Adult Human Kidney," *Journal of American Society of Nephrology*, 2006; 17(9)2443-56.
Schallert, T. et al., "Use-Dependent Structural Events in Recovery of Function," *Brain Plasticity, Adv. Neurol.*, 1997; 73:229-38.
Schouten, J.W. et al., "A Review and Rationale for the Use of Cellular Transplantation as Therapeutic Strategy for Traumatic Brain Injury," *Journal of Neorotrauma*, 2004; 21(11):1501-38.
Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54(4):409-37.
Shimizu, T. et al., "Fabrication of Pulsatile Cardiac Tissue Grafts Using a Novel 3-Dimensional Cell Sheet Manipulation Technique and Temperature-Responsive Cell Culture Surfaces", *Circulation Rsearch*, 2002; 90(3):40-48.
Shuto, T. et al., "Dexamethasone Stimulates Osteoclast-like Cell Formation by Inhibiting Granulocyte-Macrophage Colony-Stimulating Factor Production in Mouse Bone Marrow Cultures," *Endocrinology*, 1994; 134:1121-26.
Song, H. et al., "Astroglia Induce Neurogenesis From Adult Neural Stem Cells," *Nature*, 2002; 417(6884):39-44.

(56) References Cited

OTHER PUBLICATIONS

Swanson, R.A. et al., "A Semiautomated Method for Measuring Brain Infarct Volume," *J. Cereb. Blood Flow Metab.*, 1990; 10(2):290-93.
Thorsby, E. et al., "Role of HLA Molecules in the Induction of Alloimmune Responses: Clinical Significance in the Cyclosporine Era," *Transplant Proc.*, 2004; 36(2 Suppl):16S-21S.
Toma, et al., "Human Mesenchymal Stem Cells Differentiate to a Cardiomyocyte Phenotype in the Adult Murine Heart," Circulation 2002; 105:93-98.
Turner, D., "The Human Leucocyte Antigen (HLA) System," *Vox Sang.*, 2004; 87(Suppl 1):87-90.
Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.
Ulloa-Montoya, F. et al., "Culture Systems for Pluripotent Stem Cells," *Journal of Bioscience and Bioengineering*, 2005; 100(1):12-27.
Webster, T.J. et al., "Nanoceramic Surface Roughness Enhances Osteoblast and Osteoclast Functions for Improved Orthopaedic/Dental Implant Efficacy," *Scripta Materialia*, 2001; 44(8-9):1639-42.
Wenning, G.K. et al., "Neural Transplantation in Animal Models of Multiple System Atrophy: A Review," *J. Nueral Transm. Suppl.*, 1999; 55:103-13.
Williams, J.T. et al., "Cells Isolated from Adult Human Skeletal Muscle Capable of Differentiating into Multiple Mesodermal Phenotypes" Am. Surg. 1999 Jan;65(1):22-6.
Wolford, et al., "Considerations in Nerve Repair," *BUMC Proceedings*, (2003) 16:152-156.
Yamashima, "Implications of Cysteine Proteases Calpain, Cathepsin and Caspase in Ischemic Neuronal Death of Primates," *Progress in Neurobiology* (2000) 62:273-295.
Zhang, L. et al., "A Test for Detecting Long-Term Sensorimotor Dysfunction in the Mouse after Focal Cerebral Ischemia," *J. Neurosci. Methods*, 2002; 117(2):207-14.
Zhang, X. et al., "Efficient Adeno-Associated Virus-Mediated Gene Expression in Human Placenta-Derived Mesenchymal Cells, " Microbiol. Immunol., 2003; 47(1):109-16.
Zhang, Y. et al., "Comparison of Mesenchymal Stem Cells from Human Placenta and Bone Marrow," *Chinese Medical Journal*, 2004; 117(6):882-87.
Zhang, Z.G. et al., "Correlation of VEGF and Angiopoietin Expression with Disruption of Blood-Brain Barrier and Angiogenesis after Focal Cerebral Ischemia," *J. Cereb. Blood Flow Metab.*, 2002; 22(4):379-92.
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U.S. Patent and Trademark Office, Non-Final Office Action in re: U.S. Appl. No. 11/322,372, dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
Correspondence from Celgene Corporation dated Sep. 12, 2008, received Sep. 15, 2008, regarding U.S. Publication No. 2005/0058631 (U.S. Appl. No. 10/877,446) and U.S. Publication No. 2006/0154366 (U.S. Appl. No. 11/315,969).
In the U.S. Patent and Trademark Office, Final Office Action in re: U.S. Appl. No. 11/315,898, dated Sep. 16, 2008, 8 pages.
In the U.S. Patent and Trademark Office, Non-Final Office Action in re: U.S. Appl. No. 11/317,574, dated Sep. 30, 2008, 23 pages.

(56) References Cited

OTHER PUBLICATIONS

In the U.S. Patent and Trademark Office, Final Office Action in re: U.S. Appl. No. 11/315,969, dated Dec. 23, 2008, 11 pages.
In the U.S. Patent and Trademark Office, Final Office Action in re: U.S. Appl. No. 11/321,864, dated Jan. 8, 2009, 10 pages.
In the U.S. Patent and Trademark Office, Final Office Action in re: U.S. Appl. No. 11/321,863, dated Feb. 12, 2009, 15 pages.
In the U.S. Patent and Trademark Office, Non-Final Office Action in re: U.S. Appl. No. 11/315,943, dated Feb. 20, 2009, 9 pages.
In the U.S. Patent and Trademark Office, Final Office Action in re: U.S. Appl. No. 10/877,445, dated Mar. 19, 2009, 15 pages.
In the U.S. Patent and Trademark Office, Non-Final Office Action in re: U.S. Appl. No. 11/481,481, dated Mar. 20, 2009, 12 pages.
In the U.S. Patent and Trademark Office, Final Office Action in re: U.S. Appl. No. 11/315,897, dated Mar. 20, 2009, 13 pages.
In the U.S. Patent and Trademark Office, Non-Final Office Action in re: U.S. Appl. No. 11/481,480, dated Mar. 20, 2009, 13 pages.
In the U.S. Patent and Trademark Office, Final Office Action in re: U.S. Appl. No. 11/322,003 dated Feb. 13, 2009, 17 pages.
In the U.S. Patent and Trademark Office, Final Office Action in re: U.S. Appl. No. 10/876,998 dated Feb. 13, 2009, 10 pages.
In the U.S. Patent and Trademark Office, Final Office Action in re: U.S. Appl. No. 11/322,372 dated Feb. 13, 2009, 14 pages.
In the U. S. Patent and Trademark Office, Non-Final Office Action in re: U.S. Appl. No. 11/315,898 dated Feb. 18, 2009, 10 pages.
In the U.S. Patent and Trademark Office, Non-Final Office Action in re: U.S. Appl. No. 11/481,456 dated Apr. 16, 2009, 14 pages.
In the U.S. Patent and Trademark Office, Final Office Action in re: U.S. Appl. No. 11/317,574 dated Apr. 29, 2009, 21 pages.
In the U.S. Patent and Trademark Office, Advisory Action in re: U.S. Appl. No. 11/315,969 dated Sep. 29, 2009, 9 pages.
In the U.S. Patent and Trademark Office, Advisory Action in re: U.S. Appl. No. 11/322,372 dated May 12, 2009, 10 pages.
In the U. S. Patent and Trademark Office, Final Office Action in re: U.S. Appl. No. 11/322,372, dated Aug. 6, 2009, 12 pages.
In the U.S. Patent and Trademark Office, Final Office Action in re: U.S. Appl. No. 11/481,456 dated Oct. 9, 2009, 11 pages.
In the U.S. Patent and Trademark Office, Final Office Action in re: U.S. Appl. No. 10/877,445 dated Aug. 25, 2009, 18 pages.
In the U.S. Patent and Trademark Office, Final Office Action in re: U.S. Appl. No. 11/321,863 dated Aug. 7, 2009, 10 pages.
In the U.S. Patent and Trademark Office, Final Office Action in re: U.S. Appl. No. 11/321,864 dated Aug. 17, 2009, 13 pages.
In the U.S. Patent and Trademark Office, Final Office Action in re: U.S. Appl. No. 11/315,969 dated May 13, 2009, 11 pages.
In the U.S. Patent and Trademark Office, Non-Final Office Action in re: U.S. Appl. No. 11/317,574 dated Dec. 28, 2009, 26 pages.
In the U.S. Patent and Trademark Office, Non-Final Office Action in re: U.S. Appl. No. 11/321,863 dated Jan. 7, 2010, 12 pages.
In the U.S. Patent and Trademark Office, Non-Final Office Action in re: U.S. Appl. No. 11/321,864 dated Jan. 27, 2010, 12 pages.
In the U.S. Patent and Trademark Office, Non-Final Office Action in re: U.S. Appl. No. 11/315,969 dated Jan. 27, 2010, 12 pages.
In the U.S. Patent and Trademark Office, Non-Final Office Action in re: U.S. Appl. No. 11/315,943 dated Feb. 19, 2010, 13 pages.
In the U.S. Patent and Trademark Office, Final Office Action in re: U.S. Appl. No. 11/316,104 dated Mar. 24, 2010, 12 pages.
In the U.S. Patent and Trademark Office, Non-Final Office Action in re: U.S. Appl. No. 11/481,456 dated May 14, 2010, 9 pages.
In the U.S. Patent and Trademark Office, Non-Final Office Action in re: U.S. Appl. No. 11/481,481 dated May 13, 2010, 9 pages.
In the U.S. Patent and Trademark Office, Final Office Action in re: U.S. Appl. No. 11/315,897 dated May 14, 2010, 13 pages.
In the U.S. Patent and Trademark Office, Non-Final Office Action in re: U.S. Appl. No. 11/481,480 dated May 17, 2010, 10 pages.
In the U.S. Patent and Trademark Office, Final Office Action in re: U.S. Appl. No. 10/877,445 dated Jul. 8, 2010, 20 pages.
In the U.S. Patent and Trademark Office, Non-Final Office Action in re: U.S. Appl. No. 10/876,998 dated Aug. 3, 2010, 14 pages.
In the U.S. Patent and Trademark Office, Final Office Action in re: U.S. Appl. No. 11/321,863 dated Aug. 17, 2010, 15 pages.
In the U.S. Patent and Trademark Office, Final Office Action in re: U.S. Appl. No. 11/321,864 dated Aug. 31, 2010, 7 pages.
In the U.S. Patent and Trademark Office, Final Office Action in re: U.S. Appl. No. 11/315,969 dated Aug. 31, 2010, 6 pages.
In the U.S. Patent and Trademark Office, Final Office Action in re: U.S. Appl. No. 11/322,372 dated Aug. 31, 2010, 11 pages.
In the U.S. Patent and Trademark Office, Non-Final Office Action in re: U.S. Appl. No. 11/316,104 dated Sep. 21, 2010, 13 pages.
In the U.S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 12/054,718 dated Sep. 29, 2010, 18 pages.
In the U.S. Patent and Trademark Office, Non-Final Office Action in re: U.S. Appl. No. 11/322,372 dated Jan. 21, 2010, 10 pages.
In the U.S. Patent and Trademark Office, Final Office Action in re: U.S. Appl. No. 11/481,481 dated Sep. 18, 2009, 11 pages.
In the U.S. Patent and Trademark Office, Advisory Action in re: U.S. Appl. No. 11/315,897 dated Jun. 30, 2009, 3 pages.
In the U.S. Patent and Trademark Office, Non-Final Action in re: U.S. Appl. No. 11/315,897 dated Sep. 2, 2009, 12 pages.
In the U.S. Patent and Trademark Office, Final Action in re: U.S. Appl. No. 11/481,480 dated Sep. 17, 2009, 12 pages.
In the U.S. Patent and Trademark Office, Non-Final Action in re: U.S. Appl. No. 11/316,104 dated Oct. 31, 2008, 15 pages.
In the U.S. Patent and Trademark Office, Final Action in re: U.S. Appl. No. 10/876,998 dated May 27, 2009, 14 pages.
In the U.S. Patent and Trademark Office, Non-Final Action in re: U.S. Appl. No. 10/876,998 dated Nov. 24, 2009, 7 pages.
In the U.S. Patent and Trademark Office, Final Action in re: U.S. Appl. No. 11/322,003 dated Feb. 13, 2009, 17 pages.
Bruder, S. P., et al., "Mesenchymal Stem Cell Surface Antigen SB-10 Corresponds to Activated Leukocyte Cell Adhesion Molecule and Is Involved in Osteogenic Differentiation," *Journal of Bone and Mineral Research*, 1998; 13(4):655-663.
Can et al., "Concise Review: Human Umbilical Cord Stroma with Regard to the Source of Fetus-Derived Stem Cells," *Stem Cells*, 2007; 25:2886-2895.
Diao et al, "Human Umbilical Cord Mesenchymal Stem Cells: Osteogenesis *In Vivo* as Seed Cells for Bone Tissue Engineering," *J. BioMed Mater Res.*, 2009; 91A:123-131.
Haynesworth et al., "Cell Surface Antigens on Human Marrow-Derived Mesenchymal Cells are Detected by Monoclonal Antibodies," *Bone*, 1992; 13:69-80.
In the U.S. Patent and Trademark Office, Non-Final Office Action in re: U.S. Appl. No. 10/876,998 dated Feb. 1, 2011, 11 pages.
In the U.S. Patent and Trademark Office, Non-Final Office Action in re: U.S. Appl. No. 11/481,456 dated Feb. 3, 2011, 10 pages.
In the U.S. Patent and Trademark Office, Non-Final Office Action in re: U.S. Appl. No. 11/481,481 dated Feb. 3, 2011, 10 pages.
In the U.S. Patent and Trademark Office, Non-Final Office Action in re: U.S. Appl. No. 12/389,305 dated Feb. 8, 2011, 14 pages.
In the U.S. Patent and Trademark Office, Non-Final Office Action in re: U.S. Appl. No. 11/481,480 dated Feb. 3, 2011, 10 pages.
In the U.S. Patent and Trademark Office, Final Office Action in re: U.S. Appl. No. 12/389,305 dated Oct. 12, 2011, 12 pages.
In the U.S. Patent and Trademark Office, Final Office Action in re: U.S. Appl. No. 12/429,849 dated Mar. 20, 2012, 9 pages.
In the U.S. Patent and Trademark Office, Final Office Action in re: U.S. Appl. No. 11/481,456 dated Oct. 11, 2011, 6 pages.
In the U.S. Patent and Trademark Office, Non-Final Office Action in re: U.S. Appl. No. 12/697,081 dated Apr. 2, 2012, 8 pages.
Bakhshi, et al. "Mesenchymal stem cells from the Wharton's jelly of umbilical cord segments provide stromal support for the maintenance of cord blood hematopoietic stem cells during long-term ex vivo culture", *Transfusion*, 2008; 48: 2638-2644.
Cell Isolation Theory, in Tissue Dissociation Guide, Worthington Biochemical, accessible at http://www.tissuedissociation.com, accessed Aug. 8, 2007.
Daley, G.Q. et al., "Realistic Prospects for Stem Cell Therapeutics," *Hematol.*, 2003; 398-418.

(56) References Cited

OTHER PUBLICATIONS

Draper et al., "Surface Antigens of Human Embryonic Stem Cells: Changes Upon Differentiation in Culture," *J. Anat.*, 2002; 200:249-258.
Erices et al., "Mesenchymal Progenitor Cells in Human Umbilical Cord Blood," *Br. J. Haematol.*, 2000; 109:235-242.
Igura et al. "Human Placental Derived Stem Cells Differentiate into Neural Cells," Blood , 2002; 100(11): 517A (Abstract 2021).
Jorgensen, n. R. et al., "Intercellular Calcium Signaling Occurs Between Human Osteoblasts and Osteoclasts and Requires Activation of Osteoclast P2X7 Receptors," *The Journal of Biological Chemistry*, 2002; 277(9):7574-7580.
Kusama et al., "Growth and morphogenesis of mouse prostate epithelial cells in collagen gel matrix culture" *Cell Biol Int Rep*, 1989; 13:569-575.
Makino et al., "Cardiomyocytes can be generated from marrow stromal cells in vitro," *J. Clin. Invest.*, 1999; 103:697-705.
Naughton et al., "Cells isolated from Wharton's jelly of the human umbilical cord develop a cartilage phenotype when treated with TGF-b in vitro," 1997; FASEB J 11:A19 (Abstract 108).
Seaver et al. "The chick oviduct in tissue culture. I. Initial characterization of growing primary oviduct tissue cultures,"*Exp. Cell Res.*, 1984; 155: 241-251.
Seiji, T. et al., Possibility of Regenerative Medicine Using Human Amniotic Cells, *Regenerative Medicine*, 2002; 1(2):79-85. English Abstract.
Shake et al., "Mesenchymal stem cell implantation in a swine myocardial infarct model: engraftment and functional effects," *Ann Thorac Surg*, 2002; 73:1919-1926.
Wang, Y. et al., "Enhanced Recovery of Hematopoietic Progenitor and Stem Cells from Cultivated, Postpartum Human Placenta," *Blood*, 2001; 98(11): 183a (Abstract 769).
In the U.S. Patent and Trademarkk Office, Final Office Action in re: U.S. Appl. No. 12/389,305 dated Aug. 6, 2014, 57 pages.
In the U.S. Patent and Trademark Office, Final Office Action in re: U.S. Appl. No. 11/316,104 dated Aug. 6, 2014, 18 pages.
In the U.S. Patent and Trademark Office, Final Office Action in re: U.S. Appl. No. 11/321,864 dated Nov. 3, 2014, 10 pages.
In the U.S. Patent and Trademark Office, Non-Final Office Action in re: U.S. Appl. No. 13/605,716 dated Feb. 13, 2013, 13 pages.
In the U.S. Patent and Trademark Office, Non-Final Office Action in re: U.S. Appl. No. 11/317,574 dated Jul. 11, 2013, 29 pages.
In the U.S. Patent and Trademark Office, Non-Final Office Action in re: U.S. Appl. No. 11/322,372 dated Jan. 26, 2014, 17 pages.
In the U.S. Patent and Trademark Office, Non-Final Office Action in re: U.S. Appl. No. 11/321,864 dated Jan. 29, 2014, 9 pages.
In the U.S. Patent and Trademark Office Non-Final Office Action in re: U.S. Appl. No. 11/321,863 dated Jan. 31, 2014, 17 pages.
In the U.S. Patent and Trademark Office, Final Office Action in re: U.S. Appl. No. 11/317,574 dated Feb. 3, 2014, 16 pages.
In the U.S. Patent and Trademark Office, Non-Final Office Action in re: U.S. Appl. No. 10/876,998 dated Feb. 11, 2014, 14 pages.
In the U.S. Patent and Trademark Office, Non-Final Office Action in re: U.S. Appl. No. 12/389,305 dated Mar. 6, 2014, 37 pages.
In the U.S. Patent and Trademark Office, Non-Final Office Action in re: U.S. Appl. No. 11/316,104 dated Mar. 14, 2014, 11 pages.
In the U.S. Patent and Trademark Office, Non-Final Office Action in re: U.S. Appl. No. 12/389,305 dated Mar. 21, 2014, 47 pages.
In the U.S. Patent and Trademark Office, Non-Final Office Action in re: U.S. Appl. No. 10/877,446 dated Mar. 21, 2014, 21 pages.
In the U.S. Patent and Trademark Office, Non-Final Office Action in re: U.S. Appl. No. 11/316,104 dated Mar. 21, 2014, 20 pages.
In the U.S. Patent and Trademark Office, Non-Final Office Action in re: U.S. Appl. No. 11/315,969 dated Mar. 21, 2014, 15 pages.
Baksh, D. et al., "Comparison of proliferative and multilineage differentiation potential of human mesenchymal stem cells derived from umbilical cord and bone marrow." *Stem Cells*, 2007; 25: 1384-1392.

Bhatia, R. et al., "A clinically suitable ex vivo expansion culture system for LTC-IC and CFC using stroma-conditioned medium," *Exp Hematol.*, 1997; 25(9): 980-91 (Abstract only).
Ciavarella, S. et al., "Umbilical Cord Mesenchymal Stem Cells: Role of Regulatory Genes in Their Differentiation to Osteoblasts," *Stem Cells and Development*, 2009; 18:1211-1220.
Covas, D. T. et al., "Isolation and culture of umbilical vein mesenchymal stem cells," *Brazilian Journal of Medical and Biological Research*, 2003; 36: 1179-1183.
Deans, R.J. et al., "Mesenchymal stem cells: Biology and potential clinical uses," *Experimental Hematology*, 2000; 28: 875-884.
"Dulbecco's Modified Eagle's Medium (DME) Formulation." Sigma-Aldrich, available on line at <http://www.sigmaaldrich.com/life-science/cell-culture/learning-center/media-formulations/dme.printerview.html>. Accessed Mar. 17, 2014.
Henderson, Gi, et al., "Inhibition of Placental Valine Uptake after Acute and Chronic Maternal Ethanol Consumption", *J Pharmacol Exp Therap*, 1981; 216:465-472.
Kestendjieva, S. et al., "Characterization of mesenchymal stem cells isolated from the human umbilical cord," *Cell Biology International*, 2008; 32: 724-732.
Kocher, A.A. et al., "Neovascularization of ischemic myocardium by human bone-marrowderived angioblasts prevents cardiomyocyte apoptosis, reduces remodeling and improves cardiac function," *Nature Medicine*, 2001, 7: 430-6.
Nehlin et al., "Immunogenicity and immune-modulating properties of human stem cells," *Stem Cells in Clinical Research*, 2011.
In the U.S. Patent and Trademark Office Final Office Action in re: U.S. Appl. No. 11/317,574 dated Feb. 3, 2014, 12 pages.
In the U.S. Patent and Trademark Office, Final Office Action in re: U.S. Appl. No. 10/876,998 dated Dec. 16, 2014, 19 pages.
In the U.S. Patent and Trademark Office, Non-Final Office Action in re: U.S. Appl. No. 11/322,372 dated Nov. 25, 2014, 24 pages.
In the U.S. Patent and Trademark Office, Final Office Action in re: U.S. Appl. No. 11/315,969 dated Dec. 18, 2014, 30 pages.
In the U.S. Patent and Trademark Office, Final Office Action in re: U.S. Appl. No. 11/321,863 dated Jan. 31, 2014, 17 pages.
In the U.S. Patent and Trademark Office, Non-Final Office Action in re: U.S. Appl. No. 14/152,649 dated Feb. 26, 2015, 9 pages.
In the U.S. Patent and Trademark Office, Non-Final Office Action in re: U.S. Appl. No. 14/444,689 dated Mar. 24, 2015, 9 pages.
In the U.S. Patent and Trademark Office, Final Office Action in re: U.S. Appl. No. 11/317,574 dated Apr. 1, 2015, 12 pages.
In the U.S. Patent and Trademark Office, Final Office Action in re: U.S. Appl. No. 13/471,095 dated Jun. 12, 2015, 10 pages.
In the U.S. Patent and Trademark Office, Final Office Action in re: U.S. Appl. No. 14/152,649 dated Jul. 10, 2015, 7 pages.
In the U.S. Patent and Trademark Office, Final Office Action in re: U.S. Appl. No. 12/339,872 dated Aug. 3, 2015, 14 pages.
In the U.S. Patent and Trademark Office, Non-Final Office Action in re: U.S. Appl. No. 11/321,864 dated Sep. 2, 2015, 11 pages.
In the U.S. Patent and Trademark Office, Final Office Action in re: U.S. Appl. No. 12/389,305 dated Sep. 4, 2015, 63 pages.
In the U.S. Patent and Trademark Office, Non-Final Office Action in re: U.S. Appl. No. 11/316,104 dated Sep. 8, 2015, 63 pages.
In the U.S. Patent and Trademark Office, Non-Final Office Action in re: U.S. Appl. No. 14/152,649 dated Oct. 27, 2015, 7 pages.
Broxmeyer, H.E. et al., "Growth characteristics and expansion of human umbilical cord blood and estimation of its potential for transplantation in adults," *PNAS*, 1992; 89(9): 4109-4113.
Hass, R. et al., "Different populations and sources of human mesenchymal stem cells (Msc): a comparison of adult and neonatal tissue-derived MSC," *Cell Communication and Signaling*, 2011; 9:12, p. 1-14.
Ho, A.D. et al., "Heterogeneity of mesenchymal stromal cell preparations," *Cytotherapy*, 2008; 10(4):320-30.
Kern, S. et al., "Comparative analysis of mesenchymal stem cells from bone marrow, umbilical cord blood, or adipose tissue," *Stem Cells*, 2006; 24(5):1294-301.
Park, B-G et al., "Development of high density mammalian cell culture system for the production of tissue-type plasminogen activator," *Biotechnology and Bioprocess Engineering*, 2000; 5:123-129.

(56) References Cited

OTHER PUBLICATIONS

Pittenger, M.F. et al.; "Human mesenchymal stem cells: progenitor cells for cartilage, bone, fat and stroma," *Current Topics in Microbiology and Immunology*, 2000; 251:3-11.
Rachakatla, R. S. et al., "Development of Human Umbilical Cord Matrix Stem Cell-Based Gene Therapy for Experimental Lung Tumors," *Cancer Gene Therapy*, 2007; 14:828-835.
Secco, M. et al., "Multipotent Stem Cells from Umbilical Cord: Cord is Richer than Blood!" *Stem Cells*, 2008; 26:146-150.
Xu, Y et al., "Umbilical Cord-Derived Mesenchymal Stem Cells Isolated by a Novel Explantation Technique Can Differentiate into Functional Endothelial Cells and Promote Revascularization," *Stem Cells and Development*, 2010, 19(10): 1511-1522.
Zhao, Q.H. et al, "Biological characteristics of human umbilical cord-derived mesenchymal stem cells and their differentiation into chondrogenic and osteogenic cells," *Zhonghua Yi Xue Za Zhi.*, 2011;91(5):317-21 (Abstract only).
In the U.S. Patent and Trademark Office Final Office Action in re: U.S. Appl. No. 10/876,998 dated Dec. 22, 2015, 21 pages.
In the U.S. Patent and Trademark Office, Final Office Action in re: U.S. Appl. No. 11/321,864 dated Dec. 22, 2015, 15 pages.
In the U.S. Patent and Trademark Office, Non-Final Office Action in re: U.S. Appl. No. 11/317,574 dated Jan. 6, 2015, 11 pages.
In the U.S. Patent and Trademark Office, Final Office Action in re: U.S. Appl. No. 11/322,372 dated Jan. 6, 2015, 27 pages
In the U.S. Patent and Trademark Office, Final Office Action in re: U.S. Appl. No. 12/337,439 dated Mar. 17, 2016 29 pages.
In the U.S. Patent and Trademark Office, Final Office Action in re: U.S. Appl. No. 11/315,969 dated Apr. 21, 2016 20 pages.
In the U.S. Patent and Trademark Office, Final Rejection in re: U.S. Appl. No. 10/876,998 dated May 20, 2016 21 pages.
In the U.S. Patent and Trademark Office, Final Office Action in re: U.S. Appl. No. 12/389,305 dated May 24, 2016 21 pages.
In the U.S. Patent and Trademark Office, Final Office Action in re: U.S. Appl. No. 11/316,104 dated May 24, 2016 24 pages.
In the U.S. Patent and Trademark Office, Non-Final Office Action in re: U.S. Appl. No. 11/322,372 dated May 31, 2016, 29 pages.
In the U.S. Patent and Trademark Office, Final Office Action in re: U.S. Appl. No. 11/317,574 dated May 31, 2016, 18 pages.
In the U.S. Patent and Trademark Office, Final Office Action in re: U.S. Appl. No. 14/152,649 dated Jun. 14, 2016, 6 pages.
In the U.S. Patent and Trademark Office, Final Office Action in re: U.S. Appl. No. 11/317,574 dated Jul. 7, 2016, 9 pages.
Baksh, D. et al., "Adult mesenchymal stem cells: characterization, differentiation, and application in cell and gene therapy", *J Cell Mol Med.*, 2004; 8(3):301-16.
Lu, L.L. et al., "Isolation and characterization of human umbilical cord mesenchymal stem cells with hematopoiesis-supportive function and other potentials," *Haematologica*, 2006; 91(8):101-726.
Mankikar, S.D., "Stem Cells: A New Paradigm in Medical Therapeutics," *Journal of Long-Term Effects of Medical Implants*, 2010; 20:219-250.
Naughton, B.A. et al.,"Hematopoiesis on nylon mesh templates. I. Long-term culture of rat bone marrow cells," *Journal of Medicine*, 1987; 18(3-4):219-50.
Wakitani, S. et al.,"Mesenchymal cell-based repair of large, full-thickness defects of articular cartilage", *J Bone Joint Surg Am*, 1994; 76(4):579-592.
Weiss, M.L. et aL,"Stem Cells in the Umbilical Cord," *Stem Cell Rev.*, 2006; 2(2):155-162.

\* cited by examiner

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial
<220> FEATURE:
<223> OTHER INFORMATION: Synthetic Construct

<400> SEQUENCE: 1
gagaaatcca aagagcaaat gg                                          22

<210> SEQ ID NO 2
<211> LENGTH: 21
<212> TYPE: DNA
<213> ORGANISM: Artificial
<220> FEATURE:
<223> OTHER INFORMATION: Synthetic Construct
```

```
<400> SEQUENCE: 2
agaatggaaa actggaatag g                                              21

<210> SEQ ID NO 3
<211> LENGTH: 20
<212> TYPE: DNA
<213> ORGANISM: Artificial
<220> FEATURE:
<223> OTHER INFORMATION: Synthetic Construct

<400> SEQUENCE: 3
tcttcgatgc ttcggattcc                                                20

<210> SEQ ID NO 4
<211> LENGTH: 21
<212> TYPE: DNA
<213> ORGANISM: Artificial
<220> FEATURE:
<223> OTHER INFORMATION: Synthetic Construct

<400> SEQUENCE: 4
gaattctcgg aatctctgtt g                                              21

<210> SEQ ID NO 5
<211> LENGTH: 21
<212> TYPE: DNA
<213> ORGANISM: Artificial
<220> FEATURE:
<223> OTHER INFORMATION: Synthetic Construct

<400> SEQUENCE: 5
ttacaagcag tgcagaaaac c                                              21

<210> SEQ ID NO 6
<211> LENGTH: 22
<212> TYPE: DNA
<213> ORGANISM: Artificial
<220> FEATURE:
<223> OTHER INFORMATION: Synthetic Construct

<400> SEQUENCE: 6
agtaaacatt gaaaccacag cc                                             22

<210> SEQ ID NO 7
<211> LENGTH: 20
<212> TYPE: DNA
<213> ORGANISM: Artificial
<220> FEATURE:
<223> OTHER INFORMATION: Synthetic Construct

<400> SEQUENCE: 7
tctgcagctc tgtgtgaagg                                                20

<210> SEQ ID NO 8
<211> LENGTH: 22
<212> TYPE: DNA
<213> ORGANISM: Artificial
<220> FEATURE:
<223> OTHER INFORMATION: Synthetic Construct

<400> SEQUENCE: 8
cttcaaaaac ttctccacaa cc                                             22

<210> SEQ ID NO 9
```

```
<211> LENGTH: 17
<212> TYPE: DNA
<213> ORGANISM: Artificial
<220> FEATURE:
<223> OTHER INFORMATION: Synthetic Construct

<400> SEQUENCE: 9
cccacgccac gctctcc                                                    17

<210> SEQ ID NO 10
<211> LENGTH: 19
<212> TYPE: DNA
<213> ORGANISM: Artificial
<220> FEATURE:
<223> OTHER INFORMATION: Synthetic Construct

<400> SEQUENCE: 10
tcctgtcagt tggtgctcc                                                  19

<210> SEQ ID NO 11
<211> LENGTH: 20
<212> TYPE: DNA
<213> ORGANISM: Artificial
<220> FEATURE:
<223> OTHER INFORMATION: Synthetic Construct

<400> SEQUENCE: 11
ctggattggc gttgtttgtg                                                 20

<210> SEQ ID NO 12
<211> LENGTH: 21
<212> TYPE: DNA
<213> ORGANISM: Artificial
<220> FEATURE:
<223> OTHER INFORMATION: Synthetic Construct

<400> SEQUENCE: 12
tcccaaggtg gagtgctgta g                                               21

<210> SEQ ID NO 13
<211> LENGTH: 21
<212> TYPE: DNA
<213> ORGANISM: Artificial
<220> FEATURE:
<223> OTHER INFORMATION: Synthetic Construct

<400> SEQUENCE: 13
ctgttgcgca catccctgcc c                                               21

<210> SEQ ID NO 14
<211> LENGTH: 22
<212> TYPE: DNA
<213> ORGANISM: Artificial
<220> FEATURE:
<223> OTHER INFORMATION: Synthetic Construct

<400> SEQUENCE: 14
ggcagtctgg ctttctcaga tt                                              22

<210> SEQ ID NO 15
<211> LENGTH: 21
<212> TYPE: DNA
<213> ORGANISM: Artificial
<220> FEATURE:
<223> OTHER INFORMATION: Synthetic Construct

<400> SEQUENCE: 15
```

-continued

```
ccctctccct tacccttagc a                                                        21

<210> SEQ ID NO 16
<211> LENGTH: 23
<212> TYPE: DNA
<213> ORGANISM: Artificial
<220> FEATURE:
<223> OTHER INFORMATION: Synthetic Construct

<400> SEQUENCE: 16
ctgtgaaagg acctgtctgt cgc                                                      23
```

POSTPARTUM CELLS DERIVED FROM PLACENTAL TISSUE, AND METHODS OF MAKING AND USING THE SAME

CROSS-REFERENCE TO RELATED APPLICATIONS

This application claims benefit under 35 U.S.C 119(e) of U.S. Provisional Application No. 60/483,264, filed Jun. 27, 2003, the entire contents of which are incorporated by reference herein.

This application is also related to the following commonly-owned, applications, the entire contents of each of which are incorporated by reference herein: U.S. application Ser. No. 10/877,012, filed Jun. 25, 2004, now U.S. Pat No. 7,510,873, issued Mar. 31, 2009; U.S. application Ser. No. 10/877,269, filed Jun. 25, 2004, now U.S. Pat. No. 7,524,489, issued Apr. 28, 2009; U.S. application Ser. No. 10/877,445, filed Jun. 25, 2004, U.S. application Ser. No. 10/877,541, filed Jun. 25, 2004, now U.S. Pat. No. 7,413,734, issued Au. 19, 2008; U.S. application Ser. No. 10/877,009, filed Jun. 25, 2004, now U.S. Pat. No. 7,560,276, issued Jul. 14, 2009; U.S. application Ser. No. 10/876,998, filed Jun. 25, 2004 and U.S. Provisional Application No. 60/555,908, filed Mar. 24, 2004.

FIELD OF THE INVENTION

This invention relates to the field of mammalian cell biology and cell culture. In particular, the invention relates to cultured cells derived from postpartum placental tissue having the potential to differentiate into multiple lineages, and methods of preparation and use of those placenta-derived cells.

BACKGROUND OF THE INVENTION

Organ and tissue generation from cells provides promising treatments for a number of pathologies, thereby making stem cells a central focus of research in many fields. Human stem cells are capable of generating a variety of mature human cell lineages. Transplantation of such cells has provided a clinical tool for reconstituting a target tissue, thereby restoring physiologic and anatomic functionality. The application of stem cell technology is wide-ranging, including tissue engineering, gene therapy delivery, and cell therapeutics for disorders including malignancies, inborn errors of metabolism, hemoglobinopathies, and immunodeficiences.

An obstacle to realization of the therapeutic potential of stem cell technology has been difficulty in obtaining sufficient numbers of human stem cells. One source of stem cells is embryonic or fetal tissue. Embryonic stem and progenitor cells have been isolated from a number of mammalian species, including humans. The derivation of stem cells from embryonic or fetal sources, however, has raised many ethical and moral issues.

Stem cells also have been isolated from adult tissues. Methods for isolation of stem cells from adult sources often yield only limited quantities of cells and/or cells having limited ability to differentiate.

Postpartum tissues have generated interest as an alternative source for human stem cells. For example, methods for recovery of stem cells by perfusion of the placenta or collection from umbilical cord blood have been described. A limitation of stem cell procurement from these methods has been an inadequate volume of cord blood or quantity of cells obtained.

Thus, alternative sources of adequate supplies of cells having the ability to differentiate into an array of cell lineages for cryopreservation and/or use in clinical applications remain in great demand. Such cells may be used in drug screening assays, for cryopreservation and/or banking, and for diagnostic and therapeutic applications.

SUMMARY OF THE INVENTION

The present invention relates to cells derived from postpartum placenta. The cells of the invention may be characterized by any one or more of characteristics including the presence or absence of cell surface markers, methods of extraction from placental tissue, gene expression profiles, protein production profiles, secretion of factors, growth characteristics, or any combination of such characteristics.

The invention encompasses cells derived from human postpartum placental tissue substantially free of blood. In some embodiments, the cell is capable of self-renewal and expansion in culture. In some aspects of the invention, the cell has the potential to differentiate into cells of another phenotype. In some embodiments, the placenta-derived cell requires L-valine for growth. The placenta-derived cells of the invention are capable of growth in about 5% to about 20% oxygen. In some embodiments of the invention, the placenta-derived cell exhibits at least one of the following characteristics:

(a) production of at least one of tissue factor, vimentin, granulocyte chemotactic protein-2 (GCP-2), and alpha-smooth muscle actin;

(b) lack of production of at least one of GRO-alpha and oxidized low density lipoprotein receptor, as detected by flow cytometry;

(c) production of at least one of CD10, CD13, CD44, CD73, CD90, PDGFr-alpha, PD-L2 and HLA-A,B,C;

(d) lack of production of at least one of CD31, CD34, CD45, CD80, CD86, CD117, CD141, CD178, B7-H2, HLA-G, and HLA-DP, DQ, DR, as detected by flow cytometry;

(e) expression, which relative to a human cell that is a fibroblast, a mesenchymal stem cell, or an iliac crest bone marrow cell, is increased for at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113;

(f) expression, which relative to a human cell that is a fibroblast, a mesenchymal stem cell, or an iliac crest bone marrow cell, is reduced for at least one of: short stature homeobox 2; heat shock 27 kDa protein 2; chemokine (C-X-C motif) ligand 12 (stromal cell-derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, antiproliferative; cholesterol 25 -hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenikephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ 14054; cDNA DKFZp564B222 (from clone DKFZp564B222); vesicle-associated membrane protein 5; EGF-containing fibulin-like extracellular matrix protein 1; BCL2/adenovirus E1B 19 kDa interacting protein 3-like; AL binding protein 1; cytochrome c oxidase subunit VIIa polypeptide 1 (muscle); neuroblastoma, suppression of tumorigenicity 1; and insulin- like growth factor binding protein 2, 36 kDa;

(g) secretion of at least one of monocyte chemotactic protein 1 (MCP-1), interleukin-6 (IL-6), stromal-derived factor 1alpha (SDF-1alpha), interleukin 8 (IL8), granulocyte chemotactic protein-2 (GCP-2), hepatocyte growth factor (HGF), keratinocyte growth factor (KGF), heparin-binding epidermal growth factor (HB-EGF), brain-derived neurotrophic factor (BDNF), tissue inhibitor of matrix metalloproteinase 1 (TIMP1), thrombopoietin (TPO), macrophage inflammatory protein 1alpha(MIP1 a), Rantes (regulated on activation, normal T cell expressed and secreted), thymus and activation-regulated chemokine (TARC), and Eotaxin;

(h) lack of secretion of at least one of fibroblast growth factor (FGF), vascular endothelial growth factor (VEGF), angiopoietin 2 (ANG2), platelet derived growth factor (PDGF-bb), transforming growth factor beta2 (TGFbeta2), macrophage inflammatory protein 1beta (MIP1b), I309, and macrophage-derived chemokine (MDC), as detected by ELISA; and (i) the ability to undergo at least 40 population doublings in culture.

In specific embodiments, the cell has all identifying features of any one of: cell type PLA 071003 (P8) (ATCC Accession No. PTA-6074); cell type PLA 071003 (P11) (ATCC Accession No. PTA-6075); and cell type PLA 071003 (P16) (ATCC Accession No. PTA-6079). The placenta-derived cells of the invention are preferably human cells. The cells of the invention may be of neonatal lineage, maternal lineage, or a combination thereof.

The invention also provides placenta-derived cells isolated from a post-partum placenta or fragment thereof by enzymatic dissociation with a matrix metalloprotease (MMP); a matrix metalloprotease and a neutral protease; a matrix metalloprotease and a mucolytic enzyme that digests hyaluronic acid; or a matrix metalloprotease, a neutral protease, and a mucolytic enzyme that digests hyaluronic acid. Preferable matrix metalloproteases include collagenase. The neutral protease is preferably thermolysin or dispase, and most preferably is dispase. The mucolytic enzyme that digests hyaluronic acid preferably is hyaluronidase. The LIBERASE (Boehringer Mannheim Corp., Indianapolis, Ind.) Blendzyme (Roche) series of enzyme combinations are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In more preferred embodiments, the tissue is incubated at 37° C. during the enzyme treatment of the disintegration step.

In some embodiments of the invention, the placental tissue is separated into fractions prior to cell extraction, such that the cell is predominantly of neonatal or maternal derivation. In some aspects of the invention, placental tissue is mechanically dissociated prior to the step of enzymatic dissociation. In some embodiments, the method of isolation of the cells of the invention further involves growing the cells in culture medium. The culture medium preferably is RPMI1640, Ham's F10 medium, Ham's F12 medium, Mesenchymal Stem Cell Growth Medium, Iscove's modified Dulbecco's medium, Dulbecco's modified Eagle's Medium (DMEM), advanced DMEM (Gibco), DMEM/MCDB201 (Sigma), CELL-GRO FREE, DMEM/F12, or Eagle's basal medium. In some aspects of the invention, the culture medium is supplemented with about 2% to about 15% (v/v) serum, beta-mercaptoethanol, glucose, and/or an antibiotic agent and an antimycotic agent. The culture medium preferably is Growth medium comprising DMEM, glucose, beta-mercaptoethanol, serum, and an antibiotic agent. The culture medium may contain at least one of fibroblast growth factor, platelet-derived growth factor, vascular endothelial growth factor, epidermal growth factor, and leukemia inhibitory factor. The cells of the invention may be grown on an uncoated or coated surface. Surfaces for growth of the cells may be coated for example with gelatin, collagen (e.g., native or denatured), fibronectin, laminin, ornithine, vitronectin, or extracellular membrane protein (e.g., MATRIGEL (BD Discovery Labware, Bedford, Mass.)).

The invention includes within its scope placenta-derived cells characterized by growth characteristics, such as but not limited to, cells that yield greater than about $10^{17}$ cells in about 60 days upon initial seeding at about 1,000 to about 5,000 cells/cm$^2$. In some embodiments, the placenta-derived cells of the invention have the ability to undergo at least 40 population doublings in about 80 days in culture.

The placenta-derived cells of the invention may be utilized from the first subculture (passage 0) to senescence. The preferable number of passages is that which yields a cell number sufficient for a given application. In certain embodiments, the cells are passaged 2 to 25 times, preferably 4 to 20 times, more preferably 8 to 15 times, more preferably 10 or 11 times, and most preferably 11 times.

Methods for inducing differentiation of placenta-derived cells of the invention also are contemplated. In some embodiments of the invention, placenta-derived cells are induced to a mesodermal, ectodermal, or endodermal lineage. For example, the cells may be induced to differentiate to an adipogenic, a chondrogenic, an osteogenic, a neurogenic, an oculogenic, a pancreagenic, a cardiomyogenic, or a hepatogenic lineage. Methods of inducing differentiation of the cells of the invention preferably involve contacting or exposing the cells to one or more differentiation-inducing agents. In some embodiments, such contact or exposure occurs in culture. The invention includes the cells so induced.

Cells of the invention may be genetically engineered to express a gene of interest or to produce a protein of interest such as but not limited to a therapeutic protein. For example, PDCs may be genetically engineered to express an antiinflammatory compound or an anti-apoptotic agent.

Methods of the invention further include methods for producing a population of placenta-derived cells by expanding a cell or cells of the invention in culture. The PDCs may be differentiation-induced or undifferentiated. In some embodiments, a population of placenta- derived cells is mixed with another population of cells. In some embodiments, the cell population is heterogeneous. A heterogeneous cell population of the invention may comprise at least about 5%, 10%, 20%, 30%, 40%, 50%, 60%, 70%, 80%, 90%, or 95% undifferentiated or differentiation-induced PDCs of the invention. The heterogeneous cell populations of the invention may further comprise stem cells or cells of a mesodermal, endodermal, or ectodermal lineage. Cell populations of the invention may be homogeneous. Homogeneous populations of placenta-derived cells may be of neonatal or maternal lineage. Homogeneity of a cell population may be achieved by any method known in the art, for example, by cell sorting (e.g., flow cytometry) or by clonal expansion.

Some embodiments of the invention provide methods of manufacturing a tissue matrix for implantation into a patient by seeding one or more placenta-derived cells of the invention onto or into a tissue matrix for implantation into a patient. The PDCs may be differentiated or undifferentiated. The matrix may contain one or more factors including drugs, anti-apoptotic agents (e.g., erythropoietin (EPO), EPO mimetibody, thrombopoietin, insulin-like growth factor (IGF)-I, IGF-II, hepatocyte growth factor, caspase inhibitors), anti-inflammatory compounds (e.g., p38 MAP kinase inhibitors, TGF-beta inhibitors, statins, IL-6 and IL-1 inhibitors, PEMIROLAST, TRANILAST, REMICADE, SIROLIMUS, and non-steroidal anti-inflammatory drugs (NSAIDS) (such as TEPOXALIN, TOLMETIN, and SUPROFEN)) as well as local anesthetics, and growth factors. In some aspects of the invention, the matrix comprises decellularized tissue, such as extracellular matrix or cell lysates of the PDCs. In some embodiments, the matrix is biodegradable. In some aspects of the invention, the matrix comprises natural or synthetic polymers. Matrices of the invention include biocompatible scaffolds, lattices, self-assembling structures and the like, whether biodegradable or not, liquid or solid. Such matrices are known in the arts of cell-based therapy, surgical repair, tissue engineering, and wound healing. Preferably the matrices are pretreated (e.g., seeded, inoculated, contacted with) with the cells, extracellular matrix, conditioned medium, cell lysate, or combination thereof, of the invention. More preferably the matrices are populated with cells in close association to the matrix or its spaces. In some aspects of the invention, the cells adhere to the matrix. In some embodiments, the cells are contained within or bridge interstitial spaces of the matrix. Most preferred are those seeded matrices wherein the cells are in close association with the matrix and which, when used therapeutically, induce or support ingrowth of the patient's cells and/or proper angiogenesis. The seeded matrices can be introduced into a patient's body in any way known in the art, including but not limited to implantation, injection, surgical attachment, transplantation with other tissue, injection, and the like. Examples of scaffolds which may be used in the present invention include nonwoven mats, porous foams, or self-assembling peptides. Nonwoven mats may, for example, be formed using fibers comprised of a synthetic absorbable copolymer of glycolic and lactic acids (PGA/PLA) sold under the tradename VICRYL (Ethicon, Inc. Somerville, N.J.). Foams composed of, for example, poly (epsilon-caprolactone)/poly(glycolic aicd) (PCL/PGA) copolymer, formed by the processes such as freeze-drying, or lyophilized, as discussed in U.S. Pat. No. 6,355,699, also are possible scaffolds. Hydrogels such as self-assembling peptides (e.g., RAD16) may also be used. These materials are frequently used as supports for growth of tissue. The matrices of the invention may be configured to the shape and/or size of a tissue or organ in vivo. The scaffolds of the invention may be flat or tubular or may comprise sections thereof. The scaffolds of the invention may be multilayered. Organs and tissues comprising PDCs, their extracellular matrix, or cell lysate also are provided.

Also encompassed within the scope of the invention are extracellular matrices of PDCs, cell fractions (e.g., soluble cell fractions) of PDCs, and PDC-conditioned medium.

In some embodiments the invention provides compositions of PDCs and one or more bioactive factors, for example, but not limited to growth factors, anti-apoptotic agents, anti-inflammatory agents, and/or differentiation inducing factors.

The cells, matrices, tissues, and compositions of the invention may be cryopreserved. Cryopreserved cells and compositions of the invention may be banked or stored. Methods for cryopreserving and/or storing postpartum-derived cells of the invention also are contemplated.

Compositions of PDCs and related products, including for example pharmaceutical compositions, are included within the scope of the invention. Compositions of PDCs may include one or more of a differentiation-inducing factor, a cell survival factor such as caspase inhibitor, an anti-inflammatory agent such as p38 kinase inhibitor, growth factors, such as PDGF-bb, EGF, bFGF, LIF, IGF-1, or VEGF, or an angiogenic factor such as VEGF or bFGF. Pharmaceutical compositions of the placenta-derived cells, extracellular matrix produced thereby, cell lysates thereof, and PDC-conditioned medium are included within the scope of the invention. The pharmaceutical compositions preferably include a pharmaceutically acceptable carrier or excipient.

In some embodiments, methods of transplanting placenta-derived cells or matrices and methods of regenerating a tissue or organ in a patient in need thereof by transplanting cells or matrices of the invention into a patient are provided.

Further provided by the invention are methods for treating a disease or injury in a patient by administering one or more placenta-derived cells, PDC populations, matrices, cell lysates, conditioned medium, or compositions of the invention.

The invention also encompasses cell cultures of the placenta-derived cells of the invention. The cultures of the invention preferably are capable of at least 40 population doublings upon initial seeding.

The cell and compositions of the invention may be used, for example, in the treatment of conditions or repair of tissue. In some embodiments of the invention, the condition to be treated is a condition of soft tissue (e.g., skin, muscle, vasculature, tendons, ligaments, bladder, fascia, pelvic floor), bone, pancreas, kidney, liver, nervous system, eye, heart, or cartilage.

Methods of the invention further include methods for producing a population of placenta-derived cells by expanding a cell of the invention in culture.

Other features and advantages of the invention will be apparent from the detailed description and examples that follow.

DETAILED DESCRIPTION OF ILLUSTRATIVE EMBODIMENTS

Definitions

Various terms used throughout the specification and claims are defined as set forth below.

Stem cells are undifferentiated cells defined by their ability at the single cell level to both self-renew and differentiate to produce progeny cells, including self-renewing progenitors, non-renewing progenitors and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent—able to give rise to all embryonic and extraembryonic cell types; (2) pluripotent—able to give rise to all embryonic cell types; (3) multipotent—able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood); (4) oligopotent—able to give rise to a more restricted subset of cell lineages than multipotent stem cells; and (5) unipotent—able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself and, under normal circumstances, differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord, and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated or differentiation-induced cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

In a broad sense, a progenitor cell is a cell that has the capacity to create progeny that are more differentiated than itself and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase differentiates into a mesodermal, ectodermal or endodermal lineage refers to a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, cell that give rise to the lining of the intestine, and cells that give rise to pancreogenic and splanchogenic cells.

The cells of the present invention are referred to as placenta-derived cells (PDCs). They also may sometimes be referred to herein as postpartum-derived cells or postpartum cells (PPDCs). In addition, the cells may be described as being stem or progenitor cells, the latter term being used in the broad sense. The term derived is used to indicate that the cells have been obtained from their biological source and grown or otherwise manipulated in vitro (e.g., cultured in a growth medium to expand the population and/or to produce a cell line). The in vitro manipulations of placenta-derived cells and the unique features of the placenta- derived cells of the present invention are described in detail below.

Various terms are used to describe cells in culture. Cell culture refers generally to cells taken from a living organism and grown under controlled condition ("in culture"). A primary cell culture is a culture of cells, tissues or organs taken directly from organisms and before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

A conditioned medium is a medium in which a specific cell or population of cells has been cultured, and then removed. While the cells are cultured in the medium, they secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Generally, a trophicfactor is defined as a substance that promotes survival, growth, proliferation, maintenance, differentiation, and/or maturation of a cell, or stimulates increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re- introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

As used herein, the term Growth medium refers to a culture medium sufficient for expansion of placenta-derived cells. The culture medium of Growth medium preferably contains Dulbecco's Modified Essential Media (DMEM). More preferably, Growth medium contains glucose. Growth medium preferably contains DMEM-low glucose (DMEM-LG) (Invitrogen, Carlsbad, Calif.). Growth medium preferably contains about 15% (v/v) serum (e.g., fetal bovine serum, defined bovine serum). Growth medium preferably contains at least one antibiotic agent and/or antimycotic agent (e.g., penicillin, streptomycin, amphotericin B, gentamicin, nystatin; preferably 50 units/milliliter penicillin G sodium and 50 micrograms/milliliter streptomycin sulfate). Growth medium preferably contains 2-mercaptoethanol (Sigma, St. Louis Mo.). Most preferably, Growth medium contains DMEM-low glucose, serum, 2-mercaptoethanol, and an antibiotic agent and antimycotic agent.

As used herein, standard growth conditions refers to standard atmospheric conditions comprising 5% $CO_2$ and a temperature in the range of 35° C. to 39° C., more preferably, 37° C., and a relative humidity of about 100%.

The term isolated refers to a cell, cellular component, or a molecule that has been removed from its native environment. PDCs, for example, may be isolated in some embodiments of the invention.

The term about refers to an approximation of a stated value within a range of ±10%.

The term treating (or treatment of) a condition refers to ameliorating the effects of, or delaying, halting or reversing the progress of, or delaying or preventing the onset of, a condition such as but not limited to a congenital anomaly, disease, or injury.

The term effective amount refers to a concentration of a reagent or pharmaceutical composition, such as a growth factor, differentiation agent, trophic factor, cell population or other agent, that is effective for producing an intended result, including cell growth and/or differentiation in vitro or in vivo, or treatment of a condition as described herein. With respect to growth factors, an effective amount may range from about 1 nanogram/milliliter to about 1 microgram/milliliter. With respect to PDCs as administered to a patient in vivo, an effective amount may range from as few as several hundred or fewer to as many as several million or more. In specific embodiments, an effective amount may range from $10^3$-$10^{11}$. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or pharmaceutical composition to achieve its intended result.

The term patient or subject refers to animals, including mammals, preferably humans, who are treated with the pharmaceutical compositions or in accordance with the methods described herein.

The term matrix as used herein refers to a support for the PPDCs of the invention, for example, a scaffold (e.g., VICRYL, PCL/PGA, or RAD16) or supporting medium (e.g., hydrogel, extracellular membrane protein (e.g., MATRIGEL (BD Discovery Labware, Bedford, Mass.)).

The term pharmaceutically acceptable carrier (or medium), which may be used interchangeably with the term biologically compatible carrier or medium, refers to reagents, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds). As used herein, the term biodegradable describes the ability of a material to be broken down (e.g., degraded, eroded, dissolved) in vivo. The term includes degradation in vivo with or without elimination (e.g., by resorption) from the body. The semi- solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

Several terms are used herein with respect to cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

The following abbreviations are used herein:
ANG2 (or Ang2) for angiopoietin 2;
APC for antigen-presenting cells;
BDNF for brain-derived neurotrophic factor;
bFGF for basic fibroblast growth factor;
bid (BID) for "bis in die" (twice per day);
BSP for bone sialoprotein;
CK18 for cytokeratin 18;
CXC ligand 3 for chemokine receptor ligand 3;
DAPI for 4'-6-Diamidino-2-phenylindole-2HCl;
DMEM for Dulbecco's Minimal Essential Medium;
DMEM:lg (or DMEM:Lg, DMEM:LG) for DMEM with low glucose;
EDTA for ethylene diamine tetraacetic acid;
EGF (or E) for epidermal growth factor;
EPO for erythropoietin;
FACS for fluorescent activated cell sorting;
FBS for fetal bovine serum;
FGF (or F) for fibroblast growth factor;
GCP-2 for granulocyte chemotactic protein-2;
GDF-5 for growth and differentiation factor 5;
GFAP for glial fibrillary acidic protein;
HB-EGF for heparin-binding epidermal growth factor;
HCAEC for Human coronary artery endothelial cells;
HGF for hepatocyte growth factor;
hMSC for Human mesenchymal stem cells;
HNF-1 alpha for hepatocyte-specific transcription factor;
HUVEC for Human umbilical vein endothelial cells;
I309 for a chemokine and the ligand for the CCR8 receptor and is responsible for chemoattraction of TH2 type T-cells;
IGF for insulin-like growth factor;
IL-6 for interleukin-6;
IL-8 for interleukin 8;
K19 for keratin 19;
K8 for keratin 8;
KGF for keratinocyte growth factor;
MCP-1 for monocyte chemotactic protein 1;
MDC for macrophage-derived chemokine;
MIP1alpha for macrophage inflammatory protein 1alpha;
MIP1beta for macrophage inflammatory protein 1beta;
MMP for matrix metalloprotease (MMP);
MSC for mesenchymal stem cells;
NHDF for Normal Human Dermal Fibroblasts;
NPE for Neural Progenitor Expansion media;
OxLDLR for oxidized low density lipoprotein receptor;
PBMC for peripheral blood mononuclear cell;
PBS for phosphate buffered saline;
PDC for placenta-derived cell;
PDGFbb for platelet derived growth factor;
PDGFr-alpha for platelet derived growth factor receptor alpha;
PD-L2 for programmed—death ligand 2;
PE for phycoerythrin;
PO for "per os" (by mouth);
PPDC for postpartum-derived cell;
Rantes (or RANTES) for regulated on activation, normal T cell expressed and secreted;
rb for rabbit
rh for recombinant;
SC for subcutaneously;
SCID for severe combined immunodeficiency;
SDF-1alpha for stromal-derived factor 1 alpha;
SHH for sonic hedgehog;
SMA for smooth muscle actin;
SOP for standard operating procedure;
TARC for thymus and activation-regulated chemokine;
TCP for tissue culture plastic;
TGFbeta2 for transforming growth factor beta2;
TGFbeta-3 for transforming growth factor beta-3;
TIMP1 for tissue inhibitor of matrix metalloproteinase 1;
TPO for thrombopoietin;
TuJ1 for BIII Tubulin;
UDC for umbilical cord-derived cell;
VEGF for vascular endothelial growth factor;
vWF for von Willebrand factor; and
alphaFP for alpha-fetoprotein.

Description

Various patents and other publications are cited herein and throughout the specification, each of which is incorporated by reference herein in its entirety.

In one aspect, the invention provides placenta-derived cells (PDCs) derived from placental tissue washed substantially free of blood. The PDCs may be derived from placenta of a mammal including but not limited to human. The placentas from which the cells are derived are post-partum placentas. The cells are capable of self-renewal and expansion in culture. The placenta-derived cells have the potential to differentiate into cells of other phenotypes. In preferred embodiments, the cells can differentiate into a cell of ectodermal, mesodermal, or endodermal origin. The invention provides, in one of its several aspects, cells that are isolated from placental tissues, as opposed to placental blood.

The cells have been characterized as to several of their cellular, genetic, immunological, and biochemical properties. For example, the cells have been characterized by their growth, by their cell surface markers, by their gene expression, by their ability to produce certain biochemical trophic factors, and by their immunological properties.

Derivation and Expansion of Placenta-Derived Cells (PDCs)

According to the methods described herein, a mammalian placenta is recovered upon or shortly after termination of either a full-term or pre-term pregnancy, for example, after its expulsion after birth. Placental tissue can be obtained from any completed pregnancy, full- term or less than full-term, whether delivered vaginally, or through other means, for example, Cessarian section. The placenta may be transported from the birth site to a laboratory in a sterile container such as a flask, beaker, culture dish, or bag. The container may have a solution or medium, including but not limited to a salt solution, such as, for example, Dulbecco's Modified Eagle's Medium (DMEM) or phosphate buffered saline (PBS), or any solution used for transportation of organs used for transplantation, such as University of Wisconsin solution or perfluorochemical solution. One or more antibiotic and/or antimycotic agents, such as but not limited to penicillin, streptomycin, am photericin B, gentamicin, and nystatin, may be added to the medium or buffer. The placenta may be rinsed with an anticoagulant solution such as heparin-containing solution. It is preferable to keep the tissue at about 4-10° C. prior to extraction of PDCs. It is even more preferable that the tissue not be frozen prior to extraction of PDCs.

Isolation of PDCs preferably occurs in an aseptic environment. The umbilical cord is removed from the placenta by means known in the art. Placental tissue is washed substantially free of blood and debris prior to derivation of PDCs. For example, the placental tissue may be washed with buffer solution, such as but not limited to phosphate buffered saline. The wash buffer also may comprise one or more antimycotic and/or antibiotic agents, such as but not limited to penicillin, streptomycin, a mphotericin B, gentamicin, and nystatin.

In some aspects of the invention, the different cell types present in postpartum tissue are fractionated into subpopulations from which the PDCs can be isolated. This may be accomplished using techniques for cell separation including, but not limited to, enzymatic treatment to dissociate postpartum tissue into its component cells, followed by cloning and selection of specific cell types, for example but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and flow cytometry, for example, fluorescence activated cell sorting (FACS).

In a preferred embodiment, placental tissue comprising a whole placenta or a fragment or section thereof is disaggregated by mechanical force (mincing or shear forces), enzymatic digestion with single or combinatorial proteolytic enzymes, such as a matrix metalloprotease and/or neutral protease, for example, collagenase, trypsin, dispase, LIBERASE (Boehringer Mannheim Corp., Indianapolis, Ind.), hyaluronidase, and/or pepsin, or a combination of mechanical and enzymatic methods. For example, the cellular component of the placental tissue may be disaggregated by methods using collagenase-mediated dissociation. Collagenase may be type 1, 2, 3, or 4. Enzymatic digestion methods preferably employ a combination of enzymes, such as a combination of a matrix metalloprotease and a neutral protease, for example, a combination of collagenase and dispase. More preferably, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes known in the art for cell isolation include papain, deoxyribonucleases, serine proteases, such as trypsin, chymotrypsin, or elastase, that may be used either on their own or in combination with other enzymes such as matrix metalloproteases, mucolytic enzymes, and neutral proteases. Serine proteases are preferably used consecutively following use of other enzymes. The temperature and period of time tissues or cells are in contact with serine proteases is particularly important. Serine proteases may be inhibited by alpha 2 microglobulin in serum and therefore the medium used for digestion is usually serum-free. EDTA and DNAse are commonly used in enzyme digestion procedures to increase the efficiency of cell recovery. The degree of dilution of the digestion may also greatly affect the cell yield as cells may be trapped within the viscous digest.

In some embodiments of the invention, placental tissue is separated into two or more sections, each section consisting of either neonatal, neonatal and maternal, or maternal aspect. The separated sections then are dissociated by mechanical and/or enzymatic dissociation according to the methods described herein. Cells of neonatal or maternal lineage may be identified by any means known in the art, for example, by karyotype analysis or in situ hybridization for a Y chromosome. Karyotype analysis also may be used to identify cells of normal karyotype.

Isolated cells or placental tissue from which PDCs grow out may be used to initiate, or seed, cell cultures. Cells are transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)). PDCs are cultured in any culture medium capable of sustaining growth of the cells such as, but not limited to, DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMIEM/F12, RPMI 1640, advanced DMEM (Gibco), DMEM/MCDB201 (Sigma), and CELL-GRO FREE. The culture medium may be supplemented with one or more components including, for example, serum (e.g., fetal bovine serum (FBS), preferably about 2-15% (v/v); equine serum (ES); human serum(HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination. The culture medium preferably comprises Growth medium (DMEM-low glucose), serum, BME, an antimycotic agent, and an antibiotic agent).

The cells are seeded in culture vessels at a density to allow cell growth. For example, the cells may be seeded at low density (for example, about 1,000 to about 5,000 cells/cm$^2$) to high density (for example, about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25 to about 40° C., more preferably about 35° C. to about 39° C., and more preferably are cultured at 37° C. The cells are preferably cultured in an incubator. The medium in the culture vessel can be static or agitated, for example, using a bioreactor. PDCs preferably are grown under low oxidative stress (e.g., with addition of glutathione, ascorbic acid, catalase, tocopherol, N-acetylcysteine). "Low oxidative stress", as used herein, refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, CELL & ISSUE CULTURE: LABORATORY PROCEDURES, John Wiley & Sons, Chichester; and Ho and Wang (eds.), 1991, ANIMAL CELL BIOREACTORS, Butterworth-Heinemann, Boston, which are incorporated herein by reference.

The culture medium is changed as necessary, for example, by carefully aspirating the medium from the dish, for example, with a pipette, and replenishing with fresh medium. Incubation is continued until a sufficient number or density of cells accumulate in the dish. The original explanted tissue sections may be removed and the remaining cells trypsinized using standard techniques or using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be PDCs.

After culturing the cells or tissue fragments for a sufficient period of time, PDCs will have grown out, either as a result of migration from the placental tissue or cell division, or both. In some embodiments of the invention, PDCs are passaged, or removed to a separate culture vessel containing fresh medium of the same or a different type as that used initially, where the population of cells can be mitotically expanded. PDCs are preferably passaged up to about 100% confluence, more preferably about 70 to about 85% confluence. The lower limit of confluence for passage is understood by one skilled in the art. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

Cells of the invention may be cryopreserved. PDCs are preferably cryopreserved in cryopreservation medium, for example, culture medium including but not limited to Growth medium, or cell freezing medium, for example commercially available cell freezing medium, such as but not limited to C2695 (Sigma), C2639 (Sigma), or C6039 (Sigma). The cryopreservation medium preferably comprises dimethylsulfoxide (DMSO), for example about 10% (v/v). The cryopreservation medium may comprise additional cryopreservation agents including but not limited to methylcellulose and/or glycerol. The cells are preferably cooled at about 1° C./min. The preferred cryopreservation temperature is about −80° C. to about −180° C., more preferably is about −90° C. to about −160° C., and most preferably is about −125 to about −140° C. Cryopreserved cells preferably are transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., more preferably about 35° C. to about 39° C., and more preferably about 37° C.

Characterization of PDCs

PDCs may be characterized, for example, by growth characteristics (e.g., population doubling capability, doubling time, passages to senescence), karyotype analysis (e.g., maternal or neonatal lineage), flow cytometry (e.g., FACS analysis), immunohistochemistry and/or immunocytochemistry (e.g., for detection of epitopes including but not limited to vimentin, desmin, alpha-smooth muscle actin, cytokeratin 18, von Willebrand factor, CD34, GROalpha, GCP-2, oxidized low density lipoprotein receptor 1, and NOGO-A), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked ImmunoSorbent Assay (ELISA)), antibody analysis (e.g., ELISA, antibody staining for cell surface markers including but not limited to CD10, CD13, CD31, CD34, CD44, CD45, CD73, CD80, CD86, CD90, CD117, CD 141, CD 178, platelet-derived growth factor receptor alpha (PDGFr-alpha), HLA class I antigens (HLA-A, HLA-B, HLA-C), HLA class II antigens (HLA-DP, HLA-DQ, HLA-DR), B7-H2, and PD-L2), mixed lymphocyte reaction (e.g., as measure of stimulation of allogeneic peripheral blood mononuclear cells (PBMCs), for example, allogeneic lymphocytes, e.g., naïve CD4+ T cells), or other methods known in the art.

The placenta-derived cells of the invention preferably are derived from human postpartum placenta tissue substantially free of blood. PDCs are capable of self-renewal and expansion in culture and have the potential to differentiate into cells of another phenotype. PDCs require L-valine for growth. PDCs preferably are capable of growth in about 5% to about 20% oxygen. PDCs preferably comprise at least one of the following characteristics:

(a) production of at least one of tissue factor, vimentin, granulocyte chemotactic protein-2 (GCP-2), and alpha-smooth muscle actin;

(b) lack of production of at least one of GRO-alpha and oxidized low density lipoprotein receptor, as detected by flow cytometry;

(c) production of at least one of CD10, CD13, CD44, CD73, CD90, PDGFr-alpha, PD-L2 and HLA-A,B,C;

(d) lack of production of at least one of CD31, CD34, CD45, CD80, CD86, CD117, CD141, CD178, B7-H2, HLA-G, and HLA-DP, DQ, DR, as detected by flow cytometry;

(e) expression, which relative to a human cell that is a fibroblast, a mesenchymal stem cell, or an iliac crest bone marrow cell, is increased for at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113;
(f) expression, which relative to a human cell that is a fibroblast, a mesenchymal stem cell, or an iliac crest bone marrow cell, is reduced for at least one of: short stature homeobox 2; heat shock 27 kDa protein 2; chemokine (C-X-C motif) ligand 12 (stromal cell-derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, antiproliferative; cholesterol 25 -hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenikephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ 14054; cDNA DKFZp564B222 (from clone DKFZp564B222); vesicle-associated membrane protein 5; EGF-containing fibulin-like extracellular matrix protein 1; BCL2/adenovirus E1B19 kDa interacting protein 3-like; AE binding protein 1; cytochrome c oxidase subunit VIIa polypeptide 1 (muscle); neuroblastoma, suppression of tumorigenicity 1; and insulin- like growth factor binding protein 2, 36 kDa;
(g) secretion of at least one of monocyte chemotactic protein 1 (MCP-1), interleukin-6 (IL-6), stromal-derived factor 1alpha (SDF-1alpha), interleukin 8 (IL8), granulocyte chemotactic protein-2 (GCP-2), hepatocyte growth factor (HGF), keratinocyte growth factor (KGF), heparin-binding epidermal growth factor (HB-EGF), brain-derived neurotrophic factor (BDNF), tissue inhibitor of matrix metalloproteinase 1 (TIMP1), thrombopoietin (TPO), macrophage inflammatory protein 1alpha(MIPla), Rantes (regulated on activation, normal T cell expressed and secreted), thymus and activation-regulated chemokine (TARC), and Eotaxin;
(h) lack of secretion of at least one of fibroblast growth factor (FGF), vascular endothelial growth factor (VEGF), angiopoietin 2 (ANG2), platelet derived growth factor (PDGF-bb), transforming growth factor beta2 (TGFbeta2), macrophage inflammatory protein 1beta (MIP1b), I309, and macrophage-derived chemokine (MDC), as detected by ELISA; and
(i) the ability to undergo at least 40 population doublings in culture.

Population doubling may be calculated as [ln(cell final/cell initial)/ln 2]. Doubling time may be calculated as (time in culture (h)/population doubling).

In preferred embodiments, the cell comprises two or more of the foregoing characteristics. More preferred are those cells comprising three, four, or five or more of the characteristics. Still more preferred are those postpartum-derived cells comprising six, seven, or eight or more of the characteristics. Still more preferred are those cells comprising all nine of the claimed characteristics.

Also presently preferred are cells that produce at least two of GCP-2, tissue factor, vimentin, and alpha-smooth muscle actin. More preferred are those cells producing three or four of the proteins GCP-2, tissue factor, vimentin, and alpha-smooth muscle actin.

In some embodiments, the cells of the invention do not produce at least one of oxidized low density lipoprotein receptor or GRO-alpha, as detected by FACS analysis. In some embodiments, the cells produce neither protein as detected by FACS analysis.

The skilled artisan will appreciate that cell markers are subject to vary somewhat under vastly different growth conditions, and that generally herein described are characterizations in Growth Medium, or variations thereof. Postpartum-derived cells that produce of at least one, two, three, or four of CD10, CD13, CD44, CD73, CD90, PDGFr-alpha, PD-L2 and HLA-A,B,C are preferred. More preferred are those cells producing five, six, or seven of these cell surface markers. Still more preferred are postpartum-derived cells that can produce all eight of the foregoing cell surface marker proteins.

PPDCs that lack of production of at least one, two, three, four of the proteins CD31, CD34, CD45, CD80, CD86, CD117, CD141, CD178, B7-H2, HLA-G, and HLA-DR,DP, DQ, as detected by flow cytometry are preferred. PPDCs lacking production of at least five, six, seven or eight or more of these markers are preferred. More preferred are cells which lack production of at least nine or ten of the cell surface markers. Most highly preferred are those cells lacking production of eleven, twelve, or thirteen of the foregoing identifying proteins.

Presently preferred cells produce each of CD10, CD13, CD44, CD73, CD90, PDGFr-alpha, and HLA-A,B,C, and do not produce any of CD31, CD34, CD45, CD117, CD141, or HLA-DR,DP,DQ, as detected by flow cytometry.

It is preferred that postpartum-derived cells exhibit increased expression, relative to a human cell that is a fibroblast, a mesenchymal stem cell, or an iliac crest bone marrow cell, for at least one, two, or three of C-type lectin superfamily member A2, Wilms tumor 1, aldehyde dehydrogenase 1 family member A2, renin, oxidized low density lipoprotein receptor 1, protein kinase C zeta, clone IMAGE: 4179671, hypothetical protein DKFZp564F013, downregulated in ovarian cancer 1, and clone DKFZp547K1113. More preferred are those cells which exhibit increased expression for four, five, six, or seven, and still more preferred are cells capable of increased expression of eight, nine, or ten of the foregoing genes.

For some embodiments, preferred are cells, which relative to a human cell that is a fibroblast, a mesenchymal stem cell, or an iliac crest bone marrow cell, have reduced expression for at least one of the genes corresponding to: short stature homeobox 2; heat shock 27 kDa protein 2; chemokine (C-X-C motif) ligand 12 (stromal cell- derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenikephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ14054; cDNA DKFZp564B222 (from clone DKFZp564B222); vesicle-associated membrane protein 5; EGF-containing fibulin-like extracellular matrix protein 1; BCL2/adenovirus E1B 19 kDa interacting protein 3-like; AL binding protein 1; cytochrome c oxidase subunit VIIa polypeptide 1 (muscle); neuroblastoma, suppression of tumorigenicity 1; and insulin-like growth factor binding protein 2, 36 kDa. More preferred are cells that have, relative to human fibroblasts, mesenchymal stem cells, or iliac crest bone marrow cells, reduced expression of at least 5, 10, 15 or 20 genes corresponding to those listed above. Presently more preferred are cells with reduced relative expression of at least 25, 30, or 35 of the genes corresponding to the listed sequences. Also more preferred are those postpartum-derived cells having expression that is reduced, relative to that of a human fibroblast, a mesenchymal stem cell, or an iliac crest bone marrow cell, of genes corresponding to 35 or more, 40 or more, or even all of the sequences listed.

Secretion of certain growth factors and other cellular proteins can make cells of the invention particularly useful. Preferred placenta-derived cells secrete at least one, two, three, or four of monocyte chemotactic protein 1 (MCP-1), interleukin-6 (IL-6), stromal-derived factor 1alpha (SDF-1alpha), interleukin 8 (IL8), granulocyte chemotactic protein-2 (GCP-2), hepatocyte growth factor (HGF), keratinocyte growth factor (KGF), heparin-binding epidermal growth factor (HB-EGF), brain-derived neurotrophic factor (BDNF), tissue inhibitor of matrix metalloproteinase 1 (TIMP1), thrombopoietin (TPO), macrophage inflammatory protein 1alpha (MIPla), Rantes (regulated on activation, normal T cell expressed and secreted), thymus and activation-regulated chemokine (TARC), and Eotaxin. Cells which secrete more than five, six, seven or eight of the listed proteins are also useful and preferred. Cells which can secrete at least nine, ten, eleven or more of the factors are more preferred, as are cells which can secrete twelve thirteen, or fourteen, or even all of the proteins in the foregoing list.

While secretion of such factors is useful, PDCs can also be characterized by their lack of secretion of factors into the medium. Postpartum-derived cells that lack secretion of at least one, two, three, or four of fibroblast growth factor (FGF), vascular endothelial growth factor (VEGF), angiopoietin 2 (ANG2), platelet derived growth factor (PDGF-bb), transforming growth factor beta2 (TGFbeta2), macrophage inflammatory protein 1beta (MIP1b), 1309, and macrophage-derived chemokine (MDC), as detected by ELISA, are preferred for use. Cells that are characterized in their lack secretion of five, six, or seven of the foregoing proteins are more preferred. Cells which lack secretion of all of the factors listed above are also preferred.

Examples of placenta-derived cells of the invention were deposited with the American Type Culture Collection (ATCC, Manassas, Va.) and assigned ATCC Accession Numbers as follows: (1) strain designation PLA 071003 (P8) was deposited Jun. 15, 2004 and assigned Accession No. PTA-6074; (2) strain designation PLA 071003 (P11) was deposited June 15, 2004 and assigned Accession No. PTA-6075; and (3) strain designation PLA 071003 (P16) was deposited Jun. 16, 2004 and assigned Accession No. PTA-6079.

Examples of umbilical cord-derived cells of the invention were deposited with the American Type Culture Collection (ATCC, Manassas, Va.) on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

PDCs of the invention may be isolated. The invention provides compositions of PDCs, including populations of PDCs. In some embodiments, the population is heterogeneous. A heterogeneous cell population of the invention may comprise at least about 5%, 10%, 20%, 30%, 40%, 50%, 60%, 70%, 80%, 90%, or 95% PDCs of the invention. The heterogeneous cell populations of the invention may further comprise stem cells or progenitor cells. In some embodiments, the population is substantially homogeneous, i.e., comprises substantially only PPDCs (preferably at least about 96%, 97%, 98%, 99% or more PPDCs). The homogeneous cell population of the invention may comprise neonatal placenta-derived cells or maternal placenta-derived cells. Homogeneity of a cell population may be achieved by any method known in the art, for example, by cell sorting (e.g., flow cytometry), bead separation, or by clonal expansion.

The cells of the invention can be induced to differentiate to cells of mesodermal, ectodermal, or endodermal phenotype or lineage.

Culture of PDCs in a Chondrogenic Medium

PDCs may be induced to differentiate into a chondrogenic lineage by subjecting them to differentiation-inducing cell culture conditions. In some embodiments, PDCs may be induced to differentiate to a chondrogenic lineage by, for example, contacting PDCs with specific exogenous growth factors (e.g., in culture), such as, for example, one or more of GDF-5 or transforming growth factor beta3 (TGF-beta3), with or without ascorbate.

Preferred chondrogenic medium is supplemented with an antibiotic agent, amino acids including proline and glutamine, sodium pyruvate, dexamethasone, ascorbic acid, and insulin/tranferrin/selenium. Chondrogenic medium is preferably supplemented with sodium hydroxide and/or collagen. Most preferably, chondrogenic culture medium is supplemented with collagen. The cells may be cultured at high or low density. Cells are preferably cultured in the absence of serum.

Chondrogenic differentiation may be assessed, for example, by Safranin-O staining for glycosaminoglycan expression or hematoxylin/eosin staining.

Culture of PDCs in an Adipogenic Medium

PDCs may be induced to differentiate into an adipogenic lineage phenotype by subjecting them to differentiation-inducing cell culture conditions. In some embodiments, PDCs are cultured in a defined medium for inducing differentiation to an adipogenic lineage. Examples of adipogenic media include, but are not limited to, media containing one or more glucocorticoids (e.g., dexamethasone, indomethasone, hydrocortisone, cortisone), insulin, a compound which elevates intracellular levels of cAMP (e.g., dibutyryl-cAMP; 8-CPT-cAMP (8-(4)chlorophenylthio)-adenosine, 3',5' cyclic monophosphate); 8-bromo- cAMP; dioctanoyl-cAMP; forskolin) and/or a compound which inhibits degradation of cAMP (e.g., a phosphodiesterase inhibitor such as isobutylmethylxanthine (IBMX), methyl isobutylxanthine, theophylline, caffeine, indomethacin), and serum.

Adipogenesis may be assessed by Oil-Red-O staining to determine the presence of lipid droplet formation or by detecting the expression of PPAR gamma or leptin.

Culture of PDCs in an Osteogenic Medium

PDCs may be induced to differentiate into an osteogenic lineage phenotype by subjecting them to differentiation-inducing cell culture conditions. In some embodiments, PDCs are cultured in osteogenic medium such as, but not limited to, media (e.g., DMEM-low glucose) containing about $10^{-7}$ molar and about $10^{-9}$ molar dexamethasone in combination with about 10 micromolar to about 50 micromolar ascorbate phosphate salt (e.g., ascorbate-2- phosphate) and between about 10 nanomolar and about 10 millimolar beta-glycerophosphate. The medium preferably includes serum (e.g., bovine serum, horse serum). Osteogenic medium also may comprise one or more antibiotic/antimycotic agents. The osteogenic medium is preferably supplemented with transforming growth factor-beta (e.g., TGF-beta1) and/or bone morphogenic protein (e.g., BMP-2, BMP-4, or a combination thereof; most preferably BMP-4)

Cells may be analyzed for an osteogenic phenotype by any method known in the art, e.g., von Kossa staining or by detection of osteogenic markers such as osteocalcin, bone sialoprotein, or alkaline phosphatase.

Culture of PDCs in Neurogenic Medium

PDCs may be induced to differentiate into a neural lineage phenotype by subjecting them to differentiation-inducing cell culture conditions. This may be accomplished by one or more methods known in the art. For instance, as exemplified herein, PDCs may be cultured in a neurogenic medium such as a serum-free DMEMIF12 composition containing butylated hydroxanisole, potassium chloride, insulin, forskolin, valproic acid, and hydrocortisone.

Alternatively, PDCs may be plated on flasks coated with laminin in Neurobasal-A medium (Invitrogen, Carlsbad, Calif.) containing B27 (B27 supplement, Invitrogen), L-glutamine and Penicillin/Streptomycin, the combination of which is referred to herein as Neural Progenitor Expansion (NPE) media. NPE media may be further supplemented with bFGF and/or EGF.

Alternatively, PDCs may be induced to differentiate in vitro by (1) co-culturing the PDCs with neural progenitor cells, or (2) growing the PDCs in neural progenitor cell-conditioned medium.

Differentiation of the PDCs to a neurogenic lineage may be demonstrated by a bipolar cell morphology with extended processes. The induced cell populations may stain positive for the presence of nestin. Differentiated PDCs may be assessed by detection of nestin, TuJ1 (BIII tubulin), GFAP, tyrosine hydroxylase, O4, GABA, and myelin basic protein (MBP). In some embodiments, PDCs have the ability to form three-dimensional bodies characteristic of neural stem cell formation of neurospheres.

Assessment of Differentiation

PDCs may be induced to differentiate to an ectodermal, endodermal, or mesodermal lineage. Methods to characterize differentiated cells that develop from the PDCs of the invention, include, but are not limited to, histological, morphological, biochemical and immunohistochemical methods, or using cell surface markers, or genetically or molecularly, or by identifying factors secreted by the differentiated cell, and by the inductive qualities of the differentiated PDCs.

Methods of Using PDCs or Components or Products Thereof.

Genetic Engineering of PDCs

The cells of the invention can be engineered to express a therapeutic protein using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells are preferably transformed or transfected with DNA controlled by or in operative association with, one or more appropriate expression control elements such as promoter or enhancer sequences, transcription terminators, polyadenylation sites, among others, and a selectable marker.

Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines.

This method can be advantageously used to engineer cell lines which express the gene product.

Any promoter may be used to drive the expression of the inserted gene. For example, viral promoters include, but are not limited to, the CMV promoter/enhancer, SV40, papillomavirus, Epstein-Barr virus or elastin gene promoter. Preferably, the control elements used to control expression of the gene of interest should allow for the regulated expression of the gene so that the product is synthesized only when needed in vivo. If transient expression is desired, constitutive promoters are preferably used in a non-integrating and/or replication- defective vector. Alternatively, inducible promoters could be used to drive the expression of the inserted gene when necessary.

Inducible promoters include, but are not limited to, those associated with metallothionein and heat shock proteins.

Examples of transcriptional control regions that exhibit tissue specificity which have been described and could be used include but are not limited to: elastase I gene control region, which is active in pancreatic acinar cells (Swift et al., 1984, *Cell* 38:639; Ornitz et al., 1985, Cold Spring Harbor Symp. *Quant. Biol.* 50:399; MacDonald, 1987, *Hepatology* 7:42S-51S); insulin gene control region, which is active in pancreatic beta cells (Hanahan, 1985, *Nature* 315:115); myelin basic protein gene control region, which is active in oligodendrocyte cells in the brain (Readhead et al., 1987, *Cell* 48:703); myosin light chain-2 gene control region, which is active in skeletal muscle (Shani, 1985, *Nature*

314:283); and gonadotropic releasing hormone gene control region, which is active in the hypothalamus (Mason et al., 1986, *Science* 234:1372).

The cells of the invention may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a cell can be reduced or knocked out using a number of techniques including, for example, inhibition of expression by inactivating the gene completely (commonly termed "knockout") using the homologous recombination technique. Usually, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene or by deleting the entire gene. By using a construct with two regions of homology to the target gene that are far apart in the genome, the sequences intervening the two regions can be deleted (Mombaerts et al., 1991, *Proc. Nat. Acad. Sci. U.S.A.* 88:3084).

Antisense, DNAzymes, small interfering RNA, and ribozyme molecules which inhibit expression of the target gene can also be used in accordance with the invention to reduce the level of target gene activity. For example, antisense RNA molecules which inhibit the expression of major histocompatibility gene complexes (HLA) have been shown to be most versatile with respect to immune responses. Still further, triple helix molecules can be utilized in reducing the level of target gene activity.

These techniques are described in detail by L. G. Davis et al. (eds), 1994, BASIC METHODS IN MOLECULAR BIOLOGY, 2nd ed., Appleton & Lange, Norwalk, Conn., which is incorporated herein by reference.

Using any of the foregoing techniques, for example, the expression of IL-1 can be knocked out or knocked down in the cells of the invention to reduce the production of inflammatory mediators by the cells of the invention. Likewise, the expression of MHC class II molecules can be knocked out or knocked down in order to reduce the risk of rejection of the implanted tissue.

Once the cells of the invention have been genetically engineered, they may be directly implanted into the patient.

Alternatively, the genetically engineered cells may be used to produce new tissue in vitro, which is then implanted in the subject.

Secretion of Trophic Factors by PDCs

The secretion of growth factors by PDCs may provide trophic support for a second cell type in vitro or in vivo. PDCs may secrete, for example, interleukin 8 (IL8), tissue factor, hepatocyte growth factor (HGF), monocyte chemotactic protein 1 (MCP-1), keratinocyte growth factor (KGF), tissue inhibitor of matrix metalloproteinase 1 (TIMP1), thrombopoietin (TPO), heparin-binding epidermal growth factor (HB-EGF), stromal-derived factor 1alpha (SDF-1alpha), brain-derived neurotrophic factor (BDNF), interleukin-6 (IL-6), granulocyte chemotactic protein-2 (GCP-2), macrophage inflammatory protein 1alpha (MIPla), monocyte chemoattractant-1 (MCP-1), Rantes (regulated on activation, normal T cell expressed and secreted), thymus and activation-regulated chemokine (TARC), Eotaxin, NGF, NT-3, IL-7, IL-1, SCF, AMPS, or Cystatin-C in substantially homogeneous populations of cells, which can be augmented by a variety of techniques, including ex vivo cultivation of the cells in chemically defined medium.

In some aspects of the invention, a population of PDCs supports the survival, proliferation, growth, maintenance, maturation, differentiation, or increased activity of cells including stem cells, such as neural stem cells (NSC), hematopoietic stem cells (HPC, particularly CD34+stem cells), embryonic stem cells (ESC), and mixtures thereof. In other embodiments, the population supported by the PDCs is substantially homogeneous, substantially homogeneous, i.e., comprises substantially only PDCs (preferably at least about 96%, 97%, 98%, 99% or more PDCs).

Conditioned Medium of PDCs

Another embodiment of the invention features use of PDCs for production of conditioned medium, either from undifferentiated PDCs or from PDCs incubated under conditions that stimulate differentiation into a given lineage. Such conditioned media are contemplated for use in in vitro or ex vivo culture of cells, for example, stem or progenitor cells, or for use in vivo, for example, to support transplanted cells (e.g., homogeneous or heterogeneous populations of PDCs).

Co-Cultures of PDCs with Other Cell Types

PDCs have the ability to support survival, growth, and differentiation of other cell types in co-culture. Accordingly, in another embodiment, PDCs are co-cultured in vitro to provide trophic support to other cells. For co-culture, it may be desirable for the PDCs and the desired other cells to be co-cultured under conditions in which the two cell types are in contact. This can be achieved, for example, by seeding the cells as a heterogeneous population of cells in culture medium or onto a suitable culture substrate. Alternatively, the PDCs can first be grown to confluence and employed as a substrate for the second desired cell type in culture. In this latter embodiment, the cells may further be physically separated, e.g., by a membrane or similar device, such that the other cell type may be removed and used separately following the co-culture period. Use of PDCs in co-culture to promote expansion and differentiation of other cell types may find applicability in research and in clinical/therapeutic areas. For instance, PDC co- culture may be utilized to facilitate growth and differentiation of cells of a given phenotype in culture, for basic research purposes or for use in drug screening assays, for example. PDC co- culture may also be utilized for ex vivo expansion of cells of a given phenotype for later administration for therapeutic purposes. For example, cells may be harvested from an individual, expanded ex vivo in co-culture with PDCs, then returned to that individual (autologous transfer) or another individual (syngeneic or allogeneic transfer). In these embodiments, it will be appreciated that, following ex vivo expansion, the mixed population of cells comprising the PDCs could be administered to a patient in need of treatment. Alternatively, in situations where autologous transfer is appropriate or desirable, the co-cultured cell populations may be physically separated in culture, enabling removal of the autologous cells for administration to the patient.

Cell Therapy

As demonstrated herein, PDCs have been shown to be effectively transplanted into the body and to supply lost function in animal models accepted for predictability of efficacy in humans. These results support a preferred embodiment of the invention, wherein PDCs are used in cell therapy for treating a condition, injury, or disease. For example, PDCs of the invention may be used to treat patients requiring the repair or replacement of a tissue or organ resulting from disease or trauma or failure of the tissue to develop normally, or to provide a cosmetic function, such as to augment features of the body. Once transplanted into a target location in the body, PDCs may themselves differentiate into one or more phenotypes, or they may provide trophic support for other cell types in vivo, or they may exert a beneficial effect in both of those fashions, among others.

PDCs may be administered alone (e.g., as substantially homogeneous populations) or as admixtures with other cells. PDCs may be administered as formulated in a pharmaceutical preparation with a matrix, or with conventional pharmaceutically acceptable carriers. Where PDCs are administered with other cells, they may be administered simultaneously or sequentially with the other cells (either before or after the other cells). Cells that may be administered in conjunction with PDCs include, but are not limited to, other multipotent or pluripotent cells. The cells of different types may be admixed with the PDCs immediately or shortly prior to administration, or they may be co-cultured together for a period of time prior to administration.

PDCs may be administered with other beneficial drugs or biological molecules (growth factors, trophic factors). When PDCs are administered with other agents, they may be administered together in a single pharmaceutical composition, or in separate pharmaceutical compositions, simultaneously or sequentially with the other bioactive factors (either before or after administration of the other agents). Examples of bioactive factors include anti-apoptotic agents (e.g., EPO, EPO mimetibody, TPO, IGF-I and IGF-II, HGF, caspase inhibitors); anti- inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti- lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine). Drugs which may be co-administered include local anesthetics. As another example, the cells may be co-administered with scar inhibitory factor as described in U.S. Pat. No. 5,827,735, incorporated herein by reference.

In one embodiment, PDCs are administered as undifferentiated cells, i.e., as cultured in Growth Medium. Alternatively, PDCs may be administered following exposure in culture to conditions that stimulate differentiation toward a desired phenotype.

The cells of the invention may be surgically implanted, injected, delivered (e.g., by way of a catheter or syringe), or otherwise administered directly or indirectly to the site in need of repair or augmentation. Routes of administration of the cells of the invention or compositions thereof include, but are not limited to, oral, nasal, intraarterial, parenteral, intravenous, ophthalmic, intramuscular, subcutaneous, intraperitoneal, intracerebral, intraventricular, intracerebroventricular, intrathecal, intracisternal, intraspinal and/or perispinal routes of administration by delivery via intracranial or intravertebral needles and/or catheters with or without pump devices.

When cells are administered in semi-solid or solid devices, surgical implantation into a precise location in the body is typically a suitable means of administration. Liquid or fluid pharmaceutical compositions, however, may be administered to a more general location (e.g., throughout a diffusely affected area, for example), from which they migrate to a particular location, e.g., by responding to chemical signals.

Other embodiments encompass methods of treatment by administering pharmaceutical compositions comprising PDC cellular components (e.g., cell lysates or components thereof) or products (e.g., extracellular matrix, trophic and other biological factors produced naturally by PDCs or through genetic modification, conditioned medium from PDC culture). Again, these methods may further comprise administering bioactive factors, such as anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti- thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N- acetylcysteine), local anesthetics, and scar inhibitory factor as described in U.S. Pat. No. 5,827,735, incorporated herein by reference.

Dosage forms and regimes for administering PDCs or any of the other pharmaceutical compositions described herein are developed in accordance with good medical practice, taking into account the condition of the individual patient, e.g., nature and extent of the condition being treated, age, sex, body weight and general medical condition, and other factors known to medical practitioners. Thus, the effective amount of a pharmaceutical composition to be administered to a patient is determined by these considerations as known in the art.

In some embodiments of the invention, it may not be necessary or desirable to immunosuppress a patient prior to initiation of cell therapy with PDCs. In addition, PDCs have been shown not to stimulate allogeneic PBMCs (for example, allogeneic lymphocytes, e.g., naïve CD4+ T cells) in a mixed lymphocyte reaction. Accordingly, transplantation with allogeneic, or even xenogeneic, PDCs may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. PDCs may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, PDCs may be genetically modified to reduce their immunogenicity.

Survival of transplanted PDCs in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done post mortem by removing the target tissue, and examining it visually or through a microscope. Alternatively, cells can be treated with stains that are specific for cells of a specific lineage. Transplanted cells can also be identified by prior incorporation of tracer dyes such as rhodamine- or fluorescein-labeled microspheres, fast blue, bisbenzamide, ferric microparticles, or genetically introduced reporter gene products, such as beta-galactosidase or beta-glucuronidase.

Functional integration of transplanted PDCs into a subject can be assessed by examining restoration of the function that was damaged or diseased or augmentation of function.

Compositions and Pharmaceutical Compositions

Compositions of PDCs and related products (e.g., extracellular matrix, lysate, cell lysate, conditioned medium), including for example pharmaceutical compositions, are included within the scope of the invention. Compositions of the invention may include one or more bioactive factors, for example but not limited to a growth factor, a differentiation-inducing factor, a cell survival factor such as caspase inhibitor, an anti-inflammatory agent such as p38 kinase inhibitor, or an angiogenic factor such as VEGF or bFGF. Some examples of bioactive factors include PDGF-bb, EGF, FGF, IGF, and LIF. In some embodiments, undifferentiated or differentiation-induced PDCs are cultured in contact with the bioactive factor. In some embodiments, undifferentiated PDCs remain undifferentiated upon contact with the bioactive factor. In other embodiments, the bioactive factor induces differentiation of the PDCs.

Pharmaceutical compositions of the invention may comprise homogeneous or heterogeneous populations of differentiated and/or undifferentiated PDCs, cultures thereof, cell lysates thereof, extracellular matrix produced thereby, or conditioned medium derived therefrom in a pharmaceutically acceptable carrier.

Pharmaceutically acceptable carriers for the cells of the invention include organic or inorganic carrier substances which do not deleteriously react with the cells of the invention or compositions or components thereof. To the extent they are biocompatible, suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences (17$^{th}$ Ed., Mack Pub. Co., Easton, Pa.) and WO 96/05309, each of which are incorporated by reference herein.

The dosage (e.g., number of cells to be administered) and frequency of administration will depend upon a number of factors, including but not limited to, the nature of the condition to be treated, the extent of the symptoms of the condition, characteristics of the patient (e.g., age, size, gender, health).

Use of PDCs for Transplantation

The treatment methods of the subject invention involves the implantation of PDCs into individuals in need thereof. The cells of the present invention may be delivered to the site of therapeutic need or "home" to the site.

The cells of the present invention may differentiate in vivo or provide trophic support to endogenous cells. The appropriate cell implantation dosage in humans can be determined from existing information relating to, e.g., the activity of the cells. From in vitro culture and in vivo animal experiments, the amount of factors produced can be quantitated. This information is also useful in calculating an appropriate dosage of implanted material. Additionally, the patient can be monitored to determine if additional implantation can be made or implanted material reduced accordingly.

To enhance vascularization and survival of the transplanted cells, angiogenic factors such as VEGF, PDGF or bFGF can be added either alone or in combination with endothelial cells or their precursors including CD34+, CD34+/CD117+cells.

One or more other components may be added to transplanted cells, including selected extracellular matrix components, such as one or more types of collagen known in the art, and/or growth factors, platelet-rich plasma, and drugs. Alternatively, the cells of the invention may be genetically engineered to express and produce growth factors. Bioactive factors which may be usefully incorporated into the cell formulation include anti-apoptotic agents (e.g., EPO, EPO mimetibody, TPO, IGF-I and IGF-II, HGF, caspase inhibitors); anti- inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti- lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics. As another example, the cells may be co-administered with scar inhibitory factor as described in U.S. Pat. No. 5,827,735, incorporated herein by reference.

Formulation of PDCs for Transplantation

In a non-limiting embodiment, a formulation comprising the cells of the invention is prepared for injection directly to the site where the production of new tissue is desired. For example, and not by way of limitation, the cells of the invention may be suspended in a hydrogel solution for injection. Examples of suitable hydrogels for use in the invention include self-assembling peptides, such as RAD16. Alternatively, the hydrogel solution containing the cells may be allowed to harden, for instance in a mold, to form a matrix having cells dispersed therein prior to implantation. Or, once the matrix has hardened, the cell formations may be cultured so that the cells are mitotically expanded prior to implantation. The hydrogel is an organic polymer (natural or synthetic) which is cross-linked via covalent, ionic, or hydrogen bonds to create a three-dimensional open-lattice structure which entraps water molecules to form a gel. Examples of materials which can be used to form a hydrogel include polysaccharides such as alginate and salts thereof, peptides, polyphosphazines, and polyacrylates, which are crosslinked ionically, or block polymers such as polyethylene oxide- polypropylene glycol block copolymers which are crosslinked by temperature or pH, respectively. In some embodiments, the support for the PDCs of the invention is biodegradable.

In some embodiments of the invention, the formulation comprises an in situ polymerizable gel, as described, for example, in U.S. Patent Application Publication 2002/0022676; Anseth et al., J. Control Release, 78(1-3):199-209 (2002); Wang et al., Biomaterials, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazene (PCPP) can be synthesized, which is cross-linked with dissolved multivalent cations in aqueous media at room temperature or below to form hydrogel matrices.

Biodegradable polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl.

Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock, et al., *Macromolecule* 10:824 (1977). Methods of synthesis of the hydrogel materials, as well as methods for preparing such hydrogels, are known in the art.

Other components may also be included in the formulation, including but not limited to any of the following: (1) buffers to provide appropriate pH and isotonicity; (2) lubricants; (3) viscous materials to retain the cells at or near the site of administration, including, for example, alginates, agars and plant gums; and (4) other cell types that may produce a desired effect at the site of administration, such as, for example, enhancement or modification of the formation of tissue or its physicochemical characteristics, or is support for the viability of the cells, or inhibition of inflammation or rejection. The cells may be covered by an appropriate wound covering to prevent cells from leaving the site. Such wound coverings are known as those of skill in the art.

Transplantation of PDCs Using Scaffolds

The cells of the invention or co-cultures thereof may be seeded onto a three-dimensional framework or scaffold and implanted in vivo, where the seeded cells will proliferate on the surface of the framework and form a replacement tissue in vivo in cooperation with the cells of the subject. Such a framework can be implanted in combination with any one or more growth factors, cells, drugs or other components described above that stimulate tissue formation or otherwise enhance or improve the practice of the invention.

The cells of the invention can be used to produce new tissue in vitro, which can then be implanted, transplanted or otherwise inserted into a site requiring tissue repair, replacement or augmentation in a subject.

In a non-limiting embodiment, the cells of the invention are used to produce a three-dimensional tissue construct in vitro, which is then implanted in vivo. As an example of the production of three-dimensional tissue constructs, see U.S. Pat. No. 4,963,489, which is incorporated herein by reference. For example, the cells of the invention may be inoculated or "seeded" onto a three-dimensional framework or scaffold, and proliferated or grown in vitro to form a living tissue that can be implanted in vivo.

The cells of the invention can be grown freely in a culture vessel to sub-confluency or confluency, lifted from the culture and inoculated onto a three-dimensional framework. Inoculation of the three-dimensional framework with a high concentration of cells, e.g., approximately $10^5$ to $10^8$ cells per milliliter, will result in the establishment of the three-dimensional support in relatively shorter periods of time.

Examples of scaffolds which may be used in the present invention include nonwoven mats, porous foams, or self assembling peptides. Nonwoven mats may, for example, be formed using fibers comprised of a synthetic absorbable copolymer of glycolic and lactic acids (PGA/PLA), sold under the tradename VICRYL (Ethicon, Inc., Somerville, N.J.), Foams, composed of, for example, poly(epsilon-caprolactone)/poly(glycolic acid) (PCL/PGA) copolymer, formed by processes such as freeze-drying, or lyophilized, as discussed in U.S. Pat. No. 6,355,699, are also possible scaffolds. Hydrogels such as self-assembling peptides (e.g., RAD16) may also be used. These materials are frequently used as supports for growth of tissue.

The three-dimensional framework also may be made of ceramic materials including, but not limited to: mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS (University of Florida, Gainesville, Fla.), and mixtures thereof. There are a number of suitable porous biocompatible ceramic materials currently available on the commercial market such as SURGIBON (Unilab Surgibone, Inc., Canada), ENDOBON (Merck Biomaterial France, France), CEROS (Mathys, A. G., Bettlach, Switzerland), and INTERPORE (Interpore, Irvine, Calif., United States), and mineralized collagen bone grafting products such as HEALOS (Orquest, Inc., Mountain View, Calif.) and VITOSS, RHAKOSS, and CORTOSS (Orthovita, Malvern, Pa.). The framework may be a mixture, blend or composite of natural and/or synthetic materials.

According to a preferred embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling.

In another preferred embodiment the cells of the invention are seeded onto foam scaffolds that may be composite structures. In addition, the three-dimensional framework may be molded into a useful shape, such as that of the external portion of the ear, or other specific structure in the body to be repaired, replaced or augmented.

In some embodiments, the framework is treated prior to inoculation of the cells of the invention in order to enhance cell attachment. For example, prior to inoculation with the cells of the invention, nylon matrices could be treated with 0.1 molar acetic acid and incubated in polylysine, PBS, and/or collagen to coat the nylon. Polystyrene could be similarly treated using sulfuric acid.

The external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In some embodiments, the scaffold is comprised of or is treated with materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN (The Polymer Technology Group, Inc., Berkeley, Calif.). These materials can be further treated to render the scaffold non-thrombogenic. Such treatments include anti-thrombotic agents such as heparin, and treatments which alter the surface charge of the material such as plasma coating.

In some aspects of the invention, it is important to re-create in culture the cellular microenvironment found in vivo, such that the extent to which the cells of the invention are grown prior to implantation in vivo or use in vitro may vary. In addition, growth factors may be added to the culture medium prior to, during, or subsequent to inoculation of the cells to trigger differentiation and tissue formation by the PDCs.

The three-dimensional framework may be modified so that the growth of cells and the production of tissue thereon is enhanced, or so that the risk of rejection of the implant is reduced. Thus, one or more biologically active compounds, including, but not limited to, anti- inflammatories, immunosuppressants or growth factors, may be added to the framework.

Therapeutic Uses for Extracellular Matrix and Cell Lysates Derived from PDCs

As an alternative to implanting the cells of the invention, or living tissue produced therefrom, a subject in need of tissue repair, replacement, or augmentation may benefit from the administration of a component or product of PDCs, such as the extracellular matrix (ECM) or cell lysate produced by those cells.

In some embodiments, after the cells of the invention have been cultured in vitro, such as, for example, by using a three-dimensional scaffold system described herein, such that a desired amount of ECM has been secreted onto the framework. Once ECM is secreted onto the framework, the cells may be removed. The ECM may be processed for further use, for example, as an injectable preparation.

In some embodiments, the cells are killed and cellular debris (e.g., cellular membranes) is removed from the framework. This process may be carried out in a number of different ways. For example, the living tissue can be flash-frozen in liquid nitrogen without a cryopreservative, or the tissue can be immersed in sterile distilled water so that the cells burst in response to osmotic pressure. Once the cells have been killed, the cellular membranes may be disrupted and cellular debris removed by treatment with a mild detergent rinse, such as EDTA, CHAPS or a zwitterionic detergent. An advantage to using a mild detergent rinse is that it solubilizes membrane-bound proteins, which are often highly antigenic.

Alternatively, the tissue can be enzymatically digested and/or extracted with reagents that break down cellular membranes. Example of such enzymes include, but are not limited to, hyaluronidase, dispase, proteases, and nucleases (for example, deoxyribonuclease and ribonuclease). Examples of detergents include non-ionic detergents such as, for example, alkylaryl polyether alcohol (TRITON® X-100), octylphenoxy polyethoxy-ethanol (Rohm and Haas Philadelphia, Pa.), BRIJ-35, a polyethoxyethanol lauryl ether (Atlas Chemical Co., San Diego, Calif.), polysorbate 20 (TWEEN 20®), a polyethoxyethanol sorbitan monolaureate (Rohm and Haas), polyethylene lauryl ether (Rohm and Haas); and ionic detergents such as, for example, sodium dodecyl sulphate, sulfated higher aliphatic alcohols, sulfonated alkanes and sulfonated alkylarenes containing 7 to 22 carbon atoms in a branched or unbranched chain.

The scaffold comprising the ECM may be used therapeutically as described above. Alternatively, ECM may be collected from the scaffold. Collection of ECM can be accomplished in a variety of ways, depending, for example, on whether the framework is biodegradable or non-biodegradable. For example, if the framework is non-biodegradable, the ECM can be removed by subjecting the framework to sonication, high pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in toto for subsequent injection. Alternatively, the ECM can be removed from the biodegradable framework by any of the methods described above for collection of ECM from a non-biodegradable framework. All collection processes are preferably designed so as not to denature the ECM produced by the cells of the invention.

Once the ECM has been collected, it may be processed further. The ECM can be homogenized to fine particles using techniques well known in the art such as, for example, by sonication, so that they can pass through a surgical needle. ECM components can be crosslinked, if desired, by gamma irradiation. Preferably, the ECM can be irradiated between 0.25 to 2 mega rads to sterilize and crosslink the ECM. Chemical crosslinking using agents that are toxic, such as glutaraldehyde, is possible but not generally preferred.

Cell lysates prepared from the populations of the postpartum-derived cells also have many utilities. In one embodiment, whole cell lysates are prepared, e.g., by disrupting cells without subsequent separation of cell fractions. In another embodiment, a cell membrane fraction is separated from a soluble fraction of the cells by routine methods known in the art, e.g., centrifugation, filtration, or similar methods. Use of soluble cell fractions in vivo allows the beneficial intracellular milieu to be used in a patient without triggering rejection or an adverse response. Methods of lysing cells are well-known in the art and include various means of mechanical disruption, enzymatic disruption, or chemical disruption, or combinations thereof. Such cell lysates may be prepared from cells directly in their growth medium and thus containing secreted growth factors and the like, or may be prepared from cells washed free of medium in, for example, PBS or other solution. Washed cells may be resuspended at concentrations greater than the original population density if preferred. Cell lysates prepared from populations of postpartum-derived cells may be used as is, further concentrated, by for example, ultrafiltration or lyophilization, or even dried, partially purified, combined with pharmaceutically acceptable carriers or diluents as are known in the art, or combined with other compounds such as biologicals, for example pharmaceutically useful protein compositions. Cell lysates may be used in vitro or in vivo, alone or for example, with cells. The cell lysates, if introduced in vivo, may be introduced locally at a site of treatment, or remotely to provide, for example needed cellular growth factors to a patient.

The amounts and/or ratios of proteins may be adjusted by mixing the ECM or cell lysate produced by the cells of the invention with ECM or cell lysate of one or more other cell types. In addition, biologically active substances such as proteins, growth factors and/or drugs, can be incorporated into the ECM or cell lysate preparation. Exemplary biologically active substances include anti-inflammatory agents and growth factors which promote healing and tissue repair. Cells may be co-administered with the ECM or cell lysates of the invention. ECM or cell lysate of PDCs may be formulated for administration as described above for PDCs.

Use of PDCs for In Vitro Screening of Drug Efficacy or Toxicity

The cells and tissues of the invention may be used in vitro to screen a wide variety of compounds for effectiveness and cytotoxicity of pharmaceutical agents, growth/regulatory factors, anti-inflammatory agents. To this end, the cells of the invention, or tissue cultures described above, are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the number of living cells in vitro, e.g., by total cell counts, and differential cell counts. This may be accomplished using standard cytological and/or histological techniques, including the use of immunocytochemical techniques employing antibodies that define type-specific cellular antigens. The effect of various drugs on the cells of the invention either in suspension culture or in the three-dimensional system described above may be assessed.

The cells and tissues of the invention may be used as model systems for the study of physiological or pathological conditions. The cells and tissues of the invention may also be used to study the mechanism of action of cytokines, growth factors and inflammatory mediators, e.g., IL-1, TNF and prostaglandins. In addition, cytotoxic and/or pharmaceutical agents can be screened for those that are most efficacious for a particular patient. Agents that prove to be efficacious in vitro could then be used to treat the patient therapeutically.

Use of PDCs to Produce Biological Molecules

In a further embodiment, the cells of the invention can be cultured in vitro to produce biological products in high yield. For example, such cells, which either naturally produce a particular biological product of interest (e.g., a growth factor, regulatory factor, or peptide hormone), or have been genetically engineered to produce a biological product, could be clonally expanded using, for example, the three-dimensional culture system described above. If the cells excrete the biological product into the nutrient medium, the product can be readily isolated from the spent or conditioned medium using standard separation techniques, e.g., such as differential protein precipitation, ion-exchange chromatography, gel filtration chromatography, electrophoresis, and high performance liquid chromatography. A "bioreactor" may be used to take advantage of the flow method for feeding, for example, a three-dimensional culture in vitro.

Essentially, as fresh media is passed through the three-dimensional culture, the biological product is washed out of the culture and may then be isolated from the outflow, as above.

Alternatively, a biological product of interest may remain within the cell and, thus, its collection may require that the cells are lysed. The biological product may then be purified using any one or more of the above-listed techniques.

Kits

The PDCs and components and products thereof can conveniently be employed as part of a kit, for example, for culture or implantation. Accordingly, the invention provides a kit including the PDCs and additional components, such as a matrix (e.g., a scaffold), hydrating agents (e.g., physiologically-compatible saline solutions, prepared cell culture media), cell culture substrates (e.g., culture dishes, plates, vials, etc.), cell culture media (whether in liquid or powdered form), antibiotic compounds, hormones, and the like. While the kit can include any such components, preferably it includes all ingredients necessary for its intended use. If desired, the kit also can include cells (typically cryopreserved), which can be seeded into the lattice as described herein.

In another aspect, the invention provides kits that utilize the PDCs, PDC populations, components and products of PDCs in various methods for augmentation, regeneration, and repair as described above. In some embodiments, the kits may include one or more cell populations, including at least PDCs and a pharmaceutically acceptable carrier (liquid, semi-solid or solid). The kits also optionally may include a means of administering the cells, for example by injection. The kits further may include instructions for use of the cells. Kits prepared for field hospital use, such as for military use, may include full-procedure supplies including tissue scaffolds, surgical sutures, and the like, where the cells are to be used in conjunction with repair of acute injuries. Kits for assays and in vitro methods as described herein may contain one or more of (1) PDCs or components or products of PDCs, (2) reagents for practicing the in vitro method, (3) other cells or cell populations, as appropriate, and (4) instructions for conducting the in vitro method.

Cryopreservation and Banking PDCs

PDCs of the invention can be cryopreserved and maintained or stored in a "cell bank". Cryopreservation of cells of the invention may be carried out according to known methods. For example, but not by way of limitation, cells may be suspended in a "freeze medium" such as, for example, culture medium further comprising 0 to 95 percent FBS and 0 to 10 percent dimethylsulfoxide (DMSO), with or without 5 to 10 percent glycerol, at a density, for example, of about 0.5 to $10 \times 10^6$ cells per milliliter. The cryopreservation medium may comprise cryopreservation agents including but not limited to methylcellulose. The cells are dispensed into glass or plastic ampoules that are then sealed and transferred to the freezing chamber of a controlled rate freezer. The optimal rate of freezing may be determined empirically. A programmable rate freezer for example, can give a change in temperature of −1 to −10° C. per minute. The preferred cryopreservation temperature is about −80° C. to about −180° C., more preferably is about −90° C. to about −160° C., and most preferably is about −125 to about −140° C. Cryopreserved cells preferably are transferred to liquid nitrogen prior to thawing for use. In some embodiments, for example, once the ampoules have reached about −90° C., they are transferred to a liquid nitrogen storage area. Cryopreserved cells can be stored for a period of years.

The cryopreserved cells of the invention constitute a bank of cells, portions of which can be "withdrawn" by thawing and used as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as DMEM conditioned with 10 percent FBS.

In yet another aspect, the invention also provides for banking of tissues, cells, cellular components and cell populations of the invention. As discussed above, the cells are readily cryopreserved. The invention therefore provides methods of cryopreserving the cells in a bank, wherein the cells are stored frozen and associated with a complete characterization of the cells based on immunological, biochemical and genetic properties of the cells. The cells so frozen can be used for autologous, syngeneic, or allogeneic therapy, depending on the requirements of the procedure and the needs of the patient. Preferably, the information on each cryopreserved sample is stored in a computer, which is searchable based on the requirements of the surgeon, procedure and patient with suitable matches being made based on the characterization of the cells or populations. Preferably, the cells of the invention are grown and expanded to the desired quantity of cells and therapeutic cell compositions are prepared either separately or as co-cultures, in the presence or absence of a matrix or support. While for some applications it may be preferable to use cells freshly prepared, the remainder can be cryopreserved and banked by freezing the cells and entering the information in the computer to associate the computer entry with the samples. Even where it is not necessary to match a source or donor with a recipient of such cells, for immunological purposes, the bank system makes it easy to match, for example, desirable biochemical or genetic properties of the banked cells to the therapeutic needs. Upon matching of the desired properties with a banked sample, the sample is retrieved, and readied for therapeutic use. Cell lysates or components prepared as described herein may also be preserved (e.g., cryopreserved, lyophilized) and banked in accordance with the present invention.

The following examples describe several aspects of embodiments of the invention in greater detail. These examples are provided to further illustrate, not to limit, aspects of the invention described herein.

EXAMPLES

Example 1

Derivation of Cells from Postpartum Placental Tissue

Postpartum placentas were obtained upon birth of either a full term or pre-term pregnancy. Cells were harvested from five separate donors of placental tissue. Different methods of cell isolation were tested for their ability to yield cells with: 1) the potential to differentiate into cells with different phenotypes, or 2) the potential to provide critical trophic factors useful for other cells and tissues.

Methods & Materials

Isolation of cells from placenta. Placental tissue was obtained from National Disease Resarch Interchange (NDRI) (Philadelphia, Pa.). The tissues were obtained from a pregnancy at the time of a normal surgical delivery. Placental cells were isolated aseptically in a laminar flow hood. To remove blood and debris, the tissue was washed in phosphate buffered saline (PBS; Invitrogen, Carlsbad, Calif.) in the presence of 100 Units/milliliter penicillin, 100 micrograms/milliliter streptomycin, and 0.25 micrograms/milliliter amphotericin (Invitrogen Carlsbad, Calif.). The tissues were then mechanically dissociated in 150 cm² tissue culture plates in the presence of 50 milliliters of medium (DMEM-Low glucose or DMEM-High glucose; Invitrogen), until the tissue was minced into a fine pulp. The chopped tissues were transferred to 50 milliliter conical tubes (approximately 5 grams of tissue per tube).

The tissue was then digested in either DMEM-Low glucose medium or DMEM-High glucose medium, each containing 100 Units/milliliter penicillin, 100 micrograms/milliliter streptomycin, and 0.25 micrograms/milliliter amphotericin and digestion enzymes. In some experiments an enzyme mixture of collagenase and dispase was used ("C:D;" collagenase (Sigma, St Louis, Mo.), 500 Units/milliliter; and dispase (Invitrogen), 50 Units/milliliter in DMEM-Low glucose medium). In other experiments a mixture of collagenase, dispase and hyaluronidase ("C:D:H") was used (collagenase, 500 Units/milliliter; dispase, 50 Units/milliliter; and hyaluronidase (Sigma), 5 Units/milliliter, in DMEM-Low glucose). The conical tubes containing the tissue, medium and digestion enzymes were incubated at 37° C. in an orbital shaker (Environ, Brooklyn, N.Y.) at 225 rpm for 2 hours.

After digestion, the tissues were centrifuged at 150×g for 5 minutes, and the supernatant was aspirated. The pellet was resuspended in 20 milliliter of Growth medium (DMEM: Low glucose (Invitrogen), 15 percent (v/v) fetal bovine serum (FBS; defined bovine serum; Lot#AND18475; Hyclone, Logan, Utah), 0.001% (v/v) 2-mercaptoethanol (Sigma), 100 Units/milliliter penicillin, 100 micrograms/milliliter streptomycin, 0.25 micrograms/milliliter amphotericin B; Invitrogen, Carlsbad, Calif.)). The cell suspension was filtered through a 70-micrometer nylon cell strainer (BD Biosciences). An additional 5 milliliters rinse comprising Growth medium was passed through the strainer. The cell suspension was then passed through a 40-micrometer nylon cell strainer (BD Biosciences) and chased with a rinse of an additional 5 milliliters of Growth medium.

The filtrate was resuspended in Growth medium (total volume 50 milliliters) and centrifuged at 150×g for 5 minutes. The supernatant was aspirated and the cells were resuspended in 50 milliliters of fresh growth medium. This process (i.e., resuspension, centrifugation, and aspiration) was repeated twice more.

After the final centrifugation, supernatant was aspirated and the cell pellet was resuspended in 5 milliliters of fresh growth medium. The number of viable cells was determined using Trypan Blue staining. Cells were then cultured under standard conditions.

The cells isolated from placenta were seeded at 5,000 cells/cm² onto gelatin- coated T-75 cm² flasks (Corning Inc., Corning, N.Y.) in Growth medium (DMEM-Low glucose (Invitrogen), 15 percent (v/v) defined bovine serum (Hyclone, Logan, Utah; Lot#AND18475), 0.001 percent (v/v) 2-mercaptoethanol (Sigma), 100 Units/milliliter penicillin, 100 micrograms/milliliter streptomycin, and 0.25 micrograms/milliliter amphotericin (Invitrogen)). After about 2-4 days, spent medium was aspirated from the flasks. Cells were washed with PBS three times to remove debris and blood-derived cells. Cells were then replenished with Growth medium and allowed to grow to confluence (about 10 days from passage 0 to passage 1). On subsequent passages (from passage 1 to 2, etc.), cells reached sub-confluence (75-85 percent confluence) in 4-5 days. For these subsequent passages, cells were seeded at 5,000 cells/cm². Cells were grown in a humidified incubator with 5 percent carbon dioxide and 20 percent oxygen, at 37° C.

Isolation of populations of maternal-derived and neonatal-derived cells from placenta. The cell isolation protocol was performed aseptically in a laminar flow hood. The placental tissue was washed in phosphate buffered saline (PBS; Invitrogen, Carlsbad, Calif.) in the presence of antimycotic and antibiotic (100 Units/milliliter penicillin, 100 microgram/milliliter streptomycin, 0.25 microgram/milliliter amphotericin B; Invitrogen) to remove blood and debris. The placental tissue was then dissected into three sections: top-line (neonatal side or aspect), mid-line (mixed cell isolation neonatal and maternal, or villous region), and bottom line (maternal side or aspect).

The separated sections were individually washed several times in PBS with antibiotic/antimycotic to further remove blood and debris. Each section was then mechanically dissociated in 150 cm² tissue culture plates in the presence of 50 milliliters of DMEM-Low glucose (Invitrogen) to a fine pulp. The pulp was transferred to 50 milliliter conical tubes. Each tube contained approximately 5 grams of tissue. The tissue was digested in either DMEM-Low glucose or DMEM-High glucose medium containing 100 Units/milliliter penicillin, 100 micrograms/milliliter streptomycin, and 0.25 micrograms/milliliter amphotericin and digestion enzymes. In some experiments an enzyme mixture of collagenase and dispase ("C:D") was used containing collagenase (Sigma, St Louis, Mo.) at 500 Units/milliliter and dispase (Invitrogen) at 50 Units/milliliter in DMEM-Low glucose medium. In other experiments a mixture of collagenase, dispase, and hyaluronidase ("C:D:H") was used (collagenase, 500 Units/milliliter; dispase, 50 Units/milliliter; and hyaluronidase (Sigma), 5 Units/milliliter in DMEM-Low glucose). The conical tubes containing the tissue, medium, and digestion enzymes were incubated for 2 hours at 37° C. in an orbital shaker (Environ, Brooklyn, N.Y.) at 225 rpm.

After digestion, the tissues were centrifuged at 150×g for 5 minutes, and the resultant supernatant was aspirated off. The pellet was resuspended in 20 milliliters of Growth medium (DMEM-Low glucose (Invitrogen), 15% (v/v) fetal bovine serum (FBS; defined bovine serum; Lot#AND18475; Hyclone, Logan, Utah), 0.001% (v/v) 2-mercaptoethanol (Sigma, St. Louis, Mo.), 100 Units/milliliter penicillin, 100 microgram/milliliter streptomycin, 0.25 microgram/milliliter amphotericin B; Invitrogen)). The cell suspension was filtered through a 70 micrometer nylon cell strainer (BD Biosciences), chased by a rinse with an additional 5 milliliters of Growth medium. The total cell suspension was passed through a 40 micrometer nylon cell strainer (BD Biosciences) followed with an additional 5 milliliters of Growth medium as a rinse.

The filtrate was resuspended in Growth medium (total volume 50 milliliters) and centrifuged at 150×g for 5 minutes. The supernatant was aspirated, and the cell pellet was resuspended in 50 milliliters of fresh Growth medium. This process (i.e., resuspension, centrifugation, and aspiration) was repeated twice more.

After the final centrifugation, supernatant was aspirated, and the cell pellet was resuspended in 5 milliliters of fresh Growth medium. A cell count was determined using the Trypan Blue Exclusion test. Cells were then cultured at standard conditions.

Isolation of PDCs using different growth conditions. Placenta-derived cells were digested in growth medium with or without 0.001% (v/v) 2-mercaptoethanol (Sigma, St. Louis, Mo.), using the enzyme combination of C:D:H, according to the procedures provided above. Placenta-derived cells so isolated were seeded under conditions set forth in Table 1-1 and grown in the presence of penicillin/ streptomycin. Cells were passaged up to four times after seeding and cryopreserved. The cryopreserved cells were banked.

TABLE 1-1

Isolation and culture expansion of placental cells under varying conditions:

| Condition | Medium | FBS | BME | Gelatin | $O_2$ | Growth Factors |
|---|---|---|---|---|---|---|
| 1 | DMEM-Lg | 15% | Y | Y | 20% | N |
| 2 | DMEM-Lg | 15% | Y | Y | 5% | N |
| 3 | DMEM-Lg | 15% | Y | N | 20% | N |
| 4 | DMEM-Lg | 15% | Y | N | 5% | N |
| 5 | DMEM-Lg | 2% | Y | N (Laminin) | 20% | EGF/FGF (20 ng/ml) |
| 6 | DMEM-Lg | 2% | Y | N (Laminin) | 5% | EGF/FGF (20 ng/ml) |
| 7 | DMEM-Lg | 2% | Y | N (Fibronectin) | 20% | PDGF/VEGF |
| 8 | DMEM-Lg | 2% | Y | N (Fibronectin) | 5% | PDGF/VEGF |
| 9 | DMEM-Lg | 15% | N | Y | 20% | N |
| 10 | DMEM-Lg | 15% | N | Y | 5% | N |
| 11 | DMEM-Lg | 15% | N | N | 20% | N |
| 12 | DMEM-Lg | 15% | N | N | 5% | N |
| 13 | DMEM-Lg | 2% | N | N (Laminin) | 20% | EGF/FGF (20 ng/ml) |
| 14 | DMEM-Lg | 2% | N | N (Laminin) | 5% | EGF/FGF (20 ng/ml) |
| 15 | DMEM-Lg | 2% | N | N (Fibronectin) | 20% | PDGF/VEGF |
| 16 | DMEM-Lg | 2% | N | N (Fibronectin) | 5% | PDGF/VEGF |

Key:
Lg: Low glucose; N: none; Y: yes; BME: beta-mercaptoethanol; FGF: fibroblast growth factor; EGF: epidermal growth factor; PDGF: platelet-derived growth factor; VEGF: vascular endothelial growth factor.

Results

Isolation of PDCs using different growth conditions. In all conditions set forth in Table 1-1, cells attached and expanded well between passage 0 and 1. Cells in condition 5 to 8 and 13 to 16 were demonstrated to proliferate well up to at least four passages after seeding.

Isolation of cells from placenta using different enzyme combinations. Tissue digestion with collagenase:dispase and collagenase:dispase:hyaluronidase resulted in the isolation of cell populations from placental tissues that expanded readily.

Summary. PDCs can be isolated using a combination of a matrix metalloprotease and neutral protease, such as but not limited to a combination of collagenase and dispase. PDCs are preferably isolated using an enzyme combination of a matrix metalloprotease, a neutral protease, and a mucolytic enzyme that degrades hyaluronic acid, such as but not limited to a combination of collagenase, dispase, and hyaluronidase or a combination of LIBERASE (Boehringer Mannheim Corp., Indianapolis, Ind.) and hyaluronidase. Blendzyme 3, which is collagenase (4 Wunsch units/g) and thermolysin (1714 casein Units/g) may be used together with hyaluronidase to isolate cells.

Example 2

Evaluation of Growth Media for Placenta-Derived Cells

Several cell culture media were evaluated for their ability to support the growth of placenta-derived cells. The growth of placenta-derived cells in normal (20%) and low (5%) oxygen was assessed after 3 days using the MTS colorimetric assay.

Methods & Materials

Placenta-derived cells at passage 8 (P8) were seeded at $1 \times 10^3$ cells/well in 96 well plates in Growth medium (DMEM-low glucose (Gibco, Carlsbad Calif.), 15% (v/v) fetal bovine serum (Cat. #SH30070.03; Hyclone, Logan, Utah), 0.001% (v/v) betamercaptoethanol (Sigma, St. Louis, Mo.), 50 Units/milliliter penicillin, 50 microgram/milliliter streptomycin (Gibco). After 8 hours the medium was changed to that described in Table 2-1 and cells were incubated in normal (20%, v/v) or low (5%, v/v) oxygen at 37° C., 5% $CO_2$ for 48 hours. MTS was added to the culture medium (CELLTITER96 AQueous One Solution Cell Proliferation Assay, Promega, Madison, Wis.) for 3 hours and the absorbance measured at 490 nanometer (Molecular Devices, Sunnyvale Calif.).

TABLE 2-1

Culture media evaluated

| Culture Medium | Supplier | Added fetal bovine serum % (v/v) |
|---|---|---|
| DMEM-low glucose | Gibco Carlsbad CA | 0, 2, or 10 |
| DMEM-high glucose | Gibco Carlsbad CA | 0, 2, or 10 |
| RPMI 1640 | Mediatech, Inc. Herndon, VA | 0, 2, or 10 |
| Cell gro-free (Serum-free, Protein-free) | Mediatech, Inc. Herndon, VA | — |
| Ham's F10 | Mediatech, Inc. Herndon, VA | 0, 2, or 10 |
| MSCGM (complete with serum) | Cambrex, Walkersville, MD | 0, 2, or 10 |
| Complete-serum free w/albumin | Mediatech, Inc. Herndon, VA | — |
| Growth medium | NA | — |
| Ham's F12 | Mediatech, Inc. Herndon, VA | 0, 2, or 10 |
| Iscove's | Mediatech, Inc. Herndon, VA | 0, 2, or 10 |
| Basal Medium Eagle's | Mediatech, Inc. Herndon, VA | 0, 2, or 10 |
| DMEM/F12 (1:1) | Mediatech, Inc. Herndon, VA | 0, 2, or 10 |

MSCGM: Mesenchymal Stem Cell Growth Medium

Results

Standard curves for the MTS assay established a linear correlation between an increase in absorbance and an increase in cell number. The absorbance values obtained were converted into estimated cell numbers and the change (%) relative to the initial seeding was calculated.

The addition of serum to media at normal oxygen conditions resulted in a reproducible dose-dependent increase in absorbance and thus the viable cell number (extrapolated). The addition of serum to complete MSCGM resulted in a dose-dependent decrease in absorbance. In the media without added serum, cells only grew in Cellgro, Ham's F10, and DMEM.

Reduced oxygen increased the growth rate of cells in Growth medium, Ham's F10, and, MSCGM.

In decreasing order of growth, the media resulting in the best growth of the PDCs were Growth medium>MSCGM>Iscove's+10% FBS=DMEM-High glucose +10% FBS=Ham's F12+10% FBS=RPMI 1640+10% FBS.

Summary. Placenta-derived cells may be grown in a variety of culture media in normal or low oxygen. PDCs grew in serum-free conditions, for example, in Ham's F10, Cellgro-free, and DMEM. PDCs also grew in protein-free conditions, for example, in Ham's F10 and Cellgro-free. Reduced oxygen increased the growth rate of cells in Growth medium, Ham's F10, and, MSCGM.

Reference

U.S. Application Publication No. 20040005704

Example 3

Growth of Postpartum Cells in Medium Containing D-Valine

It has been reported that medium containing D-valine instead of the normal L-valine isoform can be used to selectively inhibit the growth of fibroblast-like cells in culture (Hongpaisan (2000) *Cell Biol Int.* 24:1-7; Sordillo et al. (1988) *Cell Biol Int Rep.* 12:355-64). Experiments were performed to determine whether placenta-derived cells could grow in medium containing D-valine.

Methods & Materials

Placenta-derived cells (P3) and fibroblasts (P9) were seeded at $5\times10^3$ cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a Modified Growth medium (DMEM with D-valine (special order, Gibco), 15% (v/v) dialyzed fetal bovine serum (Hyclone, Logan, Utah), 0.001% (v/v) betamercaptoethanol (Sigma), 50 Units/milliliter penicillin, 50 micrograms/milliliter streptomycin (Gibco)).

Results

Placenta-derived and fibroblast cells seeded in the D-valine-containing medium did not proliferate, unlike cells seeded in growth medium containing dialyzed serum. Fibroblast cells changed morphologically, increasing in size and changing shape. All of the cells died and eventually detached from the flask surface after 4 weeks.

Summary. PDCs require L-valine for cell growth and to maintain long-term viability.

Example 4

Cryopreservation Media for Placenta-Derived Cells

The objective of this study was to determine a suitable cryopreservation medium for the cryopreservation of placenta-derived cells.

Methods & Materials

Placenta-derived cells grown in Growth medium (DMEM-low glucose (Gibco, Carlsbad Calif.), 15% (v/v) fetal bovine serum (Cat. #SH30070.03, Hyclone, Logan, Utah), 0.001% (v/v) betamercaptoethanol (Sigma, St. Louis, Mo.), 50 Units/milliliter penicillin, 50 microgram/milliliter streptomycin (Gibco)), in a gelatin-coated T75 flask were washed with phosphate buffered saline (PBS; Gibco) and trypsinized using 1 milliliter Trypsin/EDTA (Gibco). The trypsinization was stopped by adding 10 milliliters Growth medium. The cells were centrifuged at 150×g, supernatant removed, and the cell pellet was resuspended in 1 milliliter Growth medium. An aliquot of cell suspension, 60 microliter, was removed and added to 60 microliter Otrypan blue (Sigma). The viable cell number was estimated using a hemocytometer. The cell suspension was divided into four equal aliquots each containing $88\times10^4$ cells each. The cell suspension was centrifuged and resuspended in 1 milliliter of each media below and transferred into Cryovials (Nalgene).

1.) Growth medium +10% (v/v) DMSO (Hybrimax, Sigma, St. Louis, Mo.)
2.) Cell Freezing medium w/DMSO, w/methylcellulose, serum-free (C6295, Sigma, St. Louis, Mo.)
3.) Cell Freezing medium serum-free (C2639, Sigma, St. Louis, Mo.)
4.) Cell Freezing Medium w/glycerol (C6039, Sigma, St. Louis, Mo.)

The cells were cooled at approximately 1° C./min overnight in a −80° C. freezer using a "Mr Frosty" freezing container according to the manufacturer's instructions (Nalgene, Rochester, N.Y.). Vials of cells were transferred into liquid nitrogen for 2 days before thawing rapidly in a 37° C. water bath. The cells were added to 10 milliliters Growth medium and centrifuged before the cell number and viability was estimated as before. Cells were seeded onto gelatin-coated flasks at 5,000 cells/cm$^2$ to determine whether the cells would attach and proliferate.

Results

The initial viability of the cells to be cryopreserved was assessed by trypan blue staining to be 100%.

There was a commensurate reduction in cell number with viability for C6295 due to cell lysis. The viable cells cryopreserved in all four solutions attached, divided, and produced a confluent monolayer within 3 days. There was no discernable difference in estimated growth rate.

Summary. The cryopreservation of cells is one procedure available for preparation of a cell bank or a cell product. Four cryopreservation mixtures were compared for their ability to protect human placenta-derived cells from freezing damage. Dulbecco's modified Eagle's medium (DMEM) and 10% (v/v) dimethylsulfoxide (DMSO) is a preferred medium of those compared for cryopreservation of placenta-derived cells.

Example 5

Growth Characteristics of Placenta-Derived Cells

The cell expansion potential of placenta-derived cells was compared to other populations of isolated stem cells. The process of cell expansion to senescence is referred to as Hayflick's limit (Hayflick (1974) *J. Am. Geriatr. Soc.* 22:1-12; Hayflick (1974) *Gerontologist* 14:37-45).

Materials and Methods

Gelatin-coating flasks. Tissue culture plastic flasks were coated by adding 20 milliliters 2% (w/v) porcine gelatin (Type B: 225 Bloom; Sigma, St Louis, Mo.) to a T75 flask (Corning, Corning, N.Y.) for 20 minutes at room temperature. After removing the gelatin solution, 10 milliliters phosphate-buffered saline (PBS) (Invitrogen, Carlsbad, Calif.) were added and then aspirated.

Comparison of expansion potential of placenta-derived cells with other cell populations. For comparison of growth expansion potential, the following cell populations were utilized: i) Mesenchymal stem cells (MSC; Cambrex, Walkersville, Md.); ii) Adipose-derived cells (U.S. Pat. No. 6,555,374 B1; U.S. Patent Application US20040058412); iii) Normal dermal skin fibroblasts (cc-2509 lot # 9F0844; Cambrex, Walkersville, Md.); and iv) Placenta-derived cells. Cells were initially seeded at 5,000 cells/cm$^2$ on gelatin-coated T75 flasks in Growth medium (DMEM-Low glucose (Invitrogen, Carlsbad, Calif.), 15% (v/v) defined bovine serum (Hyclone, Logan, Utah; Lot#AND18475), 0.001% (v/v) 2-mercaptoethanol (Sigma, St. Louis, Mo.), 100 Units/milliliter penicillin, 100 microgram/milliliter streptomycin, 0.25 micrograms/milliliter amphotericin B; Invitrogen, Carlsbad, Calif.)). For subsequent passages, cell cultures were treated as follows. After trypsinization, viable cells were counted after Trypan Blue staining (e.g., cell suspension (50 microliters) was combined with Trypan Blue (50 microliters, Sigma, St. Louis Mo.); viable cell numbers were estimated using a hemocytometer).

Following counting, cells were seeded at 5,000 cells/cm$^2$ onto gelatin-coated T 75 flasks in 25 milliliters of fresh growth medium. Cells were grown under standard atmosphere with 5% carbon dioxide at 37° C. The growth medium was changed twice per week. When cells reached about 85 percent confluence, they were passaged. This process was repeated until the cells reached senescence.

At each passage, cells were trypsinized and counted. The viable cell yield, population doubling [ln(cell final/cell initial)/ln 2], and doubling time (time in culture (h)/population doubling) were calculated. For the purposes of determining optimal cell expansion, the total cell yield per passage was determined by multiplying the total yield for the previous passage by the expansion factor for each passage (i.e., expansion factor=cell final/cell initial).

Expansion potential of cell banks at low density. The expansion potential of cells banked at passage 10 was tested. Normal dermal skin fibroblasts (cc-2509 lot # 9F0844; Cambrex, Walkersville, Md.) and placenta-derived cells were tested. These cell populations had been banked at passage 10 previously, having been seeded at 5,000 cell/cm$^2$ and grown to confluence at each passage to that point. The effect of cell density on the cell populations following cell thaw at passage 10 was determined. Cells were thawed under standard conditions and counted using Trypan Blue staining. Thawed cells were then seeded at 1,000 cells/cm$^2$ in Growth medium (DMEM:Low glucose (Invitrogen, Carlsbad, Calif.), 15% (v/v) defined bovine serum (Hyclone, Logan, Utah; Lot#AND18475), 0.001% 2-mercaptoethanol (Sigma, St. Louis, Mo.), 100 Units/milliliter penicillin, 100 micrograms/milliliter streptomycin, and 0.25 micrograms/milliliter amphotericin (Invitrogen, Carlsbad, Calif.)). Cells were grown under standard atmospheric conditions at 37° C. Growth medium was changed twice a week and cells were passaged as they reached about 85% confluence. Cells were subsequently passaged until senescence. Cells were trypsinized and counted at each passage. The cell yield, population doubling (ln(cell final/cell initial)/ln2), and doubling time (time in culture (h)/population doubling) were calculated for each passage. The total cell yield per passage was determined by multiplying total yield for the previous passage by the expansion factor for each passage (i.e., expansion factor=cell final/cell initial).

Expansion of placenta-derived cells at low density from initial cell seeding. The expansion potential of freshly isolated placenta-derived cell cultures under low cell seeding conditions was tested in another experiment. Placenta-derived cells were isolated as described in Example 1. Cells were seeded at 1,000 cells/cm$^2$ and passaged as described above until senescence. Cells were grown under standard atmospheric conditions at 37° C. Growth medium was changed twice per week. Cells were passaged as they reached about 85% confluence. At each passage, cells were trypsinized and counted by Trypan Blue staining. The cell yield, population doubling (ln(cell final/cell initial)/ln 2) and doubling time (time in culture (h)/population doubling) were calculated for each passage. The total cell yield per passage was determined by multiplying the total yield for the previous passage by the expansion factor for each passage (i.e., expansion factor=cell final/cell initial). Cells were grown on gelatin and non-gelatin coated flasks.

Expansion of Clonal Neonatal or Maternal Placenta-derived Cells. Cloning may be used in order to expand a population of neonatal or maternal cells successfully from placental tissue. Following isolation of three different cell populations from the placenta (neonatal aspect, maternal aspect, and villous region), these cell populations are expanded under standard growth conditions and then karyotyped to reveal the identity of the isolated cell populations. By isolating the cells from a mother who delivers a boy, it is possible to distinguish between the male and female chromosomes by performing metaphase spreads. These experiments can be used to demonstrate that top-line cells are karyotype positive for neonatal phenotype, mid-line cells are karyotype positive for both neonatal and maternal phenotypes, and bottom-line cells are karyotype positive for maternal cells.

Other growth conditions. In other experiments cells were expanded on either non-coated, collagen-coated, fibronectin-coated, laminin-coated, or extracellular membrane protein (e.g., MATRIGEL (BD Discovery Labware, Bedford, Mass.))-coated plates. Cultures have been demonstrated to expand well on these different matrices.

Results

Comparison of expansion potential of placenta-derived cells with other cell populations. Placenta-derived cells expanded for greater than 40 passages, generating cell yields of >1×10$^{17}$ cells in 60 days. In contrast, MSCs and fibroblasts senesced after <25 days and <60 days, respectively. Although both adipose-derived and omental cells expanded for almost 60 days, they generated total cell yields of 4.5×10$^{12}$ and 4.24×10$^{13}$, respectively. Thus, when seeded at 5,000 cells/cm$^2$ under the experimental conditions utilized, PDCs expanded much better than the other cell types grown under the same conditions (Table 5-1).

TABLE 5-1

Growth characteristics for different cell populations grown to senescence

| Cell Type | Senescence | Total Population Doublings | Total Cell Yield |
| --- | --- | --- | --- |
| MSC | 24 day | 8 | 4.72 × 10$^7$ |
| Adipose-derived cells (Artecel, U.S. Pat. No. 6,555,374) | 57 day | 24 | 4.5 × 10$^{12}$ |
| Fibroblasts | 53 day | 26 | 2.82 × 10$^{13}$ |
| Placenta | 80 day | 46 | 2.49 × 10$^{19}$ |

Expansion of potential of cell banks at low density. Placenta-derived and fibroblast cells expanded for greater than 10 passages generating cell yields of >1×10$^{11}$ cells in 60 days (Table 5-2). After 60 days under these conditions, the placenta- derived cells became senescent whereas the fibroblast cell populations senesced after 80 days, completing >40 population doublings.

TABLE 5-2

Growth characteristics for different cell populations using low density growth expansion from passage 10 through senescence

| Cell Type (Passage No.) | Senescence | Total Population Doublings | Total Cell Yield |
|---|---|---|---|
| Fibroblast (P10) | 80 day | 43.68 | $2.59 \times 10^{11}$ |
| Placental (P10) | 60 day | 32.96 | $6.09 \times 10^{12}$ |

Expansion of placenta-derived cells at low density from initial cell seeding. Placenta-derived cells were expanded at low density (1,000 cells/cm$^2$) on gelatin- coated and uncoated plates or flasks. Growth potential of these cells under these conditions was good. The cells expanded readily in a log phase growth. The rate of cell expansion was similar to that observed when placenta-derived cells were seeded at 5,000 cells/cm$^2$ on gelatin- coated flasks in growth medium. No differences were observed in cell expansion potential between culturing on either uncoated flasks or gelatin-coated flasks. Cells grown in gelatin-coated flasks appeared phenotypically smaller than cells grown in uncoated flasks.

Expansion of Clonal Neonatal or Maternal Placenta-Derived Cells. A clonal neonatal or maternal cell population can be expanded from placenta-derived cells isolated from the neonatal aspect or the maternal aspect, respectively, of the placenta. Cells are serially diluted and then seeded onto gelatin-coated plates in Growth medium for expansion at 1 cell/well in 96-well gelatin coated plates. From this initial cloning, expansive clones are identified, trypsinized, and reseeded in 12-well gelatin-coated plates in Growth medium and then subsequently passaged into T25 gelatin-coated flasks at 5,000 cells/cm$^2$ in Growth medium. Subcloning is performed to ensure that a clonal population of cells has been identified. For subcloning experiments, cells are trypsinized and reseeded at 0.5 cells/well. The subclones that grow well are expanded in gelatin-coated T25 flasks at 5,000 cells cm$^2$/flask. Cells are passaged at 5,000 cells cm$^2$/T75 flask. The growth characteristics of the best clone are plotted, to demonstrate cell expansion. Karyotyping analysis can confirm that the clone is either neonatal or maternal.

Summary. The current cell expansion conditions of growing isolated PDCs at densities of about 5,000 cells/cm$^2$ in growth medium on gelatin-coated or uncoated flasks under standard atmospheric oxygen are sufficient to generate large numbers of cells at passage 11. PDCs also can be readily expanded using lower density culture conditions (e.g., about 1,000 cells/cm$^2$). It is preferred to culture placenta-derived cells under standard atmospheric conditions to generate large pools of cells. Culture conditions may be altered to achieve alternative proliferative and/or differentiative capacity of placenta-derived cells.

Under the conditions utilized, while the expansion potential of MSCs and adipose-derived cells was limited, placenta-derived cells expand readily to large numbers. The data demonstrate that placenta-derived cell lines as developed herein can expand for greater than 40 doublings to provide sufficient cell numbers, for example, for cell banks, whereas mesenchymal stem cells cannot be expanded to obtain large quantities of cells.

REFERENCES

Hayflick (1974) *J. Am. Geriatr. Soc.* 22(1):1-12

Example 6

Karyotype Analysis of Placenta-Derived Cells

Cell lines used in cell therapy are preferably homogeneous and free from any contaminating cell type. Human cells used in cell therapy should have a normal chromosome number (46) and structure. To identify placenta-derived cell lines that are homogeneous and free from cells of non-placental tissue origin, karyotypes of cell samples were analyzed.

Materials and Methods

PDCs from postpartum tissue of a male neonate were cultured in Growth medium (DMEM-low glucose (Gibco Carlsbad, Calif.), 15% (v/v) fetal bovine serum (FBS) (Hyclone, Logan, Utah), 0.001% (v/v) betamercaptoethanol (Sigma, St. Louis, Mo.), and 50 Units/milliliter penicillin, 50 microgram/milliliter streptomycin (Gibco, Carlsbad, Calif.)). Postpartum tissue from a male neonate (X,Y) was selected to allow distinction between neonatal- derived cells and maternal-derived cells (X,X). Cells were seeded at 5,000 cells/cm$^2$ in Growth medium in a T25 flask (Corning, Corning, N.Y.) and expanded to about 80% confluence. A T25 flask containing cells was filled to the neck with Growth medium. Samples were delivered to a clinical cytogenetics lab by courier (estimated lab to lab transport time is one hour). Chromosome analysis was performed by the Center for Human & Molecular Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

Results

All cell samples sent for chromosome analysis were interpreted as exhibiting a normal appearance. Three of the thirteen cell lines analyzed exhibited a heterogeneous phenotype (XX and XY) indicating the presence of cells derived from both neonatal and maternal origins (Table 6-1). Cells derived from tissue Placenta-N were isolated from the neonatal aspect of placenta. At passage zero, this cell line appeared homogeneous XY. However, at passage nine, the cell line was heterogeneous (XX/XY), indicating a previously undetected presence of cells of maternal origin.

TABLE 6-1

Karyotype analysis of PDCs

| Tissue | passage | Metaphase cells counted | Metaphase cells analyzed | Number of karyotypes | ISCN Karyotype |
|---|---|---|---|---|---|
| Placenta | 22 | 20 | 5 | 2 | 46, XX |
| Placenta | 2 | 20 | 5 | 2 | 46, XX |

TABLE 6-1-continued

Karyotype analysis of PDCs

| Tissue | passage | Metaphase cells counted | Metaphase cells analyzed | Number of karyotypes | ISCN Karyotype |
|---|---|---|---|---|---|
| Placenta-N | 0 | 20 | 5 | 2 | 46, XY |
| Placenta-V | 0 | 20 | 5 | 2 | 46, XY |
| Placenta-M | 0 | 21 | 5 | 4 | 46, XY[18]/46, XX[3] |
| Placenta-M | 4 | 20 | 5 | 2 | 46, XX |
| Placenta-N | 9 | 25 | 5 | 4 | 46, XY[5]/46, XX[20] |
| Placenta-N C1 | 1 | 20 | 5 | 2 | 46, XY |
| Placenta-N C3 | 1 | 20 | 6 | 4 | 46, XY[2]/46, XX[18] |
| Placenta-N C4 | 1 | 20 | 5 | 2 | 46, XY |
| Placenta-N C15 | 1 | 20 | 5 | 2 | 46, XY |
| Placenta-N C20 | 1 | 20 | 5 | 2 | 46, XY |
| Placenta-N C22 | 1 | 20 | 5 | 2 | 46, XY |

Key:
N—Neonatal side; V—villous region; M—maternal side; C—clone

Summary. Chromosome analysis identified placenta-derived cells whose karyotypes appear normal as interpreted by a clinical cytogenetic laboratory. Karyotype analysis also identified cell lines free from maternal cells, as determined by homogeneous karyotype.

Example 7

Evaluation of Human Placenta-Derived Cell Surface Markers by Flow Cytometry

Characterization of cell surface proteins or "markers" by flow cytometry can be used to determine a cell line's identity. The consistency of expression can be determined from multiple donors and in cells exposed to different processing and culturing conditions. Postpartum cell lines derived from the placenta were characterized (by flow cytometry) providing a profile for the identification of these cell lines.

Materials and Methods

Media. Cells were cultured in Growth medium (DMEM-low glucose (Gibco Carlsbad, Calif.), 15% (v/v) fetal bovine serum (FBS); (Hylcone, Logan, Utah), 0.001% (v/v) beta-mercaptoethanol (Sigma, St. Louis, Mo.), and 50 Units/milliliter penicillin, 50 microgram/milliliter streptomycin (Gibco, Carlsbad, Calif.)).

Culture vessels. Cells were cultured in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Antibody staining. Adherent cells in flasks were washed in phosphate buffered saline (PBS); (Gibco, Carlsbad, Calif.) and detached with Trypsin/EDTA (Gibco, Carlsbad, Calif.). Cells were harvested, centrifuged, and resuspended in 3% (v/v) FBS in PBS at a cell concentration of $1\times10^7$ per milliliter. In accordance with the manufacturer's specifications, antibody to the cell surface marker of interest (Table 7-1) was added to one hundred microliters of cell suspension, and the mixture was incubated in the dark for 30 minutes at 4° C. After incubation, cells were washed with PBS and centrifuged to remove unbound antibody. Cells were resuspended in 500 microliters PBS and analyzed by flow cytometry.

Flow cytometry analysis. Flow cytometry analysis was performed with a FACScalibur instrument (Becton Dickinson, San Jose, Calif.).

Antibodies to cell surface markers. The following antibodies to cell surface markers were used.

TABLE 7-1

Antibodies to cell surface markers

| Antibody | Manufacture | Catalog Number |
|---|---|---|
| CD10 | BD Pharmingen (San Diego, CA) | 555375 |
| CD13 | BD Pharmingen (San Diego, CA) | 555394 |
| CD31 | BD Pharmingen (San Diego, CA) | 555446 |
| CD34 | BD Pharmingen (San Diego, CA) | 555821 |
| CD44 | BD Pharmingen (San Diego, CA) | 555478 |
| CD45RA | BD Pharmingen (San Diego, CA) | 555489 |
| CD73 | BD Pharmingen (San Diego, CA) | 550257 |
| CD90 | BD Pharmingen (San Diego, CA) | 555596 |
| CD117 | BD Biosciences (San Jose, CA) | 340529 |
| CD141 | BD Pharmingen (San Diego, CA) | 559781 |
| PDGFr-alpha | BD Pharmingen (San Diego, CA) | 556002 |
| HLA-A, B, C | BD Pharmingen (San Diego, CA) | 555553 |
| HLA-DR, DP, DQ | BD Pharmingen (San Diego, CA) | 555558 |
| IgG-FITC | Sigma (St. Louis, MO) | F-6522 |
| IgG-PE | Sigma (St. Louis, MO) | P-4685 |

Passage to passage comparison. Placenta-derived cells were analyzed at passages 8, 15, and 20.

Donor to donor comparison. To compare differences among donors, placenta cells from different donors were compared to each other.

Surface coating comparison. Placenta-derived cells cultured on gelatin-coated flasks was compared to placenta-derived cells cultured on uncoated flasks.

Digestion enzyme comparison. Four treatments used for isolation and preparation of cells were compared. Cells isolated from placenta by treatment with 1) collagenase; 2) collagenase/dispase; 3) collagenase/hyaluronidase; and 4) collagenase/hyaluronidase/dispase were compared.

Placental layer comparison. Cells isolated from the maternal aspect of placental tissue were compared to cells isolated from the villous region of placental tissue and cells isolated from the neonatal fetal aspect of placenta.

Results

Placenta-derived cell characterization. Placenta-derived cells analyzed by flow cytometry showed positive for production of CD10, CD13, CD44, CD73, CD 90, PDGFr-alpha and HLA-A, B, C, indicated by the increased values of fluorescence relative to the IgG control. These cells were negative for detectable for production of CD31, CD34, CD45, CD117, CD141, and HLA-DR, DP, DQ, indicated by fluorescence values comparable to the IgG control. Variations in fluorescence values of positive curves were accounted. While the mean (i.e., CD13) and range (i.e., CD90) of the positive curves showed some variation, the curves appeared normal, confirming a homogeneous population, and exhibited fluorescence values greater than the IgG control.

Passage to passage comparison. Placenta-derived cells at passages 8, 15, and 20 analyzed by flow cytometry were positive for production of CD10, CD13, CD44, CD73, CD 90, PDGFr-alpha, and HLA-A, B, C, as reflected in the increased value of fluorescence relative to the IgG control. The cells were negative for production of CD31, CD34, CD45, CD117, CD141, and HLA-DR, DP, DQ, as indicated by fluorescence values consistent with the IgG control.

Donor to donor comparison. Placenta-derived cells isolated from separate donors analyzed by flow cytometry each expressed CD10, CD13, CD44, CD73, CD 90, PDGFr-alpha, and HLA-A, B, C, with increased values of fluorescence relative to the IgG control. The cells were negative for production of CD31, CD34, CD45, CD117, CD141, and HLA-DR, DP, DQ as indicated by fluorescence value consistent with the IgG control.

The effect of surface coating with gelatin. Placenta-derived cells expanded on either gelatin-coated or uncoated flasks analyzed by flow cytometry expressed of CD 10, CD13, CD44, CD73, CD 90, PDGFr-alpha, and HLA-A, B, C, reflected in the increased values of fluorescence relative to the IgG control. These cells were negative for production of CD31, CD34, CD45, CD117, CD141, and HLA-DR, DP, DQ indicated by fluorescence values consistent with the IgG control.

Effect of enzyme digestion procedure on the cell surface marker profile. PDCs isolated using various digestion enzymes analyzed by flow cytometry expressed CD10, CD13, CD44, CD73, CD 90, PDGFr-alpha, and HLA-A, B, C, as indicated by the increased values of fluorescence relative to the IgG control. These cells were negative for production of CD31, CD34, CD45, CD117, CD 141, and HLA-DR, DP, DQ, as indicated by fluorescence values consistent with the IgG control.

Placental layer comparison. Cells isolated from the maternal, villous, and neonatal layers of the placenta, respectively, analyzed by flow cytometry showed positive for production of CD 10, CD13, CD44, CD73, CD90, PDGFr-alpha, and HLA- A, B, C, as indicated by the increased value of fluorescence relative to the IgG control. These cells were negative for production of CD31, CD34, CD45, CD117, CD141, and HLA-DR, DP, DQ, as indicated by fluorescence values consistent with the IgG control.

Summary. Analysis of placenta-derived cells by flow cytometry has established a profile useful to identify of these cell lines. Placenta-derived cells are positive for CD10, CD13, CD44, CD73, CD90, PDGFr-alpha, HLA-A,B,C and negative for CD31, CD34, CD45, CD117, CD141, and HLA-DR, DP, DQ. This identity was consistent between variations in variables including the donor, passage, culture vessel surface coating, digestion enzymes, and placental layer. Some variation in individual fluorescence value histogram curve means and ranges were observed, but all positive curves under all conditions tested were normal and expressed fluorescence values greater than the IgG control, thus confirming that the cells comprise a homogeneous population which has positive expression of the markers.

Example 8

Analysis of Placenta-Derived Cells by Affymetrix Gene Chip® Arrays

Affymetrix GeneChip® arrays were used to compare gene expression profiles of placenta-derived cells with umbilical cord-derived cells, fibroblasts, human mesenchymal stem cells, and another cell line derived from human bone marrow. This analysis provided a characterization of the postpartum cells and identified unique molecular markers for these cells.

Materials and Methods

Isolation and Culture of Cells

Postpartum tissue-derived cells. Human umbilical cords and placenta were obtained from National Disease Research Interchange (NDRI, Philadelphia, Pa.) from normal full term deliveries with patient consent. The tissues were received and cells were isolated as described in Example 1. Cells were cultured in Growth Medium (Dulbecco's Modified Essential Media (DMEM-low glucose; Invitrogen, Carlsbad, Calif.) with 15% (v/v) fetal bovine serum (Hyclone, Logan Utah), 100 Units/milliliter penicillin, 100 microgram/milliliter streptomycin (Invitrogen, Carlsbad, Calif.), and 0.001% (v/v) 2-mercaptoethanol (Sigma, St. Louis Mo.)) on gelatin-coated tissue culture plastic flasks. The cultures were incubated under standard growth conditions.

Fibroblasts. Human dermal fibroblasts were purchased from Cambrex Incorporated (Walkersville, Md.; Lot number 9F0844) and were obtained from ATCC CRL- 1501 (CCD39SK). Both lines were cultured in DMEM/F12 medium (Invitrogen, Carlsbad, Calif.) with 10% (v/v) fetal bovine serum (Hyclone) and 100 Units/milliliter penicillin, 100 microgram/milliliter streptomycin (Invitrogen). The cells were grown on standard tissue-treated plastic.

Human Mesenchymal Stem Cells (hMSC). hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. in standard atmosphere with 5% $CO_2$.

*Human Iliac Crest Bone Marrow Cells* (ICBM). Human iliac crest bone marrow was received from NDRI with patient consent. The marrow was processed according to the method outlined by Ho, et al. (International PCT Publication No. WO03/025149). The marrow was mixed with lysis buffer (155 microMolar $NH_4Cl$, 10 microMolar $KHCO_3$, and 0.1 microMolar EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 microMolar glutamine. The cells were centrifuged, and the cell pellet was resuspended in fresh medium. The viable mononuclear cells were counted using trypan-blue exclusion (Sigma, St. Louis, MO). The mononuclear cells were seeded in tissue-cultured plastic flasks at $5\times10^4$ cells/cm$^2$. The cells were incubated at 37° C. with 5% $CO_2$ at either standard atmospheric $O_2$ or at 5% $O_2$. Cells were cultured for 5 days without a medium change. Media and non-adherent cells were removed after 5 days of culture. The adherent cells were maintained in culture.

Isolation of mRNA and GeneChip Analysis. Actively growing cultures of cells were removed from the flasks with a cell scraper in cold phosphate buffered saline (PBS). The cells were centrifuged for 5 minutes at 300×g. The supernatant was removed, and the cells were resuspended in fresh PBS and centrifuged again. The supernatant was removed, and the cell pellet was immediately frozen and stored at −80° C. Cellular mRNA was extracted and transcribed into cDNA. cDNA was then transcribed into cRNA and biotin-labeled. The biotin-labeled cRNA was hybridized with HG-U133A GENECHIP oligonucleotide array (Affymetrix, Santa Clara Calif.). The hybridization and data collection was performed according to the manufacturer's specifications. Analyses were performed using "Significance Analysis of Microarrays" (SAM) version 1.21 computer software (Stanford University; Tusher, V. G. et al., 2001, Proc. Natl. Acad. Sci. USA 98: 5116-5121).

Results

Fourteen different populations of cells were analyzed in this study. The cells along with passage information, culture substrate, and culture media are listed in Table 8- 1.

TABLE 8-1

Cells analyzed by the microarray study. The cell lines are listed by their identification code along with passage at the time of analysis, cell growth substrate, and growth media.

| Cell Population | Passage | Substrate | Media |
| --- | --- | --- | --- |
| Umbilical (022803) | 2 | Gelatin | DMEM, 15% FBS, BME |
| Umbilical (042103) | 3 | Gelatin | DMEM, 15% FBS, BME |
| Umbilical (071003) | 4 | Gelatin | DMEM, 15% FBS, BME |
| Placenta (042203) | 12 | Gelatin | DMEM, 15% FBS, BME |
| Placenta (042903) | 4 | Gelatin | DMEM, 15% FBS, BME |
| Placenta (071003) | 3 | Gelatin | DMEM, 15% FBS, BME |
| ICBM (070203) (5% $O_2$) | 3 | Plastic | MEM 10% FBS |
| ICBM (062703) (std $O_2$) | 5 | Plastic | MEM 10% FBS |
| ICBM (062703 )(5% $O_2$) | 5 | Plastic | MEM 10% FBS |
| hMSC (Lot 2F1655) | 3 | Plastic | MSCGM |
| hMSC (Lot 2F1656) | 3 | Plastic | MSCGM |
| hMSC (Lot 2F1657) | 3 | Plastic | MSCGM |
| hFibroblast (9F0844) | 9 | Plastic | DMEM-F12, 10% FBS |
| hFibroblast (ATCC CRL-1501) | 4 | Plastic | DMEM-F12, 10% FBS |

The data were evaluated by a Principle Component Analysis, analyzing the 290 genes that were differentially expressed in the cells. This analysis allows for a relative comparison for the similarities between the populations. Table 8-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes.

TABLE 8-2

The Euclidean Distances for the Cell Pairs. The Euclidean distance was calculated for the cell types using the 290 genes that were differentially expressed between the cell types. Similarity between the cells is inversely proportional to the Euclidean distance.

| Cell Pair | Euclidean Distance |
| --- | --- |
| ICBM-hMSC | 24.71 |
| Placenta-umbilical | 25.52 |
| ICBM-Fibroblast | 36.44 |
| ICBM-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 8-3, 8-4, and 8-5 show the expression of genes increased in placenta-derived cells (Table 8-3), increased in umbilical cord-derived cells (Table 8-4), and reduced in umbilical cord- and placenta-derived cells (Table 8-5). The column entitled "Probe Set ID" refers to the manufacturer's identification code for the sets of several oligonucleotide probes located on a particular site on the chip, which hybridize to the named gene (column "Gene Name"), comprising a sequence that can be found within the NCBI (GenBank) database at the specified accession number (column "NCBI Accession Number").

TABLE 8-3

Genes shown to have specifically increased expression in the placenta-derived cells as compared to the other cell lines assayed.
Genes Increased in Placenta-Derived Cells

| Probe Set ID | Gene Name | NCBI Accession Number |
| --- | --- | --- |
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | renin | NM_000537 |
| 210004_at | oxidised low density lipoprotein (lectin-like) receptor 1 | AF035776 |

TABLE 8-3-continued

Genes shown to have specifically increased expression in the placenta-derived cells as compared to the other cell lines assayed.
Genes Increased in Placenta-Derived Cells

| Probe Set ID | Gene Name | NCBI Accession Number |
| --- | --- | --- |
| 214993_at | *Homo sapiens*, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | *Homo sapiens* mRNA; cDNA DKFZp547K1113 (from clone DKFZp547K1113) | AI246730 |

TABLE 8-4

Genes shown to have specifically increased expression in umbilical cord-derived cells as compared to the other cell lines assayed.
Genes Increased in Umbilical Cord-Derived Cells

| Probe Set ID | Gene Name | NCBI Accession Number |
| --- | --- | --- |
| 202859_x_at | interleukin 8 | NM_000584 |
| 211506_s_at | interleukin 8 | AF043337 |
| 210222_s_at | reticulon 1 | BC000314 |
| 204470_at | chemokine (C-X-C motif) ligand 1 (melanoma growth stimulating activity | NM_001511 |
| 206336_at | chemokine (C-X-C motif) ligand 6 (granulocyte chemotactic protein 2) | NM_002993 |
| 207850_at | chemokine (C-X-C motif) ligand 3 | NM_002090 |
| 203485_at | reticulon 1 | NM_021136 |
| 202644_s_at | tumor necrosis factor, alpha-induced protein 3 | NM_006290 |

TABLE 8-5

Genes that were shown to have decreased expression in the umbilical cord and placenta cells as compared to the other cell lines assayed.
Genes Decreased in Umbilical Cord-and Placenta-Derived Cells

| Probe Set ID | Gene name | NCBI Accession Number |
| --- | --- | --- |
| 210135_s_at | short stature homeobox 2 | AF022654.1 |
| 205824_at | heat shock 27 kDa protein 2 | NM_001541.1 |
| 209687_at | chemokine (C-X-C motif) ligand 12 (stromal cell-derived factor 1) | U19495.1 |
| 203666_at | chemokine (C-X-C motif) ligand 12 (stromal cell-derived factor 1) | NM_000609.1 |
| 212670_at | elastin (supravalvular aortic stenosis, Williams-Beuren syndrome) | AA479278 |
| 213381_at | *Homo sapiens* mRNA; cDNA DKFZp586M2022 (from clone DKFZp586M2022) | N91149 |
| 206201_s_at | mesenchyme homeobox 2 (growth arrest-specific homeobox) | NM_005924.1 |
| 205817_at | sine oculis homeobox homolog 1 (*Drosophila*) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | interleukin 11 receptor, alpha | NM_004512.1 |
| 202465_at | procollagen C-endopeptidase enhancer | NM_002593.2 |
| 203706_s_at | frizzled homolog 7 (*Drosophila*) | NM_003507.1 |
| 212736_at | hypothetical gene BC008967 | BE299456 |
| 214587_at | collagen, type VIII, alpha 1 | BE877796 |
| 201645_at | tenascin C (hexabrachion) | NM_002160.1 |
| 210239_at | iroquois homeobox protein 5 | U90304.1 |
| 203903_s_at | hephaestin | NM_014799.1 |

TABLE 8-5-continued

Genes that were shown to have decreased expression in the umbilical cord and placenta cells as compared to the other cell lines assayed.
Genes Decreased in Umbilical Cord-and Placenta-Derived Cells

| Probe Set ID | Gene name | NCBI Accession Number |
|---|---|---|
| 205816_at | integrin, beta 8 | NM_002214.1 |
| 203069_at | synaptic vesicle glycoprotein 2 | NM_014849.1 |
| 213909_at | Homo sapiens cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | sine oculis homeobox homolog 2 (Drosophila) | NM_016932.1 |
| 213435_at | KIAA1034 protein | AB028957.1 |
| 206115_at | early growth response 3 | NM_004430.1 |
| 213707_s_at | distal-less homeobox 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | biglycan | AA845258 |
| 201261_x_at | biglycan | BC002416.1 |
| 202132_at | transcriptional co-activator with PDZ-binding motif (TAZ) | AA081084 |
| 214701_s_at | fibronectin 1 | AJ276395.1 |
| 213791_at | proenkephalin | NM_006211.1 |
| 205422_s_at | integrin, beta-like 1 (with EGF-like repeat domains) | NM_004791.1 |
| 214927_at | Homo sapiens mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | Homo sapiens mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | insulin-like growth factor binding protein 2, 36 kDa | NM_000597.1 |

Tables 8-6, 8-7, and 8-8 show the expression of genes increased in human fibroblasts (Table 8-6), ICBM cells (Table 8-7), and MSCs (Table 8-8).

TABLE 8-6

Genes that were shown to have increased expression in fibroblasts as compared to the other cell lines assayed.
Genes increased in fibroblasts dual specificity phosphatase 2
KIAA0527 protein
Homo sapiens cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41

TABLE 8-6-continued

Genes that were shown to have increased expression in fibroblasts as compared to the other cell lines assayed.
Genes increased in fibroblasts HSPC019 protein
Homo sapiens cDNA: FLJ23564 fis, clone LNG10773
Homo sapiens mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [Homo sapiens]
transforming growth factor, beta 2

TABLE 8-6-continued

Genes that were shown to have increased expression in
fibroblasts as compared to the other cell lines assayed.
Genes increased in fibroblasts hypothetical protein MGC29643
antigen identified by monoclonal antibody MRC OX-2

TABLE 8-7

Genes that were shown to have increased expression in
the ICBM-derived cells as compared to
the other cell lines assayed.
Genes Increased In ICBM Cells cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1
hippocalcin-like 1
jagged 1 (Alagille syndrome)
proteoglycan 1, secretory granule

TABLE 8-8

Genes that were shown to have increased expression in
the MSC cells as compared to the other cell lines assayed.
Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
*Homo sapiens* cDNA FLJ12232 fis, clone MAMMA1001206
*Homo sapiens* cDNA FLJ34668 fis, clone LIVER2000775
jun B proto-oncogene
B-cell CLL/lymphoma 6 (zinc finger protein 51)
zinc finger protein 36, C3H type, homolog (mouse)

Summary. The GENECHIP analysis was performed to provide a molecular characterization of the postpartum cells derived from placenta. This analysis included cells derived from three different placentas. The study also included three different lines of umbilical cord-derived cells, two different lines of dermal fibroblasts, three lines of mesenchymal stem cells, and three lines of iliac crest bone marrow cells. The mRNA that was expressed by these cells was analyzed by AffyMetrix GENECHIP that contained oligonucleotide probes for 22,000 genes.

Results showed that 290 genes are differentially expressed in these five different cell types. These genes include ten genes that are specifically increased in the placenta-derived cells. Fifty-four genes were found to have specifically lower expression levels in placenta.

The expression of selected genes has been confirmed by PCR in Example 9. These results demonstrate that the placenta-derived cells have a distinct gene expression profile, for example, as compared to bone marrow-derived cells and fibroblasts.

Example 9

Cell Markers in Placenta-Derived Cells

Similarities and differences in gene expression between cells derived from the human placenta and cells derived from other sources were assessed by comparing their gene expression profiles using an Affymetrix Genechip. Six "signature" genes were identified: oxidized LDL receptor 1, interleukin-8, renin, reticulon, chemokine receptor ligand 3 (CXC ligand 3), and granulocyte chemotactic protein 2 (GCP-2). These "signature" genes were expressed at relatively high levels in placenta-derived cells. This analysis was conducted to verify the microarray data and find accordance/divergence between gene and protein expression, as well as to establish a series of reliable assay for detection of unique identifiers for placenta-derived cells.

Methods & Materials

Cells. Placenta-derived cells (three isolates, including one isolate predominately neonatal as identified by karyotyping analysis) and Normal Human Dermal Fibroblasts (NHDF; neonatal and adult) were grown in Growth medium (DMEM-low glucose (Gibco, Carlsbad, Calif.), 15% (v/v) fetal bovine serum (Cat. #SH30070.03; Hyclone, Logan, Utah), 0.001% (v/v) beta-mercaptoethanol (Sigma, St. Louis, Mo.), 50 Units/milliliter penicillin, 50 microgram/milliliter streptomycin (Gibco, Carlsbad, Calif.)) in a gelatin-coated T75 flask. Mesenchymal Stem Cells (MSCs) were grown in a Mesenchymal Stem Cell Growth Medium Bullet kit (MSCGM; Cambrex, Walkerville, Md.).

For IL-8 experiments, cells were thawed from liquid nitrogen and plated in gelatin-coated flasks at 5,000 cells/$cm^2$, grown for 48 hours in Growth medium and then grown for 8 hours in 10 milliliters of serum starvation medium [DMEM-low glucose (Gibco, Carlsbad, Calif.), 50 Units/milliliter penicillin, 50 microgram/milliliter streptomycin (Gibco, Carlsbad, Calif.) and 0.1% (w/v) Bovine Serum Albumin (BSA; Sigma, St. Louis, Mo.)]. After this treatment, RNA was extracted and the supernatants were centrifuged at 150×g for 5 minutes to remove cellular debris.

Cell culture for ELISA assay. Placenta-derived cells and human fibroblasts derived from human neonatal foreskin were cultured in Growth medium in gelatin-coated T75 flasks. Cells were frozen at passage 11 in liquid nitrogen. Cells were thawed and transferred to 15 milliliter centrifuge tubes. After centrifugation at 150×g for 5 minutes, the supernatant was discarded. Cells were resuspended in 4 milliliters culture medium and counted. Cells were grown in a 75 $cm^2$ flask containing 15 milliliters of Growth medium at 375,000 cell/flask for 24 hours. The medium was changed to a serum starvation medium for 8 hours. Serum starvation medium was collected at the end of incubation, centrifuged at 14,000×g for 5 minutes, and stored at −20° C.

To estimate the number of cells in each flask, 2 milliliters of trypsin/EDTA (Gibco, Carlsbad, Calif.) was added to each flask. After cells detached from the flask, trypsin activity was neutralized with 8 milliliters of Growth medium. Cells were transferred to a 15 milliliter centrifuge tube and centrifuged at 150×g for 5 minutes. Supernatant was removed and 1 milliliter Growth medium was added to each tube to resuspend the cells. Cell number was estimated using a hemocytometer.

ELISA assay. The amount of IL-8 secreted by the cells into serum starvation medium was analyzed using ELISA assays (R&D Systems, Minneapolis, Minn.). All assays were tested according to the instructions provided by the manufacturer.

Total RNA isolation. RNA was extracted from confluent placenta-derived cells and fibroblasts or for IL-8 expression from cells treated as described above. Cells were lysed with 350 microliter buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 U/sample) (Sigma St. Louis, Mo.). RNA was eluted with 50 microliter DEPC-treated water and stored at −80° C. RNA was extracted from human placenta. Tissue (30 milligram) was suspended in 700 microliter of buffer RLT containing beta-mercaptoethanol. Samples were mechanically homogenized, and the RNA extraction proceeded according to manufacturer's specification. RNA was extracted with 50 microliter of DEPC-treated water and stored at −80° C.

Reverse transcription. RNA was reverse transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum cells ("signature genes," including oxidized LDL receptor, interleukin-8, renin, and reticulon), were further investigated using real-time and conventional PCR.

Real-time PCR. PCR was performed on cDNA samples using ASSAYS-ON-DEMAND gene expression products: oxidized LDL receptor (Hs00234028); renin (Hs00166915); reticulon (Hs00382515); CXC ligand 3 (Hs00171061); GCP-2 (Hs00605742); IL-8 (Hs00174103); and GAPDH were mixed with cDNA and TaqMan Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 minute and 95° C. for 10 minute, followed by 40 cycles of 95° C. for 15 second and 60° C. for 1 minute. PCR data was analyzed according to manufacturer's specifications (User Bulletin #2 from Applied Biosystems for ABI Prism 7700 Sequence Detection System).

Conventional PCR. Conventional PCR was performed using an ABI PRISM 7700 (Perkin Elmer Applied Biosystems, Boston, Mass.) to confirm the results from real-time PCR. PCR was performed using 2 microliter of cDNA solution, 1×TAQ polymerase (tradename AMPLITAQ GOLD) universal mix PCR reaction buffer (Applied Biosystems, Foster City, Calif.) and initial denaturation at 94° C. for 5 minutes. Amplification was optimized for each primer set. For IL-8, CXC ligand 3, and reticulon (94° C. for 15 seconds, 55° C. for 15 seconds, and 72° C. for 30 seconds for 30 cycles); for renin (94° C. for 15 seconds, 53° C. for 15 seconds, and 72° C. for 30 seconds for 38 cycles); for oxidized LDL receptor and GAPDH (94° C. for 15 seconds, 55° C. for 15 seconds, and 72° C. for 30 seconds for 33 cycles). Primers used for amplification are listed in Table 9-1. Primer concentration in the final PCR reaction was 1 microMolar except for GAPDH which was 0.5 microMolar. GAPDH primers were the same as real-time PCR, except that the manufacturer's TaqMan probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal-length POLAROID camera (VWR International, South Plainfield, N.J.).

TABLE 9-1

Primers used

| Primer name | | Primers | |
|---|---|---|---|
| Oxidized LDL receptor | S: | 5'-GAGAAATCCAAAGAGCAAATGG-3' | (SEQ ID NO: 1) |
| | A: | 5'-AGAATGGAAAACTGGAATAGG-3' | (SEQ ID NO: 2) |
| Renin | S: | 5'-TCTTCGATGCTTCGGATTCC-3' | (SEQ ID NO: 3) |
| | A: | 5'-GAATTCTCGGAATCTCTGTTG-3' | (SEQ ID NO: 4) |
| Reticulon | S: | 5'-TTACAAGCAGTGCAGAAAACC-3' | (SEQ ID NO: 5) |
| | A: | 5'-AGTAAACATTGAAACCACAGCC-3' | (SEQ ID NO: 6) |
| Interleukin-8 | S: | 5'-TCTGCAGCTCTGTGTGAAGG-3' | (SEQ ID NO: 7) |
| | A: | 5'-CTTCAAAAACTTCTCCACAACC-3' | (SEQ ID NO: 8) |
| Chemokine (CXC) ligand 3 | S: | 5'-CCCACGCCACGCTCTCC-3' | (SEQ ID NO: 9) |
| | A: | 5'-TCCTGTCAGTTGGTGCTCC-3' | (SEQ ID NO: 10) |

Immunofluorescence. Cells were fixed with cold 4% (w/v) paraformaldehyde (Sigma-Aldrich, St. Louis, Mo.) for 10 minutes at room temperature. Placenta-derived cells at passage 0 (P0) (one isolate, directly after isolation) and passage 11 (P11) (two isolates) and fibroblasts (P11) were used. Immunocytochemistry was performed using antibodies directed against the following epitopes: vimentin (1:500, Sigma, St. Louis, Mo.), desmin (1:150; Sigma—raised against rabbit; or 1:300; Chemicon, Temecula, Calif.—raised against mouse,), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 placenta-derived cells: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the process. Primary antibodies, diluted in blocking solution, were then applied to the cultures for a period of 1 hour at room temperature. The primary antibody solutions were removed, and the cultures were washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150, Santa Cruz Biotech). Cultures were washed and 10 microMolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed, with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Preparation of cells for FACS analysis. Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended in 3% (v/v) FBS in PBS at a cell concentration of $1\times10^7$/milliliter. One hundred microliter aliquots were delivered to conical tubes. Cells stained for intracellular antigens were permeabilized with Perm/Wash buffer (BD Pharmingen, San Diego, Calif.). Antibody was added to aliquots as per manufacturer's specifications and the cells were incubated in the dark for 30 minutes at 4° C. After incubation, cells were washed with PBS and centrifuged to remove excess antibody. Cells requiring a secondary antibody were resuspended in 100 microliter of 3% FBS. Secondary antibody was added as per manufacturer's specification and the cells were incubated in the dark for 30 minutes at 4° C. After incubation, cells were washed with PBS and centrifuged to remove excess secondary antibody. Washed cells were resuspended in 0.5 milliliter PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), Donkey against Goat IgG (sc-3743; Santa Cruz, Biotech.).

FACS analysis. Flow cytometry analysis was performed with FACScalibur (Becton Dickinson San Jose, Calif.).

Results

Results of real-time PCR for selected "signature" genes performed on cDNA from cells derived from human placentas, adult and neonatal fibroblasts, and Mesenchymal Stem Cells (MSCs) indicate that both oxidized LDL receptor and renin were expressed at higher level in the placenta-derived cells as compared to other cells. The data obtained from real-time PCR were analyzed by the $\Delta C_T$ method and expressed on a logarithmic scale. No significant difference in the expression levels of CXC ligand 3 and GCP-2 were found between placenta-derived cells and controls. CXC ligand 3 was expressed at very low levels. GCP-2 was expressed at levels comparable to human adult and neonatal fibroblasts. The results of real-time PCR were confirmed by conventional PCR. Sequencing of PCR products further validated these observations. No significant difference in the expression level of CXC ligand 3 was found between postpartum cells and controls using conventional PCR CXC ligand 3 primers listed in Table 9-1.

The production of the cytokine IL-8 in placenta-derived cells is elevated in both Growth medium-cultured and serum-starved placenta-derived cells. All real-time PCR data was validated with conventional PCR and by sequencing PCR products.

When supernatants of cells grown in serum-free medium were examined for the presence of IL-8, high amounts were detected in media derived from certain isolates of placenta cells (Table 9-2). No IL-8 was detected in medium derived from human dermal fibroblasts.

TABLE 9-2

IL-8 protein production measured by ELISA

| Cell type | IL-8 |
|---|---|
| Human Fibroblasts | ND |
| Placenta Isolate 1 | ND |
| Placenta Isolate 2 | ND |
| Placenta Isolate3 (normal $O_2$) | 17.27 ± 8.63 |
| Placenta Isolate 3 (low $O_2$, W/O BME) | 264.92 ± 9.88 |

Results of the ELISA assay for interleukin-8 (IL-8) performed on placenta-derived cells and human skin fibroblasts. Values are presented here are picogram/million cells, n = 2, sem.
ND: Not Detected Placenta-derived cells were examined for the production of oxidized LDL receptor, GCP-2, and GROalpha by FACS analysis. Cells tested positive for GCP-2. Oxidized LDL receptor and GROalpha were not detected by this method.

Placenta-derived cells were tested for the production of selected proteins by immunocytochemical analysis. Immediately after isolation (passage 0), cells derived from the human placenta were fixed with 4% paraformaldehyde and exposed to antibodies for six proteins: von Willebrand Factor, CD34, cytokeratin 18, desmin, alpha-smooth muscle actin, and vimentin. Cells stained positive for both alpha-smooth muscle actin and vimentin. This pattern was preserved through passage 11. Only a few cells (<5%) at passage 0 stained positive for cytokeratin 18.

Placenta-derived cells at passage 11 were also investigated by immunocytochemistry for the production of GROalpha and GCP-2. Placenta-derived cells were GCP-2 positive, but GROalpha production was not detected by this method.

Summary. Accordance between gene expression levels measured by microarray and PCR (both real-time and conventional) has been established for four genes: oxidized LDL receptor 1, renin, reticulon, and IL-8. The expression of these genes was differentially regulated at the mRNA level in placenta-derived cells, with IL-8 also differentially regulated at the protein level. The presence of oxidized LDL receptor was not detected at the protein level by FACS analysis in cells derived from the placenta. Differential expression of GCP-2 and CXC ligand 3 was not confirmed at the mRNA level, however, GCP-2 was detected at the protein level by FACS analysis in the placenta-derived cells. Although this result may not be fully consistent with data obtained from the microarray experiment, any inconsistency may simply be due to differences in the sensitivity of the methodologies.

Immediately after isolation (passage 0), cells derived from the human placenta stained positive for both alpha-smooth muscle actin and vimentin. This pattern was also observed in cells at passage 11. These results suggest that vimentin and alpha-smooth muscle actin production is preserved in cells with passaging, for example, in the Growth medium used here.

Example 10

Immunohistochemical Characterization of PDC Phenotype

The phenotypes of cells found within human placental tissue was analyzed by immunohistochemistry.

Materials & Methods

Tissue Preparation. Human placenta tissue was harvested and immersion-fixed in 4% (w/v) paraformaldehyde overnight at 4° C. Immunohistochemistry was performed using antibodies directed against the following epitopes (see Table 10-1): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 micron thick) using a standard cryostat (Leica Microsystems) and mounted onto glass slides for staining.

TABLE 10-1

Summary of Primary Antibodies Used

| Antibody | Concentration | Vendor |
| --- | --- | --- |
| Vimentin | 1:500 | Sigma, St. Louis, MO |
| Desmin (rb) | 1:150 | Sigma |
| Desmin (m) | 1:300 | Chemicon, Temecula, CA |
| alpha-smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, CA |

TABLE 10-1-continued

Summary of Primary Antibodies Used

| Antibody | Concentration | Vendor |
| --- | --- | --- |
| GROalpha - PE | 1:100 | BD, Franklin Lakes, NJ |
| GCP-2 | 1:100 | Santa Cruz Biotech |
| Ox-LDL R1 | 1:100 | Santa Cruz Biotech |
| NOGO-A | 1:100 | Santa Cruz Biotech |

Immunohistochemistry. Immunohistochemistry was performed similar to previous studies (e.g., Messina, et al. (2003) Exper. Neurol. 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG—Texas Red (1:250; Molecular Probes, Eugene, Oreg.) and/or goat anti- rabbit IgG—Alexa 488 (1:250; Molecular Probes) or donkey anti-goat IgG—FITC (1:150; Santa Cruz Biotech). Cultures were washed, and 10 microMolar DAPI (Molecular Probes) was applied for 10 minutes to visualize cell nuclei.

Following immunostaining, fluorescence was visualized using the appropriate fluorescence filter on an Olympus inverted epi-fluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Placenta Characterization. Vimentin, desmin, SMA, CK18, vWF, and CD34 were all observed within the placenta and regionally specific.

GROalpha, GCP-2, ox-LDL R1, and NOGO-A Tissue Expression. None of these markers were observed within placental tissue.

Summary. Vimentin, desmin, alpha-smooth muscle actin, cytokeratin 18, von Willebrand Factor, and CD34 are expressed in cells within human placenta.

Example 11

In Vitro Immunology

Postpartum cell lines were evaluated in vitro for their immunological characteristics in an effort to predict the immunological response, if any, these cells would elicit upon in vivo transplantation. Postpartum cell lines were assayed by flow cytometry for the production of HLA-DR, HLA-DP, HLA-DQ, CD80, CD86, and B7-H2. These proteins are expressed by antigen-presenting cells (APC) and are required for the direct stimulation of naïve CD4+ T cells (Abbas & Lichtman, CELLULAR AND MOLECULAR IMMUNOLOGY, 5th Ed. (2003) Saunders, Philadelphia, p. 171). The cell lines were also analyzed by flow cytometry for the production of HLA-G (Abbas & Lichtman, CELLULAR AND MOLECULAR IMMUNOLOGY, 5th Ed. (2003) Saunders, Philadelphia, p. 171), CD 178 (Coumans, et. al., (1999) *Journal of Immunological Methods* 224, 185-196), and PD-L2 (Abbas & Lichtman, CELLULAR AND MOLECULAR IMMUNOLOGY, 5th Ed. (2003) Saunders, Philadelphia, p. 171; Brown, et. al. (2003) *The Journal of Immunology* 170, 1257-1266). The production of these proteins by cells residing in placental tissues is thought to mediate the immuno-privileged status of placental tissues in utero. To predict the extent to which placenta-derived cell lines elicit an immune response in vivo, the cell lines were tested in a one-way mixed lymphocyte reaction (MLR).

Materials and Methods

Cell culture. Cells were cultured in Growth Medium (DMEM-low glucose (Gibco, Carlsbad, Calif.), 15% (v/v) fetal bovine serum (FBS); (Hyclone, Logan, Utah), 0.001% (v/v) betamercaptoethanol (Sigma, St. Louis, Mo.), 50 Units/milliliter penicillin, 50 microgram/milliliter streptomycin (Gibco, Carlsbad, Calif.)) until confluent in T75 flasks (Corning, Corning, N.Y.) coated with 2% gelatin (Sigma, St. Louis, Mo.).

Antibody Staining. Cells were washed in phosphate buffered saline (PBS) (Gibco, Carlsbad, Calif.) and detached with Trypsin/EDTA (Gibco, Carlsbad, Calif.). Cells were harvested, centrifuged, and re-suspended in 3% (v/v) FBS in PBS at a cell concentration of $1 \times 10^7$ per milliliter. Antibody (Table 11-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 11-1

| Antibodies | | |
|---|---|---|
| Antibody | Manufacturer | Catalog Number |
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD 178 | Santa Cruz (San Cruz, CA) | sc-19681 |
| PD-L2 | BD Pharmingen (San Diego, CA) | 557846 |
| Mouse IgG2a | Sigma (St. Louis, MO) | F-6522 |
| Mouse IgG1kappa | Sigma (St. Louis, MO) | P-4685 |

Mixed Lymphocyte Reaction. Cryopreserved vials of passage 11 placenta-derived PDCs labeled as cell line B were sent on dry ice to CTBR (Senneville, Quebec) to conduct a mixed lymphocyte reaction using CTBR SOP no. CAC-031. Peripheral blood mononuclear cells (PBMCs) were collected from multiple male and female volunteer donors. Stimulator (donor) allogeneic PBMC, autologous PBMC, and placenta-derived cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radiolabeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the placenta-derived cell was calculated as the mean proliferation of the receiver plus mitomycin C-treated placenta-derived cell line divided by the baseline proliferation of the receiver.

Results

Mixed Lymphocyte Reaction-Placenta. Seven human volunteer blood donors were screened to identify a single allogeneic donor that would exhibit a robust proliferation response in a mixed lymphocyte reaction with the other six blood donors. This donor was selected as the allogeneic positive control donor. The remaining six blood donors were selected as recipients. The allogeneic positive control donor and placenta cell lines were treated with mitomycin C and cultured in a mixed lymphocyte reaction with the six individual allogeneic receivers. Reactions were performed in triplicate using two cell culture plates with three receivers per plate (Table 11-2). The average stimulation index ranged from 1.3 (plate 2) to 3 (plate 1) and the allogeneic donor positive controls ranged from 46.25 (plate 2) to 279 (plate 1) (Table 11-3).

TABLE 11-2

Mixed Lymphocyte Reaction Data - Cell Line B (Placenta)
DPM for Proliferation Assay

| Analytical number | Culture System | Replicates | | | Mean | SD | CV |
|---|---|---|---|---|---|---|---|
| | | 1 | 2 | 3 | | | |
| Plate ID: Plate1 | | | | | | | |
| IM03-7769 | Proliferation baseline of receiver | 79 | 119 | 138 | 112.0 | 30.12 | 26.9 |
| | Control of autostimulation (Mitomycin C treated autologous cells) | 241 | 272 | 175 | 229.3 | 49.54 | 21.6 |
| | MLR allogenic donor IM03-7768 (Mitomycin C treated) | 23971 | 22352 | 20921 | 22414.7 | 1525.97 | 6.8 |
| | MLR with cell line (Mitomycin C treated cell type B) | 664 | 559 | 1090 | 771.0 | 281.21 | 36.5 |
| SI (donor) | | | | | 200 | | |
| SI (cell line) | | | | | 7 | | |

TABLE 11-2-continued

Mixed Lymphocyte Reaction Data - Cell Line B (Placenta)
DPM for Proliferation Assay

| Analytical number | Culture System | Replicates | | | Mean | SD | CV |
|---|---|---|---|---|---|---|---|
| | | 1 | 2 | 3 | | | |
| IM03-7770 | Proliferation baseline of receiver | 206 | 134 | 262 | 200.7 | 64.17 | 32.0 |
| | Control of autostimulation (Mitomycin C treated autologous cells) | 1091 | 602 | 524 | 739.0 | 307.33 | 41.6 |
| | MLR allogenic donor IM03-7768 (Mitomycin C treated) | 45005 | 43729 | 44071 | 44268.3 | 660.49 | 1.5 |
| | MLR with cell line (Mitomycin C treated cell type B) | 533 | 2582 | 2376 | 1830.3 | 1128.24 | 61.6 |
| SI (donor) | | | | | 221 | | |
| SI (cell line) | | | | | 9 | | |
| IM03-7771 | Proliferation baseline of receiver | 157 | 87 | 128 | 124.0 | 35.17 | 28.4 |
| | Control of autostimulation (Mitomycin C treated autologous cells) | 293 | 138 | 508 | 313.0 | 185.81 | 59.4 |
| | MLR allogenic donor IM03-7768 (Mitomycin C treated) | 24497 | 34348 | 31388 | 30077.7 | 5054.53 | 16.8 |
| | MLR with cell line (Mitomycin C treated cell type B) | 601 | 643 | a | 622.0 | 29.70 | 4.8 |
| SI (donor) | | | | | 243 | | |
| SI (cell line) | | | | | 5 | | |
| IM03-7772 | Proliferation baseline of receiver | 56 | 98 | 51 | 68.3 | 25.81 | 37.8 |
| | Control of autostimulation (Mitomycin C treated autologous cells) | 133 | 120 | 213 | 155.3 | 50.36 | 32.4 |
| | MLR allogenic donor IM03-7768 (Mitomycin C treated) | 14222 | 20076 | 22168 | 18822.0 | 4118.75 | 21.9 |
| | MLR with cell line (Mitomycin C treated cell type B) | a | a | a | a | a | a |
| SI (donor) | | | | | 275 | | |
| SI (cell line) | | | | | a | | |
| IM03-7768 (allogenic donor) | Proliferation baseline of receiver | 84 | 242 | 208 | 178.0 | 83.16 | 46.7 |
| | Control of autostimulation (Mitomycin treated autologous cells) | 361 | 617 | 304 | 427.3 | 166.71 | 39.0 |
| Cell line type B | Proliferation baseline of receiver | 126 | 124 | 143 | 131.0 | 10.44 | 8.0 |
| | Control of autostimulation (Mitomycin treated autologous cells) | 822 | 1075 | 487 | 794.7 | 294.95 | 37.1 |
| Plate ID: Plate 2 | | | | | | | |
| IM03-7773 | Proliferation baseline of receiver | 908 | 181 | 330 | 473.0 | 384.02 | 81.2 |
| | Control of autostimulation (Mitomycin C treated autologous cells) | 269 | 405 | 572 | 415.3 | 151.76 | 36.5 |
| | MLR allogenic donor IM03-7768 (Mitomycin C treated) | 29151 | 28691 | 28315 | 28719.0 | 418.70 | 1.5 |
| | MLR with cell line (Mitomycin C treated cell type B) | 567 | 732 | 905 | 734.7 | 169.02 | 23.0 |
| SI (donor) | | | | | 61 | | |
| SI (cell line) | | | | | 2 | | |
| IM03-7774 | Proliferation baseline of receiver | 893 | 1376 | 185 | 818.0 | 599.03 | 73.2 |
| | Control of autostimulation (Mitomycin C treated autologous cells) | 261 | 381 | 568 | 403.3 | 154.71 | 38.4 |
| | MLR allogenic donor IM03-7768 (Mitomycin C treated) | 53101 | 42839 | 48283 | 48074.3 | 5134.18 | 10.7 |
| | MLR with cell line (Mitomycin C treated cell type B) | 515 | 789 | 294 | 532.7 | 247.97 | 46.6 |
| SI (donor) | | | | | 59 | | |
| SI (cell line) | | | | | 1 | | |
| IM03-7775 | Proliferation baseline of receiver | 1272 | 300 | 544 | 705.3 | 505.69 | 71.7 |
| | Control of autostimulation (Mitomycin C treated autologous cells) | 232 | 199 | 484 | 305.0 | 155.89 | 51.1 |
| | MLR allogenic donor IM03-7768 (Mitomycin C treated) | 23554 | 10523 | 28965 | 21014.0 | 9479.74 | 45.1 |
| | MLR with cell line (Mitomycin C treated cell type B) | 768 | 924 | 563 | 751.7 | 181.05 | 24.1 |
| SI (donor) | | | | | 30 | | |
| SI (cell line) | | | | | 1 | | |
| IM03-7776 | Proliferation baseline of receiver | 1530 | 137 | 1046 | 904.3 | 707.22 | 78.2 |
| | Control of autostimulation (Mitomycin C treated autologous cells) | 420 | 218 | 394 | 344.0 | 109.89 | 31.9 |
| | MLR allogenic donor IM03-7768 (Mitomycin C treated) | 28893 | 32493 | 34746 | 32044.0 | 2952.22 | 9.2 |
| | MLR with cell line (Mitomycin C treated cell type B) | a | a | a | a | a | a |
| SI (donor) | | | | | 35 | | |
| SI (cell line) | | | | | a | | |

TABLE 11-3

Average stimulation index of placenta cells and an allogeneic donor in a mixed lymphocyte reaction with six individual allogeneic receivers.
Average Stimulation Index

| | Recipient | Placenta |
|---|---|---|
| Plate 1 (receivers 1-3) | 279 | 3 |
| Plate 2 (receivers 4-6) | 46.25 | 1.3 |

Antigen Presenting Cell Markers—Placenta. Histograms of placenta-derived cells analyzed by flow cytometry show negative for production of HLA-DR, DP, DQ, CD80, CD86, and B7-H2, as noted by fluorescence value consistent with the IgG control, indicating that placental cell lines lack the cell surface molecules required to directly stimulate allogeneic PBMCs (e.g., CD4$^+$ T cells).

Immuno-modulating Markers—Placenta. Histograms of placenta-derived cells analyzed by flow cytometry show positive for production of PD-L2, as noted by the increased value of fluorescence relative to the IgG control, and negative for production of CD 178 and HLA-G, as noted by fluorescence value consistent with the IgG control.

Summary. In the mixed lymphocyte reactions conducted with placenta-derived cell lines, the average stimulation index ranged from 1.3 to 3, and that of the allogeneic positive controls ranged from 46.25 to 279. Placenta-derived cell lines were negative for the production of the stimulating proteins HLA-DR, HLA-DP, HLA-DQ, CD80, CD86, and B7-H2, as measured by flow cytometry. Placenta-derived cell lines were negative for the production of immuno-modulating proteins HLA-G and CD 178 and positive for the production of PD-L2, as measured by flow cytometry. Allogeneic donor PBMCs contain antigen-presenting cells expressing HLA-DP, DR, DQ, CD80, CD86, and B7-H2, thereby allowing for the stimulation of allogeneic PBMCs (e.g., naïve CD4+ T cells). The absence of antigen- presenting cell surface molecules on placenta-derived cells required for the direct stimulation of allogeneic PBMCs (e.g., naïve CD4+ T cells) and the presence of PD-L2, an immunomodulating protein, may account for the low stimulation index exhibited by these cells in a MLR as compared to allogeneic controls.

Example 12

Secretion of Trophic Factors by Placenta-Derived Cells

The secretion of selected trophic factors from PDCs was measured. Factors were selected that have angiogenic activity (i.e., hepatocyte growth factor (HGF) (Rosen et al. (1997) *Ciba Found. Symp.* 212:215-26), monocyte chemotactic protein 1 (MCP-1) (Salcedo et al. (2000) *Blood* 96;34-40), interleukin-8 (IL-8) (Li et al. (2003) *J. Immunol.* 170:3369-76), keratinocyte growth factor (KGF), basic fibroblast growth factor (bFGF), vascular endothelial growth factor (VEGF) (Hughes et al. (2004) *Ann. Thorac. Surg.* 77:812-8), tissue inhibitor of matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1alpha (SDF-1 alpha)), neurotrophic/neuroprotective activity (brain-derived neurotrophic factor (BDNF) (Cheng et al. (2003) *Dev. Biol.* 258;319-33), interleukin-6 (IL-6), granulocyte chemotactic protein-2 (GCP-2), transforming growth factor beta2 (TGFbeta2)), or chemokine activity (macrophage inflammatory protein 1alpha (MIP1a), macrophage inflammatory protein 1beta (MIP1b), monocyte chemoattractant-1 (MCP- 1), Rantes (regulated on activation, normal T cell expressed and secreted), I309, thymus and activation-regulated chemokine (TARC), Eotaxin, macrophage-derived chemokine (MDC), IL-8).

Methods & Materials

Cell culture. PDCs derived from placenta and human fibroblasts derived from human neonatal foreskin were cultured in Growth Medium (DMEM-low glucose (Gibco, Carlsbad, Calif.), 15% (v/v) fetal bovine serum (SH30070.03; Hyclone, Logan, Utah), 50 Units/milliliter penicillin, 50 microgram/milliliter streptomycin (Gibco)) on gelatin- coated T75 flasks. Cells were cryopreserved at passage 11 and stored in liquid nitrogen. After thawing of the cells, Growth Medium was added to the cells followed by transfer to a 15 milliliter centrifuge tube and centrifugation of the cells at 150×g for 5 minutes. The supernatant was discarded. The cell pellet was resuspended in 4 milliliters Growth Medium, and cells were counted. Cells were seeded at 5,000 cells/cm$^2$ on a T75 flask containing 15 milliliters of Growth Medium and cultured for 24 hours. The medium was changed to a serum-free medium (DMEM-low glucose (Gibco), 0.1% (w/v) bovine serum albumin (Sigma), 50 Units/milliliter penicillin, 50 microgram/milliliter streptomycin (Gibco)) for 8 hours. Conditioned serum-free media was collected at the end of incubation by centrifugation at 14,000×g for 5 minutes and stored at −20° C. To estimate the number of cells in each flask, cells were washed with phosphate-buffered saline (PBS) and detached using 2 milliliters trypsin/EDTA (Gibco). Trypsin activity was inhibited by addition of 8 milliliters Growth Medium. Cells were centrifuged at 150×g for 5 minutes. Supernatant was removed, and cells were resuspended in 1 milliliter Growth Medium. Cell number was estimated using a hemocytometer.

ELISA assay. Cells were grown at 37° C. in 5% carbon dioxide and atmospheric oxygen. PDCs (isolate 3) also were grown in 5% oxygen or beta-mercaptoethanol (BME). The amount of MCP-1, IL-6, VEGF, SDF-1alpha, GCP-2, IL-8, and TGF- beta2 produced by each cell sample was measured by an ELISA assay (R&D Systems, Minneapolis, Minn.). All assays were performed according to the manufacturer's instructions. Values presented are picogram/milliliter/million cells (n=2, sem).

SEARCHLIGHT Multiplexed ELISA assay. Chemokines (MIP1a, MIP1b, MCP-1, Rantes, 1309, TARC, Eotaxin, MDC, IL8), BDNF, and angiogenic factors (HGF, KGF, bFGF, VEGF, TIMP1, ANG2, PDGF-bb, TPO, HB-EGF were measured using SEARCHLIGHT Proteome Arrays (Pierce Biotechnology Inc.). The Proteome Arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a sandwich ELISA procedure, the entire plate is imaged to capture chemiluminescent signal generated at each spot within each well of the plate. The amount of signal generated in each spot is proportional to the amount of target protein in the original standard or sample.

Results

ELISA assay. MCP-1 and IL-6 were secreted by placenta-derived PDCs and dermal fibroblasts (Table 12-1). SDF-1 alpha was secreted by placenta-derived cells cultured in 5% O$_2$ and by fibroblasts. GCP-2 and IL-8 were secreted by placenta- derived cells cultured in the presence of BME or 5% O$_2$. GCP-2 also was secreted by human fibroblasts. TGF-beta2 was not detectable by ELISA assay.

TABLE 12-1

ELISA assay results

| | MCP-1 | IL-6 | VEGF | SDF-1alpha | GCP-2 | IL-8 | TGF-beta2 |
|---|---|---|---|---|---|---|---|
| Fibroblast | 17 ± 1 | 61 ± 3 | 29 ± 2 | 19 ± 1 | 21 ± 1 | ND | ND |
| Placenta - isolate 1 | 60 ± 3 | 41 ± 2 | ND | ND | ND | ND | ND |
| Placenta - isolate 2 | 125 ± 16 | 10 ± 1 | ND | ND | ND | ND | ND |
| Placenta - isolate 3, + BME | 21 ± 10 | 67 ± 3 | ND | ND | 44 ± 9 | 17 ± 9 | ND |

TABLE 12-1-continued

| | ELISA assay results | | | | | | |
|---|---|---|---|---|---|---|---|
| | MCP-1 | IL-6 | VEGF | SDF-1alpha | GCP-2 | IL-8 | TGF-beta2 |
| Placenta - isolate 3, +5% $O_2$, W/O BME | 77 ± 16 | 339 ± 21 | ND | 1149 ± 137 | 54 ± 2 | 265 ± 10 | ND |

Key:
ND: Not Detected.

SEARCHLIGHT Multiplexed ELISA assay. TIMP1, TPO, KGF, HGF, HBEGF, BDNF, MIP1a, MCP-1, RANTES, TARC, Eotaxin, and IL-8 were secreted from placenta-derived cells (Tables 12-2 and 12-3). No Ang2, VEGF, or PDGF-bb were detected.

TABLE 12-2

| | SEARCHLIGHT Multiplexed ELISA assay results | | | | | | | | |
|---|---|---|---|---|---|---|---|---|---|
| | TIMP1 | ANG2 | PDGFbb | TPO | KGF | HGF | FGF | VEGF | HBEGF | BDNF |
| HFB | 19306.3 | ND | ND | 230.5 | 5.0 | ND | ND | 27.9 | 1.3 | ND |
| P1 | 24299.5 | ND | ND | 546.6 | 8.8 | 16.4 | ND | ND | 3.8 | ND |
| P3 | 14176.8 | ND | ND | 568.7 | 5.2 | 10.2 | ND | ND | 1.9 | 33.6 |

Key:
hFB (human fibroblasts), P1 (placenta-derived cells - isolate 1), P3 (placenta-derived cells 0 isolate 3).
ND: Not Detected.

TABLE 12-3

| | SEARCHLIGHT Multiplexed ELISA assay results | | | | | | | |
|---|---|---|---|---|---|---|---|---|
| | MIP1a | MIP1b | MCP1 | RANTES | I309 | TARC | Eotaxin | MDC | IL8 |
| HFB | ND | ND | 39.6 | ND | ND | 0.1 | ND | ND | 204.9 |
| P1 | 79.5 | ND | 228.4 | 4.1 | ND | 3.8 | 12.2 | ND | 413.5 |
| P3 | ND | ND | 102.7 | ND | ND | 0.4 | ND | ND | 63.8 |

Key:
hFB (human fibroblasts), P1 (placenta-derived cells - isolate 1), P3 (placenta-derived cells - isolate 3).
ND: Not Detected.

Summary. Placenta-derived cells secreted a number of trophic factors. Some of these trophic factors, such as HGF, MCP-1, and IL-8, play important roles in angiogenesis. Other trophic factors, such as BDNF and IL-6, have important roles in neural regeneration.

Example 13

Plasma Clotting Assay

Cell therapy may be injected systemically for certain applications where cells are able to target the site of action. It is important that injected cells not cause thrombosis, which may be fatal. Tissue factor, a membrane-bound pro-coagulant glycoprotein, is the initiator of the extrinsic clotting cascade, which is the predominant coagulation pathway in vivo. Tissue factor also plays an important role in embryonic vessel formation, for example, in the formation of the primitive vascular wall (Brodsky et al. (2002) Exp. Nephrol. 10:299-306). To determine the potential for PPDCs to initiate clotting, placenta-derived PPDCs were evaluated for tissue factor production and their ability to initiate plasma clotting.

Methods & Materials

Human Tissue factor. Human tissue factor SIMPLASTIN (Organon Tekailca Corporation, Durham, N.C.), was reconstituted with 20 milliliters distilled water. The stock solution was serially diluted (1:2) in eight tubes. Normal human plasma (George King Bio- Medical, Overland Park, Kans.) was thawed at 37° C. in a water bath and then stored in ice before use. To each well of a 96-well plate was added 100 microliters phosphate buffered saline (PBS), 10 microliters diluted SIMPLASTIN (except a blank well), 30 microliters 0.1 Molar calcium chloride, and 100 microliters of normal human plasma. The plate was immediately placed in a temperature-controlled microplate reader and absorbance measured at 405 nanometer at 40 second intervals for 30 minutes.

J-82 and placenta-derived cells. J-82 cells (ATCC, MD) were grown in Iscove's modified Dulbecco's medium (IMDM; Gibco, Carlsbad, Calif.) containing 10% (v/v) fetal bovine serum (FBS; Hyclone, Logan Utah), 1 milliMolar sodium pyruvate (Sigma Chemical, St. Louis, Mo.), 2 milliMolar L-Glutamin (Mediatech Herndon, Va.), 1×non-essential amino acids (Mediatech Herndon, Va.). At about 70% confluence, cells were transferred to wells of 96-well plate at 100,000, 50,000 and 25,000 cells/well. Placenta-derived cells were cultured in Growth Medium (DMEM-low glucose (Gibco), 15% (v/v) FBS, 50 Units/milliliter penicillin, 50 microgram/milliliter streptomycin (Gibco), and 0.001% betamercaptoethanol (Sigma)) in gelatin-coated T75 flasks (Corning, Corning, N.Y.). Placenta-derived cells at passage 5 were transferred to wells at 50,000 cells/well. Culture medium was removed from each well after centrifugation at 150×g for 5 minutes. Cells were suspended in PBS without calcium and magnesium.

Tissue factor inhibition. Inhibition of the clotting reaction by preincubation of cells with CNTO 859, an antibody to tissue factor, will demonstrate that tissue factor is responsible for the clotting. Cells are incubated with 20 microgram/milliliter CNTO 859 (Centocor, Malvern, Pa.) for 30 minutes. Calcium chloride (30 microliter) is added to each well. The plate is immediately placed in a temperature-controlled microplate reader and absorbance measured at 405 nanometer at 40 second intervals for 30 minutes. Cells are washed in PBS and detached from the flask with Trypsin/EDTA (Gibco Carlsbad, Calif.). Cells are harvested, centrifuged, and re-suspended 3% (v/v) FBS in PBS at a cell concentration of $1 \times 10^7$ per milliliter. Antibody is added to 100 microliter cell suspension as per the manufacturer's specifications, and the cells are incubated in the dark for 30 minutes at 4° C. After incubation, cells are washed with PBS and centrifuged at 150×g for 5 minutes to remove unbound antibody. Cells are re-suspended in 100 microliter of 3% FBS and secondary antibody added as per the manufacturer's instructions. Cells are incubated in the dark for 30 minutes at 4° C. After incubation, cells are washed with PBS and centrifuged to remove unbound secondary antibody. Washed cells are re-suspended in 500 microliter of PBS and analyzed by flow cytometry.

Results

Flow cytometry analysis revealed that placenta-derived postpartum cells express tissue factor. Placenta-derived cells increased the clotting rate as indicated by the time to half maximal absorbance (T ½ to max; Table 13-1). The T ½ to max is inversely proportional to the number of J82 cells.

TABLE 13-1

The effect of human tissue factor (SIMPLASTIN) and placenta-derived cells (Pla) on plasma clotting was evaluated. The time to half maximal absorbance (T ½ to max) at the plateau in seconds was used as a measurement unit.

| SIMPLASTIN Dilution | T ½ to max (seconds) |
|---|---|
| 1:2 | 61 |
| 1:4 | 107 |
| 1:8 | 147 |
| 1:16 | 174 |
| 1:32 | 266 |
| 1:64 | 317 |
| 1:128 | 378 |
| 0 (negative control) | 1188 |
| J-82 cells | |
| 100,000 | 122 |
| 50,000 | 172 |
| 25,000 | 275 |
| Pla P5 | |
| 50,000 | 757 |

Summary. Placenta-derived cells express tissue factor. Tissue factor is normally found on cells in a conformation that is inactive but is activated by mechanical or chemical (e.g., LPS) stress (Sakariassen et al. (2001) *Thromb. Res.* 104:149-74; Engstad et al. (2002) *Int. Immunopharmacol.* 2:1585-97). Thus, minimization of stress during the preparation process of PDCs may prevent activation of tissue factor. In addition to the thrombogenic activity, tissue factor has been associated with angiogenic activity. Thus, tissue factor activity may be beneficial when placenta-derived cells are transplanted in tissue but should be inhibited when PDCs are injected intravenously.

Example 14

Differentiation of Placenta-Derived Cells into Hepatocytes

A variety of conditions were examined to determine a suitable combination of basic media and growth factors for the differentiation of placenta-derived cells into hepatocytes. HNF-1alpha, a hepatocyte-specific transcription factor, cytoplasmic intermediate filament proteins such as keratin 19 (K 9), keratin 8 (K8), and cytokeratin 18 (CK18), which are markers of epithelial cells and two liver-specific secreted proteins, alpha-fetoprotein (alphaFP), and albumin were selected as markers for hepatocyte differentiation (Schwartz et al. (2002) *J. Clin. Invest.* 109(10):1291-1302; Okumoto et al. (2003) *Biochem. Biophys. Res. Commun.* 304(4):691-695; Chagraoui et al. (2003) *Blood* 101(8): 2973-2982).

Methods & Materials

Placenta-derived cells isolated according to the method described in Example 1, as well as neonatal or adult Normal Human Dermal Fibroblasts (NHDF) were grown in Growth medium (DMEM-low glucose (Gibco, Carlsbad, Calif.), 15% (v/v) fetal bovine serum (Cat. #SH30070.03; Hyclone, Logan Utah), 0.001% (v/v) beta-mercaptoethanol (Sigma, St. Louis, Mo.), 50 Units/milliliter penicillin, 50 microgram/milliliter streptomycin (Gibco)), in a gelatin-coated T75 flask. Basic Fibroblast Growth Factor (bFGF), Oncostatin M, Hepatocyte Growth Factor (HGF), Stem Cell Factor (SCF), and Fibroblast Growth Factor 4 (FGF 4) were from PeproTech Inc. (Rocky Hill, N.J.). Platelet Derived Growth Factor BB (PDGF-BB) was from R&D Systems (Minneapolis, Minn.).

The following conditions were tested:

Method 1

Placenta-derived cells (P2) (predominately neonatal as analyzed by karyotyping), neonatal and adult Normal Human Dermal Fibroblasts (NHDF). Cells were plated at $22.5 \times 10^3$ cells/cm$^2$ on 1% MATRIGEL (BD Discovery Labware, Bedford, Mass.) (Becton-Dickinson and Co., Franklin Lakes, N.J.) in serum-free medium (60% (v/v) low glucose DMEM) (DMEM-LG; Gibco, Carlsbad, Calif.), 40% (v/v) MCDB-201 (Sigma, St. Louis, Mo.), supplemented with 1× insulin/transferrin/selenium, 4.7 microgram/milliliter linoleic acid, 1 milligram/milliliter bovine serum albumin, 10 nanoMolar Dexamethasone, 100 microMolar ascorbic acid phosphate (all from Sigma), 100 Units/milliliter penicillin, 100 Units/milliliter streptomycin (Gibco), 2% (v/v) FCS (Hyclone Laboratories, Logan, Utah), and 10 nanogram/milliliter each EGF and PDGF-BB). After 8 to 12 hours, medium was removed, cells were washed twice with PBS (Gibco) and cultured in the above-described medium without EGF and PDGF-BB but supplemented with 20 nanogram/milliliter HGF and/or 10 nanogram/milliliter FGF-4 (Schwartz et al. (2002) *J. Clin. Invest.* 109(10):1291-1302). Cells were cultured in standard air with 5% $CO_2$ at 37° C.

Method 2

Placenta-derived cells (P2) (predominately neonatal as analyzed by karyotyping), neonatal and adult NHDF. Cells were seeded at 22,500 cells/cm$^2$ in 24-well plates coated with gelatin and grown as described above.

Method 3

Placenta-derived cells (P10), adult NHDF, Placenta-derived cells (P3). Cells were seeded at high density (50,000 cells/cm²) in 24-well TCP plates and grown in DMEM (Gibco), B27 Supplement (Gibco), 50 Units/milliliter penicillin, 50 microgram/milliliter streptomycin, 20 nanograms/milliliter HGF and/or 10 nanograms/milliliter FGF-4. Cells were grown in these conditions for 4 weeks.

Method 4

Placenta-derived cells (P3), Placenta-derived cells (P15), Placenta-derived cells (P2) (predominately neonatal as analyzed by karyotyping), Placenta-derived cells (PS) (predominately neonatal as analyzed by karyotyping), Placenta-derived cells (P5) (predominately maternal as analyzed by karyotyping), neonatal and adult NHDF. Cells were seeded at a density of 5,000 cells/cm² in T25 flasks in Chang C medium (Irvine Scientific, Santa Ana, Calif.) on either fibronectin (PeproTech, Rocky Hill, N.J.) or gelatin (Sigma) and grown for two passages until confluence. Cells were then seeded at 1,000 cells/cm² in 24-well TCPS plates and grown as described above until they reached about 40-60% confluence.

Method 5

Placenta-derived cells (P2) (predominately neonatal as analyzed by karyotyping), and adult NHDF. Cells were plated in 24-well plates on gelatin in Growth medium supplemented with either 1 nanogram/milliliter or 10 nanogram/milliliter oncostatin M (Chagraoui (2003) *Blood* 101 (8): 2973-2982). Cells were grown in these conditions for 4 weeks.

Method 6

Placenta-derived cells (P2)(predominately neonatal as analyzed by karyotyping), and adult NHDF. Cells were plated in 24-well plates on gelatin in Growth medium supplemented with 10 nanogram/milliliter bFGF, 10 nanogram/milliliter HGF, 10 nanogram/milliliter SCF. Cells were grown in these conditions for 4 weeks (Okumoto et al. (2003) *Biochem. Biophys. Res. Commun.* 304(4):691-695.).

Total RNA isolation and quantitative RT-PCR. RNA was extracted from placenta-derived cells and fibroblasts grown as described in each protocol. Cells were lysed with 350 microliter buffer RLT containing beta-mercaptoethanol (Sigma St. Louis, Mo.) according to the manufacturer's instructions (RNeasy Mini Kit, Qiagen, Valencia, Calif.) and RNA extracted according to the manufacturer's instructions (RNeasy Mini Kit, Qiagen, Valencia, Calif.) with a 2.7 Units/sample DNase treatment (Sigma). RNA was eluted with 50 microliter DEPC- treated water and stored at −80° C. RNA was reverse transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Real-time PCR. PCR was performed on cDNA samples using ASSSAYS-ON-DEMAND gene expression products for albumin (Hs00609411), cytochrome p450 2B6 (Hs00167937), GAPDH (Applied Biosystems, Foster City, Calif.) and TaqMan Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 min and 95° C. for 10 minute followed by 40 cycles of 95° C. for 15 seconds and 60° C. for 1 minute. PCR data were analyzed according to manufacturer's specifications (User Bulletin #2 from Applied Biosystems for ABI Prism 7700 Sequence Detection System).

Immunofluorescence. Cell cultures were fixed with cold 4% (w/v) paraformaldehyde for a period of 10 minutes at room temperature. Immunocytochemistry was performed using antibodies directed against the following epitopes: keratin 8 (K8; 1:400; Chemicon, Temecula, Calif.), keratin 19 (K19; 1:400; Chemicon), cytokeratin 18 (CK18; 1:400; Sigma, St. Louis, Mo.), vimentin (1:500; Sigma), desmin (1:150; Sigma), albumin (1:200; Sigma), c-met (1:400; Santa Cruz Biotech, Santa Cruz, Calif.), and HNF-1alpha (1:400; Santa Cruz Biotech). In general, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100, Sigma) for 30 minutes to access intracellular antigens. In instances where the epitope of interest would be located on the cell surface (c-met), triton was omitted in all steps of the procedure in order to prevent epitope loss. Primary antibodies, diluted in blocking solution, were then applied to the cultures for a period of 1 hour at room temperature. Next, primary antibody solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) for K8, K19, CK18, vimentin, and albumin, goat anti-rabbit IgG—Alexa 488 (1:250; Molecular Probes) for desmin and c-met, or donkey anti-goat IgG—FITC (1:150; Santa Cruz Biotech) for HNF-1alpha staining. Cultures were washed and 10 microMolar DAPI (Molecular Probes) was applied for 10 minutes to visualize cell nuclei.

Following immunostaining, fluorescence was visualized using the appropriate fluorescence filter on an Olympus inverted epi-fluorescent microscope (Olympus, Melville, N.Y.). Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

In order to determine whether placenta-derived cells could express epithelial markers, cells were cultured in Chang C medium. Placenta-derived cells (P4), (P3), and (P8) were grown in Chang C medium for 11 days. Placenta-derived cells stained positive for cytokeratin 18 by immunocytochemistry analysis. None of the samples stained positive for keratin 8. Samples grown in Growth medium were negative for both markers.

The effect of early and late passages as well as gelatin and fibronectin substrata was investigated. Cells were grown in Chang C medium for 11 days. RNA and protein expression of epithelial/hepatocyte-specific proteins were analyzed. Immunocytochemistry staining for cytokeratinl8, keratin 8, keratin 19, c-met, albumin, desmin, and HNF-1alpha were negative in all conditions. Cells stained positive for vimentin. Expression of both albumin and cytochrome p450 2B6 at levels lower than that of human HepG2 cells was detected with assay-on-demand primers. Albumin and cytochrome p450 2B6 expression also were detected in cells grown in Growth medium.

Placenta-derived cells were treated as described in method 1 according to a protocol developed by Schwartz et al. (2002) *J. Clin. Invest.* 109(10):1291-1302.). Both albumin and cytochrome p450 2B6 were detected with assay-on-demand primers at levels lower than HepG2 positive control. No clear pattern emerged between conditions applied and gene expression levels, i.e., albumin and cytochrome p450 2B6 expression was also detected in control samples. Some expression of albumin and cytochrome p450 2B6 was detected with ASSAY-ON-DE- MAND primers however the levels were significantly lower than those observed in human HepG2 cells.

Oncostatin M at low concentration of 1 nanogram/milliliter increased expression levels of cytochrome p450 2B6 in placenta-derived cells grown in Growth medium on gelatin-coated flasks. FGF-4 and HGF treatment had little effect and may have reduced the expression of albumin and cytochrome p450 2B6.

Summary. Several differentiation protocols were tested for ability to induce differentiation of placenta-derived cells to hepatocyte phenotype. Expression of hepatocyte- specific markers such as albumin and cytochrome p450 2B6 was detected, thereby indicating that the cells underwent some differentiation into hepatocytes. Placenta-derived cells cultured in Chang C medium expressed cytokeratin 18, a marker of epithelial cells in the lower or pancreatic ducts.

Example 15

Differentiation of Placenta-Derived Cells to an Osteogenic Phenotype

Mesenchymal stem cells (MSCs) derived from bone marrow have been demonstrated to reproducibly differentiate into osteoblast-like cells that mineralize and express alkaline phosphatase. Additional markers expressed by osteoblasts, such as osteocalcin and bone sialoprotein, have been used to demonstrate differentiation into an osteoblast-like cell. The ability of placenta-derived cells to differentiate into an osteogenic phenotype was evaluated by culturing in an osteogenic medium and addition of bone morphogenic proteins (BMP) –2 (Rickard et al. (1994) Dev. Biol. 161,:218-228) or –4 and transforming growth factor beta1.

Methods & Materials

Culture of cells. Prior to initiation of osteogenesis, Mesenchymal Stem Cells (MSC) were grown in Mesenchymal Stem Cell Growth Medium Bullet kit (MSCGM, Cambrex, Walkerville, Md.). Other cells were cultured in Growth medium (DMEM-low glucose (Gibco, Carlsbad, Calif.), 15% (v/v) fetal bovine serum (SH30070.03; Hyclone, Logan, Utah), 0.001% (v/v) betamercaptoethanol (Sigma, St. Louis, Mo.), 50 Units/milliliter penicillin, 50 microgram/milliliter streptomycin (Gibco)) in a gelatin-coated T75 flask and were washed with phosphate buffered saline (PBS).

Osteoblasts (9F1721; Cambrex) were grown in osteoblast growth medium (Cambrex) and RNA was extracted as described below.

Osteogenesis

Protocol 1. Placenta-derived cells (P3) and (P4) (previously karyotyped and shown to be predominantly neonatal-derived cells) and MSCs (P3) were seeded at 5×10$^3$ cells/cm$^2$ in 24-well plates and 6-well dishes in Growth medium and incubated overnight. The medium was removed and replaced with Osteogenic medium (DMEM-low glucose, 10% (v/v) fetal bovine serum, 10 milliMolar betaglycerophosphate (Sigma), 100 nanoMolar dexamethasone (Sigma, St. Louis, Mo.), 50 microMolar ascorbate phosphate salt (Sigma), fungizone (Gibco), 50 Units/milliliter penicillin, 50 microgram/milliliter streptomycin (Gibco)). Osteogenic medium was supplemented with 20 nanogram/milliliter TGF-beta1 (Sigma), 40 nanogram/milliliter hrBMP-2 (Sigma) or 40 nanogram/milliliter hrBMP-4 (Sigma). Cultures were treated for a total of 14, 21, and 28 days, with media changes every 3-4 days.

Protocol 2. Placenta-derived cells were tested for the ability to differentiate into an osteogenic phenotype. Placenta-derived cells (P4) were seeded at 30,000 cells/well of a 6-well plate (gelatin-coated) in Growth medium. Mesenchymal stem cells (MSC) (P3 and P4), fibroblasts (P11), and iliac crest bone marrow cells (P3; International PCT Publication No. WO03/025149) were seeded at 30,000 cells/well of a 6 well plate (gelatin-coated) in mesenchymal stem cell growth medium (MSCGM, Cambrex) and Growth medium, respectively.

Osteogenic induction was initiated by removing the initial seeding media (24 h) and replacing it with osteogenic induction medium: DMEM-low glucose, 10% fetal bovine serum, 10 millimolar betaglycerophosphate (Sigma), 100 nanoMolar dexamethasone (Sigma), 50 microMolar ascorbate phosphate salt (Sigma), 50 Units/milliliter penicillin, 50 microgram/milliliter streptomycin (Gibco). In some conditions, osteogenic medium was supplemented with human recombinant (hr) BMP-2 (20 nanogram/milliliter) (Sigma,) or hrBMP-4 or with both hrBMP-2 (20 nanogram/milliliter) and hrBMP-4 (20 nanogram/milliliter) (Sigma). Cultures were treated for a total of 28 days with media changes every 3-4 days.

RNA extraction and Reverse Transcription. Cells were lysed with 350 microliter buffer RLT containing betamercaptoethanol (Sigma, St. Louis, Mo.) according to the manufacturer's instructions (RNeasy Mini kit, Qiagen, Valencia, Calif.) and stored at –80° C. Cell lysates were thawed and RNA extracted according to the manufacturer's instructions (RNeasy Mini kit, Qiagen, Valencia, Calif.) with a 2.7 Unit/sample DNase treatment (Sigma St. Louis, Mo.). RNA was eluted with 50 micoliter DEPC-treated water and stored at –80° C. RNA was reverse transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at –20° C.

PCR. PCR was performed on cDNA samples using ASSAYS-ON-DEMAND gene expression products bone sialoprotein (Hs00173720), osteocalcin (Hs00609452), GAPDH (Applied Biosystems, Foster City, Calif.), and TaqMan Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 minutes and 95° C. for 10 minutes followed by 40 cycles of 95° C. for 15 seconds and 60° C. for 1 minute.

von Kossa Staining. Cells were fixed with 10% (v/v) neutral buffered formalin (Richard-Allan, Kalamazoo, Mich.). After fixation, the cells were washed in deionized water and incubated in 5% (w/v) silver nitrate (Aldrich Chemical Company Milwaukee, Wis.) for one hour in direct sunlight. Cells were washed in deionized water and incubated in 5% (w/v) sodium thiosulfate (EM Sciences, Gibbstown, N.J.) for five minutes. Cells were then washed in distilled water and examined by light microscopy.

Results

Protocol 1. RNA extracted from osteoblasts was used as a positive control for the real-time gene expression of osteocalcin and bone sialoprotein. Osteoblast expression levels of osteocalcin and BSP relative to placenta-derived cells grown in growth medium were 2.5- and 8000-fold, respectively. MSCs grown in the osteogenic medium mineralized and gave positive von Kossa staining. MSC expression of osteocalcin and BSP was significantly increased in osteogenic medium at 21 days. The addition of BMP-2 and -4 enhanced BSP expression but had no effect on osteocalcin expression. TGF-beta1 did not augment the effect of osteogenesis medium. Extensive mineralization was observed with one placenta sample (P4) that had predominantly neonatal-derived cells. Placenta-derived cells (P3) showed induction of BSP expression levels in osteogenic media and low levels of osteocalcin induction. BMP-4 and TGF-beta1 increased osteocalcin expression by placenta-derived cells (P3).

Protocol 2. Osteogenic differentiation, as shown by positive von Kossa staining for mineralization, was observed with placenta-derived cells (P4) and ICBM (P3) incubated with osteogenic medium supplemented with BMP2 or 4, and MSCs (P3) incubated with osteogenic medium supplemented with BMP 4 (Table 15-1). None of the other cells differentiated into the osteogenic phenotype and stained by von Kossa. To ensure that von Kossa staining was related to the cell and not extracellular matrix, cells were counterstained with nuclear fast red. This stain demonstrated large lipid droplets in some MSCs consistent with an adipocyte phenotype. This suggests that MSCs do not differentiate specifically into an osteogenic phenotype in these conditions. Furthermore, the level of adipogenesis was seen to increase when MSCs were incubated in osteogenic medium supplemented with either BMP2 or BMP4.

TABLE 15-1

Results of osteogenic differentiation using von Kossa staining for Protocol 2. Placenta-derived cells (Pla), mesenchymal stem cells (MSC), fibroblasts (Fib), and iliac crest bone marrow cells (ICBM) cells were cultured in osteogenic medium (OM) alone or supplemented with BMP2 or BMP2 and BMP4.

| Number | Cell Line | Conditions | Von Kossa | Comments |
|---|---|---|---|---|
| 1 | ICBM P3 | Osteogenic medium (OM) | Neg | Normal O2 |
| 2 | ICBM P3 | OM, BMP2 | Pos | Normal O3 |
| 3 | ICBM P3 | OM, BMP4 | Pos | Normal O4 |
| 4 | MSC | Osteogenic medium (OM) | Neg | lots of fat |
| 5 | MSC | OM, BMP2 | Neg | lots of fat |
| 6 | MSC | OM, BMP4 | Pos | lots of fat |
| 7 | Pla P4 | Osteogenic medium (OM) | Neg | |
| 8 | Pla P4 | OM, BMP2 | Pos | |
| 9 | Pla P4 | OM, BMP4 | Pos | |
| 10 | MSC P4 | Osteogenic medium (OM) | Neg | Fat |
| 11 | MSC P4 | OM, BMP2 | Neg | Fat |
| 12 | MSC P4 | OM, BMP2, BMP4 | Neg | Fat |
| 13 | Pla P4 | Osteogenic medium (OM) | Neg | |
| 14 | Pla P4 | OM, BMP2 | Neg | |
| 15 | Pla P4 | OM, BMP2, BMP4 | Neg | |
| 16 | Fib 1F1853 P11 | Osteogenic medium (OM) | Neg | |
| 17 | Fib 1F1853 P11 | OM, BMP2 | Neg | |
| 18 | Fib 1F1853 P11 | OM, BMP2, BMP4 | Neg | |

Summary. Bone marrow-derived MSCs (Kadiyala et al. (1997) *Cell Transplant* 6:125-34) as well as cells derived from other tissue such as adipose (Halvorsen et al. (2001) *Tissue Eng.* 7:729-41) have been shown to differentiate into an osteoblast-like cell. MSCs have also been shown to differentiate into adipocytes or osteoblasts in response to BMPs (Chen et al. (1998) *J. Cell Biol.* 142:295-305) due to differential roles for bone morphogenic protein (BMP) receptor type IB and IA. Placenta-derived cells are also capable of expressing an osteoblast-like phenotype as previously observed with bone marrow-derived mesenchymal stem cells (MSCs) when placed in osteogenic medium containing dexamethasone, B-glycerophosphate, and ascorbic acid. Several experiments were conducted with different isolates to determine whether there was mineralization of the cultured cells by von Kossa staining and expression of bone sialoprotein (BSP) and osteocalcin, which are expressed in osteoblasts. Following induction of osteogenesis, MSCs were demonstrated to mineralize and stain with von Kossa and also have increased mRNA levels of bone sialoprotein and osteocalcin expression using real-time relative quantitation. Numerous MSCs also formed lipid droplets in the cytoplasm similar to adipocytes. Placenta-derived cells (predominantly neonatal cells) showed extensive mineralization and induction of BSP and osteocalcin in osteogenic medium, which was enhanced at 21 days with BMP-2 or -4.

Example 16

Chondrogenic Differentiation of Placenta-Derived Cells

Placenta-derived cells were tested for their ability to differentiate into chondrocytes in vitro in two different assay systems: the pellet assay culture system and collagen gel cultures. The pellet culture system has been used successfully with selected lots of human mesenchymal stem cells (MSC). MSC grown in this assay and treated with transforming growth factor-beta3 have been shown to differentiate into chondrocytes (Johnstone, et al. (1998) *Exp. Cell Res.* 238:265-272). The collagen gel system has been used to culture chondrocytes in vitro (Gosiewska, et al. (2001) *Tissue Eng.* 7:267-277.). Chondrocytes grown under these conditions form a cartilage-like structure.

Materials and Methods

Cell Culture Human placentas were received and cells were isolated as described (Example 1). Cells were cultured in Growth medium (Dulbecco's Modified Essential Media (DMEM), 15% (v/v) fetal bovine serum (Hyclone, Logan Utah), 50 Units/milliliter penicillin, 50 microgram/milliliter streptomycin (Invitrogen, Carlsbad, Calif.), 0.001% (v/v) 2-mercaptoethanol (Sigma, St. Louis, Mo.)) on gelatin-coated tissue culture plastic flasks. The cultures were incubated at 37° C. with 5% $CO_2$. For use in experiments, cells were between passages 4 and 12.

Human articular chondrocytes were purchased from Cambrex (Walkersville, Md.) and cultured in the same media as the placenta-derived cells. Twenty-four hours before the experiment, the culture media was changed to a media containing 1% FBS.

Human mesenchymal stem cells (MSCs) were purchased from Cambrex (Walkersville, Md.) and cultured in MSCGM (Cambrex). Cells used for experiments were between passages 2 and 4.

Collagen gel assays. Cultured cells were trypsinized to remove from culture plate. Cells were washed with centrifugation twice at 300×g for 5 min in DMEM without serum and counted. Cells were mixed with the following components at the final concentrations listed: rat tail collagen (1 milligram/milliliter, BD DiscoveryLabware, Bedford, Mass.), 0.01 Normal NaOH, and Chondrogenic medium (DMEM, 100 Units/milliliter penicillin, 100 microgram/milliliter streptomycin, 2 millimolar L-Glutamine, 1 millimolar Sodium Pyruvate, 0.35 millimolar L-Proline, 100 nanoMolar dexamethasone, 0.17 millimolar L- Ascorbic Acid, 1% (v/v) ITS (insulin, transferrin, selenium) (all components from Sigma Chemical Company)). The cells were gently mixed with the medium, and the samples were aliquoted into individual wells of a 24-well ultra-low cluster plate (Corning, Corning, N.Y.) at a concentration of either $2\times10^5$ per well or $5\times10^5$ per well. Cultures were placed in an incubator and left undisturbed for 24 to 48 hours. Medium was replaced with fresh chondrogenic medium supplemented with appropriate growth factor every 24-48 hours. Samples were allowed to culture for up to 28 days at which time they were removed and fixed in 10% (v/v) formalin (VWR Scientific, West Chester, Pa.) and processed for histological examination. Samples were stained with Safranin O or hematoxylin/eosin for evaluation.

Pellet culture assays. Cultured cells were trypsinized to remove from the culture plate. Cells were washed with centrifugation twice at 300×g for 5 minutes in DMEM without serum and counted. Cells were resuspended in fresh chondrogenic medium (described above) at a concentration of $5\times10^5$ cells per milliliter. Cells were aliquoted into new polypropylene tubes at $2.5\times10^5$ cells per tube. The appropriate samples were then treated with either TGF-beta3 (10 nanogram/milliliter, Sigma) or GDF-5 (100 nanogram/milliliter; R&D Systems, Minneapolis, Minn.) as growth factor. Cells were then centrifuged at 150×g for 3 minutes. Tubes were then transferred to the incubator and left undisturbed for 24 to 48 hours in standard atmosphere with 5% $CO_2$ at 37° C. and. Media was replaced with fresh chondrocyte cell media and growth factor, where appropriate, every 2 to 3 days. Samples were allowed to culture for up to 28 days at which time they were removed and fixed and stained as described above.

Results

Safranin O stains of cell pellets of placenta-derived cells treated with TGF-beta3 and GDF-5 showed positive Safranin O staining as compared to control cells, indicating glycosoaminoglycan. Placenta-derived cells also showed some chondrocyte-like morphology.

Summary. The results of the present study show that the placenta-derived cells partially differentiated into chondrocytes in vitro in the pellet culture and the collagen gel assay systems, as evidenced by glycosaminoglycan expression and similarity of cell morphology to cartilage tissue.

Example 17

Evaluation of Chondrogenic Potential of Placenta-Derived Cells in an In Vitro Pellet Culture Based Assay This example describes evaluation of the chondrogenic potential of cells derived from placental tissue using in vitro pellet culture based assays. Cells derived from placenta at early passage (P3) and late passage (P12) were used. The chondrogenic potential of the cells was assessed in pellet culture assays, under chondrogenic induction conditions, in medium supplemented with transforming growth factor beta-3 (TGF beta-3), rhGDF-5 (recombinant human growth and differentiation factor 5) or a combination of both.

Materials & Methods

Reagents. Dulbecco's Modified Essential Media (DMEM), Penicillin and Streptomycin, were obtained from Invitrogen, Carlsbad, Calif. Fetal calf serum (FCS) was obtained from HyClone (Logan, Utah). Mesenchymal stem cell growth medium (MSCGM) and hMSC chondrogenic differentiation bullet kit were obtained from Biowhittaker, Walkersville, Md. TGF beta-3 was obtained from Oncogene research products, San Diego, Calif. rhGDF-5 was obtained from Biopharm, Heidelberg, Germany (WO9601316 A1, US5994094 A).

Cells. Human mesenchymal stem cells (Lot# 2F1656) were obtained from Biowhittaker, Walkersville, Md. and were cultured in MSCGM according to manufacturer's instructions. This lot has been tested previously, and was shown to be positive in the chondrogenesis assays. Human adult and neonatal fibroblasts were obtained from American Type Culture Collection (ATCC), Manassas, Va. and cultured in growth medium (Dulbecco's Modified Essential supplemented with 15% (v/v) fetal bovine serum, 100 Units/milliliter penicillin, 100 microgram/milliliter streptomycin and 0.001% (v/v) 2- mercaptoethanol (Sigma, St. Louis, Mo.) on gelatin-coated tissue culture plastic flasks. Placenta-derived cells (Lot# 071003Plac) were utilized. Cells were cultured in Growth medium similar to fibroblasts. The cell cultures were incubated at 37° C. with 5% $CO_2$. Cells used for experiments were at passages 3 and 12.

Pellet culture assay. For pellet cultures, $0.25\times10^6$ cells were placed in a 15 milliliter conical tube and centrifuged at 150×g for 5 minutes at room temperature to form a spherical pellet according to protocol for chondrogenic assay from Biowhittaker. Pellets were cultured in chondrogenic induction medium containing TGF beta −3 (10 nanogram/milliliter), rhGDF-5 (500 nanogram/milliliter), or a combination of TGF beta −3 (10 nanogram/milliliter), and rhGDF-5 (500 nanogram/milliliter) for three weeks. Untreated controls were cultured in growth medium. During culture, pellets were re-fed with fresh medium every other day. Treatment groups included the following:

Treatment Group
  A. Placenta-derived cells early passage (P EP)+rhGDF-5
  B. Placenta-derived cells late passage (P LP)+rhGDF-5
  C. Human Mesenchymal Stem cells (HMSC)+rhGDF-5
  D. Human adult fibroblast cells (HAF)+rhGDF-5
  E. Placenta-derived cells early passage (P EP)+TGF beta −3
  F. Placenta-derived cells late passage (P LP)+TGF beta −3
  G. Human Mesenchymal Stem cells (HMSC)+TGF beta −3
  J. Human adult fibroblast cells (HAF)+TGF beta −3
  I. Placenta-derived cells early passage (P EP)+rhGDF-5+TGF beta −3, n=1
  J. Placenta-derived cells late passage (P LP)+rhGDF-5+TGF beta −3
  K. Human Mesenchymal Stem cells (HMSC)+rhGDF-5+TGF beta −3
  L. Human adult fibroblast cells (HAF)+rhGDF-5+TGF beta −3
  M. Human neonatal fibroblast cells (HNF)+rhGDF-5+TGF beta −3
  N. Placenta-derived cells early passage (P EP)
  O. Placenta-derived cells late passage (P LP)
  P. Human Mesenchymal Stem cells (HMSC)
  Q. Human adult fibroblast cells (HAF)

Histology of in vitro samples. At the end of the culture period pellets were fixed in 10% buffered formalin and sent to MPI Research (Mattawan, Mich.) for paraffin embedding, sectioning, and staining with Hematoxylin/Eosin (H/E) and Safranin O (SO) staining.

Results

Placenta-derived cells, MSCs and fibroblasts formed cell pellets in chondrogenic induction medium with the different growth factors. The size of the pellets at the end of culture period varied among the different cell types. Pellets formed with the placental cells were similar in size, or slightly larger than, those formed by MSCs and fibroblasts. Pellets formed with all cell types and cultured in control medium were smaller than pellets cultured in chondrogenic induction medium.

Examination of cross sections of pellets stained with H/E and Safranin-O provided some indication that placenta-derived cells at early and late passage may have the potential to undergo chondrogenic differentiation. Chondrogenesis as assessed by cell condensation, cell morphology and Safranin O positive staining of matrix was indistinct in the placenta-derived cells cultured in chondrogenic induction medium supplemented with TGF beta −3, rhGDF-5, or both. However, this may be due to the fact that chondrogenic induction conditions were optimized for MSCs, not for postpartum-derived cells, and it should be noted that control pellets cultured in growth medium showed no evidence of chondrogenesis. Moreover, distinct cell populations were observed in placenta-derived cells at both passages located apically or centrally. Some cell condensation was observed with fibroblast, but it was not associated with Safranin O staining.

Example 18

Adipogenic Differentiation of Placenta-Derived Cells

Stromal populations of stem cells have been demonstrated to differentiate into an adipogenic phenotype (Janderova et al. (2003) Obes. Res. 11(1):65-74; Zangani et al. (1999) Differentiation 64(2):91-101; Liu et al.(2003) Curr. Mol. Med. 3(4):325-40). The potential of placenta-derived cells to differentiate into an adipogenic phenotype was examined.

Methods & Materials

Adipose differentiation. Placenta-derived cells (P3) were seeded at 200,000 cells per well on 6-well tissue culture-treated plates in growth medium ((DMEM:Low glucose (Invitrogen, Carlsbad, Calif.), 15 percent (v/v) defined bovine serum (Hyclone, Logan, Utah; Lot#AND18475), 0.001 percent 2-mercaptoethanol (Sigma, St. Louis, Mo.), 100 Units/milliliter penicillin, 100 microgram/milliliter streptomycin, 0.25 micrograms per milliliter amphotericin B; Invitrogen, Carlsbad, Calif.). Mesenchymal stem cells (P3, IF2155), osteoblasts (P5, CC2538; Cambrex, Walkerville, Md.), omental cells (P6) (isolated from omental tissue from NDRI, following protocol used for placenta-derived cell isolation in Example 1), adipose-derived cells (U.S. Pat. No. 6,555,374 B1) (P6), and fibroblasts (P6, CC2509) (Cambrex, Walkerville, Md.) were also seeded under the same conditions. Prior to initiation of osteogenesis, Mesenchymal Stem Cells were grown in a Mesenchymal Stem Cell Growth Medium Bullet kit (Cambrex, Walkerville, Md.). After 2 days, spent medium was aspirated off and cells were washed with phosphate buffered saline (PBS). At this point, medium was switched to Dulbecco's minimal essential medium-high glucose (DMEM-Hg; Invitrogen, Carlsbad, Calif.) containing 10 percent FBS (v/v, Hyclone, Logan Utah), 0.02 milligrams per milliliter insulin (Sigma, St. Louis, Mo.), and 100 Units/milliliter penicillin, 100 microgram/milliliter streptomycin, 0.25 micrograms per milliliter amphotericin B; Invitrogen, Carlsbad, Calif.). Once the cells had reached confluence, spent medium was aspirated off. Cells were then cultured in an adipose differentiation medium (DMEM-Hg (Invitrogen, Carlsbad, Calif.), containing 10 percent defined fetal bovine serum ((v/v), Hyclone, Logan, Utah), 0.02 milligrams per milliliter insulin (Sigma, St. Louis, Mo.) and 100 Units/milliliter penicillin, 100 micrograms/milliliter streptomycin, and 0.25 micrograms/milliliter amphotericin, 5 micromolar isobutylmethylxanthine (Sigma, St. Louis, Mo.), 100 micromolar dexamethasone (Sigma, St. Louis, Mo.), and 2.5 micromolar indomethacin (Sigma, St. Louis, Mo.) for up to 4 weeks. Cells were stained with Oil-Red-O to determine the presence of lipid droplet formation.

Oil Red O Staining. Cells were fixed with 10 percent (v/v) neutral buffered formalin (Richard-Allan Kalamazoo, Mich.). After fixation, the cells were washed in deionized water and incubated for two minutes in propylene glycol (absolute; Poly Scientific, Bay Shore, N.Y.). Propylene glycol was removed by aspiration, and samples were incubated in Oil Red O (Poly Scientific, Bay Shore, N.Y.) for one hour. Staining solution was removed by aspiration and stained samples were then incubated in 85 percent (v/v) propylene glycol solution (Poly Scientific, Bay Shore, N.Y.) for one minute. Finally stained samples were washed with two changes of de-ionized water. Stained samples were counter-stained with Mayer's Hematoxylin (Poly Scientific Bay Shore, N.Y.) and examined by light microscopy. Images were taken at magnification of 20×.

Leptin Assay. Adipose-derived cells and placenta-derived cells were seeded at 200,000 cells/well in 6-well tissue culture-treated plates. Cells were initially seeded in growth medium ((DMEM:Lg; Invitrogen, Carlsbad, Calif.), 15% FBS (defined bovine serum Lot#AND18475; Hyclone, Logan, Utah), 0.001% 2-mercaptoethanol (Sigma, St. Louis, Mo.), 100 Units/milliliter penicillin, 100 microgram/milliliter streptomycin, 0.25 micrograms per milliliter amphotericin B; Invitrogen, Carlsbad, Calif.)), which was changed to an adipogenic differentiation medium (DMEM-Hg medium (Gibco, Carlsbad, Calif.) containing 1 micromolar dexamethasone (Sigma, St. Louis, Mo.), 0.2 millimolar indomethasone (Sigma, St. Louis, Mo.), 0.01 milligrams per microliter insulin (Sigma, St. Louis, Mo.), 0.5 millimolar isobutylmethylxanthine (Sigma, St. Louis, Mo.), 10 percent (v/v) fetal bovine serum (Cat. #SH30070.03; Hyclone, Logan, Utah), 100 Units/milliliter penicillin, 100 microgram/milliliter streptomycin (Gibco, Carlsbad Calif.)). At the end of the assay, the conditioned medium was collected and leptin levels were measured using an ELISA kit (Quantikine, R&D Systems, Minneapolis, Minn.).

Results

Adipose differentiation. Morphologically, MSCs and Adipose-derived cells (Artecel; U.S. Pat. No. 6,555,374) demonstrated lipid formation as early as 5 days in this assay. Large amounts of lipid droplet formation were observed in both these cultures by 15 days of culture. Cultures of osteoblasts also deposited large amounts of lipid under these conditions after 10 days in culture and extensively at 15 days. Lipid droplet formation was observed in placenta-derived and omental cell cultures after 15 days of culture. Low level lipid droplet formation was observed in the fibroblast cultures after 20 days in adipogenic-inducing conditions.

Leptin. Leptin was not detected by ELISA in placenta-derived cell conditioned medium.

Summary. The potential of placenta-derived cells to differentiate into an adipose phenotype was examined. The data demonstrate that placenta-derived cells undergo a low level of adipose differentiation when compared to cultures of mesenchymal stem cells, adipose-derived cells, or osteoblasts. No leptin was detected in placenta-derived cells by ELISA following the adipogenic differentiation protocol used.

Example 19

Differentiation of Placenta-Derived Cells to Beta Cells

The pancreas contains endocrine cells, organized in islets of Langerhans, which produce insulin, glucagon, somatostatin, and pancreatic polypeptide (PP). The ability of placenta-derived cells to differentiate towards cells with an insulin-producing phenotype was tested under eight different induction protocols.

Methods & Materials

Placenta-derived cells as well as neonatal or adult Normal Human Dermal Fibroblasts (NHDF) were grown in Growth medium (DMEM-low glucose (Gibco, Carlsbad, Calif.), 15% (v/v) fetal bovine serum (Cat. #SH30070.03, Hyclone; Logan, Utah), 0.001% (v/v) betamercaptoethanol (Sigma, St. Louis, Mo.), 50 Units/milliliter penicillin, 50 microgram/milliliter streptomycin (Gibco, Carlsbad, Calif.)) in a gelatin-coated T75 flask as well as in different beta-cell promoting differentiation conditions. Flasks were coated with 2% (w/v) gelatin solution (Sigma, St. Louis, Mo.) for 20 minutes at room temperature. Gelatin solution was aspirated off, and flasks were washed with PBS. Basic Fibroblast Growth Factor (bFGF), Epidermal Growth Factor (EGF), Transforming Growth Factor beta (TGFbeta) and Fibroblast Growth Factor 10 (FGF-10) were purchased from Pepro-Tech Inc. (Rocky Hill, N.J.). GLP- 1 was purchased from Sigma (St. Louis, Mo.)

Protocol 1: Placenta-derived cells (isolate 1; P2), adipose-derived cells (U.S. Pat. No. 6,555,374), placenta-derived cells (isolate 2; P4) (predominately neonatal as analyzed by karyotyping—data not shown), and adult Normal Human Dermal Fibroblasts (NHDF) (P10). Cells were maintained under either normal or 5% $O_2$ conditions. Cells were seeded at low density (5,000 cells/cm$^2$) in gelatin-coated T75 flasks on gelatin and grown in Ham's F12 medium (Clonetics, Santa Rosa, Calif.), 2% (v/v) FBS, 50 Units/milliliter penicillin, 50 microgram/milliliter streptomycin, 10 nanograms/milliliter EGF, and 20 nanograms/milliliter bFGF until confluence. Confluent cells were trypsinized and plated at 50,000 cells/cm$^2$ in 24-well Tissue Culture Polystyrene (TCPS; BD Biosciences, Bedford, Mass.) plates with or without gelatin or collagen coating. Cells were grown in Ham's F12 medium, 2% FBS, 50 Units/milliliter penicillin, 50 microgram/milliliter streptomycin, 10 nanograms/milliliter EGF, 20 nanograms/milliliter bFGF, and 15 nanoMolar GLP-1 (7-37 isoform) for up to 3 weeks.

Protocol 2: Placenta-derived cells (isolate 3; P3) and placenta-derived cells (isolate 2; P3) (predominately neonatal as identified by karyotyping analysis). Cells were seeded at low density (5,000 cells/cm$^2$) in T75 flasks on gelatin and grown in Ham's F12 medium, 2% FBS, 50 Units/milliliter penicillin, 50 microgram/milliliter streptomycin, 10 nanograms/milliliter EGF, 20 nanograms/milliliter bFGF until confluence. Confluent cells were trypsinized and plated at 50,000 cells/cm$^2$ in 24-well TCPS plates with or without gelatin coating. Cells were grown in Ham's F12 medium, 2% FBS, P/S, 15 nanoMolar GLP- 1 (7-37 isoform) for up to 3 weeks.

Protocol 3: Placenta-derived cells (isolate 1; P10), adult NHDF P10, and placenta-derived cells (isolate 2; P3). Cells were seeded at high density (50,000 cells/cm$^2$) in 24-well TCPS plates and grown in DMEM:Ham's F12 (1:1) medium, B-27 supplement (Gibco, Carlsbad, Calif.), 50 Units/milliliter penicillin, 50 microgram/milliliter streptomycin, 20 nanograms/milliliter EGF, 40 nanograms/milliliter bFGF. Spherical clusters were generated within about 4-6 days. Following that period, the spherical clusters were collected, centrifuged, and replated onto laminin-coated, 24-well plates (BD Biosciences, Bedford, Mass.), and cultured up to 3 weeks in B-27-supplemented medium containing 10 nanoMolar GLP-1 (7-37) with no other growth factors (i.e., no bFGF and no EGF).

Protocol 4: Placenta-derived cells (isolate 1; P10), adult NHDF (P10), placenta-derived cells (isolate 2; P3). Cells were set up at high density (50,000 cells/cm$^2$) in 24-well TCPS plates and grown in DMEM:Ham's F12 (1:1) medium, B-27 supplement, 50 Units/milliliter penicillin, 50 microgram/milliliter streptomycin, 20 nanograms/milliliter EGF, 40 nanograms/milliliter bFGF. Spherical clusters were generated, usually in about 4-6 days. Following that period, the spherical clusters were collected, centrifuged, and replated onto laminin-coated, 24-well plates and cultured up to 3 weeks in B-27-supplemented medium containing 10 nanoMolar GLP-1 (1-37 isoform) but no other growth factors (i.e., no bFGF and no EGF).

Protocol 5: Adult NHDF (P15) and placenta-derived cells (isolate 1; P15). Cells were seeded at high density (50,000 cells/cm$^2$) in 24-well TCPS gelatin- coated plates and grown in DMEM:Ham's F12 (1:1) medium, B-27 supplement, 50 Units/milliliter penicillin, 50 microgram/milliliter streptomycin, 10 nanograms/milliliter FGF-10, and/or 40 nanograms/milliliter TGFbeta for >two weeks.

Protocol 6: Adult NHDF and placenta-derived cells (isolate 1; P15). Cells were seeded at high density (50,000 cells/cm$^2$) in 24-well TCPS gelatin-coated plates and grown in EBM-2 medium, 10 nanograms/milliliter FGF-10, and/or 40 nanograms/milliliter TGFbeta for >two weeks.

Protocol 7: Placenta-derived cells (isolate 3; P3) were seeded at low density (5,000 cells/cm$^2$) in T75 flasks on gelatin and grown either in Growth medium or in Ham's F12 medium, 2% FBS, 50 Units/milliliter penicillin, 50 microgram/milliliter streptomycin, 10 nanograms/milliliter EGF, 20 nanograms/milliliter bFGF until confluence. Confluent cells were trypsinized and plated at 50,000 cells/cm$^2$ in 24-well TCPS plates, with or without gelatin coating. Three types of basic media were used for up to 3 weeks:

betaI medium: Ham's F12 medium, 2% FBS, 10 millimolar nicotinamide,
    50 Units/milliliter penicillin, 50 microgram/milliliter streptomycin, 25 milliMolar glucose
    betaII medium: Equal parts of DMEM/Ham's F12 media, 2% FBS, 10 millimolar nicotinamide, 25 milliMolar glucose
    Endothelial Cell Basal Medium (EBM), (Clonetics, Santa Rosa, Calif.).

The following growth factors were added to each of the media: 10 nanograms/milliliter EGF, 20 nanograms/milliliter bFGF, 10 nanoMolar GLP-1 (7-37 isoform).

Protocol 8: Placenta-derived cells (isolate 2; P2) (predominately neonatal as identified by karyotyping analysis), placenta-derived cells (isolate 2; P1), clone #22. Cells were seeded at low density (5,000 cells/cm$^2$) in T25 TCPS flasks and grown in DMEM, 20% FBS, 50 Units/milliliter penicillin, 50 microgram/milliliter streptomycin until confluence.

Total RNA isolation and quantitative RT-PCR. RNA was extracted from placenta-derived cells and fibroblasts grown as described in each protocol. Cells were lysed with 350 microliter buffer RLT containing beta-mercaptoethanol (Sigma St. Louis, Mo.) according to the manufacturer's instructions (RNeasy Mini kit, Qiagen, Valencia, Calif.) and RNA extracted according to the manufacturer's instructions (RNeasy Mini kit, Qiagen, Valencia, Calif.) with a 2.7 Units/sample DNase treatment (Sigma St. Louis, Mo.). RNA was eluted with 50 microliter DEPC-treated water and stored at −80° C. RNA was reverse transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Real-time PCR. PCR was performed on cDNA samples using ASSAYS-ON-DEMAND gene expression products PDX-1 (Hs00426216), pro-insulin (Hs00355773), Ngn-3 (Hs00360700), Glut-2 (Hs00165775), GAPDH (Applied Biosystems, Foster City, Calif.) and TaqMan Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 minutes and 95° C. for 10 minutes followed by 40 cycles of 95° C. for 15 seconds and 60° C. for 1 minute. In addition another set of primers designed in-house for PDX-1 and Ngn-3 was tested. Table 19-1 contains primers' sequences. PCR using these primers was performed as described above. Pancreas total RNA (Ambion, Austin, Tex.) was used as control. PCR data was analyzed according to the AACT method recommended by Applied Biosystems (User Bulletin #2 from Applied Biosystems for ABI Prism 7700 Sequence Detection System).

TABLE 19-1

Primers

| Primer name | Sequence |
|---|---|
| PDX-1 Forward primer | 5'-CTGGATTGGCGTTGTTTGTG-3' (SEQ ID NO: 11) |
| PDX-1 Reverse primer | 5'-TCCCAAGGTGGAGTGCTGTAG-3' (SEQ ID NO: 12) |
| PDX-1-TaqMan probe | 5'-CTGTTGCGCACATCCCTGCCC-3' (SEQ ID NO: 13) |
| Ngn-3 Forward primer | 5'-GGCAGTCTGGCTTTCTCAGATT-3' (SEQ ID NO: 14) |
| Ngn-3 Reverse primer | 5'-CCCTCTCCCTTACCCTTAGCA-3' (SEQ ID NO: 15) |
| Ngn-3 TaqMan probe | 5'-CTGTGAAAGGACCTGTCTGTCGC-3' (SEQ ID NO: 16) |

Results

For placenta-derived cells treated according to protocols 1-8, expression of pancreas-specific marker was not detected using real-time PCR and the assay-on-demand primers, with the exception that low levels of Ngn-3 were detected in cells from protocol 7. The same primers produced positive results with cDNA derived from pancreatic tissue RNA. Results of real-time PCR for PDX-1 and Ngn-3 performed on cDNA samples derived from human placenta were compared to results for adipose-derived cells grown according to protocol 1. PCR was also performed using in-house designed primers (Table 19-1). Results of real-time PCR using these primers for PDX-1 and Ngn-3 performed on cDNA samples derived from human placenta were compared to results from adipose-derived cells. Data obtained from real-time PCR was analyzed by the $\Delta C_T$ method (User Bulletin #2 from Applied Biosystems for ABI Prism 7700 Sequence Detection System) and expressed on a logarithmic scale.

Experimental conditions in Protocols 3 and 8 applied to placenta-derived cells, but not fibroblasts, produced structures resembling the cellular assembly of pancreatic epithelial cells into islets. These structures emerged about 3-5 days after the implementation of the protocol. Expression of pancreatic markers PDX-1, Ngn3, Glut-2 and pro-insulin were not detected by real-time PCR.

Summary. Limited expression of PDX-1 and Ngn-3 was observed in placenta-derived cells treated with a variety of experimental protocols. There were differences in results between in-house designed and commercially available primers. For example, while protocol number 1 gave positive data for PDX-1 and Ngn-3 using in-house designed primers, ASSAYS-ON-DEMAND primers for the same genes produced negative data. The results were not directly verified by immunological techniques. Notwithstanding such differences, expression of several pancreatic markers has been accomplished, suggesting the potential of placenta-derived cells to differentiate towards the pancreatic phenotypes.

Example 20

Differentiation of Placenta-Derived Cells to the Cardiomyocyte Phenotype

There is a tremendous need for therapy that will slow the progression of and/or cure heart disease, such as ischemic heart disease and congestive heart failure. Cells that can differentiate into cardiomyocytes that can fully integrate into the patient's cardiac muscle without arrhythmias are highly desirable. Rodent mesenchymal stem cells treated with 5-azacytidine have been shown to express markers of cardiomyocytes (Fukuda et al. (2002) *C. R. Biol.* 325:1027-38). This has not been shown for adult human stem cells. Additional factors have been used to improve stem cell differentiation including low oxygen (Storch (1990) *Biochim. Biophys. Acta* 1055:126-9), retinoic acid (Wobus et al. (1997) *J. Mol. Cell Cardiol.* 29:1525-39), DMSO (Xu et al. (2002) *Circ. Res.* 91:501-8), and chelerythrine chloride (International PCT Publication No. WO03/025149), which effects the translocation of PKC from the cytosol to plasma membrane and is an inhibitor of PKC activity. In this example, placenta-derived cells were treated with 5-azacytidine either alone or in combination with DMSO or chelerythrine chloride and markers of cardiomyocytes measured by real-time PCR.

Methods & Materials

Cells. Cryopreserved placenta-derived cells (P24) were grown in Growth medium (DMEM-low glucose (Gibco, Carlsbad Calif.), 15% (v/v) fetal bovine serum (Cat. #SH30070.03, Hyclone, Logan Utah), 0.001% (v/v) beta-mercaptoethanol (Sigma, St. Louis, Mo.), 50 Units/milliliter penicillin, 50 microgram/milliliter streptomycin (Gibco)), in a gelatin-coated flask. Cells were seeded at $5 \times 10^4$ cells/well in 96-well plates in Growth medium for 24 hours. The medium was changed to 0, 3, 10 and 30 uM 5-azacytidine (Sigma, St. Louis, Mo.) alone or with 5 microMolar chelerythrine chloride (Sigma), 1% (v/v) dimethylsulfoxide (DMSO) (Sigma), or 1 microMolar retinoic acid (Sigma) in MEM-alpha (Sigma), insulin, transferrin, and selenium (ITS; Sigma), 10% (v/v) fetal bovine serum, 50 Units/milliliter penicillin, 50 microgram/milliliter streptomycin, and cells incubated at 37° C., 5% (v/v) $O_2$ for 48 or 72 hours. Media was then changed to MEM-alpha, insulin, transferrin, and selenium, 10% (v/v) fetal bovine serum, 50 Units/ milliliter penicillin, 50 microgram/milliliter streptomycin, and cells incubated at 37° C., 5% (v/v) $O_2$ for 14 days.

RNA extraction and Reverse Transcription. Cells were lysed with 150 microliter buffer RLT containing beta-mercaptoethanol (Sigma St. Louis, Mo.) according to the manufacturer's instructions (RNeasy 96 kit, Qiagen, Valencia, Calif.) and stored at −80° C. Cell lysates were thawed and RNA extracted according to the manufacturer's instructions (RNeasy 96 kit, Qiagen, Valencia, Calif.) with a 2.7 Units/sample DNase treatment (Sigma St. Louis, Mo.). RNA was eluted with 50 microliter DEPC-treated water and stored at −80° C. RNA was reverse transcribed using random hexamers with the TaqMan reverse transcription reagents (Applied Biosystems, Foster City, Calif.) at 25° C. for 10 minutes, 37° C. for 60 minutes and 95° C. for 10 minutes. Samples were stored at −20° C.

PCR. PCR was performed on cDNA samples using ASSAYS-ON-DEMAND gene expression products cardiac myosin (Hs00165276 ml), skeletal myosin (Hs00428600), GATA 4 (Hs00171403 ml), GAPDH (Applied Biosystems, Foster City, Calif.), and TaqMan Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 minutes and 95° C. for 10 minutes followed by 40 cycles of 95° C. for 15 seconds and 60° C. for 1 minute. cDNA from heart and skeletal muscle (Ambion Austin Tex.) were used as a control.

Results

Control RNA from cardiac muscle showed expression of cardiac myosin and GATA 4, skeletal muscle RNA showed skeletal myosin and cardiac myosin but no GATA 4 expression. Placenta-derived cells (P24) treated for 72 h with factors and grown for an additional 14 days expressed GATA 4, but no skeletal myosin or cardiac myosin. Additional samples from placenta that were analyzed showed expression of GATA 4.

Summary. Untreated placenta-derived cells constitutively express GATA 4, a nuclear transcription factor in cardiomyocytes, sertoli cells, and hepatocytes.

Example 21

Treatment of Placenta-Derived Cells with Progesterone and cAMP

Placenta comprises both neonatal and maternal cells. The maternal cells are derived from the uterine wall during the process of implantation. Endometrial cells of the uterus undergo a process called decidualization after conception that is driven by steroid hormones and embryonic signals that changes the cell's morphology, phenotype and function. The morphology of the cells changes from fibroblastic to polygonal. Expression of alpha-smooth muscle actin is reduced, and cells begin to express desmin, prolactin, and insulin growth factor binding protein-1 (IGFBP-1) (Fazleabas and Strakova (2002) Mol. Cellular. Endo. 186:143-147). In the present study the effects of progesterone and 8-bromoadenosine 3',5'-cyclicmonophosphate, a cAMP analogue, were investigated. It has been previously shown that these compounds promote endometrium decidualization in vitro (Gellersen and Brosens (2003) J. Endocrinol. 178:357-372). Fibroblasts, mesenchymal stem cells (MSC), and placenta-derived cells were treated with progesterone and a cAMP analogue for 3 and 6 days and stained for desmin, a marker of decidualization, and vimentin for mesenchymal stromal cells.

Methods & Materials

Mesenchymal stem cells (P3) (Cambrex, Walkersville, Md.), placenta-derived cells (P3) (maternal karyotype), and dermal fibroblasts (P10) (Cambrex,) were seeded onto gelatin-coated LabTek II chamber slides (Nalgene, Rochester, N.Y.) at 10,000 cells/well in Growth medium (DMEM-low glucose (Gibco Carlsbad Calif.), 15% (v/v) fetal bovine serum (Hyclone, Logan, Utah), 0.001% (v/v) betamercaptoethanol (Sigma, St Loius, Mo.), 50 Units/milliliter penicillin, 50 microgram/milliliter streptomycin (Gibco)). Cells became confluent in 4 days and the medium was changed to either 1) control basal medium (DMEM-low glucose (Gibco), 10% (v/v) fetal bovine serum charcoal/dextran-treated (Hyclone), 50 Units/milliliter penicillin, 50 microgram/milliliter streptomycin (Gibco), Fungizone (Gibco)) or 2) basal medium containing 63.5 microMolar progesterone (Sigma) and 0.76 milliMolar 8-bromoadenosine 3'5'-cyclic-monophosphate (Sigma). Cells were incubated for 3 or 6 days with media changed at 3 days. Cells were washed with PBS (Gibco) and fixed with 4% (w/v) paraformaldehyde (Sigma) for 20 minutes and stored at 4° C. in phosphate buffered saline.

Immunocytochemistry was performed to evaluate expression of vimentin (1:500, Sigma,) and desmin (1:150, Sigma). Briefly, fixed cultures were washed with phosphate-buffered saline (PBS) and exposed to a protein blocking solution containing PBS, 4% goat serum (Chemicon, Temecula, Calif.), and 0.3% Triton (Triton X-100, Sigma) for 30 minutes. Primary antibody solutions were then applied to the samples containing blocking solution plus vimentin antibody (1:500) and desmin (1:150) for a period of 1 hour at room temperature. Next, primary antibody solutions were removed and samples washed with PBS prior to application of secondary antibody solutions (1 hour at room temperature) containing blocking solution along with goat anti-mouse IgG—Texas Red (1:250) and goat anti-rabbit IgG—Alexa 488 (1:250; Molecular Probes, Eugene, Oreg.). Samples were washed and 10 microMolar DAPI (Molecular Probes) applied for 10 minutes to visualize cell nuclei.

Following immunostaining, fluorescence was visualized using the appropriate fluorescence filter on an Olympus inverted epi-fluorescent microscope. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

All cells, with the exception of MSCs, in the control medium showed no vimentin or desmin staining at day 3 or 6. Maternal placenta-derived cells at 3 and 6 days showed a change in morphology when treated with progesterone and 8-bromoadenosine 3'5'-cyclicmonophosphate. Placenta-derived cells became phase bright and had a significantly reduced proliferation rate resulting in a lower density culture. Placenta-derived cells were the only cells to stain strongly for vimentin when treated with progesterone and 8-bromoadenosine 3'5'-cyclicmonophosphate for 3 or 6 days. MSCs showed weakly positive staining for vimentin under both conditions at 3 and 6 days.

Summary. Placenta-derived cells and fibroblasts grown in DMEM-low glucose with 10% fetal bovine serum normally express vimentin. In the present analysis, there was no staining for vimentin when cells were grown in 10% charcoal/dextran-treated fetal calf serum for as little as 3 days. Maternal placenta-derived cells showed a change in morphology and vimentin expression with progesterone and 8-bromoadenosine 3'5'-cyclicmonophosphate treatment. Expression of desmin was not detected.

Gene chip analysis revealed that there is little or no expression of the progesterone receptor in the cells tested. Expression of a putative steroid receptor, progesterone membrane components 1 and 2 (Gerdes et al. (1998) *Biol. Chem.* 379:907-11) was detected.

Example 22

Short-Term Neural Differentiation of Placenta-Derived Cells

The ability of placenta-derived cells to differentiate into neural lineage cells was examined.
Materials & Methods Isolation and Expansion of Placenta-derived Cells. Placenta-derived cells were isolated and expanded as described in Example 1.

Modified Woodbury-Black Protocol. (A) This assay was adapted from an assay originally performed to test the neural induction potential of bone marrow stromal cells (1). Placenta-derived cells (P3) were thawed and expanded in Growth Medium at 5,000 cells/cm$^2$ until sub-confluence (75%) was reached. Cells were then trypsinized and seeded at 6,000 cells per well of a Titretek II glass slide (VWR International, Bristol, Conn.). As controls, mesenchymal stem cells (P3; 1F2155; Cambrex, Walkersville, Md.), osteoblasts (P5; CC2538; Cambrex), omental cells (P6; (041003)), Artecel cells (U.S. Pat. No. 6,555,374 B1) (P6; Donor 2) and neonatal human dermal fibroblasts (P6; CC2509; Cambrex) were also seeded under the same conditions.

All cells were initially expanded for 4 days in DMEM/F12 medium (Invitrogen, Carlsbad, Calif.) containing 15% (v/v) fetal bovine serum (FBS; Hyclone, Logan, Utah), basic fibroblast growth factor (bFGF; 20 nanogram/milliliter; Peprotech, Rocky Hill, N.J.), epidermal growth factor (EGF; 20 nanogram/milliliter; Peprotech) and 50 Units/milliliter penicillin, 50 microgram/milliliter streptomycin (Invitrogen). After 4 days, cells were rinsed in phosphate-buffered saline (PBS; Invitrogen) and were subsequently cultured in DMEM/F12 medium+20% (v/v) FBS+50 Units/milliliter penicillin, 50 microgram/milliliter streptomycin for 24 hours. After 24 hours, cells were rinsed with PBS. Cells were then cultured for 1 to 6 hours in an induction medium which was comprised of DMEM/F12 (serum-free) containing 200 milliMolar butylated hydroxyanisole, 10 nanoMolar ☐potassium chloride, 5 milligram/milliliter insulin, 10 nanoMolarforskolin, 4 nanoMolarvalproic acid, and 2 nanoMolar☐hydrocortisone (all chemicals from Sigma, St. Louis, Mo.). Cells were then fixed in –20° C. 100% methanol and immunocytochemistry was performed (see methods below) to assess human nestin protein expression.

(B) Placenta-derived cells (P11) and adult human dermal fibroblasts (1F1853, P11) were thawed and culture expanded in Growth Medium at 5,000 cells/cm2 until sub-confluence (75%) was reached. Cells were then trypsinized and seeded at similar density as in (A), but onto (1) 24 well tissue culture-treated plates (TCP, Falcon brand, VWR International), (2) TCP wells+2% (w/v) gelatin adsorbed for 1 hour at room temperature, or (3) TCP wells+20 nanogram/milliliter adsorbed mouse laminin (adsorbed for a minimum of 2 hours at 37° C.; Invitrogen).

Exactly as in (A), cells were initially expanded and media switched at the aforementioned timeframes. One set of cultures was fixed, as before, at 5 days and six hours, this time with 4° C. 4% (w/v) paraformaldehyde (Sigma) for 10 minutes at room temperature. In the second set of cultures, media was removed and switched to Neural Progenitor Expansion medium (NPE) consisting of Neurobasal-A medium (Invitrogen) containing B27 (B27 supplement; Invitrogen), L-glutamine (4 milliMolar), and 50 Units/milliliter penicillin, 50 microgram/milliliter streptomycin (Invitrogen). NPE medium was further supplemented with retinoic acid (RA; 1 micromolar; Sigma). This medium was removed 4 days later and cultures were fixed with 4° C. 4% (w/v) paraformaldehyde (Sigma) for 10 minutes at room temperature, and stained for nestin, GFAP, and TuJ1 protein expression (see Table 22-1).

TABLE 22-1

Summary of Primary Antibodies Used

| Antibody | Concentration | Vendor |
|---|---|---|
| Rat 401 (nestin) | 1:200 | Chemicon, Temecula, CA |
| Human Nestin | 1:100 | Chemicon |
| TuJ1 (BIII Tubulin) | 1:500 | Sigma, St. Louis, MO |
| GFAP | 1:2000 | DakoCytomation, Carpinteria, CA |
| Tyrosine hydroxylase (TH) | 1:1000 | Chemicon |
| GABA | 1:400 | Chemicon |
| Desmin (mouse) | 1:300 | Chemicon |
| alpha - smooth muscle actin | 1:400 | Sigma |
| Human nuclear protein (hNuc) | 1:150 | Chemicon |

Two Stage Differentiation Protocol. Placenta-derived cells (P11), adult human dermal fibroblasts (P11; 1F1853; Cambrex) were thawed and culture expanded in Growth Medium at 5,000 cells/cm$^2$ until sub-confluence (75%) was reached. Cells were then trypsinized and seeded at 2,000 cells/cm$^2$, but onto 24 well plates coated with laminin (BD Biosciences, Franklin Lakes, N.J.) in the presence of NPE media supplemented with bFGF (20 nanogram/milliliter; Peprotech, Rocky Hill, N.J.) and EGF (20 nanogram/milliliter; Peprotech) [whole media composition further referred to as NPE+F+E]. At the same time, adult rat neural progenitors isolated from hippocampus (P4; (062603); see Example 23)) were also plated onto 24 well laminin-coated plates in NPE+F+E media. All cultures were maintained in such conditions for a period of 6 days (cells were fed once during that time) at which time media was switched to the differentiation conditions listed in Table 22-2 for an additional period of 7 days. Cultures were fixed with ice-cold 4% (w/v) paraformaldehyde (Sigma) for 10 minutes at room temperature, and stained for human or rat nestin, GFAP, and TuJ1 protein expression.

TABLE 22-2

Summary of Conditions for Two-Stage Differentiation Protocol

| COND. # | A<br>PRE-<br>DIFFERENTIATION | B<br>2$^{nd}$<br>STAGE DIFF |
|---|---|---|
| 1 | NPE + F + E | NPE + SHH (200 nanogram/milliliter) + F8 (100 nanogram/milliliter) |
| 2 | NPE + F + E | NPE + SHH (200 nanogram/milliliter) + F8 (100 |

TABLE 22-2-continued

Summary of Conditions for Two-Stage Differentiation Protocol

| COND. # | A<br>PRE-<br>DIFFERENTIATION | B<br>$2^{nd}$<br>STAGE DIFF |
|---|---|---|
| | | nanogram/milliliter) + RA (1 micromolar) |
| 3 | NPE + F + E | NPE + RA (1 micromolar) |
| 4 | NPE + F + E | NPE + F (20 nanogram/milliliter) + E (20 nanogram/milliliter) |
| 5 | NPE + F + E | Growth Medium |
| 6 | NPE + F + E | Condition 1B + rhGDF-5 (20 nanogram/milliliter) |
| 7 | NPE + F + E | Condition 1B + BMP7 (20 nanogram/milliliter) |
| 8 | NPE + F + E | Condition 1B + GDNF (20 nanogram/milliliter) |
| 9 | NPE + F + E | Condition 2B + rhGDF-5 (20 nanogram/milliliter) |
| 10 | NPE + F + E | Condition 2B + BMP7 (20 nanogram/milliliter) |
| 11 | NPE + F + E | Condition 2B + GDNF (20 nanogram/milliliter) |
| 12 | NPE + F + E | Condition 3B + rhGDF-5 (20 nanogram/milliliter) |
| 13 | NPE + F + E | Condition 3B + BMP7 (20 nanogram/milliliter) |
| 14 | NPE + F + E | Condition 3B + GDNF (20 nanogram/milliliter) |
| 15 | NPE + F + E | NPE + rhGDF-5 (20 nanogram/milliliter) |
| 16 | NPE + F + E | NPE + BMP7 (20 nanogram/milliliter) |
| 17 | NPE + F + E | NPE + GDNF (20 nanogram/milliliter) |

Neural Progenitor Co-Culture Protocol. Adult rat hippocampal progenitors (062603) were plated as neurospheres or single cells (10,000 cells/well) onto laminin-coated 24 well dishes (BD Biosciences) in NPE+F (20 nanogram/milliliter)+E (20 nanogram/milliliter).

Separately, placenta-derived cells (022803) P11 were thawed and culture expanded in NPE+F (20 nanogram/milliliter)+E (20 nanogram/milliliter) at 5,000 cells/cm$^2$ for a period of 48 hours. Cells were then trypsinized and seeded at 2,500 cells/well onto existing cultures of neural progenitors. At that time, existing medium was exchanged for fresh medium. Four days later, cultures were fixed with ice-cold 4% (w/v) paraformaldehyde (Sigma) for 10 minutes at room temperature, and stained for human nuclear protein (hNuc; Chemicon) (Table 221-1 above) to identify PPDCs.

Immunocytochemistry. Immunocytochemistry was performed using the antibodies listed in Table 22-1. Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibody solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Woodbury-Black Protocol. (A) Upon incubation in this neural induction composition, all cell types transformed into cells with bipolar morphologies and extended processes. Other larger non-bipolar morphologies were also observed. Furthermore, the induced cell populations stained positively for nestin, a marker of multipotent neural stem and progenitor cells.

(B) When repeated on tissue culture plastic (TCP) dishes, nestin expression was not observed unless laminin was pre-adsorbed to the culture surface. To further assess whether nestin-expressing cells could then go on to generate mature neurons, PPDCs and fibroblasts were exposed to NPE+RA (1 microMolar), a media composition known to induce the differentiation of neural stem and progenitor cells into such cells (2,3,4). Cells were stained for TuJ1, a marker for immature and mature neurons, GFAP, a marker of astrocytes, and nestin, a marker for neural progenitors. Under no conditions was TuJ1 expression turned on nor were cells with neuronal morphology observed, suggesting that neurons were not generated in the short term. Furthermore, nestin and GFAP expression were no longer expressed by PDCs, as determined by immunocytochemistry.

Two Stage Differentiation Results. Placenta derived cells (as well as human fibroblasts and rodent neural progenitors as negative and positive control cell types, respectively) were plated on laminin (neural promoting)-coated dishes and exposed to 13 different growth conditions (and two control conditions) known to promote differentiation of neural progenitors into neurons and astrocytes. In addition, two conditions were added to examine the influence of GDF5, and BMP7 on PPDC differentiation. Generally, a two-step differentiation approach was taken, where the cells were first placed in neural progenitor expansion conditions for a period of 6 days followed by full differentiation conditions for 7 days. Morphologically, placenta-derived cells exhibited fundamental changes in cell morphology throughout the time-course of this procedure. However, in no cases were neuronal or astrocytic-shaped cells observed except for in control, neural progenitor-plated conditions. Immunocytochemistry, negative for human nestin, TuJ1, and GFAP confirmed these morphological observations.

Neural Progenitor and PDC Co-culture Procedures. Placenta-derived cells were plated onto cultures of rat neural progenitors seeded two days earlier in neural expansion conditions (NPE+F+E). While visual confirmation of plated placenta-derived cells proved that these cells were plated as single cells, human-specific nuclear staining (hNuc) 4 days post-plating (6 days total length of exposure) showed that they tended to ball up and avoid contact with the neural progenitors. Furthermore, where placental cells attached, these cells spread out and appeared to be innervated by differentiated neurons that were of rat origin suggesting that the placental cells may have differentiated into muscle cells. This observation was based upon morphology under phase contrast microscopy. Another observation was that typically large cell bodies (larger than neural progenitors) possessed morphologies resembling neural progenitors, with thin processes spanning out in multiple directions. HNuc staining (found in one half of the cell's nucleus) suggested that in some cases these human cells may have fused with rat progenitors and assumed their phenotype. Controls wells containing neural progenitors only had fewer total progenitors and apparent differentiated cells than did co-culture wells containing placental cells, further indicating that placenta-derived cells influenced the differentiation and behavior of neural progenitors either by release of chemokines and cytokines, or by contact-mediated effects.

Summary. Multiple protocols were conducted to determine the short term potential of placenta-derived PPDCs to differentiate into neural lineage cells. These included phase contrast imaging of morphology in combination with immunocytochemistry for nestin, TuJ1, and GFAP, proteins associated with multipotent neural stem and progenitor cells, immature and mature neurons, and astrocytes, respectively. Evidence was observed to suggest that neural differentiation occurred in certain instances in these short-term protocols.

Several notable observations were made in co-cultures of PPDCs with neural progenitors. This approach, using human PPDCs along with a xenogeneic cell type allowed for absolute determination of the origin of each cell in these cultures. First, some cells were observed in these cultures where the cell cytoplasm was enlarged, with neurite-like processes extending away from the cell body, yet only half of the body labeled with hNuc protein. Those cells may be human PPDCs that have differentiated into neural lineage cells or they may be PPDCs that have fused with neural progenitors of rat origin. Second, it appeared that neural progenitors extended neurites to PPDCs in a way that indicates the progenitors differentiated into neurons and innervated the PPDCs. Third, cultures of neural progenitors and PPDCs had more cells of rat origin and larger amounts of differentiation than control cultures of neural progenitors alone, further indicating that plated PPDCs provided soluble factors and or contact-dependent mechanisms that stimulated neural progenitor survival, proliferation, and/or differentiation.

References for Example 22

(1) Woodbury, D. et al. (2000). *J Neurosci. Research.* 61(4): 364-70.
(2) Jang, Y. K. et al. (2004). *J. Neurosci. Research.* 75(4): 573-84.
(3) Jones-Villeneuve, E. M. et al. (1983). *Mol Cel Biol.* 3(12): 2271-9.
(4) Mayer-Proschel, M. et al. (1997). *Neuron.* 19(4): 773-85.

Example 23

Placenta-Derived Cellular Trophic Factors for Neural Progenitor Support

The influence of placenta-derived cells on adult neural stem and progenitor cell survival and differentiation through non-contact dependent (trophic) mechanisms was examined.

Materials & Methods

Adult Neural Stem and Progenitor Cell Isolation. Fisher 344 adult rats were sacrificed by $CO_2$ asphyxiation followed by cervical dislocation. Whole brains were removed intact using bone rongeurs and hippocampus tissue dissected based on coronal incisions posterior to the motor and somatosensory regions of the brain (1). Tissue was washed in Neurobasal-A medium (Invitrogen, Carlsbad, Calif.) containing B27 (B27 supplement; Invitrogen), L-glutamine (4 milli-Molar; Invitrogen), and 50 Units/milliliter penicillin, 50 microgram/milliliter streptomycin (Invitrogen), the combination of which is herein referred to as Neural Progenitor Expansion (NPE) medium. NPE medium was further supplemented with bFGF (20 nanogram/milliliter, Peprotech, Rocky Hill, N.J.) and EGF (20 nanogram/milliliter, Peprotech, Rocky Hill, N.J.), herein referred to as NPE+bFGF+EGF.

Following wash, the overlying meninges were removed, and the tissue minced with a scalpel. Minced tissue was collected and trypsin/EDTA (Invitrogen) added as 75% of the total volume. DNAse (100 microliter per 8 milliliters total volume, Sigma, St. Louis, Mo.) was also added. Next, the tissue/media was sequentially passed through an 18 gauge needle, 20 gauge needle, and finally a 25 gauge needle one time each (all needles from Becton Dickinson, Franklin Lakes, N.J.). The mixture was centrifuged for 3 minutes at 250×g. Supernatant was removed, fresh NPE+bFGF+EGF was added and the pellet resuspended. The resultant cell suspension was passed through a 40 micron cell strainer (BD Biosciences), plated on laminin-coated T-75 flasks (Becton Dickinson) or low cluster 24-well plates (Becton Dickinson), and grown in NPE+bFGF+EGF media until sufficient cell numbers were obtained for the studies outlined.

Placenta-Derived Cell Plating. Placenta-derived cells (P12) previously grown in Growth medium were plated at 5,000 cells/transwell insert (sized for 24 well plate) and grown for a period of one week in Growth medium in inserts to achieve confluence.

Adult Neural Progenitor Plating. Neural progenitors, grown as neurospheres or as single cells, were seeded onto laminin-coated 24 well plates at an approximate density of 2,000 cells/well in NPE+bFGF+EGF for a period of one day to promote cellular attachment. One day later, transwell inserts containing placenta-derived cells were added according to the following scheme:

(1) Transwell (placenta in Growth medium, 200 microliter)+neural progenitors (NPE+bFGF+EGF, 1 milliliter)
(2) Transwell (adult human dermal fibroblasts [1F1853; Cambrex, Walkersville, Md.] P12 in Growth medium, 200 microliter)+neural progenitors (NPE+bFGF+EGF, 1 milliliter)
(3) Control: neural progenitors alone (NPE+bFGF+EGF, 1 milliliter)
(4) Control: neural progenitors alone (NPE only, 1 milliliter)

Immunocytochemistry. After 7 days in co-culture, all conditions were fixed with cold 4% (w/v) paraformaldehyde (Sigma) for a period of 10 minutes at room temperature. Immunocytochemistry was performed using antibodies directed against the epitopes listed in Table 23-1. Briefly, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 microMolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 23-1

Summary of Primary Antibodies Used

| Antibody | Concentration | Vendor |
|---|---|---|
| Rat 401 (nestin) | 1:200 | Chemicon, Temecula, CA |
| TuJ1 (BIII Tubulin) | 1:500 | Sigma, St. Louis, MO |
| Tyrosine hydroxylase (TH) | 1:1000 | Chemicon |
| GABA | 1:400 | Chemicon |
| GFAP | 1:2000 | DakoCytomation, Carpintena, CA |
| Myelin Basic Protein (MBP) | 1:400 | Chemicon |

Quantitative Analysis of Neural Progenitor Differentiation. Quantification of hippocampal neural progenitor differentiation was examined. A minimum of 1000 cells were counted per condition or if less, the total number of cells observed in that condition. The percentage of cells positive for a given stain was assessed by dividing the number of positive cells by the total number of cells as determined by DAPI (nuclear) staining.

Mass Spectrometry Analysis & 2D Gel Electrophoresis. In order to identify unique, secreted factors as a result of co-culture, conditioned media samples taken prior to culture fixation were frozen down at −80° C. overnight. Samples were then applied to ultrafiltration spin devices (MW cutoff 30 kD). Retentate was applied to immunoaffinity chromatography (anti-Hu-albumin; IgY) (immunoaffinity did not remove albumin from the samples). Filtrate was analyzed by MALDI. The pass through was applied to Cibachron Blue affinity chromatography. Samples were analyzed by SDS-PAGE and 2D gel electrophoresis.

Results

Placenta-derived cell co-culture stimulates adult neural progenitor differentiation. Following culture with placenta-derived cells, co-cultured neural progenitor cells derived from adult rat hippocampus exhibited differentiation along all three major lineages in the central nervous system. This effect was clearly observed after five days in co-culture, with numerous cells elaborating complex processes and losing their phase bright features characteristic of dividing progenitor cells. Conversely, neural progenitors grown alone in the absence of bFGF and EGF appeared unhealthy and survival was limited.

After completion of the procedure, cultures were stained for markers indicative of undifferentiated stem and progenitor cells (nestin), immature and mature neurons (TuJ1), astrocytes (GFAP), and mature oligodendrocytes (MBP). Differentiation along all three lineages was confirmed while control conditions did not exhibit significant differentiation as evidenced by retention of nestin-positive staining amongst the majority of cells. Though differentiation also appeared to be influenced by adult human fibroblasts, such cells were not able to promote the differentiation of mature oligodendrocytes nor were they able to generate an appreciable quantity of neurons. Though not quantified, fibroblasts did, however, appear to enhance the survival of neural progenitors and their progeny similar to findings for placenta-derived postpartum cells.

Identification of Unique Compounds. Conditioned media from placental test conditions along with the appropriate controls (NPE media ±1.7% serum, media from co- culture with fibroblasts) were examined for differences. Potentially unique compounds were identified and excised from their respective 2D gels.

Summary. Co-culture of adult neural progenitor cells with placenta-derived postpartum cells results in differentiation of those cells. In view of the lack of contact between the PPDCs and the neural progenitors, this result appears to be a function of soluble factors released from the PPDCs (trophic effect).

Several other observations were made. First, there were very few cells in the control condition where EGF and bFGF were removed. Most cells died and on average, there were about 100 cells or fewer per well. Second, it is to be expected that there would be very little differentiation in the control condition where EGF and bFGF was retained in the medium throughout, since this is normally an expansion medium. While approximately 70% of the cells were observed to retain their progenitor status (nestin+), about 30% were GFAP+(indicative of astrocytes). This may be due to the fact that such significant expansion occurred throughout the course of the procedure that contact between progenitors induced this differentiation. Similar findings have been reported in the literature (2).

References for Example 23

(1) Paxinos, G. & Watson, C. (1997). THE RAT BRAIN IN STEREOTAXIC COORDINATES.
(2) Song, H. et al. (2002). Nature. 417(6884): 39-44.

Example 24

Endothelial Network Formation Assay

Angiogenesis, or the formation of new vasculature, is necessary for the growth of new tissue. Induction of angiogenesis is an important therapeutic goal in many pathological conditions. The present study was aimed at identifying potential angiogenic activity of the placenta-derived cells in in vitro assays. The study followed a well-established method of seeding endothelial cells onto a culture plate coated with MATRIGEL (BD Discovery Labware, Bedford, Mass.), a basement membrane extract (Nicosia and Ottinetti (1990) In Vitro Cell Dev. Biol. 26(2):119-28). Treating endothelial cells on MATRIGEL (BD Discovery Labware, Bedford, Mass.) with angiogenic factors will stimulate the cells to form a network that is similar to capillaries. This is a common in vitro assay for testing stimulators and inhibitors of blood vessel formation (Ito et al. (1996) Int. J. Cancer 67(1):148-52). The protocols utilized in this example made use of a co-culture system with the placenta-derived cells seeded onto culture well inserts. These permeable inserts allow for the passive exchange of media components between the endothelial and the placenta-derived culture media.

Material & Methods

Cell Culture.

Placenta-derived cells. Human placentas were received and cells were isolated as previously described (Example 1). Cells were cultured in Growth medium (Dulbecco's Modified Essential Media (DMEM; Invitrogen, Carlsbad, Calif.), 15% (v/v) fetal bovine serum (Hyclone, Logan Utah), 100 Units/milliliter penicillin, 100 microgram/milliliter streptomycin Invitrogen), 0.001% (v/v) 2-mercaptoethanol (Sigma, St. Louis, Mo.)) on gelatin- coated tissue culture plastic flasks. The cultures were incubated at 37° C. with 5% $CO_2$. Cells used for experiments were between passages 4 and 12.

Actively growing placenta-derived cells were trypsinized, counted, and seeded onto COSTAR TRANSWELL 6.5 millimeter diameter tissue culture inserts (Corning, Corning, N.Y.) at 15,000 cells per insert. Cells were cultured on the inserts for 48 to 72 hours in growth media in standard air with 5% $CO_2$ at 37° C.

Human mesenchymal stem cells (hMSC). hMSCs were purchased from Cambrex (Walkersville, Md.) and cultured in MSCGM (Cambrex). The cultures were incubated in standard air with 5% $CO_2$ at 37° C.

Actively growing MSCs were trypsinized and counted and seeded onto Costar® Transwell® 6.5 millimeter diameter tissue culture inserts (Corning, Corning, N.Y.) at 15,000 cells per insert. Cells were cultured on the inserts for 48 to 72 hours in growth media in standard air with 5% $CO_2$ at 37° C.

Human umbilical vein endothelial cells (HUVEC). HUVEC were obtained from Cambrex (Walkersville, Md.). Cells were grown in separate cultures in either EBM or EGM endothelial cell media (Cambrex). Cells were grown on standard tissue cultured plastic in standard air with 5% $CO_2$ at 37° C. Cells used in the assay were between passages 4 and 10.

Human coronary artery endothelial cells (HCAEC). HCAEC were purchased from Cambrex Incorporated (Walkersville, Md.). These cells were also maintained in separate cultures in either the EBM or EGM media formulations. Cells were grown on standard tissue cultured plastic in standard air with 5% $CO_2$ at 37° C. Cells used for experiments were between passages 4 and 8.

Endothelial Network Formation (MATRIGEL) assays. Culture plates were coated with MATRIGEL (BD Discovery Labware, Bedford, Mass.) according to manufacturer's specifications. Briefly, MATRIGEL (BD Discovery Labware, Bedford, Mass.) was thawed at 4° C. and approximately 250 microliter was aliquoted and distributed evenly onto each well of a chilled 24-well culture plate (Corning). The plate was then incubated at 37° C. for 30 minutes to allow the material to solidify. Actively growing endothelial cell cultures were trypsinized and counted. Cells were washed twice in Growth media with 2% FBS, followed by centrifugation, resuspension, and aspiration of the supernatant. Cells were seeded onto the coated wells 20,000 cells per well in approximately 0.5 milliliter Growth medium with 2% (v/v) FBS. Cells were then incubated for approximately 30 minutes to allow cells to settle.

Endothelial cell cultures were then treated with either 10 nanoMolar human bFGF (Peprotech, Rocky Hill, N.J.) or 10 nanoMolar human VEGF (Peprotech, Rocky Hill, N.J.) to serve as a positive control for endothelial cell response. Transwell inserts seeded with placenta-derived cells were added to appropriate wells with Growth medium with 2% FBS in the insert chamber. Cultures were incubated in standard air with 5% $CO_2$ at 37° C. for approximately 24 hours. The well plate was removed from the incubator, and images of the endothelial cell cultures were collected with an Olympus inverted microscope (Olympus, Melville, N.Y.).

Results

In a co-culture system with placenta-derived cells, HUVEC form cell networks. HUVEC cells form limited cell networks in co-culture experiments with hMSC and with 10 nanoMolar bFGF. HUVEC cells without any treatment showed very little or no network formation. These results suggest that the placenta-derived cells release angiogenic factors that stimulate the HUVEC.

In a co-culture system with placenta-derived cells, CAECs form cell networks.

Table 24-1 shows levels of known angiogenic factors released by PDCs in Growth medium. Placenta-derived cells were seeded onto inserts as described above. The cells were cultured at 37° C. in atmospheric oxygen for 48 hours on the inserts and then switched to a 2% FBS medium and returned at 37° C. for 24 hours. Media was removed, immediately frozen and stored at −80° C., and analyzed by the SEARCHLIGHT multiplex ELISA assay (Pierce Chemical Company, Rockford, Ill.). Results shown are the averages of duplicate measurements. The results show that the placenta-derived cells do not release detectable levels of platelet- derived growth factor-bb (PDGF-bb) or heparin-binding epidermal growth factor (HBEGF). The cells do release measurable quantities of tissue inhibitor of metalloprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

TABLE 24-1

Potential angiogenic factors released from placenta-derived cells. Cells were cultured in 24 hours in media with 2% FBS in atmospheric oxygen. Media was removed and assayed by the SEARCHLIGHT multiplex ELISA assay (Pierce). Results are the means of a duplicate analysis. Values are concentrations in the media reported in picograms per milliliter of culture media.

| | TIMP1 (pg/ml) | ANG2 (pg/ml) | PDGF-BB (pg/ml) | TPO (pg/ml) | KGF (pg/ml) | HGF (pg/ml) | FGF (pg/ml) | VEGF (pg/ml) | HB-EGF (pg/ml) |
|---|---|---|---|---|---|---|---|---|---|
| Plac (P4) | 91655.3 | 175.5 | <2.0 | 275.5 | 3.0 | 58.3 | 7.5 | 644.6 | <1.2 |
| Plac (P11) | 1592832.4 | 28.1 | <2.0 | 1273.1 | 193.3 | 5960.3 | 34.8 | 12361.1 | 1.7 |
| Media alone | <9.8 | 25.1 | <2.0 | <6.4 | <2.0 | <3.2 | <5.4 | <4.0 | <1.2 |

Table 24-2 shows levels of known angiogenic factors released by PDCs. PDCs were seeded onto inserts as described above. The cells were cultured in Growth medium at 5% oxygen for 48 hours on the inserts and then switched to a 2% FBS medium and returned to 5% $O_2$ incubation for 24 hours. Media was removed, immediately frozen, and stored at −80° C., and analyzed by the SEARCHLIGHT multiplex ELISA assay (Pierce Chemical Company, Rockford, Ill.). Results shown are the averages of duplicate measurements. The results show that the placenta-derived cells do not release detectable levels of platelet-derived growth factor-bb (PDGF-BB), or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF) and vascular endothelial growth factor (VEGF).

TABLE 24-2

Potential angiogenic factors released from placenta-derived cells. Cells were cultured in 24 hours in media with 2% FBS in 5% oxygen. Media was removed and assayed by the SEARCHLIGHT multiplex ELISA assay (Pierce). Results are the means of a duplicate analysis. Values are concentrations in the media reported in picograms per milliter of culture media.

|  | TIMP1 (pg/ml) | ANG2 (pg/ml) | PDGF-BB (pg/ml) | TPO (pg/ml) | KGF (pg/ml) | HGF (pg/ml) | FGF (pg/ml) | VEGF (pg/ml) | HB-EGF (pg/ml) |
|---|---|---|---|---|---|---|---|---|---|
| Plac (P4) | 72972.5 | 253.6 | <2.0 | 743.1 | 2.5 | 30.2 | 15.1 | 1495.1 | <1.2 |
| Plac (P11) | 458023.1 | 55.1 | <2.0 | 2562.2 | 114.2 | 2138.0 | 295.1 | 7521.3 | 1.8 |
| Media alone | <9.8 | 25.1 | <2.0 | <6.4 | <2.0 | <3.2 | <5.4 | <4.0 | <1.2 |

Summary. The results show that placenta-derived cells can stimulate both human umbilical vein and coronary artery endothelial cells to form networks in an in vitro MATRIGEL (BD Discovery Labware, Bedford, Mass.) assay. This effect is similar to that seen with known angiogenic factors in this assay system. These results suggest that PDCs are useful for stimulating angiogenesis in vivo.

Example 25

Transplantation of Placenta-Derived Cells under the Kidney Capsule

Transplantation of pancreatic islets to the kidney capsule is routinely performed to evaluate transplantation methodologies for the treatment of diabetes (Refaie et al. (1998) Trans. Proc. 30:400-403). In addition to pancreatic islets, other cells may be differentiated into insulin-secreting cells capable of blood glucose homeostasis. The purpose of this study was to determine whether cells derived from human placenta could survive when implanted under the kidney capsule in immune-deficient mice. In addition, placenta-derived cells were mixed with GM-CSF mobilized CD34+ cells to determine whether these cells could promote vascularization and survival of the placenta-derived cells.

Methods & Materials

Cell Culture. Cryopreserved placenta-derived cells (isolate 1, P10) were removed from liquid nitrogen storage and grown in Growth medium (DMEM-low glucose (Gibco Carlsbad Calif.), 15% (v/v) fetal bovine serum (Hyclone, Logan, Utah), 0.001% (v/v) betamercaptoethanol (Sigma, St Louis, Mo.), 50 Units/milliliter penicillin, 50 microgram/milliliter streptomycin (Gibco)) on gelatin (Sigma)-coated T225 (Corning, Corning, N.Y.) flasks until confluent.

Cells from two flasks were washed with Phosphate buffered saline (PBS) and a single cell suspension was obtained by using Trypsin/EDTA (Gibco). Cryopreserved GM-CSF mobilized CD34+ cells were purchased from Cambrex, Walkersville, Md. (lot 1F0174 donor 7956). CD34+ cells were thawed and washed in DMEM medium.

The cell suspension was washed twice in DMEM. Cell number and viability was estimated after trypan blue (Sigma) staining using a hemocytometer. Aliquots of the cell suspension containing ~300,000 viable cells were centrifuged at 150×g, and the cells were resuspended in approximately 6 microliter of DMEM and drawn into a 20 microliter pipette tip connected to a 1 milliliter syringe. The tip of the pipette tip containing the cells was clamped using a small Ligaclip (Ethicon Endosurgery, Cincinnati Ohio).

Animal Preparation.

Mice (Mus Musculus)/Fox Chase SCID/Male (Harlan Sprague Dawley, Inc., Indianapolis, Ind.), 8 weeks of age. All handling of the SCID mice took place under a hood. The mice were individually weighed and anesthetized with an intraperitoneal injection of a mixture of 60 milligrams/kilogram KETASET (ketamine hydrochloride, Aveco Co., Inc., Fort Dodge, Iowa) and 10 milligrams/kilogram ROMPUN (xylazine, Mobay Corp., Shawnee, Kans.) and saline. After induction of anesthesia, the entire back of the animal from the dorsal cervical area to the dorsal lumbosacral area was clipped free of hair using electric animal clippers. The area was scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period. The anesthetized and surgically prepared animal was placed in the desired recumbent position. A transverse incision was made on the left abdominal side approximately 2 cm caudal to the rib cage of animal. The kidney was exposed and the capsule pierced with a 26-gauge needle. A capsule lance (modified glass pipette tip) was used to create a space beneath the kidney capsule into which the cells were introduced. The cells were injected via a syringe with a micropipette tip attached. The pocket was closed by passing an ophthalmic cautery pen (Aaron medical Industries, St. Petersburg, Fla.) over the opening (not touching the kidney). The kidney was placed back in the correct anatomical position and the muscle layer sutured closed. The skin was closed with wound clips.

The experimental design comprised one transplantation of cells per mouse (Table 25-1); four treatments with n-value of 4 per treatment; and three time-points (1, 14, and 30 days).

Mice were euthanized at their designated intervals by carbon dioxide inhalation. The kidney implantation sites were excised and frozen for histology.

Immunohistochemistry. Frozen kidney implantation sites were embedded on edge in O.C.T. Compound (Sakura, Torrance, Calif.). The kidney tissue was trimmed by cryosectioning to yield a five-micron section of the implantation site and adjacent tissue. Yielded sections were fixed in freshly prepared 4% paraformaldehyde (EM Sciences Gibbstown, N.J.) in phosphate buffered saline (Gibco) for 15 minutes. Sections were washed in PBS and incubated in 3% goat serum in PBS blocking solution for one hour. Blocking solution was removed by gentle aspiration. Sections were incubated in anti-human nuclei antibody (Chemicon International, Temecula, Calif.) diluted 1:100 in blocking solution for one hour. Sections were washed with PBS and incubated in fluorescent labeled goat anti-mouse IgG antibody (Molecular Probes Eugene, Oreg.) diluted 1:200 in blocking solution for 30 minutes in absence of light. Sections were washed in PBS and incubated in 10 microMolar DAPI (Molecular Probes Eugene, Oreg.) for five minutes. Sections were washed in PBS and examined by fluorescent microscopy.

Tri-Chrome Staining. Frozen kidney implantation sites were embedded on edge in O.C.T. Compound (Sakura Torrance, Calif.). The kidney tissue was trimmed by cryosectioning to yield a five-micron section of the implantation site and adjacent tissue. Yielded sections were fixed in 10% neutral buffered formalin (Richard-Allan Scientific Kalamazoo, Mich.) for 15 minutes. Sections were stained tri-chrome (Poly Scientific Bay Shore, N.Y.) using manufacturer's methods.

TABLE 25-1

SCID Mouse Kidney Capsule Cell Transplantation Scheme

| Animal (#) | Post-Transplantation Days | Kidney Capsule (left) |
|---|---|---|
| 1 | 1 | 1 |
| 2 | 1 | 1 |
| 3 | 1 | 1 |
| 4 | 1 | 1 |
| 5 | 14 | 1 |
| 6 | 14 | 1 |
| 7 | 14 | 1 |
| 8 | 14 | 1 |
| 9 | 30 | 1 |
| 10 | 30 | 1 |
| 11 | 30 | 1 |
| 12 | 30 | 1 |
| 13 | 1 | 2 |
| 14 | 1 | 2 |
| 15 | 1 | 2 |
| 16 | 1 | 2 |
| 17 | 14 | 2 |
| 18 | 14 | 2 |
| 19 | 14 | 2 |
| 20 | 14 | 2 |
| 21 | 30 | 2 |
| 22 | 30 | 2 |
| 23 | 30 | 2 |
| 24 | 30 | 2 |

Treatments:
1. $3 \times 10^3$ cells from placenta
2. $3 \times 10^3$ cells from placenta + $3 \times 10^3$ CD34 + cells
Added animal # 25-27 as control (No cells)

Results

The viability of the placenta-derived cells was ~75% and the CD34+ cells was 95%. Initial attempts to transplant $1 \times 10^6$ viable cells were unsuccessful due to inadequate size of the kidney capsule to accommodate the cells. Cells were transplanted within 3 hours of trypsinization. The localization of placenta-derived cells under the kidney capsule was observed microscopically. There were no apparent differences in the number and distribution of placenta- derived cells with or without CD34+ cells at each time point. There was an apparent decrease in cell numbers over time.

Staining of cells under the kidney capsule showed the retention of transplanted cells. Human cells were detected using the human nuclear antigen. All cells (human and mouse) were detected using DAPI.

Summary. Transplantation of cells into the renal capsule was successful. Undifferentiated placenta-derived cells ($3 \times 10^3$) pre-treated with growth factors with or without $3 \times 10^3$ GM-CSF mobilized CD34+ cells were transplanted beneath the capsule of the kidney. Animals were sacrificed at 1, 14, and 30 days following cell transplantation. Cells survived at 1, 14, and 30 days with a reduction in apparent cell numbers at 30 days. The presence of GM-CSF mobilized CD34+ cells did not effect the survival of placenta-derived cells. This study demonstrates that placenta-derived cells can be transplanted to the kidney capsule.

Example 26

Transplantation of Placenta-Derived Cells

Cells derived from the postpartum placenta are useful for regenerative therapies. The tissue produced by placenta-derived cells transplanted into SCID mice with a biodegradable material was evaluated. The materials evaluated were VICRYL nonwoven, 35/65 PCLJPGA foam, and RAD 16 self-assembling peptide hydrogel.

Methods & Materials

Cell Culture. Placenta-derived cells were grown in Growth medium (DMEM-low glucose (Gibco, Carlsbad Calif.), 15% (v/v) fetal bovine serum (Cat. #SH30070.03; Hyclone, Logan, Utah), 0.001% (v/v) betamercaptoethanol (Sigma, St. Louis, Mo.), 50 Units/milliliter penicillin, 50 microgram/milliliter streptomycin (Gibco)) in a gelatin-coated flasks.

Matrix Preparation. A nonwoven scaffold was prepared using a traditional needle punching technique as described below. Fibers, comprised of a synthetic absorbable copolymer of glycolic and lactic acids (PGA/PLA), sold under the tradename VICRYL were obtained from Ethicon, Inc. (Somerville, N.J.). The fibers were filaments of approximately 20 microns in diameter. The fibers were then cut and crimped into uniform 2-inch lengths to form 2-inch staple fiber. A dry lay needle-punched nonwoven matrix was then prepared utilizing the VICRYL staple fibers. The staple fibers were opened and carded on standard nonwoven machinery. The resulting mat was in the form of webbed staple fibers. The webbed staple fibers were needle-punched to form the dry lay needle-punched nonwoven scaffold. The nonwoven scaffold was rinsed in water followed by another incubation in ethanol to remove any residual chemicals or processing aids used during the manufacturing process.

Foams, composed of 35/65 poly(epsilon-caprolactone)/poly(glycolic acid) (35/65 PCUPGA) copolymer, werer formed by the process of lyophilized, as discussed in U.S. Pat. No. 6,355,699.

Sample Preparation. One million viable cells were seeded in 15 microliter Growth medium onto 5 millimeter diameter, 2.25 millimeter thick nonwoven scaffolds (64.33 milligram/cubic centimeters) or 5 millimeter diameter 35/65 PCUPGA foam disks. Cells were allowed to attach for two hours before adding more Growth medium to cover the scaffolds.

Cells were grown on scaffolds overnight. Scaffolds without cells were also incubated in medium.

RAD16 self-assembling peptides (3D Matrix, Cambridge, Mass. under a material transfer agreement) was obtained as a sterile 1% (w/v) solution in water, which was mixed 1:1 with $1\times10^6$ cells in 10% (w/v) sucrose (Sigma, St Louis, Mo.), 10 millimolar HEPES in Dulbecco's modified medium (DMEM; Gibco) immediately before use. The final concentration of cells in RAD16 hydrogel was $1\times10^6$ cells/100 microliter.

TEST MATERIAL (N=4/Rx)
1. VICRYL nonwoven+$1\times10^6$ placenta-derived cells
2. 35/65 PCL/PGA foam+$1\times10^6$ placenta-derived cells
3. RAD 16 self-assembling peptide+$1\times10^6$ placenta-derived cells
4. 35/65 PCL/PGA foam
5. VICRYL nonwoven Animal Preparation. The animals utilized in this study were handled and maintained in accordance with the current requirements of the Animal Welfare Act. Compliance with the above Public Laws were accomplished by adhering to the Animal Welfare regulations (9 CFR) and conforming to the current standards promulgated in the Guide for the Care and Use of Laboratory Animals, 7th edition.

Mice (*Mus Musculus*)/Fox Chase SCID/Male (Harlan Sprague Dawley, Inc., Indianapolis, Ind.), 5 weeks of age. All handling of the SCID mice took place under a hood. The mice were individually weighed and anesthetized with an intraperitoneal injection of a mixture of 60 milligram/kilogram KETASET (ketamine hydrochloride, Aveco Co., Inc., Fort Dodge, Iowa) and 10 milligram/kilogram ROMPUN (xylazine, Mobay Corp., Shawnee, Kans.) and saline. After induction of anesthesia, the entire back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period.

Subcutaneous Implantation Technique. Four skin incisions, each approximately 1.0 cm in length, were made on the dorsum of the mice. Two cranial sites were located transversely over the dorsal lateral thoracic region, about 5-millimeter caudal to the palpated inferior edge of the scapula, with one to the left and one to the right of the vertebral column. Another two were placed transversely over the gluteal muscle area at the caudal sacro- lumbar level, about 5-mm caudal to the palpated iliac crest, with one on either side of the midline. Implants were randomly placed in these sites. The skin was separated from the underlying connective tissue to make a small pocket and the implant placed (or injected for RAD16) about 1-cm caudal to the incision. The appropriate test material was implanted into the subcutaneous space. The skin incision was closed with metal clips.

Animal Housing. Mice were individually housed in microisolator cages throughout the course of the study within a temperature range of 64° F.-79° F. and relative humidity of 30% to 70% and were maintained on an approximate 12 hour light/12 hour dark cycle. The temperature and relative humidity were maintained within the stated ranges to the greatest extent possible. Diet consisted of Irradiated Pico Mouse Chow 5058 (Purina Co.) and water fed ad libitum.

Mice were euthanized at their designated intervals by carbon dioxide inhalation. The subcutaneous implantation sites with their overlying skin were excised and frozen for histology.

Histology. Excised skin with implant was fixed with 10% neutral buffered formalin (Richard-Allan Kalamazoo, Mich.). Samples with overlying and adjacent tissue were centrally bisected, paraffin-processed, and embedded on cut surface using routine methods. Five- micron tissue sections were obtained by microtome and stained with hematoxylin and eosin (Poly Scientific Bay Shore, N.Y.) using routine methods.

Results

There was minimal ingrowth of tissue into foams implanted subcutaneously in SCID mice after 30 day. In contrast there was extensive tissue fill in foams implanted with placenta-derived cells.

There was some tissue in growth in VICRYL nonwoven scaffolds. Nonwoven scaffolds seeded with placenta-derived cells showed increased matrix deposition and mature blood vessels.

It was not possible to identify the point of injection of RAD16 and cells.

Summary. The purpose of this study was to determine the type of tissue formed by cells derived from human placenta in scaffolds in immune deficient mice. Synthetic absorbable nonwoven/foam discs (5.0 millimeter diameter×1.0 millimeter thick) or self-assembling peptide hydrogel were seeded with cells derived from human placenta and implanted subcutaneously bilaterally in the dorsal spine region of SCID mice. It has been demonstrated that placenta-derived cells can dramatically increase good quality tissue formation in biodegradable scaffolds.

Example 27

Assessment of Placenta-Derived Cells for Cardiovascular Therapy in a Rodent Coronary Ligation Model The efficacy of intracardiac human placenta-derived cell treatment when administered 15 minutes post-coronary artery occlusion was evaluated in a rodent model of myocardial ischemia/infarction.

Methods & Materials

The Charles River Worcester, Mass. test facility is accredited by the Association for the Assessment and Accreditation of Laboratory Animal Care, International (AAALAC) and registered with the United States Department of Agriculture to conduct research in laboratory animals. All the conditions of testing will conform to the Animal Welfare Act (9 CFR) and its amendments. The protocol was reviewed and approved by the Institutional Animal Care and Use Committee (IACUC) at the Test Facility for compliance with regulations prior to study initiation.

The animals having characteristics identified in Table 27-1 were individually housed in micro-isolator cages on autoclaved bedding. The cages conform to standards set forth in The Guide for the Care and Use of Laboratory Animals.

TABLE 27-1

Animal characteristics

| | |
|---|---|
| Species | *Rattus norvegicus* |
| Strain | Rnu |

TABLE 27-1-continued

Animal characteristics

| | |
|---|---|
| Source | Charles River Laboratories |
| Age at Dosing | 6-8 weeks |
| Weight at Dosing | ~200-250 grams |
| Number of Males (including spares) | 40 + 10 |

Purina Certified Diet (irradiated) was provided to the animals ad libitum. This diet was routinely analyzed by the manufacturer for nutritional components and environmental contaminants. Results of the manufacturer's analyses are on file at the Test Facility. Autoclaved Filtered tap water was provided ad libitum. Samples of the filtered water were analyzed for total dissolved solids, hardness, specified microbiological content, and selected environmental contaminants. Results of these analyses are on file at the Test Facility.

Environmental controls were set to maintain temperatures of 18 to 26° C. (64 to 79° F.) with a relative humidity of 30% to 70%. A 12:12 hour light:dark cycle was maintained. Ten or greater air changes per hour were maintained in the animal rooms. Upon receipt and prior to use on the study, the animals were held for a minimum of four days for conditioning according to the Test Facility Vendor Management Program as described in the Test Facility Standard Operating Procedure, Receipt, Conditioning, and Quarantine of Laboratory Animals.

Each animal was identified by a unique number and this number was indicated by an ear punch. Animals were randomly assigned to groups by a weight-ordered distribution such that individual body weights did not exceed ±20% of mean weight.

The animals were anesthetized with sodium pentobarbital (40 milligram/kilogram) and buprenorphine (0.05 milligram/kilogram) as a single cocktail given intramuscularly (IM). Following the establishment of anesthesia, animals were intubated using an 18-16 gauge, 2-inch length angiocath, or appropriate sized angiocath, and maintained on room air respiration (supplemented with oxygen) and a positive pressure ventilator throughout the surgical procedure. Additional anesthesia was given incrementally as needed. Preoperative antibiotic therapy was also administered, Benzathine/Procaine penicillin G, 40,000 Units/kilogram, IM. Additional antibiotic therapy was administered every 48 hours.

Electrode pads were placed around the appropriate paws of the animals to receive a useable electrocardiogram (ECG) signal. Animals were positioned on a heating pad to help maintain body temperature throughout the procedure. A rectal temperature probe was inserted into the animal to monitor body temperature. Ophthalmic ointment was administered to each eye. The surgical sites (thoracic area) were prepared for aseptic surgery by removing any excess fur, and gently wiping the area with sponges that have been soaked in 70% isopropyl alcohol, which was allowed to dry. Medi Sepps™ or similar solution was then applied to the area and also allowed to dry. The area was appropriately draped for strict aseptic surgery.

A surgical incision was made on the skin over the fourth intercostal space. Blunt dissection through the muscle layers was used to access the thoracic cavity. A retractor was carefully inserted into the fourth intercostal space and opened to allow access to the interior cavity. The pericardium was carefully opened via gentle teasing with cotton swabs dampened in sterile saline solution. A damp cotton swab was used to gently push the apex of the heart into the opening where a length of 6-0 silk suture was attached into the myocardium for manipulation of the heart. After a pause to allow the heart to recover, the suture placed in the apex was used to ease the heart out of the chest cavity and to place sufficient tension on the heart to allow access to the upper heart and the left anterior descending coronary artery (LAD). Another length of 6-0 silk suture was placed into the myocardium so as to surround the LAD. The pressure on the apical suture was released and the heart allowed to return to the interior of the chest cavity.

Once the heart rate and ECG returned to baseline values, the ligatures around the LAD were tied off to occlude the LAD. This was a permanent occlusion with the suture tied off and the ends trimmed. Once the ligature was tied, the surgeon looked for the following indications of successful occlusion: change in color of the area of the heart directly below the ligature to a white/grayish white as a result of the termination of blood flow to the area and a significant change in the ECG corresponding to occlusion of the LAD. Arrhythmias may have developed within the first 10 minutes of the occlusion. The rat was monitored closely during this time period in the event that resuscitation was necessary. In the event of severe arrhythmia and failure of the rat to convert to normal sinus rhythm without assistance, aid was rendered via cardiac massage. Approximately 15 minutes following the initiation of the LAD occlusion, the area of left ventricle made ischemic was treated with either vehicle or test article by direct injection into the ischemic myocardium. Treatment consisted of three to ten intramyocardial injections (100 microliter/injection) into the ischemic zone of myocardium.

Human cells were grown in Growth medium (DMEM-low glucose (Gibco, Carlsbad Calif.), 15% (v/v) fetal bovine serum (Cat. #SH30070.03, Hyclone, Logan Utah), 0.001% (v/v) betamercaptoethanol (Sigma, St. Louis, Mo.), 50 Units/milliliter penicillin, 50 microgram/milliliter streptomycin (Gibco, Carlsbad Calif.), in a gelatin-coated T300 flasks. Cells were washed with phosphate buffered saline (PBS, Gibco, Carlsbad Calif.) and trypsinized using Trypsin/EDTA (Gibco, Carlsbad Calif.). The trypsinization was stopped by adding Growth medium. The cells were centrifuged at 150×g, supernatant removed, and the cell pellet was resuspended in approximately 1 milliliter Growth medium per million cells. An aliquot of cells was removed and added to trypan blue (Sigma, St. Louis, Mo.). The viable cell number was estimated using a hemocytometer. The cell suspension was centrifuged and resuspended in 1 milliliter Growth containing 10% (v/v) DMSO (Hybrimax, Sigma, St. Louis, Mo.) per 5 million cells and transferred into Cryovials (Nalgene). The cells were cooled at approximately 1° C./minute overnight in a −80° C. freezer using a "Mr Frosty" freezing container (Nalgene, Rochester, N.Y.). Vials of cells were transferred into liquid nitrogen. Vials were shipped from CBAT, Somerville, N.J. to Charles River, Worcester, Mass. on dry ice and stored at −80° C. Approximately 1-2 hours before injection of cells into the animal, a vial of cells was thawed rapidly in a 37° C. water bath. Under aseptic conditions in a BSL2 biosafety cabinet, cells were added to 40 milliliters PBS with magnesium and calcium (Sigma St. Louis, Mo.) and centrifuged at 150×g for 5 minutes before resuspending the cell pellet in 10 milliliters PBS. The cell number and viability was estimated as described above. The cells were centrifuged at 150×g for 5 minutes and resuspended in PBS at a final concentration of $10^6$ viable cells/100 microliter. The cell suspension was loaded into 1 milliliter syringes with a 30G needle and kept on ice. Viability was assessed again up to 5 hours on ice.

Following the administration of treatment (Table 27-2) and stabilization of the heart, the surgeon began closing the surgical incision. The retractor was removed. The lungs were over-inflated for 3-4 breaths and visually inspected as much as possible to ensure that they were fully re-inflated. This created a negative pressure necessary to prevent pneumothorax post-recovery. To evacuate fluid and excess air from the thoracic cavity after closing the cavity, an intravenous catheter (i.e., 20 gauge, 2 millimeter in length) was placed through the skin and muscle layers so that the tip remains in the thoracic cavity. Care was taken so that the tip did not pierce the lung or heart. The separated ribs and associated muscle was sutured together with appropriate suture. The upper layers of muscle was sutured using a simple continuous pattern. The skin was closed with 4-0 silk using a horizontal mattress pattern. A 10 milliliter syringe was attached to the intravenous catheter that had been previously placed in the thoracic cavity and the plunger slowly pulled back to withdraw fluids and air from the cavity. At the same time, the catheter was slowly withdrawn from the entry site, thereby allowing the surrounding muscle mass and skin to seal the puncture. The surgical drape was removed and fluids (i.e., lactated Ringers solution, 25 milliliter/kilogram subcutaneously [SC] or intraperitoneally [IP]) were given.

lature, and wall thickness. These images were saved on optical disk for further analysis. After examination, the gel medium was removed from the skin with gauze or paper towel. The rat was removed from the ventilator and placed in a warmed recovery cage until mobile.

At the conclusion of the surgical procedures, respiratory ventilation was turned off. The animals were observed for pedal reflex. The rectal probe and ECG electrodes subsequently were removed, and the animal was extubated and placed in a warmed oxygenated recovery cage. After complete recovery from anesthesia, the animals were given buprenorphine (0.05 milligram/kilogram, SC). Observations were made regularly until the animals showed full mobility and an interest in food and water. The animals then were placed in a clean housing cage and returned to the animal housing room. Animals were monitored for surgical incision integrity twice daily post-surgery.

Analgesics (i.e., Buprenorphine, 0.05 milligram/kilogram SC) were given twice daily for 4 days post-operatively and thereafter as needed. Visual indications of post- operative pain include lack of normal body postures and movement (e.g., animal remains in hunched position), antipathy, lack of eating/drinking, lack of grooming, etc.

Body weight was recorded for each animal prior to initial treatment, weekly thereafter, and on the day of necropsy. Animals found dead were weighed and necropsied.

TABLE 27-2

Treatment regimens

| Gr. No. | No. of Males | Test Article | Dosage Level (cells/animal) | Dose Conc. (cells/mL) | Route/Dose Regimen | Time of Treatment Administration | Necropsy Day |
|---------|--------------|-------------|------------------------------|----------------------|---------------------|----------------------------------|--------------|
| 1 | 8 | Vehicle | 0 | 0 | Direct injection(s) into the ischemic region of the left ventricle of the heart, consisting of 3 to 10 intramyocardial injections of 100 microliters total. | 15 minutes after coronary artery ligation | Day 28 (±1 Day) |
| 2 | 8 | Placenta #4 (P10) (A) | 1 million | 10 million | | | |
| 3 | 8 | Placenta #3 (P10) (C) | | | | | |
| 4 | 8 | Human fibroblasts 1F1853 (P10) (D) | | | | | |

Gr. = Group; No. = Number; Conc. = Concentration

Immediately after each rat had undergone treatment with test article and the incision sutured, the animal underwent an echocardiography (ECG) examination. Anesthesia was maintained throughout the completion of the echo examination. Upon the completion of the echo examination, ventilation was discontinued, and the rat was returned to the recovery area to recover in a heated, oxygenated recovery cage.

A second echo examination of each surviving animal was completed at the end of the study (approximately 28 days post-treatment), prior to termination. During the second examination, the animals were anesthetized as described previously.

For each echo examination, the left thoracic area was shaved, and warmed, ultrasonic gel was applied to the skin to enhance contact with the transducer. Electrode pads were placed around the appropriate extremities to receive an ECG signal. Echocardiographic images included short axis and long axis views to allow for the determination of ventricular cavity dimensions, contractility, blood flow through vascu- In order for the heart to be harvested, each rat was anesthetized as was done for surgery. The jugular vein was cannulated. The heart was arrested in diastole with potassium chloride infused via the jugular cannula. The heart was then removed from the thoracic cavity. A limited necropsy was then performed on the heart after which the heart was placed in 10% neutral buffered formalin. The remainder of each carcass was then discarded with no further evaluation.

Hearts of all animals that were found dead or euthanized moribund were placed in 4% paraformaldehyde until evaluated. The remainder of each carcass was then discarded with no further evaluation.

Histology and Image Analysis. Fixed tissues sectioned with a stainless steel coronal heart matrix (Harvard Apparatus Holliston, Mass.) yielded four two-millimeter thick serial tissue sections. Sections were processed and serially embedded in paraffin using routine methods. Five-micron sections were obtained by microtome and stained Masson's Tri-chrome for Connective Tissue (Poly Scientific Bay Shore, N.Y.) using manufacturer's methods. Electronic photomicrographs were captured and analyzed using image analysis methods developed by Phase 3 Imaging System (Glen Mills, Pa.). Photomicrographs of the tri-chrome stained sections were color-metrically analyzed electronically to determine the overall area of the ventricle and free wall and the area of the differential staining.

Results

There was no loss in the initial viability of cells over 5 hours in the vehicle when kept on ice. Cells were injected into the infarct with one to three needle entry points and multiple changes in direction of needle orientation.

Echocardiography measurements were taken from the infarct-treated rats. Fractional shortening of the vehicle-treated animals had a significant decrease from 47.7%±8.3% at Day 0 to 23.5%±30.2% at Day 28 ($p<0.05$). The animals that were treated with placenta-derived cells showed small, non-significant differences between the fractional shortening between Day 0 and 28. There was no significant difference between the fractional shortening between the groups at Day 0. Each group had eight animals at the start but some did not survive the experiment. The fibroblast-treated animals experienced greater mortality than those treated with PDCs.

Hearts collected at the study termination were subjected to histological analysis. The hearts were arrested in diastole and fixed. The results were calculated from an algorithm to estimate the percentage of total heart area that comprises the infarct. The infarct size in the vehicle-treated animals was 22.9%±6.7% of heart area, while the infarct size in hearts treated with two different isolates of placenta-derived cells was 13.9%±3.7% and 12.9%±3.4%, respectively, and with fibroblasts was 19.3%±8.0%. The difference of infarct size of cell-treated animals relative to vehicle-treated animals was not statistically significant, as determined by t-test/ANOVA.

Summary. The results of the present study suggest that the placenta-derived cells have some benefit in reducing the damage of a surgically induced myocardial infarction in rats. The vehicle-treated animals showed a significant reduction in cardiac function at day 28 as compared to day 0, as measured by fractional shortening, while the placenta-derived cell- treated animals showed minimal change over the 28-day study. The fibroblast-treated animals showed minimal change but only two animals survived the study. Evaluation of infarct size suggested that there may be some modest, but not statistically significant, reduction in the infarct size in the placenta-derived cell-treated animals as compared to the vehicle controls at Day 28. Taken together, these data support efficacy of the placenta-derived cells in reducing damage from a myocardial infarction.

Example 28

Use of Placenta-Derived Cells in the Treatment of Retinitis Pigmentosa

Currently no real treatment exists for blinding disorders that stem from the degeneration of cells in the retina. Loss of photoreceptors as a result of apoptosis or secondary degeneration lead to progressive deterioration of vision, and ultimately to blindness. Diseases in which this occurs include age-related macular degeneration (AMD) and retinitis pigmentosa (RP). RP is most commonly associated with a single gene mutation, which contributes to photoreceptor cell death.

The retinal photoreceptors and adjacent retinal pigment epithelium form a functional unit. The Royal College of Surgeons (RCS) rat presents with a tyrosine receptor kinase (Merkt) defect affecting outer segment phagocytosis, leading to photoreceptor cell death (D'Cruz et al. (2000) *Hum. Mol. Genet.* 9(4):645-51).

Transplantation of retinal pigment epithelial (RPE) cells into the subretinal space of RCS rats was found to limit the progress of photoreceptor loss and preserve visual function (Li and Turner (1988) *Exp Eye Res.* 47(6):911-7). In this example, it is demonstrated that placenta-derived cells can be used to promote photoreceptor rescue in a RCS model.

Methods & Materials

Cell transplants. Cultures of human placental and adult fibroblast cells (passage 10) were expanded for 1 passage. All cells were initially seeded at 5,000 cells/cm$^2$ on gelatin-coated T75 flasks in growth medium ((DMEM:Low glucose (Invitrogen, Carlsbad, Calif.), 15% (v/v) defined bovine serum (Hyclone, Logan, Utah; Lot#AND18475), 0.001% 2-mercaptoethanol (Sigma, St. Louis, Mo.), 50 Units/milliliter penicillin, 50 microgram/milliliter streptomycin, 0.25 micrograms per milliliter amphotericin B; Invitrogen, Carlsbad, Calif.)). For subsequent passages, all cells were treated as follows. After trypsinization, viable cells were counted after trypan Blue staining. Briefly, 50 microliter of cell suspension was combined with 50 microliter of 0.04% w/v trypan Blue (Sigma, St. Louis Mo.) and the viable cell number, was estimated using a heamocytometer. Cells were trypsinized and washed three times in supplement free-DMEM:Low glucose medium (Invitrogen, Carlsbad, Calif.). Cultures of human placental and fibroblast cells at passage 11 were trypsinized and washed twice in Leibovitz's L-15 medium (Invitrogen, Carlsbad, Calif.). For the transplantation procedure, dystrophic RCS rats were anesthetized with xylazine-ketamine (1 milligram/kilogram intraperitoneal (i.p.) of the following mixture: 2.5 milliliters xylazine at 20 milligram/milliliter, 5 milliliters ketamine at 100 milligram/milliliter, and 0.5 milliliter distilled water) and their heads secured by a nose bar. Cells devoid of serum were resuspended ($2 \times 10^5$ cells per injection) in 2 microliter of Leibovitz, L-15 medium (Invitrogen, Carlsbad, Calif.) and transplanted using a fine glass pipette (internal diameter 75 to 150 microliter) trans-scerally. Cells were delivered into the dorso- temporal subretinal space of anesthetized 3 week old dystrophic-pigmented RCS rats (total N=10/cell type).

Cells were injected unilaterally into the right eye, while the left eye was injected with carrier medium alone (Sham control; Leibovitz's L-15 medium). Viability of residual transplant cells remained at greater than 95% as assessed by trypan blue exclusion at the end of the transplant session. After cell injections were performed, animals were injected with dexamethasone (2 milligram/kilogram) for 10 days post transplantation. For the duration of the study, animals were maintained on oral cyclosporine A (210 milligram/liter of drinking water; resulting blood concentration: 250-300 microgram/liter) (Bedford Labs, Bedford, Ohio) from 2 days pre-transplantation until end of the study. Food and water were available ad libitum. Animals were sacrificed at 60 or 90 days postoperatively, with some animals being sacrificed at earlier timepoints for histological assessment of short-term changes associated with cell transplantation.

ERG recordings. Following overnight dark adaptation, animals were prepared for ERG recording under dim red light, as previously described (Sauve et al.(2004) *Vision Res.* January; 44(1):9-18). In brief, under anesthesia (with a mixture of 150 milligram/kilogram i.p ketamine, and 10 milligram/kilogram i.p. xylazine), the head was secured with a stereotaxic head holder and the body temperature monitored through a rectal thermometer and maintained at 38° C. using a homeothermic blanket. Pupils were dilated using equal parts of topical 2.5% phenylephrine and 1% tropicamide. Topical anesthesia with 0.75% bupivacaine was used to prevent any corneal reflexes and a drop of 0.9% saline was frequently applied on the cornea to prevent its dehydration and allow electrical contact with the recording electrode (gold wire loop). A 25-gauge needle inserted under the scalp, between the two eyes, served as the reference electrode. Amplification (at 1-1000 Hz bandpass, without notch filtering), stimulus presentation, and data acquisition were provided by the UTAS-3000 system from LKC Technologies (Gaithersburg, Md.). ERGs were recorded at 60 days.

Mixed a- and b-wave recording. For the quantification of dark-adapted b-waves, recordings consisted of single flash presentations (10 microseconds duration), repeated 3 to 5 times to verify the response reliability and improve the signal-to-noise ratio, if required. Stimuli were presented at six increasing intensities in one log unit steps varying from −3.6 to 1.4 log candila/m$^2$ in luminance. To minimize the potential bleaching of rods, inter-stimulus intervals were increased as the stimulus luminance was elevated from 10 sec at lowest stimulus intensity to 2 minutes at highest stimulus intensity. The maximum b-wave amplitude was defined as that obtained from the flash intensity series, regardless of the stimulus intensity. The true $V_{max}$ from fitting the data with a Naka-Rushton curve was not used because ERG responses were often erratic at higher luminance levels in dystrophic animals and showed tendencies for depressed responses around 0.4 and 1.4 log candila/m$^2$. In order to determine the age at which ERG components were obtained or lost, criterion amplitudes were used: 20 microVolt for a- and b-waves, and 10 microVolt for STR-like responses. The amplitude of the b-wave was measured from the a-wave negative peak up to the b-wave positive apex, and not up to the peak of oscillations, which can exceed the b-wave apex (Nusinowitz et al. (1999) *Invest Ophthalmol Vis Sci.* 40(12):2848-58).

Isolation of rod and cone responses. The double flash protocol was used to determine the isolation of rod and cone responses (Nixon et al. (2001) *Clin. Experiment Ophthalmol.* 29(3): 193-6). A probe flash was presented 1 sec after a conditioning flash, using a specific feature of the UTAS-3000 system (LKC Technologies) with calibrated ganzfeld; assuring complete recharge of the stimulator under the conditions used. The role of the conditioning flash in the procedure was to transiently saturate rods so that they were rendered unresponsive to the probe flash. Response to the probe flash was taken as reflecting cone-driven activity. A rod-driven b-wave was obtained by subtracting the cone-driven response from the mixed response (obtained following presentation of a probe flash alone, i.e., not preceded by any conditioning flash).

Histology. Animals were sacrificed with an overdose of urethane (12.5 gram/kilogram). The orientation of the eye was maintained by placing a 6.0 suture through the superior rectus muscle prior to enucleation. After making a corneal incision, the eyes were fixed with 2.5% parafomaldehyde, 2.5% glutaraldehyde, 0.01% picric acid in 0.1 M cacodylate buffer (pH 7.4). After fixation, the cornea and lens were removed by cutting around the cilliary body. A small nick was made in the periphery of the dorsal retina prior to removal of the superior rectus to assist in maintaining orientation. The retinas were then post-fixed in 1% osmium tetroxide for 1 hour. After dehydration through a series of alcohols to epoxypropane, the retinas were embedded in TAAB embedding resin (TAAB Laboratories, Aldemarston, UK). Semi-thin sections were stained with 1% toluidine Blue in 1% borate buffer and the ultra thin sections were contrasted with uranyl acetate and lead citrate.

For Nissl staining, sections were stained with 0.75% cresyl violet (Sigma, St. Louis, Mo.) after which they were dehydrated through graded alcohols at 70, 95 and 100% twice. They were then placed in xylene (Sigma, St. Louis, Mo.), rinsed with PBS (pH 7.4) (Invitrogen, Carlsbad, Calif.), coverslipped and mounted with DPX mountant (Sigma, St. Louis, Mo.).

Results

ERG Recordings. At 60 days post-transplant, animals that received placenta-derived cell injections (n=4) showed no improvement in a-wave (20±20) versus sham controls (0), but showed improvement in mixed b-wave (81±72) versus sham controls (1.5±2), and good improvement in cone-b-wave (50±19) versus sham controls (7±7), and in rod contribution (30%) versus sham controls (0). These results indicated improvement in visual responsiveness when compared to sham controls. In contrast to transplantation of placenta-derived cells, fibroblast transplantations showed no improvement in any of the parameters tested.

TABLE 28-1

ERG data

| Group | a-wave | | mixed b-wave | | cone b-wave | | % rod contribution | |
|---|---|---|---|---|---|---|---|---|
| | Untreated | Treated | Untreated | Treated | Untreated | Treated | Untreated | Treated |
| Sham 60 days | 0 | 0 | 7 ± 9 | 0 | 23 ± 5 | 12 ± 16 | N/A | N/A |
| P (n = 4) 60 days | 0 | 20 ± 20 | 1.5 ± 2 | 81 ± 72 | 7 ± 7 | 50 ± 19 | N/A | 30 |

N.B.
Sham = control (medium only), P = Placental cell transplant

Histology. Following transplantation, there was no histological evidence of an inflammatory reaction and infiltrating immune cells were not observed in Nissl-stained sections in the placental cell groups. However, fibroblast implantations resulted in animal death (n=7) and indications of early stage inflammatory responses.

REFERENCES

Lund et al. (2001) *Proc Natl Acad Sci U.S.A.* 98(17):9942-7.

Example 29

Chondrogenic Potential of Postpartum-Derived Cells on Implantation in SCID Mice

The chondrogenic potential of cells derived from umbilical cord or placenta tissue was evaluated following seeding on bioresorbable growth factor-loaded scaffolds and implantation into SCID mice.

Materials & Methods

Reagents. Dulbecco's Modified Essential Media (DMEM), Penicillin and Streptomycin, were obtained from Invitrogen, Carlsbad, Calif. Fetal calf serum (FCS) was obtained from HyClone (Logan, Utah). Mesenchymal stem cell growth medium (MSCGM) was obtained from Biowhittaker, Walkersville, Md. TGFbeta-3 was obtained from Oncogene research products, San Diego, Calif. GDF-5 was obtained from Biopharm, Heidelberg, Germany (International PCT Publication No. WO96/01316 A1, U.S. Pat. No. 5,994,094A). Chondrocyte growth medium comprised DMEM-High glucose supplemented with 10% fetal calf serum (FCS), 10 milliMolar HEPES, 0.1 milliMolar nonessential amino acids, 20 microgram/milliliter L-proline, 50 microgram/milliliter ascorbic acid, 100 Unit/milliliter penicillin, 100 microgram/milliliter streptomycin, and 0.25 microgram/milliliter amphotericin B. Bovine fibrinogen was obtained from Calbiochem.

Cells. Human mesenchymal stem cells (hMSC, Lot# 2F1656) were obtained from Biowhittaker, Walkersville, Md. and were cultured in MSCGM according to the manufacturer's instructions. This lot was tested in the laboratory previously in in vitro experiments and was shown to be positive in the chondrogenesis assays. Human adult fibroblasts were obtained from American Type Culture Collection (ATCC), Manassas, Va. and cultured in Growth Medium on gelatin-coated tissue culture plastic flasks. Postpartum-derived cells isolated from human umbilical cords (Lot# 022703Umb) and placenta (Lot# 071003Plac) were prepared as previously described (Example 1). Cells were cultured in Growth Medium on gelatin-coated tissue culture plastic flasks. The cell cultures were incubated in standard growth conditions. Cells used for experiments were at passages 5 and 14.

Scaffold. 65/35 Polyglycolic acid (PGA)/Polycaprolactone (PCL) foam scaffolds [4×5 centimeters, 1millimeter thick, Ethylene Oxide (ETO) sterilized] reinforced with Polydioxanone (PDS) mesh (PGA/PCL foam-PDS mesh) were obtained from Center for Biomaterials and Advanced Technologies (CBAT, Somerville, N.J.). Punches (3.5 millimeters) made from scaffolds were loaded with either GDF-5 (3.4 micrograms/scaffold), TGFbeta- 3 (10 nanograms/scaffold), a combination of GDF-5 and TGFbeta-3, or control medium, and lyophilized.

Cell seeding on scaffolds. Placenta- and umbilical cord-derived cells were treated with trypsin, and cell number and viability was determined. $0.75 \times 10^6$ cells were resuspended in 15 microliters of Growth Medium and seeded onto 3.5 millimeter scaffold punches in a cell culture dish. The cell-seeded scaffold was incubated in a cell culture incubator in standard air with 5% $CO_2$ at 37° C. for 2 hours after which they were placed within cartilage explant rings.

Bovine Cartilage Explants. Cartilage explants 5 millimeter in diameter were made from cartilage obtained from young bovine shoulder. Punches (3 millimeter) were excised from the center of the explant and replaced with cells seeded 3.5 millimeter resorbable scaffold. Scaffolds with cells were retained within the explants using fibrin glue (60 microliter of bovine fibrinogen, 3 milligram/milliliter). Samples were maintained in chondrocyte growth medium overnight, rinsed in Phosphate Buffered Saline the following day, and implanted into SCID mice.

Animals. SCID mice ((*Mus musculus*)/Fox Chase SCID/Male), 5 weeks of age, were obtained from Harlan Sprague Dawley, Inc. (Indianapolis, Ind.) and Charles River Laboratories (Portage, Mich.). Animals used in the study were selected without any apparent systematic bias. A tag was placed on each individual animal cage listing the accession number, implantation technique, animal number, species/strain, surgery date, in vivo period, and date of euthanasia. The animals were identified by sequential numbers marked on the ear with an indelible ink marker.

Experimental Design. A total of 42 mice were tested. Two scaffolds were implanted subcutaneously in each mouse as described below; 42 mice for subcutaneous implantation; 28 treatments with n-value of 3 per treatment. The study corresponds to IACUC Approval Number: Skillman IACUC 01-037. The study lasted six weeks.

SCID Implantation.

A. Body Weights

Each animal was weighed prior to being anesthetized and at necropsy.

B. Anesthesia and Surgical Preparation:

All handling of the SCID mice occurred under a hood. The mice were individually weighed and anesthetized with an intraperitoneal injection of a mixture of KETASET (ketamine hydrochloride [60 milligram/kilogram]), ROMPUN (xylazine [10 milligram/kilogram]), and saline.

After induction of anesthesia, the entire back of the animal from the dorsal cervical area to the dorsal lumbosacral area was clipped free of hair using electric animal clippers. The area was scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period. The anesthetized and surgically prepared animal was placed in the desired recumbent position.

C. Subcutaneous Implantation Technique:

An approximate 2-cm skin incision was made just lateral to the thoracic spine parallel to the vertebral column. The skin was separated from the underlying connective tissue via blunt dissection. Each SCID mouse received 2 treatments that were placed in subcutaneous pockets created by blunt dissection in each hemithorax through one skin incision. Tacking sutures of 5-0 ETHIBOND EXCEL (polyester) were used to tack the skin to musculature around each scaffold to prevent subcutaneous migration. Scaffolds were implanted for 6 weeks and then harvested. The experimental design is outlined in Table 29-1.

TABLE 29-1

Experimental Design: Treatment (N = 3 per treatment)

A. 65/35 PGA/PCL Foam + PDS mesh cultured with Placenta-derived cells, EP, TGFbeta3
B. 65/35 PGA/PCL Foam + PDS mesh cultured with Placenta-derived cells, EP, rhGDF-5
C. 65/35 PGA/PCL Foam + PDS mesh cultured with Placenta-derived cells, EP, rhGDF-5 + TGFbeta3
D. 65/35 PGA/PCL Foam + PDS mesh cultured with Placenta-derived cells, EP, control
E. 65/35 PGA/PCL Foam + PDS mesh cultured with Placenta-derived cells, LP, TGFbeta3
F. 65/35 PGA/PCL Foam + PDS mesh cultured with Placenta-derived cells, LP, rhGDF-5
G. 65/35 PGA/PCL Foam + PDS mesh cultured with Placenta-derived cells, LP, rhGDF-5 + TGFbeta3
H. 65/35 PGA/PCL Foam + PDS mesh cultured with Placenta-derived cells, LP, control
I. 65/35 PGA/PCL Foam + PDS mesh cultured with Umbilical cord-derived cells, EP, TGFbeta3
J. 65/35 PGA/PCL Foam + PDS mesh cultured with Umbilical cord-derived cells, EP, rhGDF-5
K. 65/35 PGA/PCL Foam + PDS mesh cultured with Umbilical cord-derived cells, EP, rhGDF-5 + TGFbeta3
L. 65/35 PGA/PCL Foam + PDS mesh cultured with Umbilical cord-derived cells, EP, control
M. 65/35 PGA/PCL Foam + PDS mesh cultured with Umbilical cord-derived cells, LP, TGFbeta3
N. 65/35 PGA/PCL Foam + PDS mesh cultured with Umbilical cord-derived cells, LP, rhGDF-5
O. 65/35 PGA/PCL Foam + PDS mesh cultured with Umbilical cord-derived cells, LP, rhGDF-5 + TGFbeta3
P. 65/35 PGA/PCL Foam + PDS mesh cultured with Umbilical cord-derived cells, LP, control
Q. 65/35 PGA/PCL Foam + PDS mesh cultured with hMSC, TGFbeta3
R. 65/35 PGA/PCL Foam + PDS mesh cultured with hMSC, rhGDF-5
S. 65/35 PGA/PCL Foam + PDS mesh cultured with hMSC, rhGDF-5 + TGFbeta3
T. 65/35 PGA/PCL Foam + PDS mesh cultured with hMSC, control
U. 65/35 PGA/PCL Foam + PDS mesh cultured with fibroblasts, Adult TGFbeta3
V. 65/35 PGA/PCL Foam + PDS mesh cultured with fibroblasts, Adult rhGDF-5
W. 65/35 PGA/PCL Foam + PDS mesh cultured with fibroblasts, Adult rhGDF-5 + TGFbeta3
X. 65/35 PGA/PCL Foam + PDS mesh cultured with fibroblasts, Adult control
Y. 65/35 PGA/PCL Foam + PDS mesh, TGFbeta3
Z. 65/35 PGA/PCL Foam + PDS mesh, rhGDF-5
AA. 65/35 PGA/PCL Foam + PDS mesh, rhGDF-5 + TGFbeta3
BB. 65/35 PGA/PCL Foam + PDS mesh, control D. Necropsy and Histologic Preparation Gross examination was performed on any animals that died during the course of the study or were euthanized in moribund condition. Selected tissues were saved at the discretion of the study director and/or pathologist.

Mice were euthanized by $CO_2$ inhalation at their designated intervals. Gross observations of the implanted sites were recorded. Samples of the subcutaneous implantation sites with their overlying skin were excised and fixed in 10% buffered formalin. Each implant was bisected into halves, and one half was sent to MPI Research (Mattawan, Mich.) for paraffin embedding, sectioning, and staining with Hematoxylin & Eosin (H&E) and Safranin O (SO).

The data obtained from this study were not statistically analyzed.

Results

New cartilage and bone formation was observed in the majority of the samples including growth factor-loaded, cell-seeded scaffolds, cell-seeded control scaffolds, and scaffolds loaded with growth factor alone. The extent of new cartilage and bone formation varied within the treatment and control groups.

Early and Late passage placenta-derived cell seeded scaffolds showed new cartilage and bone formation within the scaffolds. No obvious differences in new cartilage and bone formation was observed between the different growth factor-loaded, cell-seeded scaffolds and scaffolds seeded with cells alone. Compared to control scaffolds (without growth factors and without cells), it appeared that there was greater extent of new cartilage formation in cell-seeded scaffolds both with and without growth factors and in growth factor-loaded scaffolds alone. New cartilage formation with placenta-derived cell-seeded scaffolds was similar to MSC- and fibroblast-seeded scaffolds.

In growth factor-treated and control scaffolds seeded with umbilical cord-derived cells at early and late passage, new cartilage and bone formation were observed. The extent of cartilage formation appeared to be less than that seen with placenta-derived cells. No one sample showed extensive cartilage formation as seen with the placenta-derived cells. Bone formation appeared to be higher in scaffolds seeded with umbilical cord-derived cells on scaffolds containing both TGFbeta-3 and rhGDF-5.

hMSC-loaded scaffolds also showed new cartilage and bone formation. The extent of new cartilage and bone formation was similar for all the hMSC treatment groups. Human adult fibroblast seeded scaffolds also demonstrated new cartilage and bone formation. Results were similar to those obtained with placenta-derived cells and hMSCs In the control group, in which growth factor-loaded scaffolds or scaffold alone were placed in cartilage rings and implanted, new cartilage and bone formation were also observed. Not surprisingly, the extent of new cartilage formation was greater in scaffolds with growth factor than in scaffolds without growth factor. Increased bone formation was present in the control with the combination of the two tested growth factors.

New cartilage formation was observed adjacent to the cartilage explant rings as well as within the scaffolds. New cartilage formation within the scaffolds adjacent to the cartilage rings could be a result of chondrocyte migration. Cartilage formation seen as islands within the scaffolds may be a result of either migration of chondrocytes within the scaffolds, differentiation of seeded cells or differentiation of endogenous mouse progenitor cells. This observation stems from the fact that in control growth factor-loaded scaffolds with no seeded cells, islands of chondrogenic differentiation were observed. New bone formation was observed within the scaffolds independently and also associated with chondrocytes. Bone formation may have arisen from osteoblast differentiation as well as endochondral ossification.

It is difficult to separate new cartilage and bone formation associated with chondrocytes that migrated versus that from any chondrogenic and osteogenic differentiation of seeded cells that may have occurred. Staining of sections with specific human antibodies may distinguish the contribution of the seeded cells to the observed chondrogenesis and osteogenesis. It is also possible that placenta-derived cells and umbilical cord-derived cells stimulated chondrocyte migration.

Abundant new blood vessels were observed with the scaffolds loaded with placenta-derived cells and umbilical cord-derived cells. Blood vessels were abundant in areas of bone formation. New blood vessels were also observed within the hMSC- and fibroblast-seeded scaffolds associated with new bone formation.

Systemic effects of the adjacent scaffold (with growth factor (GF)) on the control scaffolds (no GF, no cells) on promoting new cartilage and bone formation cannot be ruled out. Analysis of new cartilage and bone formation in scaffolds, taking into consideration the scaffolds implanted adjacent to it in SCID mice, showed no clear pattern of systemic effect of growth factor from the adjacent scaffold.

Summary. Results showed that new cartilage and bone formation were observed in growth factor and control scaffolds seeded with placenta- and umbilical cord-derived cells. Results with placenta-derived cells were similar to that seen with human mesenchymal stem cells, while the extent of new cartilage like tissue formation was slightly less pronounced in umbilical cord-derived cells. Growth factor-loaded scaffolds implanted without cells also demonstrated new cartilage and bone formation. These data indicate that new cartilage formation within the scaffolds may arise from chondrocytes that migrated from the bovine explants, from chondrogenic differentiation of endogenous progenitor cells, and from chondrogenic differentiation of seeded cells.

These results suggest that placenta- and umbilical cord-derived cells undergo chondrogenic and osteogenic differentiation. These results also suggest that placenta- and umbilical cord-derived cells may promote migration of chondrocytes from the cartilage explant into the scaffolds. Abundant new blood vessels were also observed in the scaffolds especially associated with new bone formation.

Example 30

Use of Postpartum-Derived Cells in Nerve Repair

Retinal ganglion cell (RGC) lesions have been extensively used as models for various repair strategies in the adult mammalian CNS. It has been demonstrated that retrobulbar section of adult rodent RGC axons results in abortive sprouting (Zeng et al., 1995) and progressive death of the parent cell population (Villegas-Perez et al., 1993). Numerous studies have demonstrated the stimulatory effects of various exogenous and endogenous factors on the survival of axotomized RGC's and regeneration of their axons (Yip and So, 2000; Fischer et al., 2001). Furthermore, other studies have demonstrated that cell transplants can be used to promote regeneration of severed nerve axons (L1 et al., 2003; Ramon-Cueto et al., 2000). Thus, these and other studies have demonstrated that cell based therapy can be utilized for the treatment of neural disorders that affect the spinal cord, peripheral nerves, pudendal nerves, optic nerves or other diseases/trauma due to injury in which nervous damage can occur.

Self-assembling peptides (PuraMatrix™, U.S. Pat. Nos. 5,670,483, 5,955,343, U.S. Published Application No. 2002/0160471, International Patent Publication No. WO 02/062969) have been developed to act as a scaffold for cell-attachment to encapsulate cells in 3-D, plate cells in 2-D coatings, or as microcarriers in suspension cultures. Three-dimensional cell culture has required either animal-derived materials (mouse sarcoma extract), with their inherent reproducibility and cell signaling issues, or much larger synthetic scaffolds, which fail to approximate the physical nanometer-scale and chemical attributes of native ECM. RAD 16 ($NH_2$-RADARADARADA-COOH) and KLD ($NH_2$-KLD-LKLDLKLDL-COOH) are synthesized in small (RAD16 is 5 nanometers) oligopeptide fragments that self- assemble into nanofibers on a scale similar to the in vivo extracellular matrix (ECM) (3D Matrix, Inc Cambridge, Mass.). The self-assembly is initiated by mono- or di-valent cations found in culture media or the physiological environment. In the protocols described in this example, RAD 16 was used as a microcarrier for the implantation of postpartum cells into the ocular defect. In this example, it is demonstrated that transplants of postpartum-derived cells PPDCs) can provide efficacy in an adult rat optic nerve axonal regeneration model.

Methods & Materials

Cells. Cultures of human adult PPDCs (umbilical cord and placenta) and fibroblast cells (passage 10) were expanded for 1 passage. All cells were initially seeded at 5,000 cells/$cm^2$ on gelatin-coated T75 flasks in Growth Medium ((DMEM:Low glucose (Invitrogen, Carlsbad, Calif.), 15% (v/v) defined bovine serum (Hyclone, Logan, Utah; Lot#AND18475), 0.001% 2-mercaptoethanol (Sigma, St. Louis, Mo.), 100 Units per milliliter penicillin, 100 micrograms per milliliter streptomycin, 0.25 micrograms per milliliter amphotericin B; Invitrogen, Carlsbad, Calif.). At passage 11 cells were trypsinized and viability was determined using trypan blue staining. Briefly, 50 microlitres of cell suspension was combined with 50 microlitres of 0.04% w/v trypan blue (Sigma, St. Louis Mo.) and the viable cell number, was estimated using a hemocytometer. Cells were then washed three times in supplement free-Leibovitz's L-15 medium (Invitrogen, Carlsbad, Calif.). Cells were then suspended at a concentration of 200,000 cells in 25 microliters of RAD-16 (3DM Inc., Cambridge, Mass.) which was buffered and made isotonic as per manufacturer's recommendations. One hundred microliters of supplement free Leibovitz's L-15 medium was added above the cell/matrix suspension to keep it wet till use. These cell/matrix cultures were maintained under standard atmospheric conditions until transplantation occurred. At the point of transplantation the excess medium was removed.

Animals and Surgery. Long Evans female rats (220-240 gram body weight) were used. Under intraperitoneal tribromoethanol anesthesia (20 milligram/100 grams body weight), the optic nerve was exposed, and the optic sheath was incised intraorbitally at approximately 2 millimeter from the optic disc, the nerve was lifted from the sheath to allow complete transsection with fine scissors (L1 et al., 2003). The completeness of transection was confirmed by visually observing complete separation of the proximal and distal stumps. The control group consisted of lesioned rats without transplants. In transplant rats cultured postpartum cells seeded in RAD-16 were inserted between the proximal and distal stumps using a pair of microforceps. Approximately 75,000 cells in RAD-16 were implanted into the severed optic nerve. Cell/matrix was smeared into the severed cut using a pair of fine microforceps. The severed optic nerve sheath was closed with 10/0 black monofilament nylon (ETHICON, Edinburgh, UK). Thus, the gap was closed by drawing the cut proximal and distal ends of the nerve in proximity with each other.

After cell injections were performed, animals were injected with dexamethasone (2 milligrams/kilogram) for 10 days post transplantation. For the duration of the study, animals were maintained on oral cyclosporine A (210 milligrams/liter of drinking water; resulting blood concentration: 250-300 micrograms/liter) (Bedford Labs, Bedford, Ohio) from 2 days pre-transplantation until end of the study. Food and water were available ad libitum. Animals were sacrificed at either 30 or 60 days posttransplantation.

CTB Application. Three days before animals were sacrificed, under anesthesia, a glass micropipette with a 30-50 millimeter tip was inserted tangentially through the sclera behind the lens, and two 4-5 microliter aliquots of a 1% retrograde tracer-cholera toxin B (CTB) aqueous solution (List Biologic, Campbell, Calif.) was injected into the vitreous. Animals were perfused with fixative and optic nerves were collected in the same fixative for 1 hour. The optic nerves were transferred into sucrose overnight. Twenty micrometer cryostat sections were incubated in 0.1 molar glycine for 30 minutes and blocked in a PBS solution containing 2.5% bovine serum albumin (BSA) (Boeringer Mannheim, Mannheim, Germany) and 0.5% triton X-100 (Sigma, St. Louis, Mo.), followed by a solution containing goat anti-CTB antibody (List Biologic, Campbell, Calif.) diluted 1:4000 in a PBS containing 2% normal rabbit serum (NRS) (Invitrogen, Carlsbad, Calif.), 2.5% BSA, and 2% Triton X-100 (Sigma, St. Louis, Mo.) in PBS, and incubated in biotinylated rabbit anti-goat IgG antibody (Vector Laboratories, Burlinghame, Calif.) diluted 1:200 in 2% Triton-X100 in PBS for 2 hours at room temperature. This was followed by staining in 1:200 streptavadin-green (Alexa Flour 438; Molecular Probes, Eugene, Oreg.) in PBS for 2 hours at room temperature. Stained sections were then washed in PBS and counterstained with propidium iodide for confocal microscopy.

Histology Preparation. Briefly, 5 days after CTB injection, rats were perfused with 4% paraformaldehyde. Rats were given 4 cubic centimeters of urethane and were then perfused with PBS (0.1 molar) then with 4% Paraformaldehyde. The spinal cord was cut and the bone removed from the head to expose the colliculus. The colliculus was then removed and placed in 4% Paraformaldehyde. The eye was removed by cutting around the outside of the eye and going as far back as possible. Care was given not to cut the optic nerve that lies on the underside of the eye. The eye was removed and the muscles were cut exposing the optic nerve this was then placed in 4% Paraformaldehyde.

Results

Lesions alone. One month after retrotubular section of the optic nerve, a number of CTB-labeled axons were identified in the nerve segment attached to the retina. In the 200 micrometers nearest the cut, axons were seen to emit a number of collaterals at right angles to the main axis and terminate as a neuromatous tangle at the cut surface. In this cut between the proximal and distal stumps, the gap was observed to be progressively bridged by a 2-3 millimeter segment of vascularized connective tissue; however, no axons were seen to advance into this bridged area. Thus, in animals that received lesion alone no axonal growth was observed to reach the distal stump.

RAD-16 transplantation. Following transplantation of RAD-16 into the cut, visible ingrowth of vascularized connective tissue was observed. However, no axonal in growth was observed between the proximal and distal stumps. The results demonstrate that application of RAD-16 alone is not sufficient for inducing axonal regeneration in this situation.

Transplantation of postpartum-derived cells. Transplantation of postpartum-derived cells into the severed optic nerve stimulated optic nerve regrowth. Some regrowth was also observed in conditions in which fibroblast cells were implanted, although this was minimal as compared with the regrowth observed with the transplanted placenta-derived cells. Optic nerve regrowth was observed in 4/5 animals transplanted with placenta-derived cells, 3/6 animals transplanted with adult dermal fibroblasts, and in 1/4 animals transplanted with umbilical cord-derived cells. In situations where regrowth was observed, CTB labeling confirmed regeneration of retinal ganglion cell axons, which were demonstrated to penetrate through the transplant area. GFAP labeling was also performed to determine the level of glial scarring. The GFAP expression was intensified at the proximal stump with some immunostaining being observed through the reinervated graft.

Summary. These results demonstrate that transplanted human adult postpartum-derived cells are able to stimulate and guide regeneration of cut retinal ganglion cell axons.

REFERENCES

1) Zeng B Y, Anderson P N, Campbell G, Lieberman A R. 1995. J. Anat. 186:495-508.
2) Villegas-Perez M P, Vidal-Sanz M, Bray G M, Aguayo A J. 1988. J Neurosci. 8:265-80.
3) Yip HK, So K F. 2000. Prog Retin Eye Res. 19: 559-75.
4) Fischer D, Heiduschka P, Thanos S. 2001. Exp Neurol. 172: 257-72.
5) Ramon-Cueto A, Cordero M I, Santos-Benito F F, Avila J. 2000. Neuron 25: 425-35.

While the present invention has been particularly shown and described with reference to the presently preferred embodiments, it is understood that the invention is not limited to the embodiments specifically disclosed and exemplified herein. Numerous changes and modifications may be made to the preferred embodiment of the invention, and such changes and modifications may be made without departing from the scope and spirit of the invention as set forth in the appended claims.

What is claimed:

1. A cell culture comprising an isolated homogeneous cell population and a culture medium, wherein said isolated cell population is obtained from human postpartum placenta substantially free of blood, wherein said cell population self-renews and expands in culture; is multipotent; produces CD10, CD13, CD44, CD73, CD90, PDGFr-alpha, PD-L2 and HLA-A,B,C; does not produce CD31, CD34, CD45, CD80, CD86, CD117, CD141, CD178, B7-H2, HLA-G or HLA-DR-DP,DQ; expresses, relative to a human fibroblast, mesenchymal stem cell, or iliac crest bone marrow cell, increased levels of oxidized low density lipoprotein receptor 1 mRNA and renin; produces granulocyte chemotactic protein-2 (GCP-2); and has the ability to undergo at least 40 population doublings in culture, and wherein the culture medium comprises Dulbecco's modified Eagle's medium (DMEM)-low glucose, DMEM-high glucose, RPMI1640, serum- and protein-free DMEM, DMEM/MCDB201, Ham's F10 medium, Ham's F12 medium, DMEM/F12, Iscove's modified Dulbecco's medium, or Eagle's basal medium.

2. The cell of claim 1 wherein said cell lacks production of GRO-alpha and oxidized low density lipoprotein receptor, as detected by flow cytometry.

3. The cell culture of claim 1 wherein said cell population further has the following characteristics:
   (a) secretion of monocyte chemotactic protein 1 (MCP-1), interleukin-6 (IL-6), interleukin 8 (IL8), hepatocyte growth factor (HGF), keratinocyte growth factor (KGF), heparin-binding epidermal growth factor (HB-EGF), brain-derived neurotrophic factor (BDNF), tissue inhibitor of matrix metalloproteinase 1 (TIMP1), thrombopoietin (TPO), macrophage inflammatory protein 1 alpha(MIP 1 a), Rantes (regulated on activation, normal T cell expressed and secreted), thymus and activation-regulated chemokine (TARC), and Eotaxin; and
   (b) lack of secretion of fibroblast growth factor (FGF), vascular endothelial growth factor (VEGF), angiopoietin 2 (ANG2), platelet derived growth factor (PDGF-bb), transforming growth factor beta2 (TGFbeta2), macrophage inflammatory protein 1beta (MIP1b), I309, and macrophage-derived chemokine (MDC), as detected by ELISA.

4. The cell of claim 1 wherein said cell population is of a neonatal origin.

5. The cell of claim 1 wherein said cell population is of a maternal origin.

6. The cell culture of claim 1 wherein the culture medium comprises serum.

7. The cell of claim 6 wherein said culture medium comprises 2% -15% (v/v) serum.

8. The cell culture of claim 7 further comprising at least one growth factor of platelet derived growth factor-bb, epidermal growth factor, vascular endothelial growth factor, fibroblast growth factor, or leukemia inhibitory factor.

9. The cell culture of claim 6 wherein said culture medium comprises at least one of fibroblast growth factor, platelet-derived growth factor, vascular endothelial growth factor, and epidermal growth factor.

10. The culture of claim 6 that can undergo at least 40 population doublings in culture.

11. The cell culture of claim 1 wherein said culture medium comprises betamercaptoethanol.

12. The cell culture of claim 1 wherein said culture medium comprises at least one antibiotic agent.

13. The cell culture of claim 1 wherein said cell population expands in the following culture media in order of growth: Growth medium>Mesenchymal Stem Cell Growth Medium (MSCGM)>Iscove's+10% serum=DMEM-high glucose+10% serum=Ham's F12+10% serum=RPMI1640+ 10% serum.

14. The cell culture of claim 1 wherein said culture medium is protein-free culture medium.

15. The cell culture of claim 1 wherein said culture medium is serum-free culture medium.

16. The cell culture of claim 1 wherein said cell population cannot expand in the absence of L-valine.

17. The cell culture of claim 7 wherein the cell population has the ability to differentiate into a mesodermal, ectodermal, or endodermal phenotype.

18. The cell culture of claim 1 further comprising at least one growth factor of platelet derived growth factor-bb, epidermal growth factor, vascular endothelial growth factor, fibroblast growth factor, or leukemia inhibitor factor.

19. The cell culture of claim 1 wherein the culture medium further comprises at least one antimycotic agent.

20. The cell culture of claim 1 wherein said cell population characteristics are stable with passage of said cell population.

21. The cell culture of claim 1 wherein the cell population is genetically engineered to produce a protein of interest.

22. The cell culture of claim 1, wherein the cell population has undergone at least one doubling in culture.

23. The cell culture of claim 1 wherein said cell population obtained from human postpartum placenta substantially free of blood is produced by contacting said human postpartum placenta substantially free of blood with a composition comprising a matrix metalloprotease and a neutral protease and obtaining the cells yielded by said contacting.

24. The cell culture of claim 23 wherein said composition further comprises a mucolytic enzyme that digests hyaluronic acid.

25. The cell culture of claim 1 wherein the isolated homogeneous cell population is identified by ATCC Accession No. PTA-6074.

26. The cell culture of claim 1 wherein the isolated homogeneous cell population is identified by ATCC Accession No. PTA-6075.

27. The cell culture of claim 1 wherein the isolated homogeneous cell population is identified by ATCC Accession No. PTA-6079.

28. A cell culture comprising an isolated homogeneous cell population and a culture medium, wherein said isolated cell population is obtained from human postpartum placenta substantially free of blood, wherein said cell population self-renews and expands in culture; is multipotent; produces CD10, CD13, CD44, CD73, CD90, PDGFr-alpha, PD-L2 and HLA-A,B,C; does not produce CD31, CD34, CD45, CD80, CD86, CD117, CD141, CD178, B7-H2, HLA-G or HLA-DR-DP,DQ; expresses, relative to a human fibroblast, mesenchymal stem cell, or iliac crest bone marrow cell, increased levels of oxidized low density lipoprotein receptor 1 mRNA and renin; produces granulocyte chemotactic protein-2 (GCP-2); and has the ability to undergo at least 40 population doublings in culture.

29. A matrix comprising a cell culture,
wherein the matrix comprises a nonwoven scaffold comprising a copolymer of glycolic and lactic acids, a 35/65 PCL/PGA foam, an in situ polymerizable gel, or a self-assembling peptide hydrogel, and
wherein the cell culture comprises an isolated homogeneous cell population and a culture medium, wherein said isolated cell population is obtained from human postpartum placenta substantially free of blood, wherein said cell population self-renews and expands in culture; is multipotent; produces CD10, CD13, CD44, CD73, CD90, PDGFr-alpha, PD-L2 and HLA-A,B,C; does not produce CD31, CD34, CD45, CD80, CD86, CD117, CD141, CD178, B7-H2, HLA-G or HLA-DR-DP,DQ; expresses, relative to a human fibroblast, mesenchymal stem cell, or iliac crest bone marrow cell, increased levels of oxidized low density lipoprotein receptor 1 mRNA and renin; and produces granulocyte chemotactic protein-2 (GCP-2).

30. The matrix of claim 29 wherein said matrix comprises a nonwoven scaffold comprising a copolymer of glycolic and lactic acids.

31. The matrix of claim 29 wherein the matrix comprises a self-assembling peptide hydrogel.

32. A kit comprising the cell culture comprising an isolated homogeneous cell population, a culture medium and at least one additional component selected from the group consisting of a scaffold, a hydrating agent, and a cell culture substrate, wherein the cell population is cryopreserved, and wherein said isolated cell population is obtained from human postpartum placenta substantially free of blood, wherein said cell population self-renews and expands in culture; is multipotent; produces CD10, CD13, CD44, CD73, CD90, PDGFr- alpha, PD-L2 and HLA-A,B,C; does not produce CD31, CD34, CD45, CD80, CD86, CD117, CD141, CD178, B7-H2, HLA-G or HLA-DR-DP,DQ; expresses, relative to a human fibroblast, mesenchymal stem cell, or iliac crest bone marrow cell, increased levels of oxidized low density lipoprotein receptor 1 mRNA and renin; and produces granulocyte chemotactic protein-2 (GCP-2).

33. The kit of claim 32 wherein said cell culture is seeded on said scaffold.

34. A cryopreserved composition comprising an isolated homogeneous cell population, wherein said isolated cell population is obtained from human postpartum placenta substantially free of blood, wherein said cell population self-renews and expands in culture; is multipotent; produces CD10, CD13, CD44, CD73, CD90, PDGFr-alpha, PD-L2 and HLA- A,B,C; does not produce CD31, CD34, CD45, CD80, CD86, CD117, CD141, CD178, B7-H2, HLA-G or HLA-DR-DP,DQ; expresses, relative to a human fibroblast, mesenchymal stem cell, or iliac crest bone marrow cell, increased levels of oxidized low density lipoprotein receptor 1 mRNA and renin; produces granulocyte chemotactic protein-2 (GCP-2); and has the ability to undergo at least 40 population doublings in culture.

35. The cryopreserved composition of claim 34, wherein said cell population lacks production of GRO-alpha and oxidized low density lipoprotein receptor, as detected by flow cytometry.

36. The cryopreserved composition of claim 34, wherein said cell population further has the following characteristics:
(a) secretion of monocyte chemotactic protein 1 (MCP-1), interleukin-6 (IL-6), interleukin 8 (IL8), hepatocyte growth factor (HGF), keratinocyte growth factor (KGF), heparin-binding epidermal growth factor (HB-EGF), brain-derived neurotrophic factor (BDNF), tissue inhibitor of matrix metalloproteinase 1 (TIMP1), thrombopoietin (TPO), macrophage inflammatory protein 1 alpha(MIP 1a), Rantes (regulated on activation, normal T cell expressed and secreted), thymus and activation-regulated chemokine (TARC), and Eotaxin; and
(b) lack of secretion of fibroblast growth factor (FGF), vascular endothelial growth factor (VEGF), angiopoietin 2 (ANG2), platelet derived growth factor (PDGF-bb), transforming growth factor beta2 (TGFbeta2), macrophage inflammatory protein 1beta (MIP1b), I309, and macrophage-derived chemokine (MDC), as detected by ELISA.

37. The cryopreserved composition of claim 34, further comprising a matrix, wherein the matrix comprises a nonwoven scaffold comprising a copolymer of glycolic and lactic acids, a 35/65 PCL/PGA foam, an in situ polymerizable gel, or a self-assembling peptide hydrogel.

38. The cryopreserved composition of claim 37, wherein said matrix comprises a nonwoven scaffold comprising a copolymer of glycolic and lactic acids.

39. The cryopreserved composition of claim 37, wherein the matrix comprises a self- assembling peptide hydrogel.

40. The cryopreserved composition of claim 34, wherein said cell population obtained from human postpartum placenta substantially free of blood is produced by contacting said human postpartum placenta substantially free of blood with matrix metalloprotease enzyme and a neutral protease enzyme and obtaining the cells yielded by said contacting.

41. The cryopreserved composition of claim 40, further comprising contacting said human postpartum placenta with a mucolytic enzyme that digests hyaluronic acid.

42. The cryopreserved composition of claim 34, wherein the isolated homogeneous cell population is identified by ATCC Accession No. PTA-6074.

43. The cryopreserved composition of claim 34, wherein the isolated homogeneous cell population is identified by ATCC Accession No. PTA-6075.

44. The cryopreserved composition of claim 34, wherein the isolated homogeneous cell population is identified by ATCC Accession No. PTA-6079.

* * * * *